United States Patent
Chan et al.

(10) Patent No.: US 7,528,132 B2
(45) Date of Patent: May 5, 2009

(54) KINASE INHIBITORS

(75) Inventors: Tin-Yau Chan, Edison, NJ (US); Thierry O. Fischmann, Scotch Plains, NJ (US); Mark A. McCoy, Randolph, NJ (US); Brian A. McKittrick, Vernon, NJ (US); Andrew J. Prongay, Stewartsville, NJ (US); Haiyan Pu, Morris Plains, NJ (US); Li Wang, Nanuet, NY (US); Li Xiao, Cranbury, NJ (US)

(73) Assignee: Schering Corporation, Kenilworth, NJ (US)

( * ) Notice: Subject to any disclaimer, the term of this patent is extended or adjusted under 35 U.S.C. 154(b) by 317 days.

(21) Appl. No.: 11/338,501

(22) Filed: Jan. 24, 2006

(65) Prior Publication Data
US 2008/0004257 A1 Jan. 3, 2008

Related U.S. Application Data

(60) Provisional application No. 60/647,096, filed on Jan. 26, 2005.

(51) Int. Cl.
C07D 403/12 (2006.01)
C07D 403/14 (2006.01)
A61K 31/53 (2006.01)
A61P 35/00 (2006.01)

(52) U.S. Cl. .................................. 514/241; 544/182
(58) Field of Classification Search .............. 544/182; 514/241
See application file for complete search history.

(56) References Cited

U.S. PATENT DOCUMENTS

2003/0004164 A1* 1/2003 Bebbington et al. ......... 514/242

FOREIGN PATENT DOCUMENTS

| WO | WO 03/077921 | 9/2003 |
| WO | WO 03/078427 | 9/2003 |

OTHER PUBLICATIONS

Cecil Textbook of Medicine, edited by Bennet, J.C., and Plum F., 20th edition, vol. 1, 1004-1010, 1996.*
West, Anthony R., Solid State Chemistry and its Applications, Wiley, New York, 1988, pp. 358 & 365.*
Vippagunta et al., Advanced Drug Delivery Reviews 48: 3-26, 2001.*
Mass, R. D., Int. J. Radiation Oncology Bio. Phys. vol. 58(3): 932-940, 2004.*
Fabbro et al. Pharmacology & therapeutics 93, 79-98, 2002.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
International Search Report for International Application No. PCT/US2006/002437, mailed Jul. 12, 2006—5pgs.
Jin Quan Cheng et al., *AKT2*, a putative oncogene encoding a member of a subfamily of protein-serine/threonine kinases, is amplified in human ovarian carcinomas, Proc. Natl. Acad. Sci. USA, 1992, 9627-9271, 89.
Jin Quan Cheng et al., Amplification of *AKT2* in human pancreatic cancer cells and inhibition of *AKT2* expression and tumorigenicity by antisense RNA, Proc. Natl. Acad. Sci. USA, 1996, 3636-3641, 93.
Kaname Nakatani et al., Up-regulation of Akt3 in Estrogen Receptor-deficient Breast Cancers and Androgen-independent Prostate Cancer Lines, The Journal of Biological Chemistry, 1999, 21528-21532, 274(31).

* cited by examiner

*Primary Examiner*—Venkataraman Balasubramanian
(74) *Attorney, Agent, or Firm*—Krishna G. Banerjee

(57) ABSTRACT

A compound having the general structure of Formula (I):

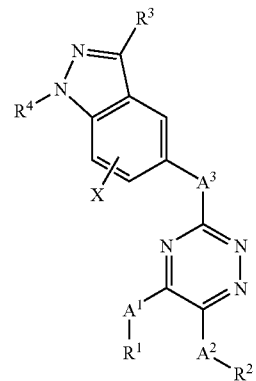

or a pharmaceutically acceptable salt, solvate, or ester thereof, are useful in treating diseases, disorders, or conditions such as immunodeficiencies, cancers, cardiovascular diseases, endocrine disorders, Parkinson's disease, metabolic diseases, tumorigenesis, Alzheimer's disease, heart disease, diabetes, neurodegeneration, inflammation, kidney disease, atherosclerosis and airway disease.

35 Claims, No Drawings

KINASE INHIBITORS

This application claims the benefit of U.S. provisional application Ser. No. 60/647,096, filed on Jan. 26, 2005, which is incorporated herein by reference in its entirety.

FIELD OF THE INVENTION

The present invention relates to indazolyl [1,2,4]triazine compounds useful as protein kinase inhibitors, pharmaceutical compositions comprising such compounds, and methods of treatment using the compounds and compositions to treat conditions such as cancer and proliferative diseases.

BACKGROUND OF THE INVENTION

Kinases are essential cellular signaling molecules. Mutations in kinases can lead to diseases or conditions including immunodeficiencies, cancers, cardiovascular diseases and endocrine disorders, such as Parkinson's disease, metabolic diseases, tumorigenesis, Alzheimer's disease, heart disease, diabetes, neurodegeneration, inflammation, kidney disease, atherosclerosis and airway disease.

Cancers result from deregulated signaling pathways that mediate cell growth and programmed cell death (apoptosis). Protein kinases are a large family of proteins that play an important role in signaling pathways that regulate a number of different cellular functions, such as cell growth, differentiation, and death (e.g., Kumar et al., *Expert Opin. Emerging Drugs* (2001) 6(2) pp. 1-13; U.S. Pat. Publ. No. 2003/0199511, WO 2004/030671, WO 2004/094386, WO 2004/096130, WO 2004/041162, WO 2004/022562, WO 2004/048343, and references cited therein). Protein kinases include those classified as tyrosine, serine/threonine (e.g., Akt or PKB), or dual specific, based on acceptor residue. Protein tyrosine kinases include intracellular domains of transmembrane growth factor receptors such as EGF receptor (EGFR), PDGF receptor (PDGFR), VEGF receptor (VEGFR), and FGF receptor (FGFR), and cytosolic kinases such as src, abl, and lck. Serine/threonine kinases include, for example, MAP kinase, MAPK kinase (MEK), Akt/PKB, Jun kinase (JNK), CDKs, protein kinase A (PKA) and protein kinase C (PKC).

Hyperactivity of protein kinases is implicated in a variety of human cancers. For example, the Akt2 kinase has been found to be over-expressed in ovarian tumors (J. Q. Cheung et al., *Proc. Natl. Acad. Sci. U.S.A.* 89: 9267-9271 (1992)) and pancreatic cancers (J. Q. Cheung et al., *Proc. Natl. Acad. Sci. U.S.A.* 93: 3636-3641 (1996)), and the Akt3 kinase was found to be over-expressed in breast and prostate cancer cell lines (Nakatani et al., *J. Biol. Chem.* 274: 21528-21532 (1999)).

Various protein kinase inhibitors have been shown to effectively treat certain cancers. For example, Gleevec™ (imantinib, Novartis), can be used to treat chronic myeloid leukemia (CML) (Kumar et al.), flavopiridol (Aventis) has been evaluated for treating mantle cell lymphoma and fludar refractory chronic lymphocytic leukemia, and a Raf kinase inhibitor (BAY-43-9006) has been evaluated for treating solid tumors and myeloid leukemia (WO 2004/022562).

Thus, drugs targeted against protein kinases represent a new generation of chemotherapy agents directed toward specific molecular targets, and thus have the potential for greater efficacy in treating various cancers, with fewer side effects than conventional chemotherapeutic agents.

Various pharmaceutically active [1,2,4]triazines are known. For example, U.S. Pat. No. 4,560,687 and U.S. Pat. No. 4,311,701 provide 3,5-diamino-6-aryl-[1,2,4]triazines useful for treating CNS disorders; EP 0021121 provides 3-amino-6-aryl-[1,2,4]triazines useful for treating CNS disorders; U.S. Pat. No. 4,190,725 provides anti-inflammatory 5,6-diaryl-[1,2,4]triazines; U.S. Pat. No. 3,948,894 provides anti-inflammatory 3-amino-5,6-diaryl-[1,2,4]triazines; U.S. 2004/0102436 provides various 2-amino-5,6-diaryl-[1,2,4]triazine $PGI_2$ receptor agonists; WO 00/66568 provides various 3-aryl-[1,2,4]triazine pesticides; WO 2004/074266 provides various 3-phenylamino- or 3-halo-[1,2,4]triazine HIV replication inhibitors; WO 97/20827 provides various 3,5-diamino-6-fluorophenyl-[1,2,4]triazine as inhibitors of glutamate release from the central nervous system; U.S. Pat. No. 4,649,139 provides 3,5-diamino-6-aryl-[1,2,4]triazines useful as cardiovascular agents; WO 2004/096129 provides 5,6-diaryl-[1,2,4]triazines useful for inhibiting Akt; U.S. Pat. No. 6,159,974 and WO 98/42686 provide 3-pyridyl-6-aryl-[1,2,4]triazine LDL receptor gene expression promoters; WO 03/077921 provides various 5-amino-[1,2,4]triazines useful as protein kinase inhibitors; EP 0088593 and U.S. Pat. No. 4,585,861 provide various 3-heterocyclo-5,6-diaryl-[1,2,4]triazines useful as activators of gamma-aminobutyric acid and benzodiazepine binding in the central nervous system; DD 248363 provides ampicillin derivatives having a 1,2,4-triazinyl moiety; GB 759014 describes improved methods of preparing 3,5-diamino-6-aryl-[1,2,4]triazines; Abdel-Rahman et al., *Bollettino Chimico Farmaceutico* (1999), 138(4), 176-185, describe the synthesis of (triazinyl)triazines; Dinakaran et al., *Biological & Pharmaceutical Bulletin* (2003), 26(9), 1278-1282, describe the synthesis of 3-quinazolinone-[1,2,4]triazines; Heinisch, *Journal fuer Praktische Chemie (Leipzig)* (1969), 311(3), 438-444 describe the synthesis of morpholine-[1,2,4]triazines; Yoneda et al., *Chemical & Pharmaceutical Bulletin* (1978), 26(10), 3154-3160, describe the synthesis of 3-aryl-5,6-diamino-[1,2,4]triazines; Yondea et al., *Chemical & Pharmaceutical Bulletin* (1973), 21(5), 926-930, describe the synthesis of [1,2,4]triazine-6-carbothioamides; Li et al., *Huaxue Xuebao* (1980), 38(6), 581-583 describe 3-substituted-5-hydroxy-6-methyl-[1,2,4]triazines; Neunhoeffer et al., *Liebigs Annalen der Chemie* (1990), (7), 631-640 describe 3-pyridyl-5-alkynyloxy-[1,2,4]triazines; Pochat, *Tetrahedron Letters* (1981), 22(37), 3595-3596 describes 3,6-diaryl-5-hydroxy-[1,2,4]triazines; Heinisch, *Journal fuer Praktische Chemie (Leipzig)* (1987), 329(2), 290-300 describes [1,2,4]triazine-6-carboxylic acids; Li, *J. Org. Chem.* (1993), 58, 516-519 describes pyrrolyl [1,2,4]triazines; Paudler et al., *J. Org. Chem.* (1966), 31, 1720-1722 describe the synthesis of various [1,2,4]triazines; Benson et al., *J. Org. Chem.*, (1992), 57, 5285-5287 describe intramolecular cycloadditions of indole and [1,2,4]triazine; and Limanto et al., *Organic Letters* (2003), 5(13), 2271-2274 describe 5-substituted-3-amino-1,2,4,-triazines. The triazines of the above references all have structures which differ substantially from the compounds of the present invention, described below.

U.S. 2003/0199511 and U.S. 2004/0127538 describe various indazoles which lack the [1,2,4]triazine ring of the compounds of the present invention, described below.

SUMMARY OF THE INVENTION

In one embodiment, the present invention is directed to a compound of Formula (I):

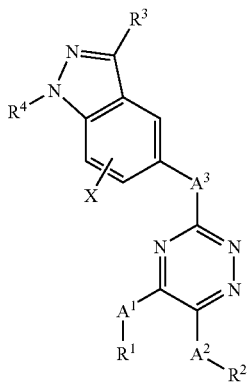

(I)

or a pharmaceutically acceptable salt, solvate, or ester thereof, wherein:

$A^1$ is selected from the group consisting of a covalent bond, alkylene, alkenylene, alkynylene, cycloalkylene, —O—, —N($R^5$)—, —C(O)—, —S—, —S(O)—, —S(O)$_2$—, —S(O)$_2$—N($R^6$)—, —N($R^6$)—S(O)$_2$—, —C($R^7$)$_2$—N($R^5$)—, —N($R^5$)—C($R^7$)$_2$—, —C(O)—N($R^6$)—, —N($R^6$)—C(O)—, —N($R^6$)—C(O)—N($R^6$)—, —C($R^6$)$_2$—C=N—, and —N=C—C($R^6$)$_2$—;

$A^2$ is selected from the group consisting of a covalent bond, alkylene, alkenylene, alkynylene, cycloalkylene, —O—, —N($R^5$)—, —C(O)—, —S—, —S(O)—, —S(O)$_2$—, —S(O)$_2$—N($R^6$)—, —N($R^6$)—S(O)$_2$—, —C($R^7$)$_2$—N($R^5$)—, —N($R^5$)—C($R^7$)$_2$—, —C(O)—N($R^6$)—, —N($R^6$)—C(O)—, —N($R^6$)—C(O)—N($R^6$)—, —C($R^7$)$_2$—C=N—, and —N=C—C($R^7$)$_2$—;

$A^3$ is selected from the group consisting of a covalent bond, cyclopropylene, alkenylene, alkynylene, —N($R^5$)—, —O—, —S—, —S(O)$_2$—, —C(O)N($R^6$)—, and —N($R^6$)C(O)—;

$R^1$ and $R^2$ are each independently selected from the group consisting of H, alkyl, haloalkyl, one or more hydroxyl substituted alkyl, alkenyl, alkynyl, alkoxy, -alkylene-O-alkyl, aryl, -alkylene-aryl, —CN, halogen, heteroaryl, -alkylene-heteroaryl, cycloalkyl, heterocyclyl, and -alkylene-heterocyclyl, wherein said aryl, heteroaryl, the aryl portion of said -alkylene-aryl, or the heteroaryl portion of said -alkylene-heteroaryl of $R^1$ or $R^2$ are unsubstituted or substituted with one or more groups Y which are independently selected; said heterocyclyl or the heterocyclyl portion of said -alkylene-heterocyclyl of $R^1$ or $R^2$ are unsubstituted or substituted with one or more groups Z which are independently selected; and with the proviso that:
1) if $R^1$ and/or $R^2$ are alkoxy, the oxygen atom of said alkoxy is not bonded to a S, N, or O atom of $A^1$ or $A^2$,
2) if $R^1$ and/or $R^2$ are —CN, said —CN is not bonded to a S, N, or O atom of $A^1$ or $A^2$,
3) if $R^1$ is halogen, $A^1$ is a covalent bond, and
4) if $R^2$ is halogen, $A^2$ is a covalent bond;

$R^3$ is selected from the group consisting of H, alkyl, haloalkyl, cycloalkyl, alkoxy, —N($R^8$)$_2$, —N($R^8$)—C(O)—$R^8$, —C(O)—N($R^6$)$_2$, —N($R^6$)—C(O)—N($R^6$)$_2$, —N($R^6$)—S(O)$_2$—$R^6$, —C(O)-alkyl, -alkylene-O-alkyl, —CN, halogen, aryl, heteroaryl, heterocyclyl, -alkylene-aryl, -alkylene-heteroaryl, alkylene-heterocyclyl, and alkynyl, wherein said aryl, heteroaryl, the aryl portion of said -alkylene-aryl, or the heteroaryl portion of said -alkylene-heteroaryl of $R^3$ are unsubstituted or substituted with one or more groups Y which are independently selected; said heterocyclyl or the heterocyclyl portion of said alkylene-heterocyclyl of $R^3$ are unsubstituted or substituted with one or more groups Z which are independently selected;

$R^4$ is selected from the group consisting of H, alkyl, —C(O)-alkyl, —C(O)—O-alkyl, alkylene-O-alkyl, and -alkylene-O—C(O)-alkyl;

$R^5$ is selected from the group consisting of H, alkyl, cycloalkyl, haloalkyl, -alkylene-N($R^8$)$_2$, alkoxy, aryl, heteroaryl, -alkylene-aryl, -alkylene-heteroaryl, —C(O)-alkyl, —S(O)$_2$-alkyl, —C(O)-aryl, —C(O)N($R^9$)$_2$, —C(O)-aryl, —C(O)-alkylene-aryl, —C(O)-heteroaryl, C(O)-alkylene-heteroaryl, —S(O)$_2$-aryl, —S(O)$_2$-alkylene-aryl, —S(O)$_2$-heteroaryl, and —S(O)$_2$-alkylene-heteroaryl, wherein said aryl, the aryl portion of —C(O)-aryl, the aryl portion of -alkylene-aryl, or the aryl portion of —S(O)$_2$-aryl of $R^5$ are unsubstituted or substituted with one or more groups Y which are independently selected;

each $R^6$ is independently selected from the group consisting of H, alkyl, cycloalkyl, haloalkyl, heterocyclyl, aryl, heteroaryl, -alkylene-heterocyclyl, -alkylene-aryl, and -alkylene-heteroaryl, wherein said aryl or the aryl portion of alkylene-aryl of $R^6$ are unsubstituted or substituted with one or more groups Y which are independently selected;

each $R^7$ is independently selected from the group consisting of H, alkyl, cycloalkyl, haloalkyl, alkenyl, alkynyl, —N($R^8$)$_2$, —CN, halo, aryl, heteroaryl, heterocyclyl, -alkylene-heterocyclyl, -alkylene-aryl, and -alkylene-heteroaryl, wherein said aryl, the aryl portion of said -alkylene-aryl, and said heteroaryl of $R^7$ are unsubstituted or substituted with one or more groups Y which are independently selected;

each $R^8$ is independently selected from the group consisting of H, alkyl, cycloalkyl, heterocyclyl, -alkylene-heterocyclyl, haloalkyl, -alkylene-aryl, aryl, heteroaryl, and -alkylene-heteroaryl, wherein said aryl of $R^8$ is unsubstituted or substituted with one or more groups Y which are independently selected;

X is one or more substituents independently selected from the group consisting of hydrogen, halogen, alkyl, alkoxy, haloalkyl, —O$R^9$, —N($R^5$)$^2$, and —C(O)N($R^6$)$_2$;

Y is one or more substituents independently selected from the group consisting of halogen, alkyl, haloalkyl, aryl, -alkylene-aryl, —OH, —O$R^9$, —CN, —N($R^9$)$_2$, —N($R^9$)—C(O)—$R^9$, —N($R^9$)—C(O)—N($R^9$)$_2$, —C(O)N($R^9$)$_2$, —C(O)OH, —C(O)O-alkyl, —N($R^9$)—S(O)$_2$—($R^9$)$_2$ and —S(O)$_2$N($R^9$)$_2$;

each $R^9$ is independently selected from the group consisting of H, alkyl, cycloalkyl, haloalkyl, heterocyclyl, -alkylene-heterocyclyl, aryl, -alkylene-aryl, heteroaryl, -alkylene-heteroaryl; and Z is one or more substituents independently selected from the group consisting of alkyl, one or more hydroxy substituted alkyl, aryl, -alkylene-aryl, -alkylene-O-alkyl, -alkylene-O-alkylene-aryl, -alkylene-O-aryl, —CN, haloalkyl, -alkylene-C(O)—N($R^8$)$_2$, —C(O)—N($R^8$)$_2$, —C(O)OH, —C(O)O-alkyl, —N($R^8$)$_2$, and -alkylene-N($R^8$)$_2$, —S(O)$_2$—N($R^8$)$_2$, -alkylene-S(O)$_2$—N($R^8$)$_2$, —N($R^8$)—C(O)—$R^8$, —N($R^8$)—C(O)—N($R^8$)$_2$, -alkylene-N($R^8$)—C(O)—N($R^8$)$_2$, -alkylene-N($R^8$)—C(O)—$R^8$, -alkylene-S $(O)_2$—$R^8$, —$N(R^8)$—$S(O)_2$—$R^8$, and -alkylene-$N(R^8)$—$S(O)_2$—$R^8$, cycloalkyl, heterocyclyl, -alkylene-heterocyclyl, heteroaryl, and -alkylene-heteroaryl, or wherein two Z substitutents on adjacent carbon atoms, on a carbon atom and an adjacent heteroatom, or on a single carbon atom, together with the carbon atom(s) and/or the combination of the carbon atom and the adjacent heteroatom to which said Z substituents are attached form a four to seven-membered cycloalkyl, cycloalkenyl, heterocyclyl, aryl, or heteroaryl ring, wherein said aryl, heteroaryl, the aryl portion of said -alkylene-aryl, -alkylene-O-alkylene-aryl, -alkylene-O-aryl, and the heteroaryl portion of said -alkylene-heteroaryl are unsubstituted or substituted with one or more $R^{10}$ substitutents which are independently selected; and $R^{10}$ is one or more substituents independently selected from the group consisting of halogen, cyano, alkyl, alkoxy, haloalkyl, haloalkoxy, nitro, —$NH_2$, —NH(alkyl), —$N(alkyl)_2$, hydroxyl, aryl, aryloxy, —O-alkylene-aryl, —NH(alkyl), —$N(alkyl)_2$, —NH(aryl), —$N(aryl)_2$, —NH-alkylene-aryl, —N(alkyl)-alkylene-aryl, -alkylene-aryl, —$C(O)NH_2$, —C(O)NH(alkyl), —$C(O)N(alkyl)_2$, —$S(O)_2NH_2$, —$S(O)_2NH(alkyl)$, —$S(O)_2N(alkyl)_2$, —NHC(O)-alkyl, —N(alkyl)C(O)-alkyl, —NHC(O)-aryl, —N(alkyl)C(O)-aryl, —NH—$S(O)_2$-alkyl, —N(alkyl)-$S(O)_2$-alkyl, —NH—$S(O)_2$-aryl, and —N(alkyl)-$S(O)_2$-aryl.

In another embodiment, the present invention is directed to the compound of Formula (I), or a pharmaceutically acceptable salt, solvate, or ester thereof, wherein:

$A^1$ is selected from the group consisting of a covalent bond, alkylene, alkenylene, alkynylene, cycloalkylene, —O—, —$N(R^5)$—, —C(O)—, —S—, —S(O)—, —$S(O)_2$—, —$S(O)_2$—$N(R^6)$—, —$N(R^6)$—$S(O)_2$—, —$C(R^7)_2$—$N(R^5)$—, —$N(R^5)$—$C(R^7)_2$—, —C(O)—$N(R^6)$—, —$N(R^6)$—C(O)—, —$N(R^6)$—C(O)—$N(R^6)$—, —$C(R^6)_2$—C=N—, and —N=C—$C(R^6)_2$—;

$A^2$ is selected from the group consisting of a covalent bond, alkylene, alkenylene, alkynylene, cycloalkylene, —O—, —$N(R^5)$—, —C(O)—, —S—, —S(O)—, —$S(O)_2$—, —$S(O)_2$—$N(R^6)$—, —$N(R^6)$—$S(O)_2$—, —$C(R^7)_2$—$N(R^5)$—, —$N(R^5)$—$C(R^7)_2$—, —C(O)—$N(R^6)$—, —$N(R^6)$—C(O)—, —$N(R^6)$—C(O)—$N(R^6)$—, —$C(R^7)_2$—C=N—, and —N=C—$C(R^7)_2$—;

$A^3$ is selected from the group consisting of a covalent bond, alkylene, —$N(R^5)$—, —$C(O)N(R^6)$—, and —$N(R^6)C(O)$—;

$R^1$ and $R^2$ are each independently selected from the group consisting of H, alkyl, haloalkyl, alkyl substituted with one or more —OH, alkenyl, alkynyl, alkoxy, -alkylene-O-alkyl, aryl, -alkylene-aryl, —CN, halogen, heteroaryl, -alkylene-heteroaryl, cycloalkyl, heterocyclyl, and -alkylene-heterocyclyl, wherein said aryl, heteroaryl, the aryl portion of said -alkylene-aryl, or the heteroaryl portion of said -alkylene-heteroaryl of $R^1$ or $R^2$ are unsubstituted or substituted with one or more groups Y which are independently selected; said heterocyclyl or the heterocyclyl portion of said -alkylene-heterocyclyl of $R^1$ or $R^2$ are unsubstituted or substituted with one or more groups Z which are independently selected; and with the proviso that:
1) if $R^1$ and/or $R^2$ are alkoxy, the oxygen atom of said alkoxy is not bonded to a S, N, or O atom of $A^1$ or $A^2$,
2) if $R^1$ and/or $R^2$ are —CN, said —CN is not bonded to a S, N, or O atom of $A^1$ or $A^2$,
3) if $R^1$ is halogen, $A^1$ is a covalent bond, and
4) if $R^2$ is halogen, $A^2$ is a covalent bond;

$R^3$ is selected from the group consisting of H, alkyl, alkoxy, —$N(R^8)_2$, —$N(R^8)$—C(O)—$R^8$, —C(O)—$N(R^6)_2$, —$N(R^6)$—C(O)—$N(R^6)_2$, —$N(R^6)$—$S(O)_2$—$R^6$, —C(O)-alkyl, -alkylene-O-alkyl, —CN, halogen, aryl, heteroaryl, heterocyclyl, -alkylene-aryl, -alkylene-heteroaryl, alkylene-heterocyclyl, and alkynyl, wherein said aryl, heteroaryl, the aryl portion of said -alkylene-aryl, or the heteroaryl portion of said -alkylene-heteroaryl of $R^3$ are unsubstituted or substituted with one or more groups Y which are independently selected; said heterocyclyl or the heterocyclyl portion of said alkylene-heterocyclyl of $R^3$ are unsubstituted or substituted with one or more groups Z which are independently selected;

$R^4$ is selected from the group consisting of H, alkyl, —C(O)-alkyl, —C(O)—O-alkyl, alkylene-O-alkyl, and -alkylene-O—C(O)-alkyl;

$R^5$ is selected from the group consisting of H, alkyl, -alkylene-$N(R^8)_2$, alkoxy, aryl, -alkylene-aryl, —C(O)-alkyl, —$S(O)_2$-alkyl, —C(O)-aryl, and —$S(O)_2$-aryl, wherein said aryl, the aryl portion of —C(O)-aryl, the aryl portion of -alkylene-aryl, or the aryl portion of —$S(O)_2$-aryl of $R^5$ are unsubstituted or substituted with one or more groups Y which are independently selected;

each $R^6$ is independently selected from the group consisting of H, alkyl, aryl, and -alkylene-aryl, wherein said aryl or the aryl portion of alkylene-aryl of $R^6$ are unsubstituted or substituted with one or more groups Y which are independently selected;

each $R^7$ is independently selected from the group consisting of H, alkyl, alkenyl, alkynyl, —$N(R^8)_2$, —CN, halo, aryl, heteroaryl, heterocyclyl, and -alkylene-aryl, wherein said aryl, the aryl portion of said -alkylene-aryl, and said heteroaryl of $R^7$ are unsubstituted or substituted with one or more groups Y which are independently selected;

each $R^8$ is independently selected from the group consisting of H, alkyl, and aryl, wherein said aryl of $R^8$ is unsubstituted or substituted with one or more groups Y which are independently selected;

X is one or more substituents independently selected from the group consisting of hydrogen, halogen, alkyl, alkoxy, and haloalkyl;

Y is one or more substituents independently selected from the group consisting of halogen, alkyl, haloalkyl, aryl, -alkylene-aryl, —OH, —O-alkyl, —CN, —$N(R^9)_2$, —$C(O)N(R^9)_2$, and —$S(O)_2N(R^9)_2$;

each $R^9$ is independently selected from the group consisting of H, alkyl, aryl, and -alkylene-aryl; and Z is one or more substituents independently selected from the group consisting of alkyl, alkyl substituted with one or more —OH, aryl, -alkylene-aryl, -alkylene-O-alkyl, -alkylene-O-alkylene-aryl, -alkylene-O-aryl, —CN, haloalkyl, —C(O)—$N(R^8)_2$, —$S(O_2)$—$N(R^8)_2$, -alkylene-$N(R^8)$—C(O)—$R^8$, -alkylene-$S(O)_2$—$R^8$, cycloalkyl, heterocyclyl, -alkylene-heterocyclyl, heteroaryl, and -alkylene-heteroaryl.

In another embodiment, the present invention is directed to a pharmaceutical composition comprising a therapeutically effective amount of at least one compound of Formula (I), or a pharmaceutically acceptable salt, solvate, or ester thereof, and at least one pharmaceutically acceptable carrier.

In another embodiment, the present invention is directed to a method of treating a disease or disorder in a patient, such as cancer or a proliferative disorder. The method comprises administering to the patient an effective amount of at least one compound of Formula (I), or a pharmaceutically acceptable salt, solvate, or ester thereof.

In another embodiment, the present invention is directed to a method of treating a disease or disorder in a patient, such as cancer or a proliferative disorder. The method comprises administering to the patient an effective amount of at least one compound of Formula (I), or a pharmaceutically acceptable salt, solvate, or ester thereof, in combination with at least one additional active ingredient selected from the group consisting of a second kinase inhibitor, an estrogen receptor modulator, an androgen receptor modulator, a retinoid receptor modulator, a cyclotoxic agent, a prenyl-protein transferase inhibitor, an HMG-CoA reductase inhibitor, an HIV protease inhibitor, a reverse transcriptase inhibitor, an angiogenesis inhibitor, an inhibitor of inherent multidrug resistance, an anti-emetic agent, an agent useful in the treatment of anemia, an agent useful in the treatment of neutropenia, and an immunologic-enhancing drug.

DETAILED DESCRIPTION OF THE INVENTION

In a first embodiment, the present invention is directed to a compound of Formula (I), or a pharmaceutically acceptable salt, solvate, or ester thereof, as described herein.

In another embodiment of the compounds of Formula (I), $A^1$ is a covalent bond or —O—.

In another embodiment of the compounds of Formula (I), $A^2$ is a covalent bond or —N($R^5$)—.

In another embodiment of the compounds of Formula (I), $A^3$ is a covalent bond.

In another embodiment of the compounds of Formula (I), $R^1$ is H or $(C_2-C_6)$heterocyclyl.

In another embodiment of the compounds of Formula (I), $R^2$ is H, —$(C_1-C_4)$alkylene-$(C_6-C_{10})$aryl, —$(C_1-C_4)$alkylene-$(C_2-C_{10})$heteroaryl or halogen.

In another embodiment of the compounds of Formula (I), $R^3$ is H, $(C_1-C_6)$alkyl, $(C_3-C_6)$cycloalkyl, —$(C_6-C_{10})$aryl, halogen, or —$NH_2$.

In another embodiment of the compounds of Formula (I), $R^4$ is H.

In another embodiment of the compounds of Formula (I), $R^5$ is H or —$(C_1-C_4)$alkylene-$(C_6-C_{10})$aryl.

In another embodiment of the compounds of Formula (I), X is H or $(C_1-C_6)$alkyl.

In another embodiment of the compounds of Formula (I), Y is one or more substituents independently selected from the group consisting of halogen, alkyl, haloalkyl, aryl, —O-alkyl, —CN, and —$NO_2$.

In another embodiment of the compounds of Formula (I), Z is one or more substituents independently selected from the group consisting of $(C_1-C_6)$alkyl, $(C_6-C_{10})$aryl, —$(C_1-C_4)$alkylene-$(C_6-C_{10})$aryl, —$(C_1-C_4)$alkylene-$(C_2-C_{10})$heteroaryl, —$(C_1-C_4)$alkylene-O—$(C_1-C_4)$alkylene-$(C_6-C_{10})$aryl, —$(C_1-C_6)$alkylene-OH, —N$(R^8)_2$, —$(C_1-C_4)$alkylene-N$(R^8)_2$, —C(O)O—$(C_1-C_6)$alkyl, and —C(O)OH, or wherein two Z substitutents on adjacent carbon atoms, on a carbon atom and an adjacent heteroatom, or on a single carbon atom, together with the carbon atom(s) and/or the combination of the carbon atom and the adjacent heteroatom to which said Z substituents are attached together form a four to seven-membered cycloalkyl or heterocyclyl ring, wherein said aryl, heteroaryl, the aryl portion of said -alkylene-aryl, -alkylene-O-alkylene-aryl, -alkylene-O-aryl, and the heteroaryl portion of said -alkylene-heteroaryl are unsubstituted or substituted with one or more $R^{10}$ substitutents which are independently selected; and $R^{10}$ is one or more substituents independently selected from the group consisting of halogen, alkyl, haloalkyl, alkoxy, haloalkoxy, and hydroxyalkyl.

In another embodiment of the compounds of Formula (I), $A^1$ is a covalent bond or —O—; $A^2$ is a covalent bond or —N($R^5$)—; $A^3$ is a covalent bond; $R^1$ is H or $(C_2-C_6)$heterocyclyl; wherein said $(C_2-C_6)$heterocyclyl of $R^1$ is unsubstituted or substituted with one of more groups Z; $R^2$ is H, —$(C_1-C_4)$alkylene-$(C_6-C_{10})$aryl, —$(C_1-C_4)$alkylene-$(C_2-C_{10})$heteroaryl or halogen; wherein said $(C_6-C_{10})$aryl portion of —$(C_1-C_4)$alkylene-$(C_6-C_{10})$aryl of $R^2$ and said $(C_2-C_{10})$ heteroaryl portion of —$(C_1-C_4)$alkylene-$(C_2-C_{10})$heteroaryl of $R^2$ are independently unsubstituted or substituted with one or more groups Y;

$R^3$ is H, $(C_1-C_6)$alkyl, $(C_3-C_6)$cycloalkyl, —$(C_6-C_{10})$aryl, halogen, or —$NH_2$; $R^4$ is H; $R^5$ is H or —$(C_1-C_4)$alkylene-$(C_6-C_{10})$aryl; X is H or $(C_1-C_6)$alkyl; Y is one or more substituents independently selected from the group consisting of halogen, alkyl, haloalkyl, aryl, —O-alkyl, —CN, and —$NO_2$; Z is one or more substituents independently selected from the group consisting of $(C_1-C_6)$alkyl, $(C_6-C_{10})$aryl, —$(C_1-C_4)$alkylene-$(C_6-C_{10})$aryl, —$(C_1-C_4)$alkylene-$(C_2-C_{10})$heteroaryl, —$(C_1-C_4)$alkylene-O—$(C_1-C_4)$alkylene-$(C_6-C_{10})$aryl, —$(C_1-C_6)$alkylene-OH, —N$(R^8)_2$, —$(C_1-C_4)$alkylene-N$(R^8)_2$, —C(O)O—$(C_1-C_6)$alkyl, and —C(O)OH, or wherein two Z substitutents on adjacent carbon atoms, on a carbon atom and an adjacent heteroatom, or on a single carbon atom, together with the carbon atom(s) and/or the combination of the carbon atom and the adjacent heteroatom to which said Z substituents are attached together form a four to seven-membered cycloalkyl or heterocyclyl ring.

In another embodiment of the compounds of Formula (I), $A^1$ is a covalent bond and $R^1$ is $(C_2-C_6)$heterocyclyl; wherein said $(C_2-C_6)$heterocyclyl of $R^1$ is unsubstituted or substituted with one of more groups Z.

In another embodiment of the compounds of Formula (I), $A^1$ is a covalent bond and $R^1$ is piperazyl.

In another embodiment of the compounds of Formula (I), $A^1$ is a covalent bond and $R^1$ is 1,4-diazapanyl (e.g.,

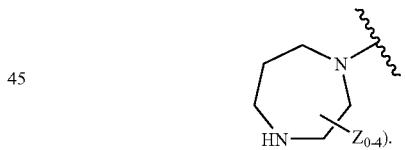

).

In another embodiment of the compounds of Formula (I), $A^1$ is a covalent bond and $R^1$ is 2,5-diaza-bicyclo[2.2.1]heptenyl.

In another embodiment of the compounds of Formula (I), $A^1$ is —O— and $R^1$ is H.

In another embodiment of the compounds of Formula (I), $A^1$ is a covalent bond and $R^1$ is $(C_2-C_6)$heterocyclyl which is selected from the group consisting of unsubstituted piperazinyl, unsubstituted piperidinyl, unsubstituted pyrrolidinyl, and piperazinyl, piperidinyl and pyrrolidinyl each of which is substituted with one or more Z substituents which are independently selected, or wherein two Z substitutents on adjacent carbon atoms, on a carbon atom and an adjacent nitrogen atom, or on a single carbon atom, together with the carbon atom(s) and/or the combination of the carbon atom and the adjacent nitrogen atom to which said Z substituents are attached form a four to seven-membered cycloalkyl or heterocyclyl ring.

In another embodiment of the compounds of Formula (I), $A^2$ is —N($R^5$)—; $R^2$ is H or —($C_1$-$C_4$)alkylene-($C_6$-$C_{10}$)aryl; and $R^5$ is H or —($C_1$-$C_4$)alkylene-($C_6$-$C_{10}$)aryl.

In another embodiment of the compounds of Formula (I), $A^2$ is —N($R^5$)—; $R^2$ is H or —$CH_2$-phenyl; and $R^5$ is H or —$CH_2$-phenyl.

In another embodiment of the compounds of Formula (I), $A^2$ is —N($R^5$)— and $R^2$ and $R^5$ are both H.

In another embodiment of the compounds of Formula (I), $A^2$ is —N($R^5$)—, $R^2$ is H, and $R^5$ is —$CH_2$-phenyl.

In another embodiment of the compounds of Formula (I), $A^2$ is —N($R^5$)— and $R^2$ and $R^5$ are both —$CH_2$-phenyl.

In another embodiment of the compounds of Formula (I), $A^2$ is a covalent bond; and $R^2$ is H or halogen.

In another embodiment of the compounds of Formula (I), $A^2$ is a covalent bond; and $R^2$ is H or halogen, wherein said halogen is chlorine.

In another embodiment of the compounds of Formula (I), $A^1$ is a covalent bond; $R^1$ is selected from the group consisting of unsubstituted piperazinyl, unsubstituted piperidinyl, unsubstituted pyrrolidinyl, and piperazinyl, piperidinyl and pyrrolidinyl each of which is substituted with one or more Z substituents which are independently selected, or wherein two Z substitutents on adjacent carbon atoms, on a carbon atom and an adjacent nitrogen atom, or on a single carbon atom, together with the carbon atom(s) and/or the combination of the carbon atom and the adjacent nitrogen atom to which said Z substituents are attached form a four to seven-membered cycloalkyl or heterocyclyl ring; $A^2$ is —N($R^5$)—; $R^2$ is H or —($C_1$-$C_4$)alkylene-($C_6$-$C_{10}$)aryl; and $R^5$ is H or —($C_1$-$C_4$)alkylene-($C_6$-$C_{10}$)aryl.

In another embodiment of the compounds of Formula (I), $A^1$ is a covalent bond; $R^1$ is unsubstituted piperazinyl or piperazinyl substituted with one group Z; $A^2$ is —N($R^5$)—; $R^2$ is H or —($C_1$-$C_4$)alkylene-($C_6$-$C_{10}$)aryl; and $R^5$ is H or —($C_1$-$C_4$)alkylene-($C_6$-$C_{10}$)aryl.

In another embodiment of the compounds of Formula (I), $A^1$ is a covalent bond; $R^1$ is unsubstituted piperazinyl or piperazinyl substituted with one group Z; $A^2$ is —N($R^5$)—; $R^2$ is H or —$CH_2$-phenyl; and $R^5$ is H or —$CH_2$-phenyl.

In another embodiment of the compounds of Formula (I), $A^1$ is a covalent bond; $R^1$ is unsubstituted piperazinyl or piperazinyl substituted with one group Z; $A^2$ is —N($R^5$)—; and $R^2$ and $R^5$ are both H.

In another embodiment of the compounds of Formula (I), $A^1$ is a covalent bond; $R^1$ is unsubstituted piperazinyl or piperazinyl substituted with one group Z; $A^2$ is —N($R^5$)—; and $R^2$ and $R^5$ are both —$CH_2$-phenyl.

In another embodiment of the compounds of Formula (I), $A^1$ is a covalent bond; $R^1$ is unsubstituted piperazinyl or piperazinyl substituted with one group Z; $A^2$ is —N($R^5$)—; $R^2$ is H; and $R^5$ is —$CH_2$-phenyl.

In another embodiment of the compounds of Formula (I), $A^1$ is a covalent bond; $R^1$ is unsubstituted piperazinyl; $A^2$ is —N($R^5$)—; $R^2$ is H or —$CH_2$-phenyl; and $R^5$ is H or —$CH_2$-phenyl.

In another embodiment of the compounds of Formula (I), $A^1$ is a covalent bond; $R^1$ is piperazinyl substituted with one group Z; $A^2$ is —N($R^5$)—; $R^2$ is H or —$CH_2$-phenyl; and $R^5$ is H or —$CH_2$-phenyl.

In another embodiment of the compounds of Formula (I), $A^1$ is a covalent bond; $R^1$ is piperazinyl substituted with one group Z; $A^2$ is —N($R^5$)—; $R^2$ is H or —$CH_2$-phenyl; $R^5$ is H or —$CH_2$-phenyl; and Z is methyl, i-propyl, iso-butyl, phenyl, —$CH_2$-phenyl, —$CH_2$—O—$CH_2$-phenyl, or —$CH_2$—OH.

In another embodiment of the compounds of Formula (I), $A^1$ is a covalent bond; $R^1$ is

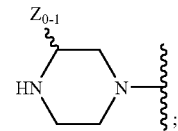

$A^2$ is —N($R^5$)—; $R^2$ is H or —($C_1$-$C_4$)alkylene-($C_6$-$C_{10}$)aryl; and $R^5$ is H or —($C_1$-$C_4$)alkylene-($C_6$-$C_{10}$)aryl.

In another embodiment of the compounds of Formula (I), $R^1$ is selected from the group consisting of

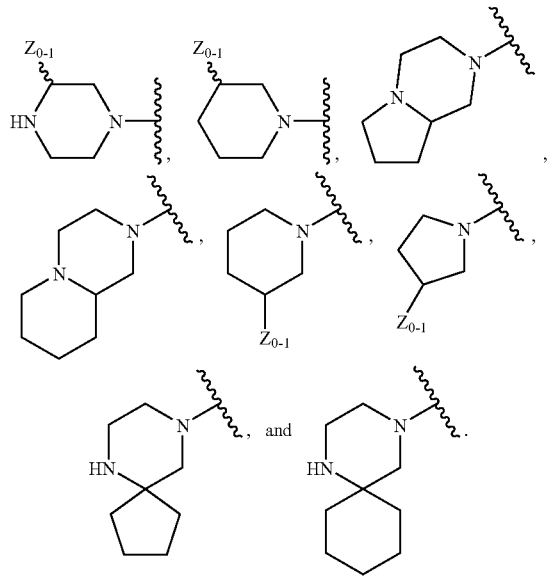

In another embodiment of the compounds of Formula (I), $A^1$ is a covalent bond; $R^1$ is selected from the group consisting of unsubstituted piperazinyl, unsubstituted piperidinyl, unsubstituted pyrrolidinyl, and piperazinyl, piperidinyl and pyrrolidinyl each of which is substituted with one or more Z substituents which are independently selected, or wherein two Z substitutents on adjacent carbon atoms, on a carbon atom and an adjacent nitrogen atom, or on a single carbon atom, together with the carbon atom(s) and/or the combination of the carbon atom and the adjacent nitrogen atom to which said Z substituents are attached form a four to seven-membered cycloalkyl or heterocyclyl ring; $A^2$ is a covalent bond; and $R^2$ is H or halogen.

In another embodiment of the compounds of Formula (I), $A^1$ is a covalent bond; $R^1$ is piperazinyl substituted with one group Z; $A^2$ is a covalent bond; and $R^2$ is H or halogen.

In another embodiment of the compounds of Formula (I), $A^1$ is a covalent bond; $R^1$ is piperazinyl substituted with one group Z; $A^2$ is a covalent bond; and $R^2$ is H or Cl.

In another embodiment of the compounds of Formula (I), $A^1$ is a covalent bond; $R^1$ is piperazinyl substituted with one or more groups Z; $A^2$ is a covalent bond; $R^2$ is H or halogen; and Z is independently selected from the group consisting of ($C_1$-$C_6$)alkyl, ($C_6$-$C_{10}$)aryl, —($C_1$-$C_4$)alkylene-($C_6$-$C_{10}$)aryl, —($C_1$-$C_4$)alkylene-O—($C_1$-$C_4$)alkylene-($C_6$-$C_{10}$)aryl, and —($C_1$-$C_6$)alkylene-OH.

In another embodiment of the compounds of Formula (I), $A^1$ is a covalent bond; $R^1$ is piperazinyl substituted with one group Z; $A^2$ is a covalent bond; $R^2$ is H or halogen; and Z is $(C_1$-$C_6)$alkyl, $(C_6$-$C_{10})$aryl, —$(C_1$-$C_4)$alkylene-$(C_6$-$C_{10})$aryl, —$(C_1$-$C_4)$alkylene-O—$(C_1$-$C_4)$alkylene-$(C_6$-$C_{10})$aryl, or —$(C_1$-$C_6)$alkylene-OH.

In another embodiment of the compounds of Formula (I), $A^1$ is a covalent bond; $R^1$ is piperazinyl substituted with one group Y; $A^2$ is a covalent bond; $R^2$ is H or Cl; and Z is methyl, i-propyl, iso-butyl, phenyl, —$CH_2$-indolyl, —$CH_2$-phenyl, —$CH_2$—O—$CH_2$-phenyl, or —$CH_2$—OH.

In another embodiment of the compounds of Formula (I), Z is selected from the group consisting of $(C_1$-$C_6)$alkyl, $(C_6$-$C_{10})$aryl, —$(C_1$-$C_4)$alkylene-$(C_6$-$C_{10})$aryl, —$(C_1$-$C_4)$alkylene-O—$(C_1$-$C_4)$alkylene-$(C_6$-$C_{10})$aryl, —$N(R^8)_2$, -$(C_1$-$C_4)$alkylene-$N(R^8)_2$, —C(O)OH, —C(O)O—$(C_1$-$C_6)$alkyl, and —$(C_1$-$C_6)$alkylene-OH, or wherein two Z substitutents on adjacent carbon atoms, on a carbon atom and an adjacent nitrogen atom, or on a single carbon atom, together with the carbon atom(s) and/or the combination of the carbon atom and the adjacent nitrogen atom to which said Z substituents are attached form a four to seven-membered cycloalkyl or heterocyclyl ring.

In another embodiment, the compounds of the present invention have the following structure of Formula (IA):

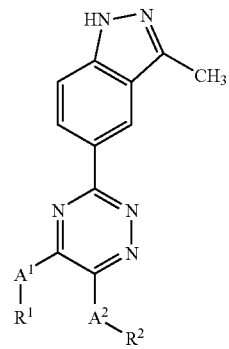

wherein $A^1$, $A^2$, $R^1$, $R^2$ are defined as shown in the Table below:

| Structure | $A^1$ | $A^2$ | $R^1$ | $R^2$ |
|---|---|---|---|---|
| A | covalent bond | —NH— | piperazinyl (HN-piperazine-N-) | H |
| B | —O— | —NH— | H | H |
| C | covalent bond | —NH— | piperazinyl (HN-piperazine-N-) | —CH₂-phenyl |
| D | covalent bond | | N(benzyl) | piperazinyl (HN-piperazine-N-) | —CH₂-phenyl |
| E | covalent bond | —NH— | 3-benzyl-piperazinyl | H |

-continued
| Structure | A¹ | A² | R¹ | R² |
|---|---|---|---|---|
| F | covalent bond | —NH— | 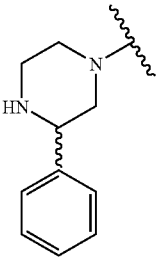 | H |
| G | covalent bond | —NH— | 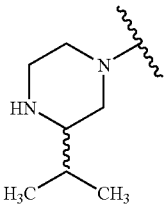 | H |
| H | covalent bond | —NH— | 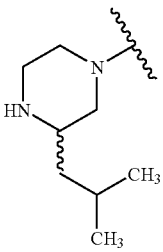 | H |
| I | covalent bond | —NH— | 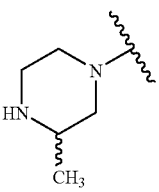 | H |
| J | covalent bond | —NH— | 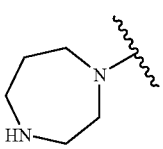 | H |
| K | covalent bond | —NH— | 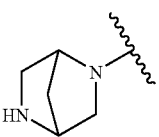 | H |
| L | covalent bond | covalent bond | 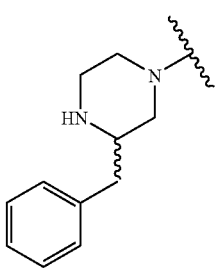 | H |

-continued
| Structure | A¹ | A² | R¹ | R² |
|---|---|---|---|---|
| M | covalent bond | covalent bond | 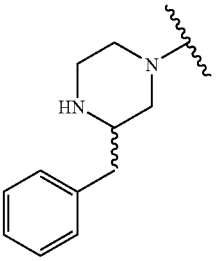 | Cl |
| N | covalent bond | —NH— | 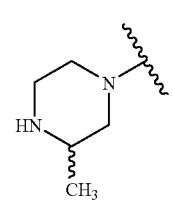 | 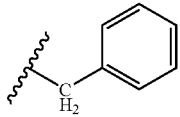 |
| O | covalent bond | —NH— | 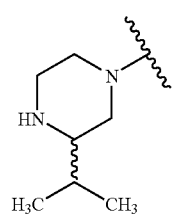 | 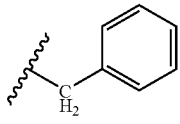 |
| P | covalent bond | —NH— | 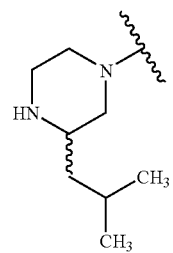 | 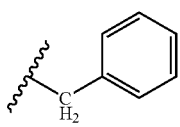 |
| Q | covalent bond | —NH— | 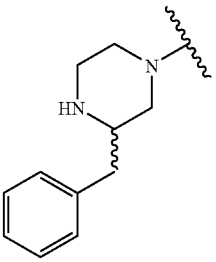 | 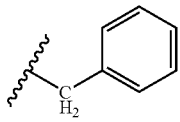 |
| R | covalent bond | covalent bond | 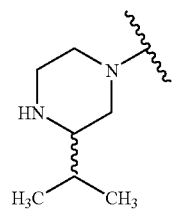 | H |

-continued
| Structure | A¹ | A² | R¹ | R² |
|---|---|---|---|---|
| S | covalent bond | covalent bond | 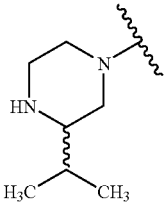 | Cl |
| T | covalent bond | covalent bond | 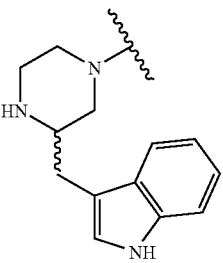 | H |
| U | covalent bond | covalent bond | 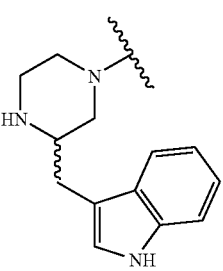 | Cl |
| V | covalent bond | covalent bond | 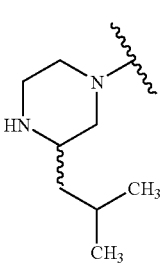 | H |
| W | covalent bond | covalent bond | 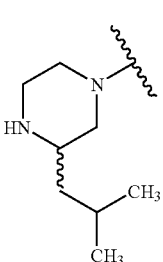 | Cl |
| X | covalent bond | covalent bond | 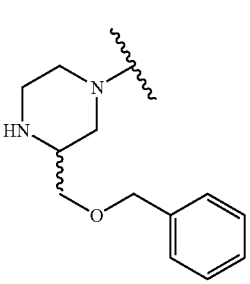 | Cl |

-continued
| Structure | A¹ | A² | R¹ | R² |
|---|---|---|---|---|
| Y | covalent bond | covalent bond | 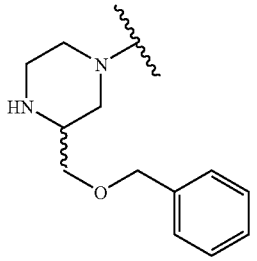 | H |
| Z | covalent bond | covalent bond | 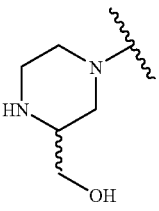 | H |
| AA | covalent bond | covalent bond | 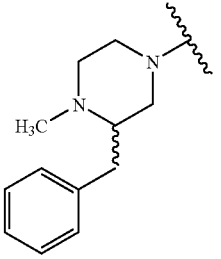 | H |
| AB | covalent bond | covalent bond | 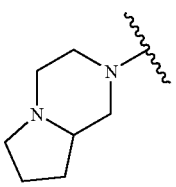 | H |
| AC | covalent bond | covalent bond | 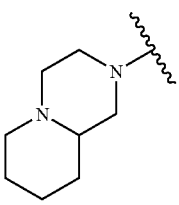 | H |
| AD | covalent bond | covalent bond | 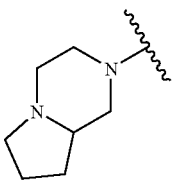 | Cl |
| AE | covalent bond | covalent bond | 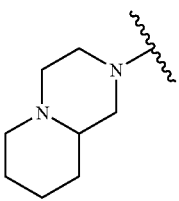 | Cl |

-continued

| Structure | A¹ | A² | R¹ | R² |
|---|---|---|---|---|
| AF | covalent bond | covalent bond | 3-aminopiperidin-1-yl | H |
| AG | covalent bond | covalent bond | 3-aminopiperidin-1-yl | Cl |
| AH | covalent bond | covalent bond | 3-(aminomethyl)piperidin-1-yl | H |
| AI | covalent bond | covalent bond | 3-(aminomethyl)piperidin-1-yl | Cl |
| AJ | covalent bond | covalent bond | 3-aminopyrrolidin-1-yl | H |
| AK | covalent bond | covalent bond | 3-aminopyrrolidin-1-yl | Cl |
| AL | covalent bond | covalent bond | 2-(methoxycarbonyl)piperazin-1-yl | H |

-continued
| Structure | A¹ | A² | R¹ | R² |
|---|---|---|---|---|
| AM | covalent bond | covalent bond | 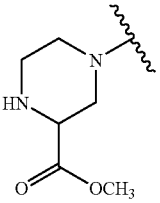 | Cl |
| AN | covalent bond | covalent bond | 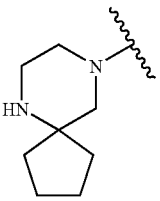 | H |
| AO | covalent bond | covalent bond | 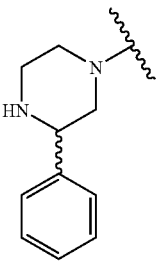 | H |
| AP | covalent bond | covalent bond | 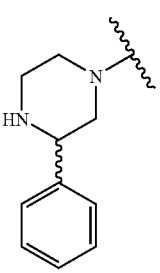 | Cl |
| AQ | covalent bond | covalent bond | 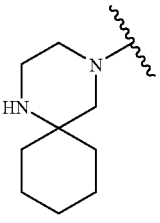 | H |
| AR | covalent bond | covalent bond | 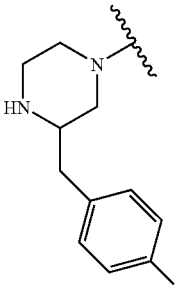 | H |

-continued
| Structure | A¹ | A² | R¹ | R² |
|---|---|---|---|---|
| AS | covalent bond | covalent bond | 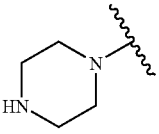 | H |
| AT | covalent bond | covalent bond | 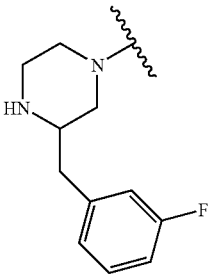 | H |
| AU | covalent bond | covalent bond | 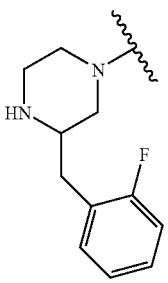 | H |
| AV | covalent bond | covalent bond | 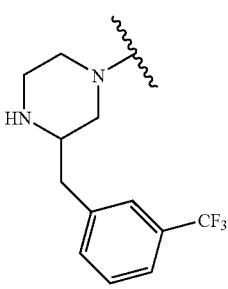 | H |
| AW | covalent bond | covalent bond | 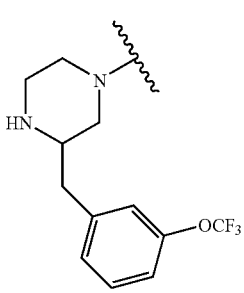 | H |
| AX | covalent bond | covalent bond | 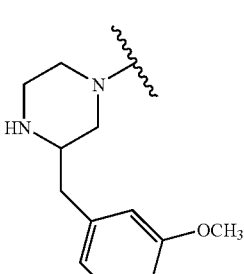 | H |

-continued
| Structure | A¹ | A² | R¹ | R² |
|---|---|---|---|---|
| AY | covalent bond | covalent bond | 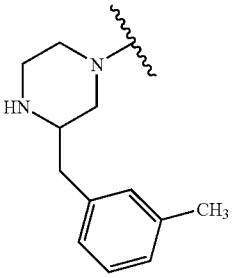 | H |
| AZ | covalent bond | covalent bond | 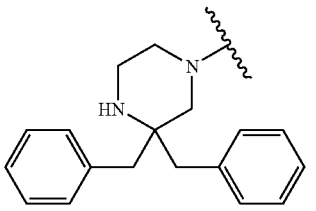 | H |
| AAA | covalent bond | covalent bond | 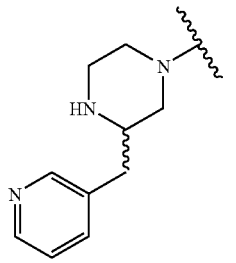 | H |
| AAB | covalent bond | covalent bond | 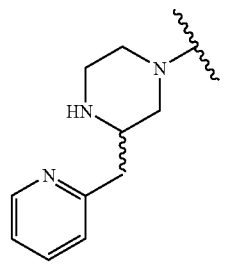 | H |
| AAC | covalent bond | covalent bond | 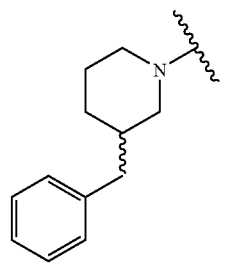 | H |

-continued
| Structure | A¹ | A² | R¹ | R² |
|---|---|---|---|---|
| AAD | covalent bond | covalent bond | 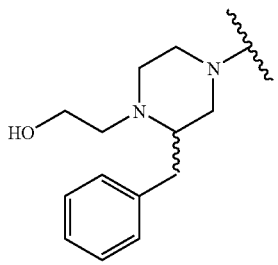 | H |
| AAE | covalent bond | covalent bond | 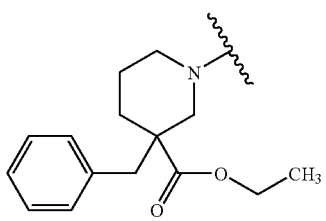 | H |
| AAF | covalent bond | covalent bond | 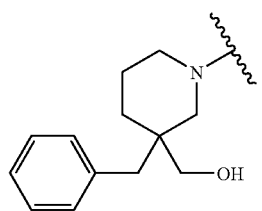 | H |
| AAG | covalent bond | covalent bond | 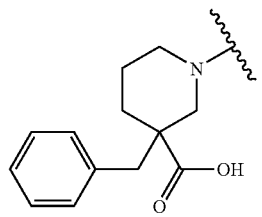 | H |
| AAH | covalent bond | covalent bond | 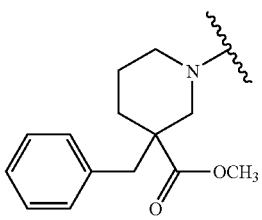 | H |
| AAI | covalent bond | covalent bond | 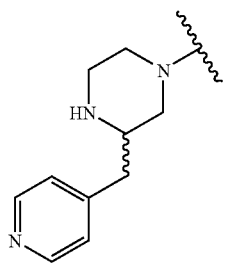 | H |

-continued
| Structure | A¹ | A² | R¹ | R² |
|---|---|---|---|---|
| AAJ | covalent bond | covalent bond |  | H |
| AAK | covalent bond | covalent bond | 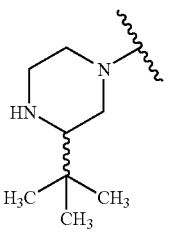 | H |
| AAL | covalent bond | —NH— | 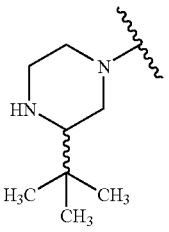 | H |
| AAM | covalent bond | —NH— | 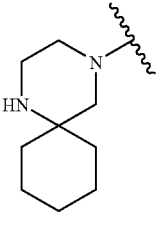 | H |
| AAN | covalent bond | —NH— | 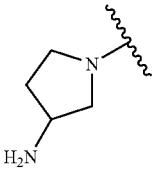 | H |
| AAO | covalent bond | —NH— | 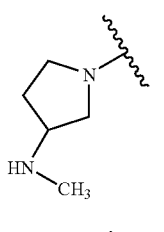 | H |
| AAP | covalent bond | —NH— | 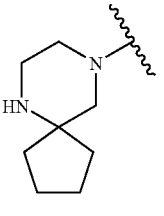 | H |

-continued
| Structure | A¹ | A² | R¹ | R² |
|---|---|---|---|---|
| AAQ | covalent bond | —NH— | 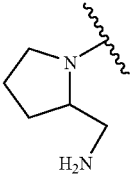 | H |
| AAR | covalent bond | —NH— | 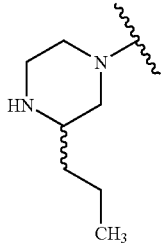 | H |
| AAT | covalent bond | —NH— | 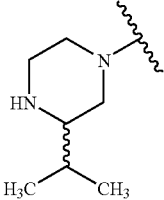 | H |
| AAU | covalent bond | —NH— | 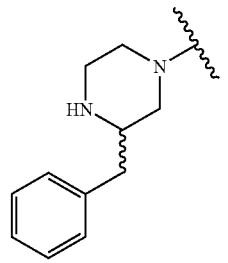 | H |
| AAV | covalent bond | covalent bond | 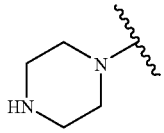 | —CH₂CH₂-phenyl |
| AAW | covalent bond | covalent bond | 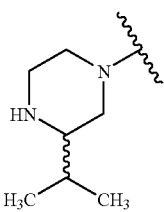 | —CH₂CH₂-phenyl |
| AAX | covalent bond | covalent bond | 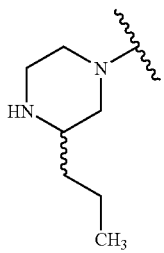 | —CH₂CH₂-phenyl |

-continued
| Structure | A¹ | A² | R¹ | R² |
|---|---|---|---|---|
| AAY | covalent bond | —NH— | 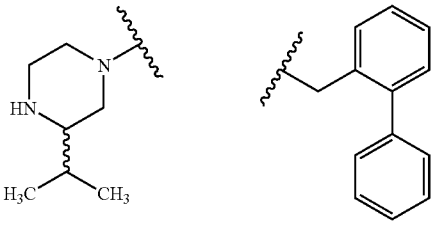 | 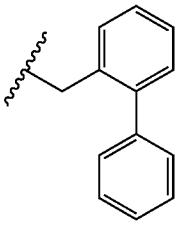 |
| AAZ | covalent bond | —NH— | 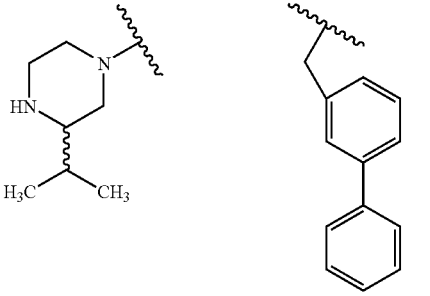 | 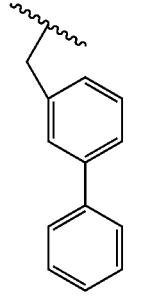 |
| AAAA | covalent bond | —NH— | 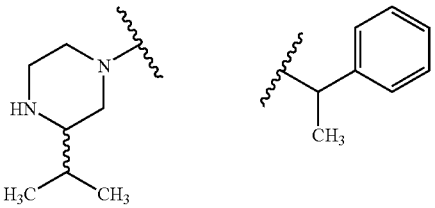 | 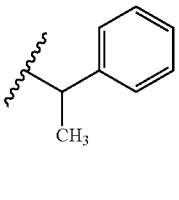 |
| AAAB | covalent bond | —NH— | 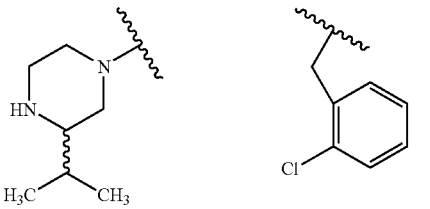 | 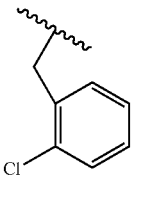 |
| AAAC | covalent bond | 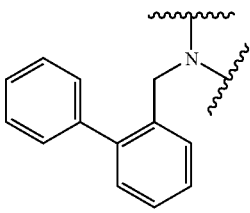 | 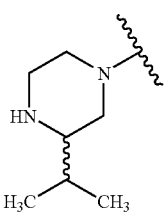 | 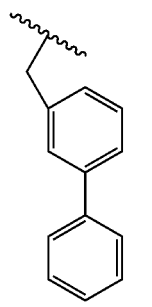 |
| AAAD | covalent bond | 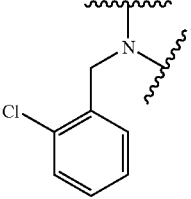 | 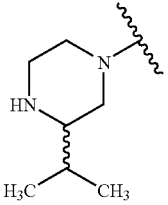 | 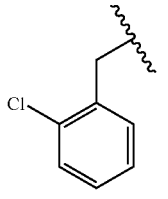 |

-continued
| Structure | A¹ | A² | R¹ | R² |
|---|---|---|---|---|
| AAAE | covalent bond | —NH— | 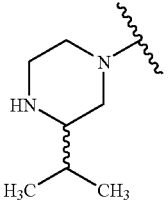 | 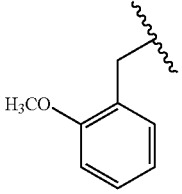 |
| AAAF | covalent bond | —NH— | 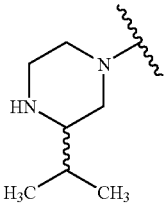 | 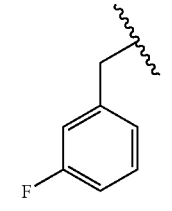 |
| AAAG | covalent bond | 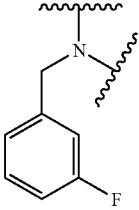 | 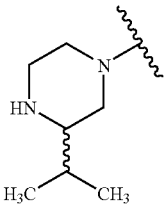 | 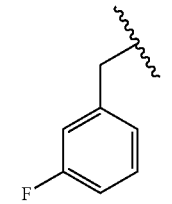 |
| AAAH | covalent bond | —NH— | 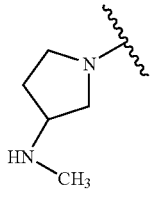 | 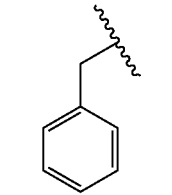 |
| AAAI | covalent bond | —NH— | 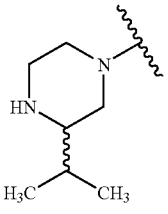 | 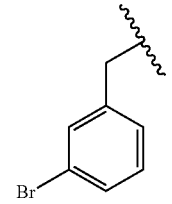 |
| AAAJ | covalent bond | 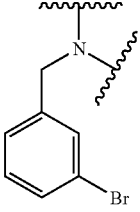 | 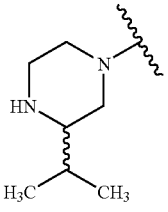 | 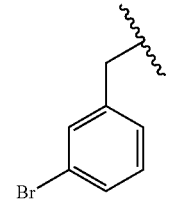 |
| AAAK | covalent bond | —NH— | 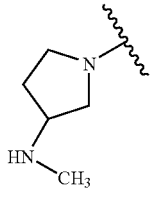 | 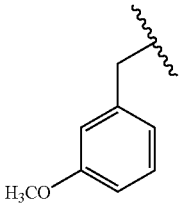 |

-continued
| Structure | A¹ | A² | R¹ | R² |
|---|---|---|---|---|
| AAAL | covalent bond | —NH— | 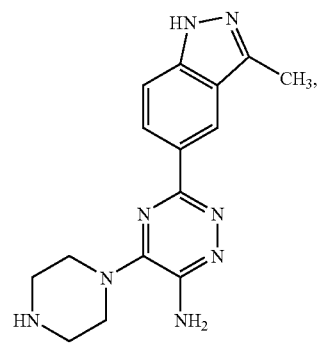 | 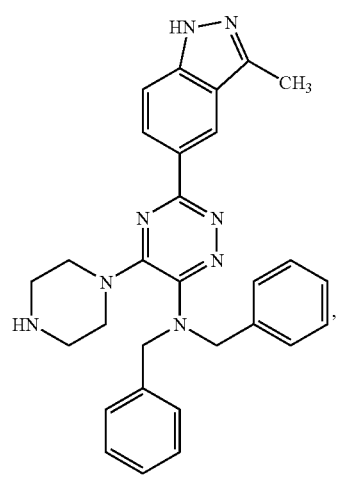 |
or pharmaceutically acceptable salts, solvates, or esters of the above.
In yet another embodiment, the compounds of the present invention are selected from the following:
1
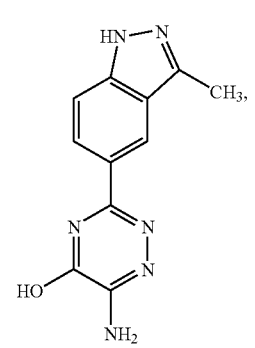
2
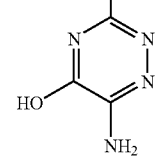
3
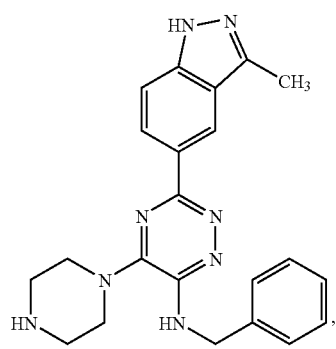
4
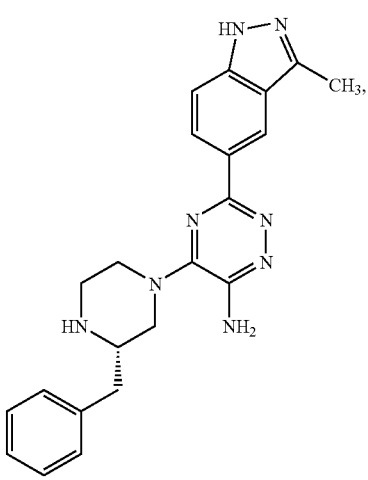
5

-continued
6
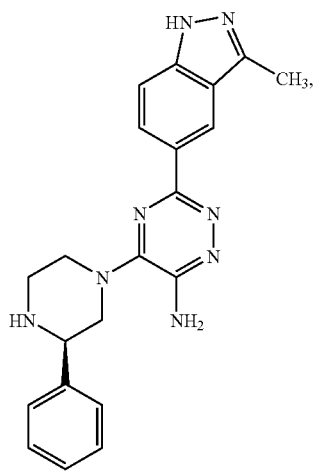
7
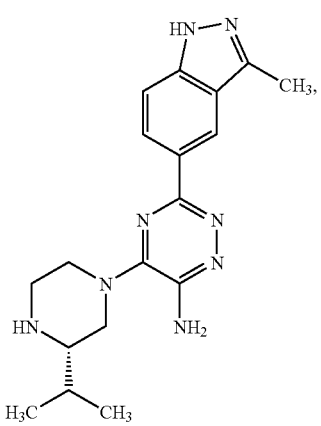
8
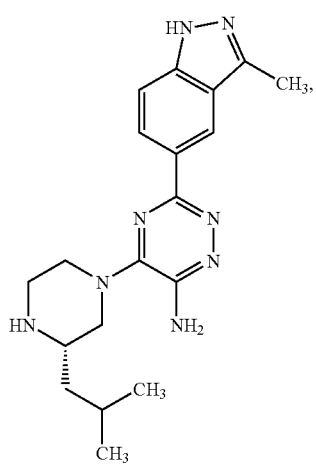
-continued
9
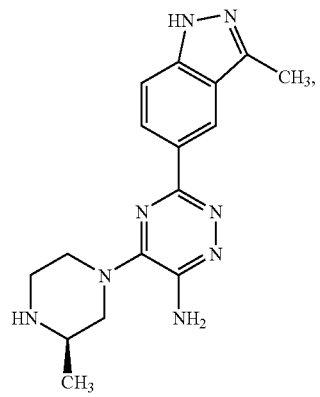
10
11
12
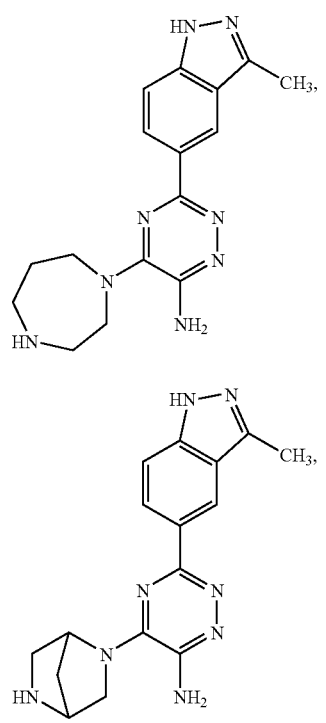

13
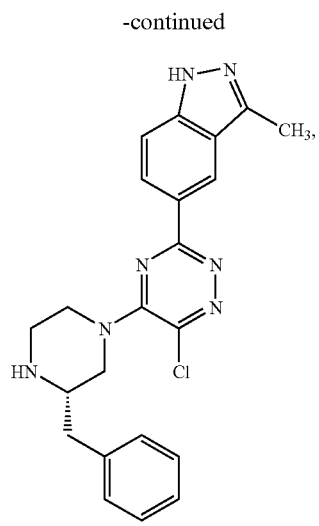
14
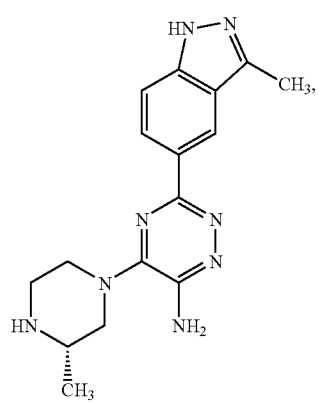
15
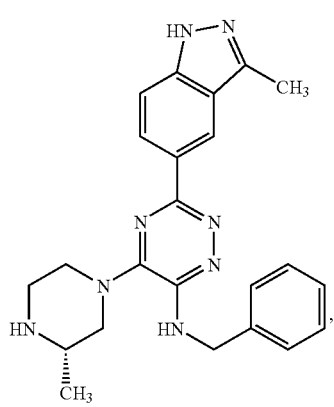
16
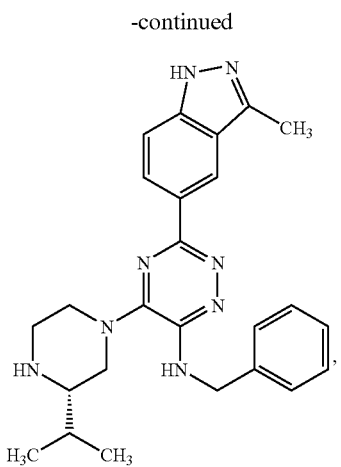
17
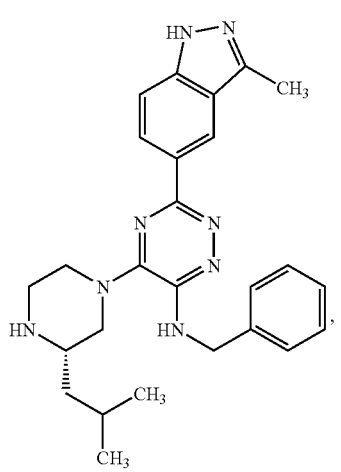
18
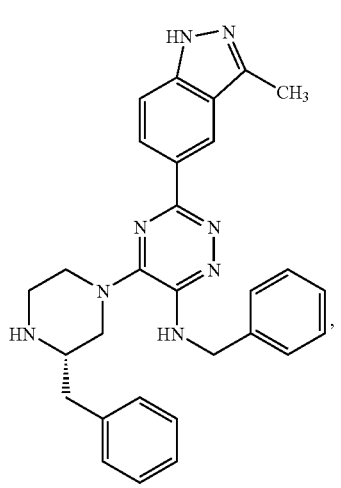

-continued
19
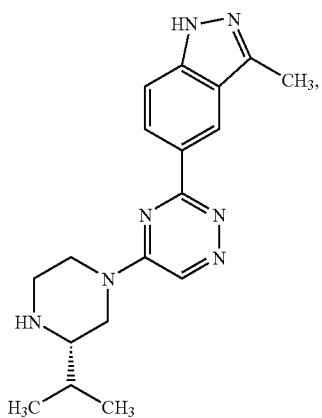
20
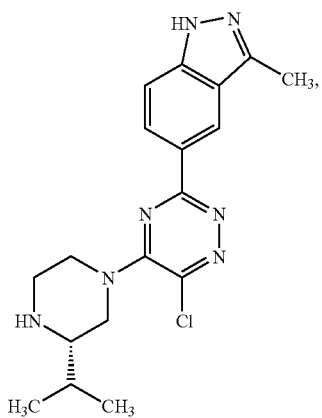
21
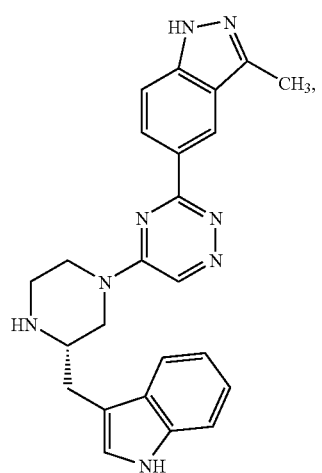
-continued
22
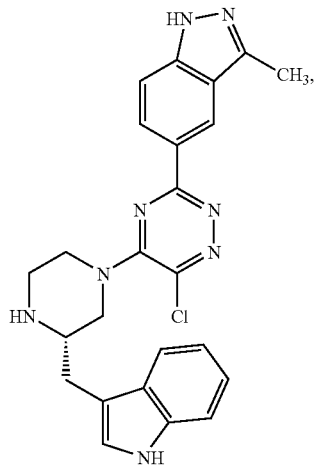
23
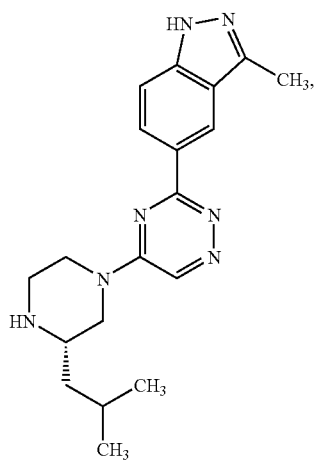
24
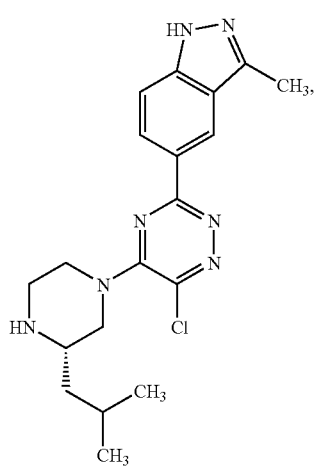

25 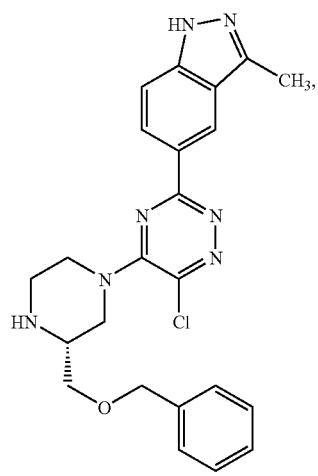
28 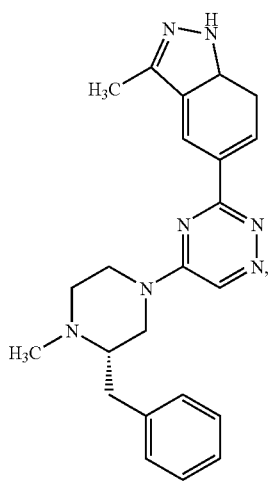
26 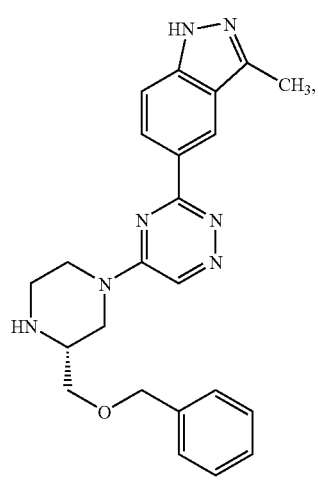
29 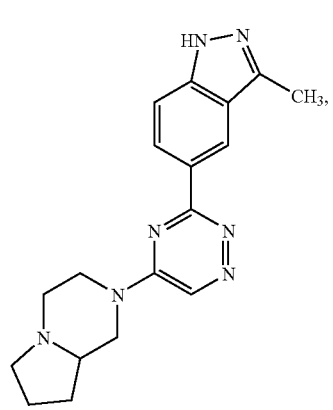
27 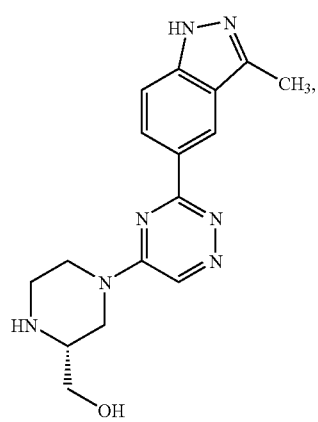
30 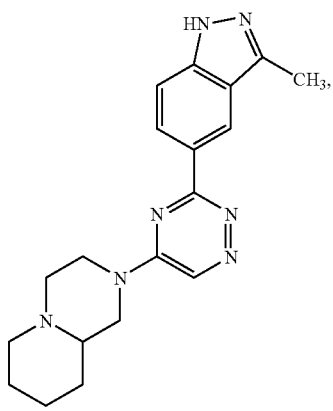

31 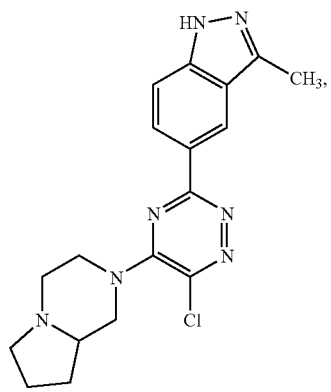
32 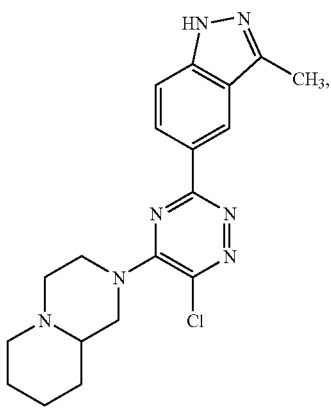
33 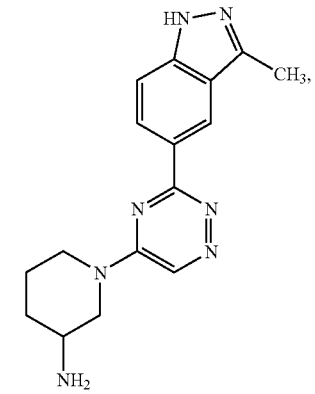
34 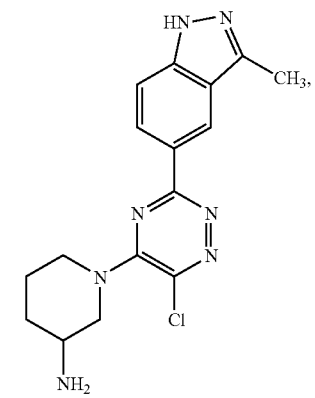
35 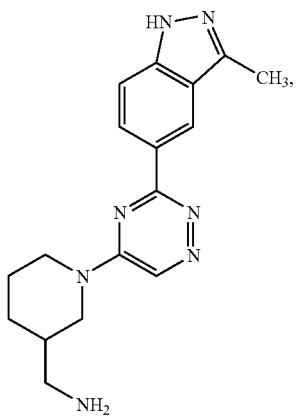
36 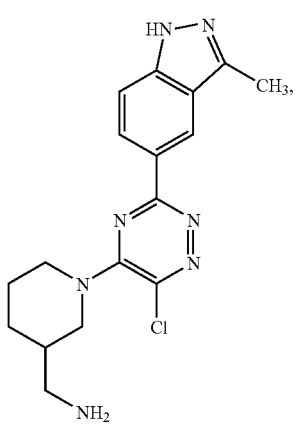
37 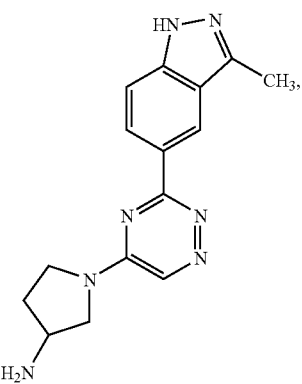
38 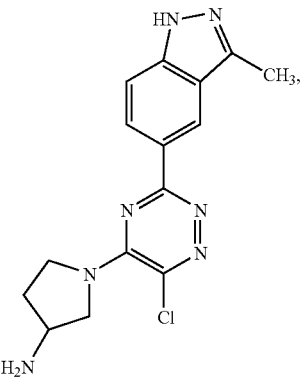

39
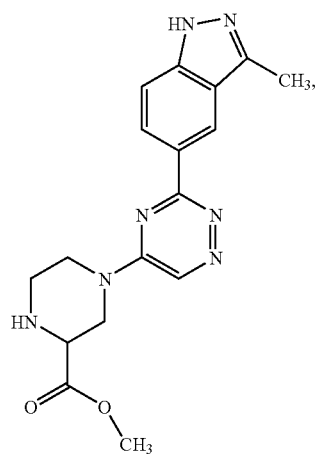
40
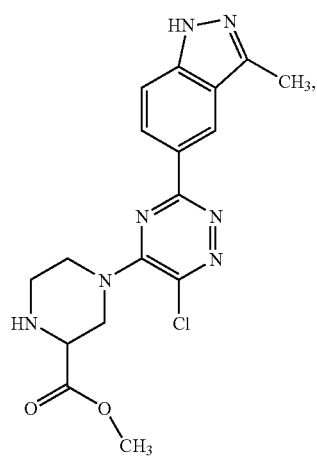
41
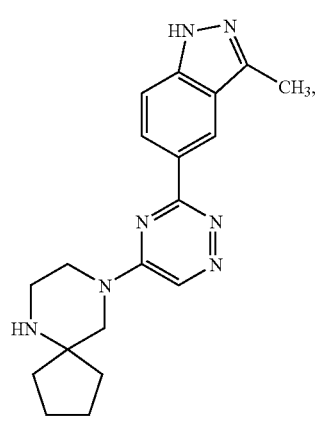
42
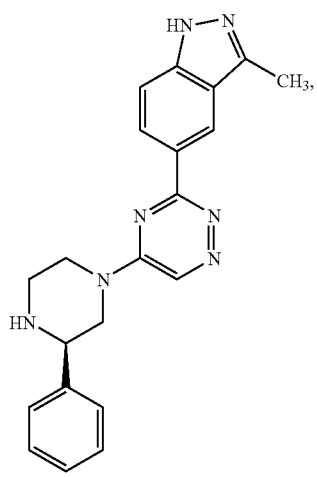
43
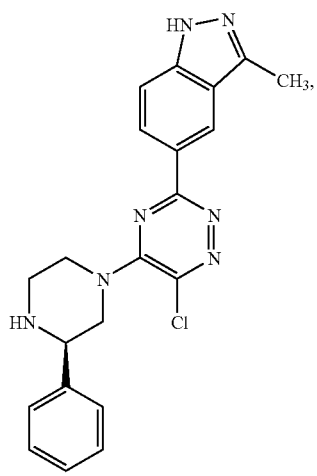

-continued

45

46

47

-continued

48

49

50

51
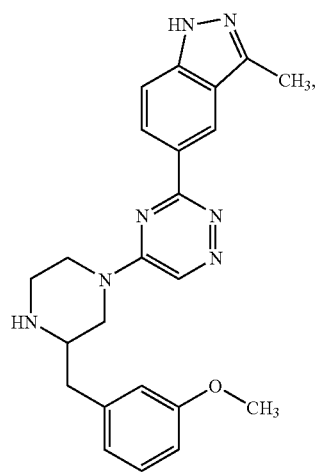
52
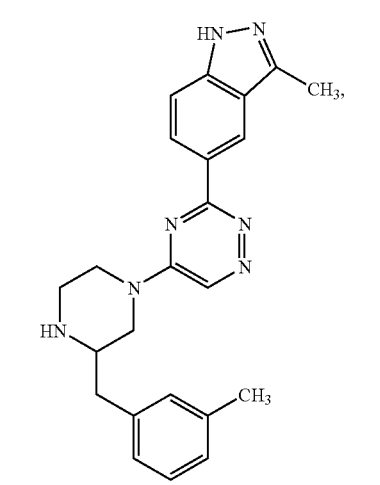
53
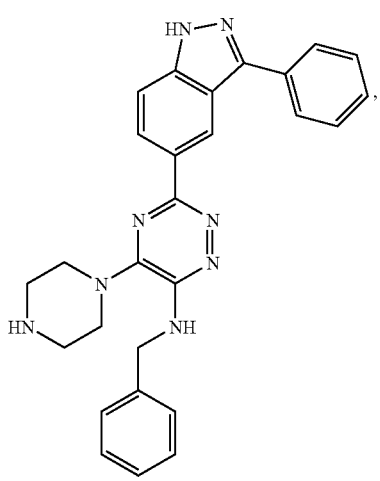
54
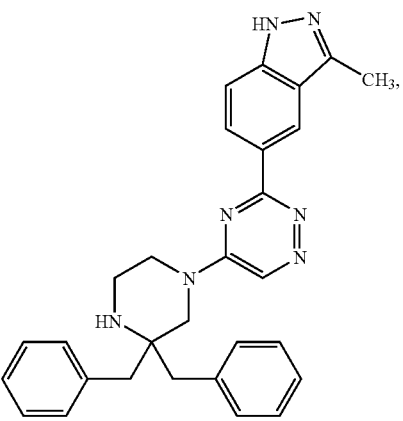
55
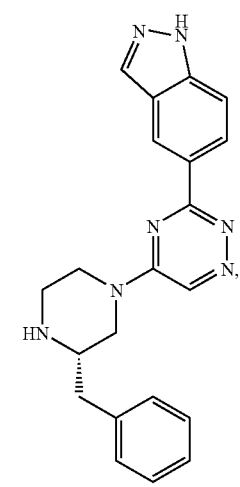
56
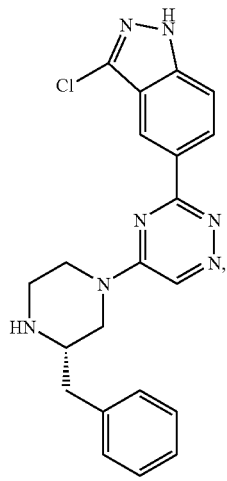

57
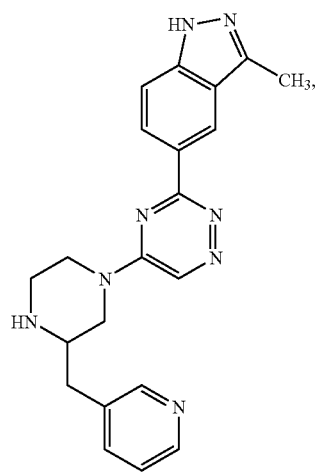
58
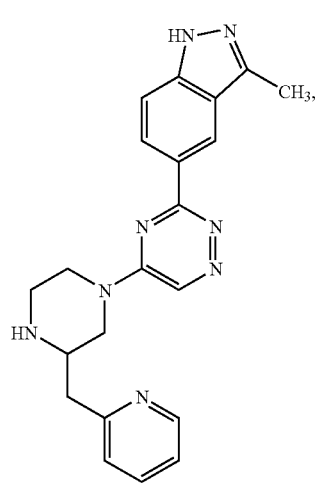
59
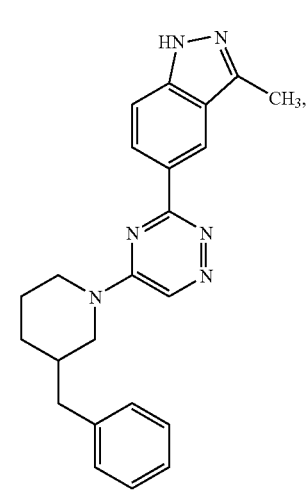
60
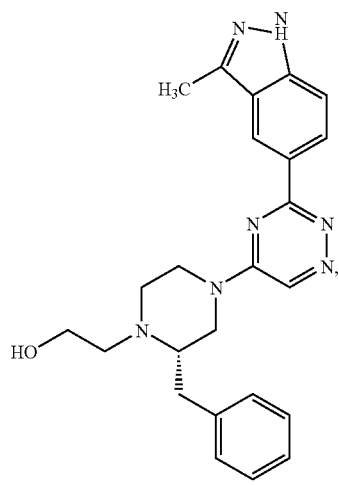
61
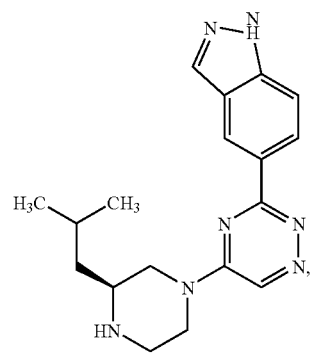
62
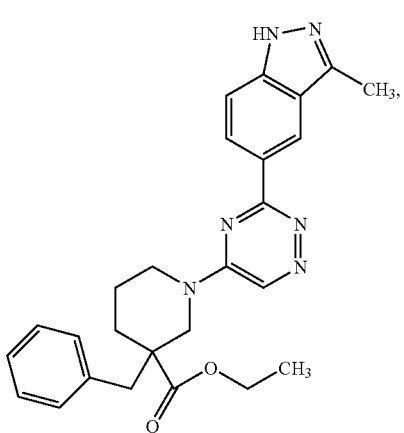

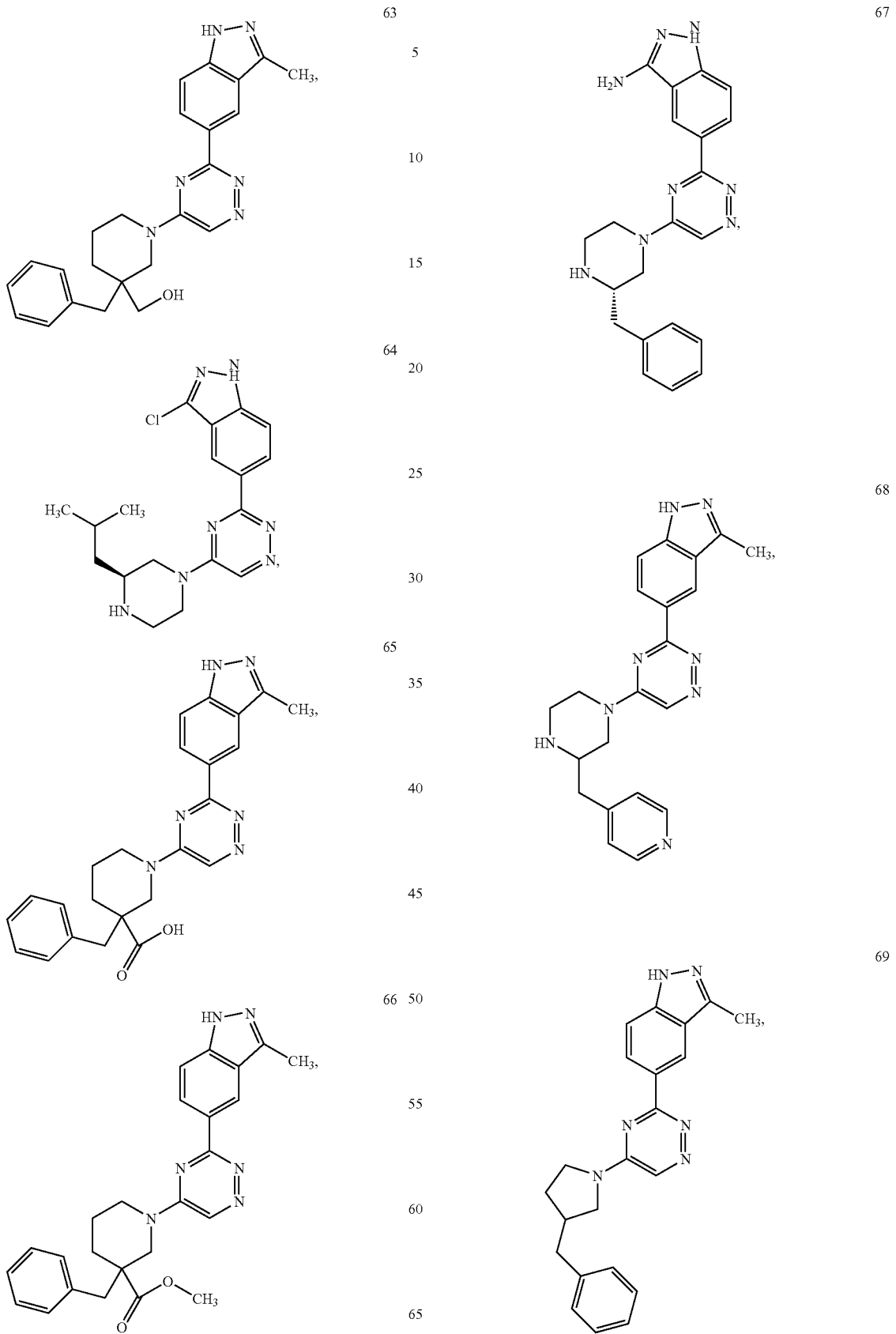

-continued
70
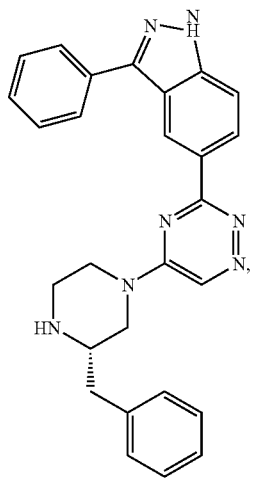
71
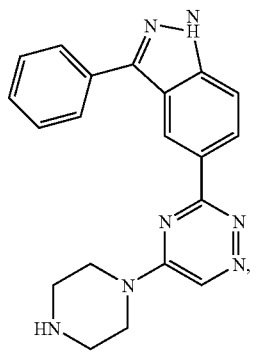
72
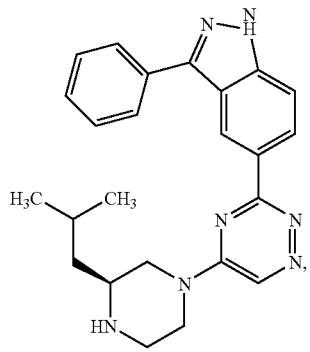
73
-continued
74
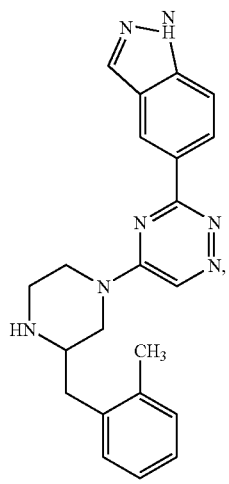
75
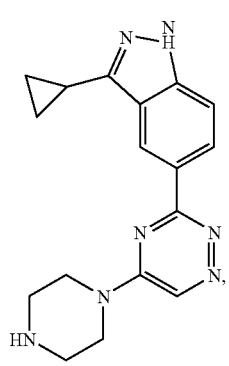
76
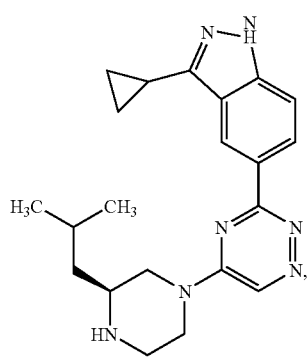

77
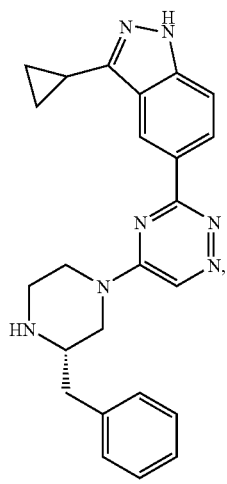
78
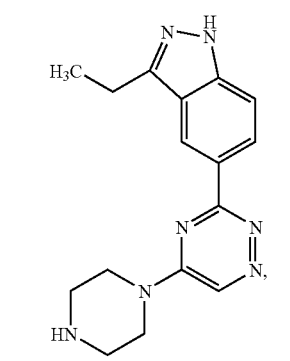
79
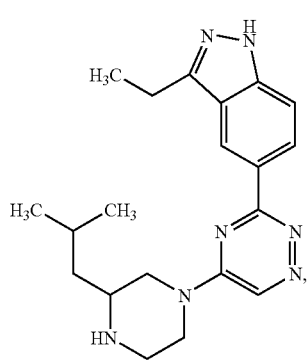
80
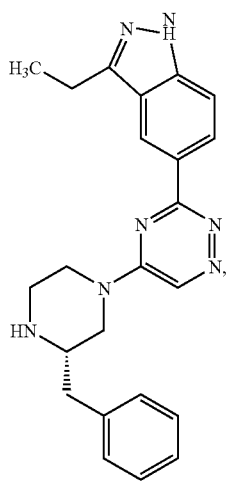
81
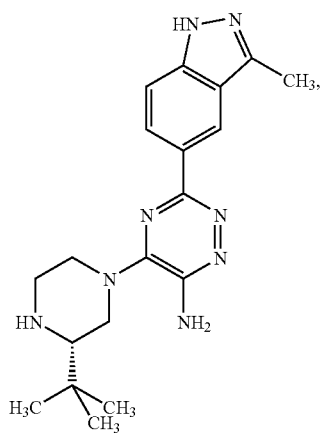
82
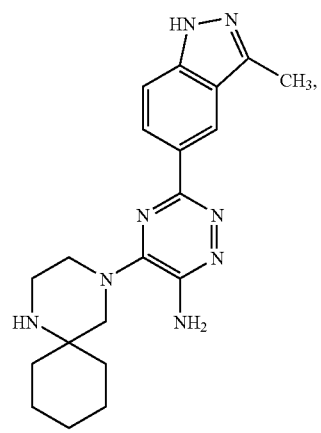

-continued
83
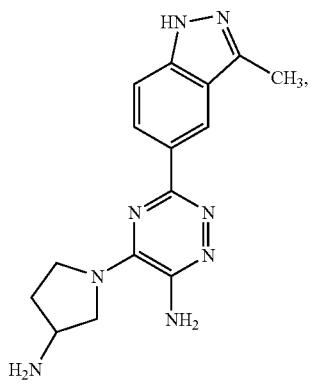
84
85
86
-continued
87
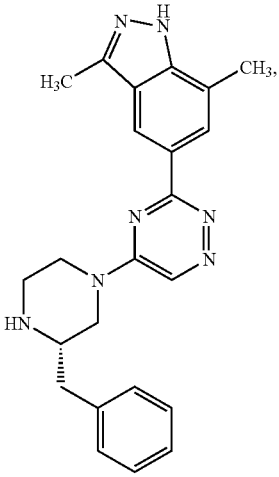
88
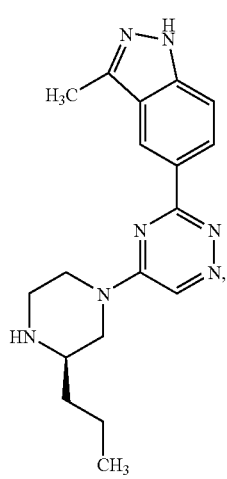
89
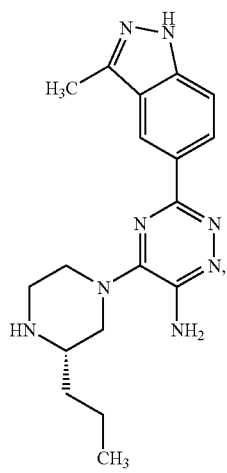

-continued
90
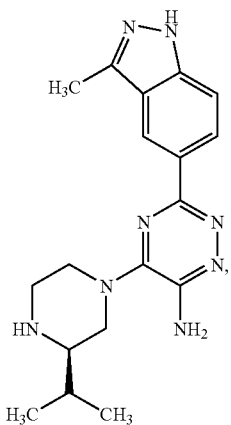
91
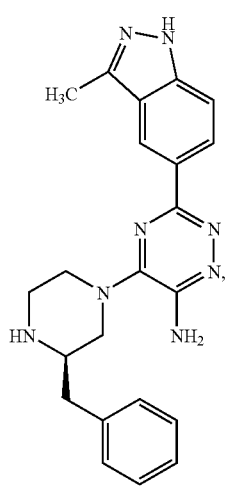
92
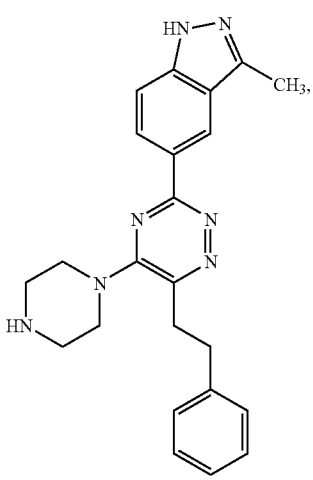
-continued
93
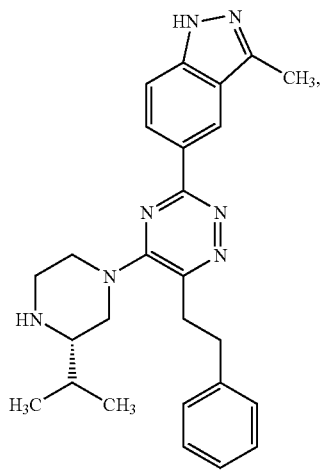
94
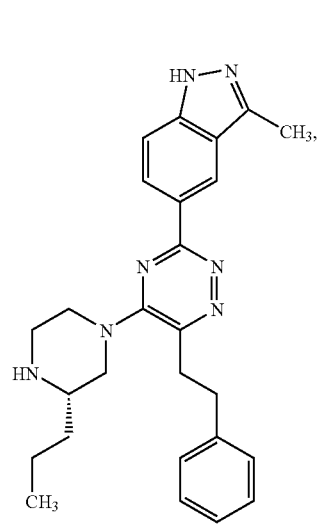
95
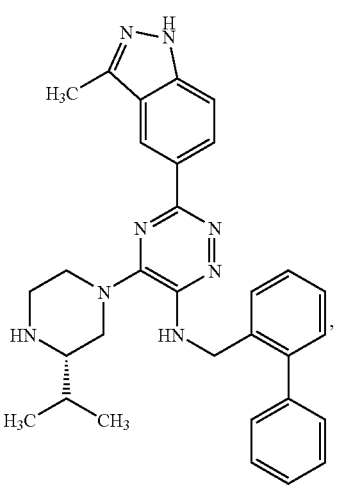

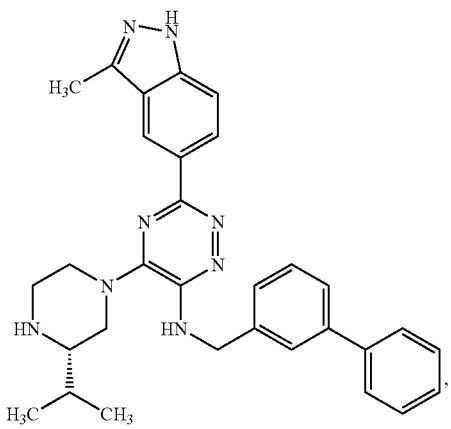
96
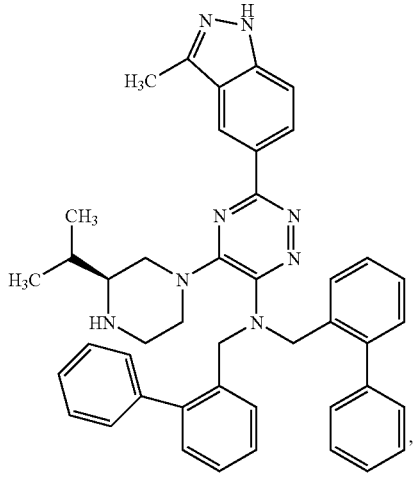
99
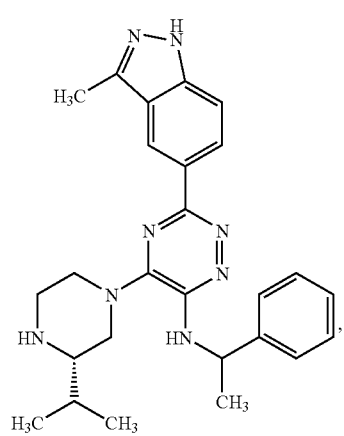
97
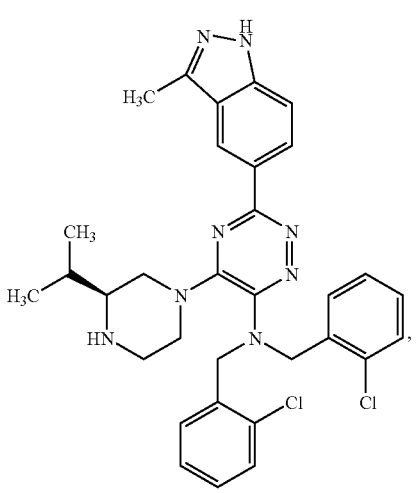
100
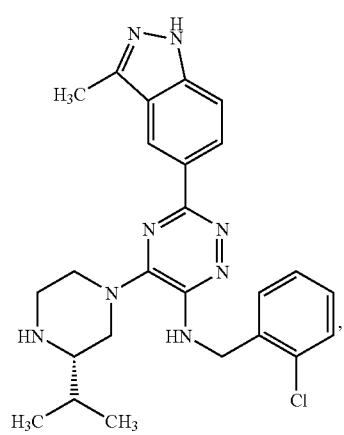
98
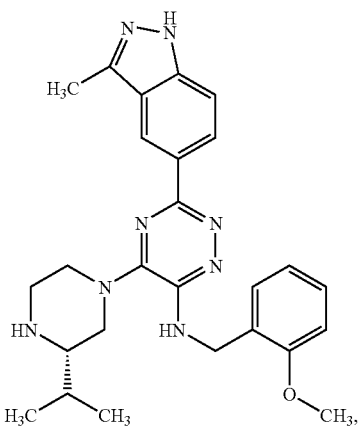
181

-continued

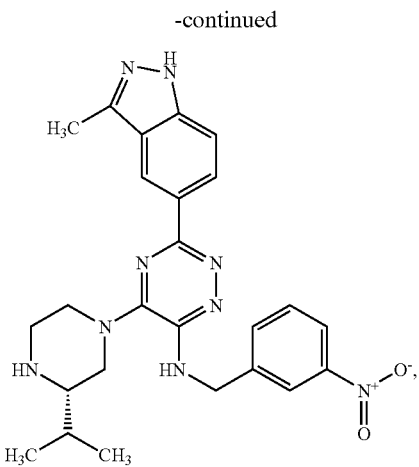

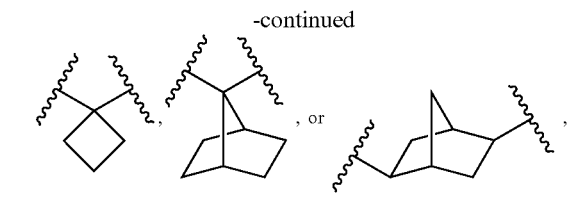

or pharmaceutically acceptable salts, solvates, or esters thereof.

The compounds of Formula (I) are preferably purified to a degree suitable for use as a pharmaceutically active substance. That is, the compounds of Formula (I) can have a purity of 95 wt % or more (excluding adjuvants such as pharmaceutically acceptable carriers, solvents, etc., which are used in formulating the compound of Formula (I) into a conventional form, such as a pill, capsule, IV solution, etc. suitable for administration into a patient). More preferably, the purity can be 97 wt % or more, even more preferably, 99 wt % or more. A purified compound of Formula (I) includes a single isomer having a purity, as discussed above, of 95 wt % or more, 97 wt % or more, or 99 wt % or more, as discussed above. For example, the purified compound of Formula (I) can include a compound of Structure A (above) having a purity of 95 wt % or more, 97 wt % or more, or 99 wt % or more.

Alternatively, the purified compound of Formula (I) can include a mixture of isomers, each having a structure according to Formula (I), where the amount of impurity (i.e., compounds or other contaminants, exclusive of adjuvants as discussed above) is 5 wt % or less, 3 wt % or less, or 1 wt % or less. For example, the purified compound of Formula (I) can be an isomeric mixture of compounds of Structure (I), where the ratio of the amounts of the two isomers is approximately 1:1, and the combined amount of the two isomers is 95 wt % or more, 97 wt % or more, or 99 wt % or more.

In one embodiment, $A^1$ and $A^2$ are each independently selected from the group consisting of a covalent bond, alkylene (e.g., $(C_1-C_6)$alkylene such as —$CH_2$—, —$CH_2CH_2$—, —$CH(CH_3)$—, or —$C(CH_3)_2$—, etc.), alkenylene (e.g., $(C_2$-$C_6)$alkenylene such as —$CH$=$CH$— or —$CH_2CH$=$CH$—, etc.), alkynylene (e.g., $(C_2-C_6)$alkynylene such as —$C$≡$C$— or —$CH_2C$≡$C$—, etc.), cycloalkylene (e.g., $(C_3-C_8)$cycloalkylenes such as

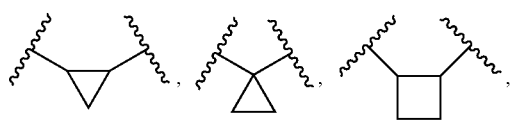

etc.), —O—, —$N(R^5)$—, —$C(O)$—, —S—, —$S(O)$—, —$S(O)_2$—, —$S(O)_2$—$N(R^6)$—, —$N(R^6)$—$S(O)_2$—, —$C(R^7)_2$—$N(R^5)$—, —$N(R^5)$—$C(R^7)_2$—, —$C(O)$—$N(R^6)$—, —$N(R^6)$—$C(O)$—, —$N(R^6)$—$C(O)$—$N(R^6)$—, —$C(R^6)_2$—$C$=$N$—, and —$N$=$C$—$C(R^6)_2$—.

In one embodiment, $A^3$ is a covalent bond, an alkylene (e.g., $(C_1-C_6)$alkylene such as —$CH_2$—, —$CH_2CH_2$—, —$CH(CH_3)$—, or —$C(CH_3)_2$—, etc.), —$N(R^5)$—, —$C(O)$$N(R^6)$—, or —$N(R^6)C(O)$—.

In one embodiment, $R^1$ and $R^2$ are each independently selected from the group consisting of H, alkyl (e.g., $(C_1-C_6)$ alkyl such as methyl, ethyl, n-propyl, i-propyl, n-butyl, sec-butyl, i-butyl, t-butyl, n-pentyl, n-hexyl, etc.), haloalkyl (e.g., $(C_1-C_6)$haloalkyl such as —$CF_3$, —$CF_2H$, —$CH_2F$, —$CH_2CF_3$, etc.), alkyl substituted with one or more —OH (e.g., $(C_1-C_6)$alkyl substituted with one or more —OH, such as —$CH_2OH$, —$CH(OH)CH_3$, —$CH_2CH_2OH$, —$CH(OH)$$CH_2CHOH$, etc.), alkenyl (e.g., $(C_2-C_6)$alkenyl such as —$CH$=$CH_2$, —$CH_2CH$=$CH_2$, —$CH$=$CHCH_3$, etc.), alkynyl (e.g., $(C_2-C_6)$alkynyl such as —$C$≡$CH$, —$CH_2C$≡$CH$, —$CH_2C$≡$CCH_3$, etc.), alkoxy (e.g., $(C_1-C_6)$ alkoxy such as —$OCH_3$, —$OCH_2CH_3$, —$OCH_2CH_2CH_3$, —$OCH(CH_3)_2$, etc.), -alkylene-O-alkyl (e.g., —$(C_2-C_6)$ alkylene-O—$(C_1-C_6)$alkyl such as —$CH_2$—O—$CH_3$, —$CH_2$—O—$CH_2CH_3$, —$CH_2CH_2$—O—$CH_3$, —$CH_2CH_2$—O—$CH_2CH_3$, etc.), aryl (e.g., $(C_6-C_{12})$aryl such as phenyl, naphthyl, biphenyl, etc, each of which can be optionally substituted with one or more groups Y as defined herein), -alkylene-aryl (e.g., —$(C_1-C_6)$alkylene-$(C_6-C_{12})$ aryl such as —$CH_2$-phenyl, —$CH_2CH_2$-phenyl, —$CH_2$-naphthyl, —$CH_2CH_2$-naphthyl, etc., where the $(C_6-C_{12})$aryl can be optionally substituted with one or more groups Y as defined herein), —CN, halogen (e.g., F, Cl, Br, or I), heteroaryl (e.g., $(C_2-C_{10})$heteroaryl such as azaindolyl, benzimidazolyl, benzofuranyl, benzothiophenyl, cinnolinyl, furanyl, furazanyl, indolyl, pyridyl, isoquinolyl, pyrazinyl, pyridazinyl, pyrimidinyl, pyrrolyl, quinolinyl, thiophenyl, isoxazolyl, triazolyl, thiazolyl; each of which can optionally be substituted with one or more groups Y as defined herein), -alkylene-heteroaryl (e.g., —$(C_2-C_6)$alkylene-$(C_2-C_{10})$heteroaryl such as —$CH_2$-pyridyl, —$CH_2CH_2$-pyridyl, —$CH_2$-pyrrolyl, —$CH_2CH_2$-pyrrolyl, etc., where the $(C_2-C_{10})$heteroaryl can optionally be substituted with one or more groups Y as defined herein), cycloalkyl (e.g., $(C_3-C_6)$cycloalkyl such as cyclopropyl, cyclobutyl, cyclopentyl, cyclohexyl, etc.), heterocyclyl (e.g., $(C_2-C_{10})$heterocyclyl such as morpholinyl, piperazinyl, piperidinyl, pyrrolidinyl, pyrrolidin-2-onyl, tetrahydrofuranyl, tetrahydrothiophenyl, azetidinyl, etc., where the $(C_2-C_{10})$heterocyclyl can be optionally substituted with one or more groups Z as defined herein), and -alkylene-heterocyclyl (e.g., —$(C_2-C_6)$alkylene-$(C_2-C_{10})$heterocyclyl such as —$CH_2$-piperazinyl, —$CH_2CH_2$-piperazinyl, —$CH_2$-piperidinyl, —$CH_2CH_2$-piperidinyl, etc.), where the —$(C_2$-$C_{10})$heterocyclyl portion of the —$(C_2-C_6)$alkylene-$(C_2-C_{10})$ heterocyclyl can be optionally substituted with one or more groups Z as defined herein.

In one embodiment, $R^3$ is selected from the group consisting of H, alkyl (e.g., $(C_1-C_6)$alkyl such as methyl, ethyl, n-propyl, i-propyl, n-butyl, sec-butyl, i-butyl, t-butyl, n-pentyl, n-hexyl, etc.), alkoxy (e.g., $(C_1-C_6)$alkoxy such as —OCH$_3$, —OCH$_2$CH$_3$, —OCH$_2$CH$_2$CH$_3$, —OCH(CH$_3$)$_2$, etc.), —N(R$^8$)$_2$, —N(R$^8$)—C(O)—R$^8$, —C(O)—N(R$^6$)$_2$, —N(R$^6$)—C(O)—N(R$^6$)$_2$, —N(R$^6$)—S(O)$_2$—R$^6$, —C(O)-alkyl (e.g., —C(O)—(C$_1$-C$_6$)alkyl such as —C(O)—CH$_3$, —C(O)—CH$_2$CH$_3$, —C(O)—CH$_2$CH$_2$CH$_3$, —C(O)—CH$_2$CH$_2$CH$_2$CH$_3$, —C(O)—CH$_2$CH(CH$_3$)$_2$, —C(O)—CH(CH$_3$)CH$_2$CH$_3$, —C(O)—C(CH$_3$)$_3$, etc.), -alkylene-O-alkyl (e.g., —(C$_2$-C$_6$)alkylene-O—(C$_1$-C$_6$)alkyl such as —CH$_2$—O—CH$_3$, —CH$_2$—O—CH$_2$CH$_3$, —CH$_2$CH$_2$—O—CH$_3$, —CH$_2$CH$_2$—O—CH$_2$CH$_3$, etc.), —CN, halogen (e.g., F, Cl, Br, or I), aryl (e.g., $(C_6-C_{12})$aryl such as phenyl, naphthyl, biphenyl, etc, each of which can be optionally substituted with one or more groups Y as defined herein), heteroaryl (e.g., $(C_2-C_{10})$heteroaryl such as azaindolyl, benzimidazolyl, benzofuranyl, benzothiophenyl, cinnolinyl, furanyl, furazanyl, indolyl, pyridyl, isoquinolyl, pyrazinyl, pyridazinyl, pyrimidinyl, pyrrolyl, quinolinyl, thiophenyl, isoxazolyl, triazolyl, thiazolyl; each of which can optionally be substituted with one or more groups Y as defined herein), heterocyclyl (e.g., $(C_2-C_{10})$heterocyclyl such as morpholinyl, piperazinyl, piperidinyl, pyrrolidinyl, pyrrolidin-2-onyl, tetrahydrofuranyl, tetrahydrothiophenyl, azetidinyl, etc., where the $(C_2-C_{10})$heterocyclyl can be optionally substituted with one or more groups Z as defined herein), -alkylene-aryl (e.g., —(C$_1$-C$_6$)alkylene-(C$_6$-C$_{12}$)aryl such as —CH$_2$-phenyl, —CH$_2$CH$_2$-phenyl, —CH$_2$-naphthyl, —CH$_2$CH$_2$-naphthyl, etc., where the $(C_6-C_{12})$aryl can be optionally substituted with one or more groups Y as defined herein), -alkylene-heteroaryl (e.g., —(C$_2$-C$_6$)alkylene-(C$_2$-C$_{10}$)heteroaryl such as —CH$_2$-pyridyl, —CH$_2$CH$_2$-pyridyl, —CH$_2$-pyrrolyl, —CH$_2$CH$_2$-pyrrolyl, etc., where the $(C_2-C_{10})$heteroaryl can optionally be substituted with one or more groups Y as defined herein), -alkylene-heterocyclyl (e.g., —(C$_2$-C$_6$)alkylene-(C$_2$-C$_{10}$)heterocyclyl such as —CH$_2$-piperazinyl, —CH$_2$CH$_2$-piperazinyl, —CH$_2$-piperidinyl, —CH$_2$CH$_2$-piperidinyl, etc.), where the —(C$_2$-C$_{10}$)heterocyclyl portion of the —(C$_2$-C$_6$)alkylene-(C$_2$-C$_{10}$)heterocyclyl can be optionally substituted with one or more groups Z as defined herein, and alkynyl (e.g., $(C_2-C_6)$alkynyl such as —C≡CH, —CH$_2$C≡CH, —CH$_2$C≡CCH$_3$, etc.).

In one embodiment, $R^4$ is selected from the group consisting of H, alkyl (e.g., $(C_1-C_6)$alkyl such as methyl, ethyl, n-propyl, i-propyl, n-butyl, sec-butyl, i-butyl, t-butyl, n-pentyl, n-hexyl, etc.), —C(O)-alkyl (e.g., —C(O)—(C$_1$-C$_6$)alkyl such as —C(O)—CH$_3$, —C(O)—CH$_2$CH$_3$, —C(O)—CH$_2$CH$_2$CH$_3$, —C(O)—CH$_2$CH$_2$CH$_2$CH$_2$CH$_3$, —C(O)—CH$_2$CH(CH$_3$)$_2$, —C(O)—CH(CH$_3$)CH$_2$CH$_3$, —C(O)—C(CH$_3$)$_3$, etc.), —C(O)—O-alkyl (e.g., —C(O)—O—(C$_1$-C$_6$)alkyl such as —C(O)—O—CH$_3$, —C(O)—O—CH$_2$CH$_3$, —C(O)—O—CH$_2$CH$_3$, —C(O)—O—CH$_2$CH$_2$CH$_2$CH$_3$, —C(O)—O—CH$_2$CH(CH$_3$)$_2$, —C(O)—O—CH(CH$_3$)CH$_2$CH$_3$, —C(O)—O—C(CH$_3$)$_3$, etc.), -alkylene-O-alkyl (e.g., —(C$_2$-C$_6$)alkylene-O—(C$_1$-C$_6$)alkyl such as —CH$_2$—O—CH$_3$, —CH$_2$—O—CH$_2$CH$_3$, —CH$_2$CH$_2$—O—CH$_3$, —CH$_2$CH$_2$—O—CH$_2$CH$_3$, etc.), and -alkylene-O—C(O)-alkyl (e.g., —(C$_2$-C$_6$)alkylene-O—C(O)—(C$_1$-C$_6$)alkyl such as —CH$_2$—O—C(O)—CH$_3$, —CH$_2$—O—C(O)—CH$_2$CH$_3$, —CH$_2$CH$_2$—O—C(O)—CH$_3$, —CH$_2$CH$_2$—O—C(O)—CH$_2$CH$_3$, etc.).

In one embodiment, $R^5$ is selected from the group consisting of H, alkyl (e.g., $(C_1-C_6)$alkyl such as methyl, ethyl, n-propyl, i-propyl, n-butyl, sec-butyl, i-butyl, t-butyl, n-pentyl, n-hexyl, etc.), -alkylene-N(R$^8$)$_2$ (e.g., $(C_1-C_6)$alkylene-N(R$^8$)$_2$ such as —CH$_2$—N(R$^8$)$_2$, —CH$_2$CH$_2$—N(R$^8$)$_2$, —CH(CH$_3$)—N(R$^8$)$_2$, or —C(CH$_3$)$_2$—N(R$^8$)$_2$, etc.), alkoxy (e.g., $(C_1-C_6)$alkoxy such as —OCH$_3$, —OCH$_2$CH$_3$, —OCH$_2$CH$_2$CH$_3$, —OCH(CH$_3$)$_2$, etc.), aryl (e.g., $(C_6-C_{12})$aryl such as phenyl, naphthyl, biphenyl, etc., each of which can be optionally substituted with one or more groups Y as defined herein), -alkylene-aryl (e.g., —(C$_2$-C$_6$)alkylene-(C$_6$-C$_{12}$)aryl such as —CH$_2$-phenyl, —CH$_2$CH$_2$-phenyl, —CH$_2$-naphthyl, —CH$_2$CH$_2$-naphthyl, etc., where the $(C_6-C_{12})$aryl can be optionally substituted with one or more groups Y as defined herein), —C(O)-alkyl (e.g., —C(O)—(C$_1$-C$_6$)alkyl such as —C(O)—CH$_3$, —C(O)—CH$_2$CH$_3$, —C(O)—CH$_2$CH$_2$CH$_3$, —C(O)—CH(CH$_3$)$_2$, —C(O)—CH$_2$CH$_2$CH$_2$CH$_3$, —C(O)—CH$_2$CH(CH$_3$)$_2$, —C(O)—CH(CH$_3$)CH$_2$CH$_3$, —C(O)—C(CH$_3$)$_3$, —C(O)—CH$_2$CH$_2$CH$_2$CH$_2$CH$_3$, —C(O)—CH$_2$CH$_2$CH$_2$CH$_2$CH$_2$CH$_3$, etc.), —S(O)$_2$-alkyl (e.g., —S(O)$_2$—(C$_1$-C$_6$)alkyl such as —S(O)$_2$—CH$_3$, —S(O)$_2$—CH$_2$CH$_3$, —S(O)$_2$—CH$_2$CH$_2$CH$_3$, —S(O)$_2$—CH(CH$_3$)$_2$, —S(O)$_2$—CH$_2$CH$_2$CH$_2$CH$_3$, —S(O)$_2$—CH$_2$CH(CH$_3$)$_2$, —S(O)$_2$—CH(CH$_3$)CH$_2$CH$_3$, —S(O)$_2$—C(CH$_3$)$_3$, —S(O)$_2$—CH$_2$CH$_2$CH$_2$CH$_2$CH$_3$, —S(O)$_2$—CH$_2$CH$_2$CH$_2$CH$_2$CH$_2$CH$_3$, etc.), —C(O)-aryl (e.g., —C(O)—(C$_6$-C$_{12}$)aryl such as —C(O)-phenyl, —C(O)-naphthyl, —C(O)-biphenyl, etc. where the $(C_6-C_{12})$aryl can be optionally substituted with one or more group Y as defined herein), and —S(O)$_2$-aryl (e.g., —S(O)$_2$—(C$_6$-C$_{12}$)aryl such as —S(O)$_2$-phenyl, —S(O)$_2$-naphthyl, —S(O)$_2$-biphenyl, etc. where the $(C_6-C_{12})$aryl can be optionally substituted with one or more group Y as defined herein).

In one embodiment, each $R^6$ is independently selected from the group consisting of H, alkyl (e.g., $(C_1-C_6)$alkyl such as methyl, ethyl, n-propyl, i-propyl, n-butyl, sec-butyl, i-butyl, t-butyl, n-pentyl, n-hexyl, etc.), unsubstituted aryl (e.g., $(C_6-C_{12})$aryl such as phenyl, naphthyl, biphenyl, etc.), aryl substituted with one or more groups Y (e.g., $(C_6-C_{12})$aryl such as phenyl, naphthyl, biphenyl, etc., substituted with one or more groups Y as defined herein), and -alkylene-aryl (e.g., —(C$_1$-C$_6$)alkylene-(C$_6$-C$_{12}$)aryl such as —CH$_2$-phenyl, —CH$_2$CH$_2$-phenyl, —CH$_2$-naphthyl, —CH$_2$CH$_2$-naphthyl, etc., where the $(C_6-C_{12})$aryl can be optionally substituted with one or more groups Y as defined herein).

In one embodiment, each $R^7$ is independently selected from the group consisting of H, alkyl (e.g., $(C_1-C_6)$alkyl such as methyl, ethyl, n-propyl, i-propyl, n-butyl, sec-butyl, i-butyl, t-butyl, n-pentyl, n-hexyl, etc.), alkenyl (e.g., $(C_2-C_6)$alkenyl such as —CH=CH$_2$, —CH$_2$CH=CH$_2$, —CH=CHCH$_3$, etc.), alkynyl (e.g., $(C_2-C_6)$alkynyl such as —C≡CH, —CH$_2$C≡CH, —CH$_2$C≡CCH$_3$, etc.), —N(R$^8$)$_2$, —CN, halo (e.g., F, Cl, Br, or I), aryl (e.g., $(C_6-C_{12})$aryl such as phenyl, naphthyl, biphenyl, etc., where the $(C_6-C_{12})$aryl is optionally substituted with one or more groups Y as defined herein), heteroaryl (e.g., $(C_2-C_{10})$heteroaryl such as azaindolyl, benzimidazolyl, benzofuranyl, benzothiophenyl, cinnolinyl, furanyl, furazanyl, indolyl, pyridyl, isoquinolyl, pyrazinyl, pyridazinyl, pyrimidinyl, pyrrolyl, quinolinyl, thiophenyl, isoxazolyl, triazolyl, thiazolyl; each of which can optionally be substituted with one or more groups Y as defined herein), and heterocyclyl (e.g., $(C_2-C_{10})$heterocyclyl such as morpholinyl, piperazinyl, piperidinyl, pyrrolidinyl, pyrrolidin-2-onyl, tetrahydrofuranyl, tetrahydrothiophenyl, azetidinyl, etc., where the $(C_2-C_{10})$heterocyclyl can be optionally substituted with one or more groups Z as defined herein) and -alkylene-aryl (e.g., —(C$_1$-C$_6$)alkylene-(C$_6$-C$_{12}$)aryl such as —CH$_2$-phenyl, —CH$_2$CH$_2$-phenyl, —CH$_2$-naphthyl, —CH$_2$CH$_2$-naphthyl, etc., where the (C$_6$-C$_{12}$)aryl can be optionally substituted with one or more groups Y as defined herein).

In one embodiment, each R$^8$ is independently selected from the group consisting of H, alkyl (e.g., (C$_1$-C$_6$)alkyl such as methyl, ethyl, n-propyl, i-propyl, n-butyl, sec-butyl, i-butyl, t-butyl, n-pentyl, n-hexyl, etc.), and aryl (e.g., (C$_6$-C$_{12}$) aryl such as phenyl, naphthyl, biphenyl, etc., where the (C$_6$-C$_{12}$)aryl is optionally substituted with one or more groups Y as defined herein).

In one embodiment, X is one or more substituents independently selected from the group consisting of hydrogen, halogen (e.g., F, Cl, Br, or I), alkyl (e.g., (C$_1$-C$_6$)alkyl such as methyl, ethyl, n-propyl, i-propyl, n-butyl, sec-butyl, i-butyl, t-butyl, n-pentyl, n-hexyl, etc.), alkoxy (e.g., (C$_1$-C$_6$)alkoxy such as —OCH$_3$, —OCH$_2$CH$_3$, —OCH$_2$CH$_2$CH$_3$, —OCH(CH$_3$)$_2$, etc.), and haloalkyl (e.g., (C$_1$-C$_6$)haloalkyl such as —CF$_3$, CF$_2$H, CH$_2$F, —CH$_2$CF$_3$, etc.).

In one embodiment, Y is one or more substituents independently selected from the group consisting of halogen (e.g., F, Cl, Br, or I), alkyl (e.g., (C$_1$-C$_6$)alkyl such as methyl, ethyl, n-propyl, i-propyl, n-butyl, sec-butyl, i-butyl, t-butyl, n-pentyl, n-hexyl, etc.), haloalkyl (e.g., (C$_1$-C$_6$)haloalkyl such as —CF$_3$, —CF$_2$H, —CH$_2$F, —CH$_2$CF$_3$, etc.), aryl (e.g., (C$_6$-C$_{12}$)aryl such as phenyl, naphthyl, biphenyl, etc.), -alkylene-aryl (e.g., —(C$_2$-C$_6$)alkylene-(C$_6$-C$_{12}$)aryl such as —CH$_2$-phenyl, —CH$_2$CH$_2$-phenyl, —CH$_2$-naphthyl, —CH$_2$CH$_2$-naphthyl, etc.), —OH, alkoxy (e.g., (C$_1$-C$_6$)alkoxy such as —OCH$_3$, —OCH$_2$CH$_3$, —OCH$_2$CH$_2$CH$_3$, —OCH(CH$_3$)$_2$, etc.), —CN, —N(R$^9$)$_2$, —C(O)N(R$^9$)$_2$, and —S(O$_2$)N(R$^9$)$_2$.

In one embodiment, each R$^9$ is independently selected from the group consisting of H, alkyl (e.g., (C$_1$-C$_6$)alkyl such as methyl, ethyl, n-propyl, i-propyl, n-butyl, sec-butyl, i-butyl, t-butyl, n-pentyl, n-hexyl, etc.), aryl (e.g., (C$_6$-C$_{12}$)aryl such as phenyl, naphthyl, biphenyl, etc.), and -alkylene-aryl (e.g., —(C$_2$-C$_6$)alkylene-(C$_6$-C$_{12}$)aryl such as —CH$_2$-phenyl, —CH$_2$CH$_2$-phenyl, —CH$_2$-naphthyl, —CH$_2$CH$_2$-naphthyl, etc.).

In one embodiment, Z is one or more substituents independently selected from the group consisting of alkyl (e.g., (C$_1$-C$_6$)alkyl such as methyl, ethyl, n-propyl, i-propyl, n-butyl, sec-butyl, i-butyl, t-butyl, n-pentyl, n-hexyl, etc.), alkyl substituted with one or more —OH (e.g., (C$_1$-C$_6$)alkyl substituted with 1, 2 or 3 —OH groups, such as —CH$_2$—OH, —CH$_2$CH$_2$—OH, —CH(OH)CH$_2$—OH, etc.), aryl (e.g., (C$_6$-C$_{12}$)aryl such as phenyl, naphthyl, biphenyl, etc.), -alkylene-aryl (e.g., —(C$_2$-C$_6$)alkylene-(C$_6$-C$_{12}$)aryl such as —CH$_2$-phenyl, —CH$_2$CH$_2$-phenyl, —CH$_2$-naphthyl, —CH$_2$CH$_2$-naphthyl, etc.), alkylene-O-alkyl (e.g., —(C$_2$-C$_6$)alkylene-O—(C$_1$-C$_6$)alkyl such as —CH$_2$—O—CH$_3$, —CH$_2$—O—CH$_2$CH$_3$, —CH$_2$—O—CH(CH$_3$)$_2$, —CH$_2$—O—CH$_2$CH$_2$CH$_3$, —CH$_2$—O—CH$_2$CH$_2$CH$_2$CH$_3$, —CH$_2$—O—CH(CH$_3$)CH$_2$CH$_3$, —CH$_2$—O—C(CH$_3$)$_3$, —CH$_2$CH$_2$—O—CH$_3$, —CH$_2$CH$_2$—O—CH$_2$CH$_3$, —CH$_2$CH$_2$—CH(CH$_3$)$_2$, —CH$_2$CH$_2$—O—CH$_2$CH$_2$CH$_3$, —CH$_2$CH$_2$—O—CH$_2$CH$_2$CH$_2$CH$_3$, —CH$_2$CH$_2$—O—CH(CH$_3$)CH$_2$CH$_3$, —CH$_2$CH$_2$—O—C(CH$_3$)$_3$, etc.), alkylene-O-alkylene-aryl (e.g., —(C$_2$-C$_6$)alkylene-O—(C$_2$-C$_6$)alkylene-(C$_6$-C$_{12}$)aryl such as —CH$_2$—O—CH$_2$-phenyl, —CH$_2$CH$_2$—OCH$_2$-phenyl, —CH$_2$—OCH$_2$CH$_2$-phenyl, —CH$_2$—O—CH$_2$-naphthyl, —CH$_2$CH$_2$—OCH$_2$-naphthyl, —CH$_2$—OCH$_2$CH$_2$-naphthyl etc.), alkylene-O-aryl (e.g., —(C$_2$-C$_6$)alkylene-O—(C$_6$-C$_{12}$)aryl such as —CH$_2$—O-phenyl, —CH$_2$CH$_2$—O-phenyl, —CH$_2$—O-naphthyl, —CH$_2$CH$_2$—O-naphthyl, etc.), —CN, haloalkyl (e.g., (C$_1$-C$_6$)haloalkyl such as —CF$_3$, —CF$_2$H, —CH$_2$F, —CH$_2$CF$_3$, etc.), —C(O)—N(R$^8$)$_2$, —S(O$_2$)—N(R$^8$)$_2$, alkylene-N(R$^8$)—C(O)—R$^8$ (e.g., —(C$_2$-C$_6$)alkylene-N(R$^8$)—C(O)—R$^8$ such as —CH$_2$—N(R$^8$)—C(O)—R$^8$, —CH$_2$CH$_2$—N(R$^8$)—C(O)—R$^8$, etc.), alkylene-S(O$_2$)—R$^8$ (e.g., —(C$_2$-C$_6$) alkylene-S(O$_2$)—R$^8$ such as —CH$_2$—S(O$_2$)—R$^8$, —CH$_2$CH$_2$—S(O$_2$)—R$^8$, etc.), cycloalkyl (e.g., (C$_3$-C$_6$)cycloalkyl such as cyclopropyl, cyclobutyl, cyclopentyl, cyclohexyl, etc.), heterocyclyl (e.g., (C$_2$-C$_{10}$)heterocyclyl such as morpholinyl, piperazinyl, piperidinyl, pyrrolidinyl, pyrrolidin-2-onyl, tetrahydrofuranyl, tetrahydrothiophenyl, azetidinyl, etc.), alkylene-heterocyclyl (e.g., —(C$_2$-C$_6$)alkylene-(C$_2$-C$_{10}$)heterocyclyl such as —CH$_2$-morpholinyl, —CH$_2$-piperazinyl, —CH$_2$-piperidinyl, —CH$_2$-pyrrolidinyl, —CH$_2$-pyrrolidin-2-onyl, —CH$_2$-tetrahydrofuranyl, —CH$_2$-tetrahydrothiophenyl, —CH$_2$-azetidinyl, —CH$_2$CH$_2$-morpholinyl, —CH$_2$CH$_2$-piperazinyl, —CH$_2$CH$_2$-piperidinyl, —CH$_2$CH$_2$-pyrrolidinyl, —CH$_2$CH$_2$-pyrrolidin-2-onyl, —CH$_2$CH$_2$-tetrahydrofuranyl, —CH$_2$CH$_2$-tetrahydrothiophenyl, —CH$_2$CH$_2$-azetidinyl, etc.), heteroaryl (e.g., (C$_2$-C$_{10}$)heteroaryl such as azaindolyl, benzimidazolyl, benzofuranyl, benzothiophenyl, cinnolinyl, furanyl, furazanyl, indolyl, pyridyl, isoquinolyl, pyrazinyl, pyridazinyl, pyrimidinyl, pyrrolyl, quinolinyl, thiophenyl, isoxazolyl, triazolyl, thiazolyl, etc.), and alkylene-heteroaryl (e.g., —(C$_2$-C$_6$)alkylene-(C$_2$-C$_{10}$)heteroaryl such as —CH$_2$-azaindolyl, —CH$_2$-benzimidazolyl, —CH$_2$-benzofuranyl, —CH$_2$-benzothiophenyl, —CH$_2$-cinnolinyl, —CH$_2$-furanyl, —CH$_2$-furazanyl, —CH$_2$-indolyl, —CH$_2$-pyridyl, —CH$_2$-isoquinolyl, —CH$_2$-pyrazinyl, —CH$_2$-pyridazinyl, —CH$_2$-pyrimidinyl, —CH$_2$-pyrrolyl, —CH$_2$-quinolinyl, —CH$_2$-thiophenyl, —CH$_2$-isoxazolyl, —CH$_2$-triazolyl, —CH$_2$-thiazolyl, —CH$_2$CH$_2$-azaindolyl, —CH$_2$CH$_2$-benzimidazolyl, —CH$_2$CH$_2$-benzofuranyl, —CH$_2$CH$_2$-benzothiophenyl, —CH$_2$CH$_2$-cinnolinyl, —CH$_2$CH$_2$-furanyl, —CH$_2$CH$_2$-furazanyl, —CH$_2$CH$_2$-indolyl, —CH$_2$CH$_2$-pyridyl, —CH$_2$CH$_2$-isoquinolyl, —CH$_2$CH$_2$-pyrazinyl, —CH$_2$CH$_2$-pyridazinyl, —CH$_2$CH$_2$-pyrimidinyl, —CH$_2$CH$_2$-pyrrolyl, —CH$_2$CH$_2$-quinolinyl, —CH$_2$CH$_2$-thiophenyl, —CH$_2$CH$_2$-isoxazolyl, —CH$_2$CH$_2$-triazolyl, —CH$_2$CH$_2$-thiazolyl, etc.).

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O) O-alkyl. Non-limiting examples of suitable alkyl groups include methyl, ethyl, n-propyl, isopropyl and t-butyl.

"Alkylene" means a difunctional group obtained by removal of a hydrogen atom from an alkyl group that is defined above. Non-limiting examples of alkylene include methylene, ethylene and propylene.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkenylene" means a difunctional group obtained by removal of a hydrogen from an alkenyl group that is defined above. Non-limiting examples of alkenylene include —CH=CH—, —C(CH$_3$)=CH—, and —CH=CHCH$_2$—.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Alkynylene" means a difunctional group obtained by removal of a hydrogen from an alkynyl group that is defined above. Non-limiting examples of alkenylene include —C≡C— and —CH$_2$C≡C—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl, indazolyl, and the like, in which there is at least one aromatic ring.

"Aralkyl", "arylalkyl", or "-alkylene-aryl" means an arylalkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkylene" means a difunctional group obtained by removal of a hydrogen atom from a cycloalkyl group that is defined above. Non-limiting examples of cycloalkylene include

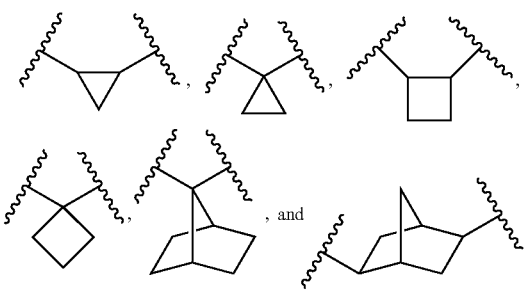

"Halogen" or "halo" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

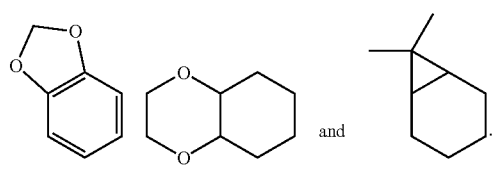

"Ring system substituent" also includes substituents off of an heterocyclyl ring, wherein said substituents on adjacent carbon atoms, on a carbon atom and an adjacent heteroatom, or on a single carbon atom, together with the carbon atom(s) and/or the combination of the carbon atom and the adjacent heteroatom to which said substituents are attached, form a four to seven-membered cycloalkyl, cycloalkenyl, heterocyclyl, aryl or heteroaryl ring. Non-limiting examples of such ring-system substituent together with the heterocyclyl ring from which the substituents are derived include:

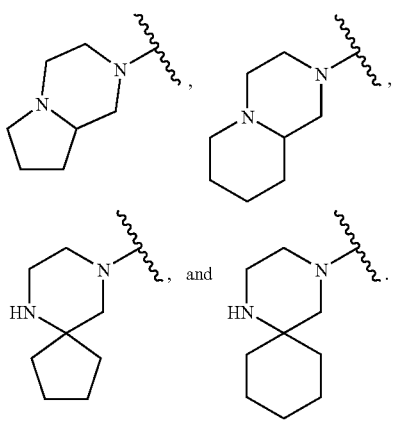

"Heterocyclyl" means a monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Heterocyclyls may be completely saturated, partially unsaturated, or aromatic. Aromatic heterocyclyls are termed "heteroaryl", as defined above. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include saturated heterocyclyls, for example piperidyl, pyrrolidinyl, piperazinyl, morpholinyl, thiomorpholinyl, thiazolidinyl, 1,4-dioxanyl, tetrahydrofuranyl, tetrahydrothiophenyl, lactams, lactones, and the like. Non-limiting examples of partially unsaturated monocyclic heterocyclyl rings include, for example, thiazolinyl, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

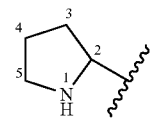

there is no —OH attached directly to carbons marked 2 and 5.

It should also be noted that tautomeric forms such as, for example, the moieties:

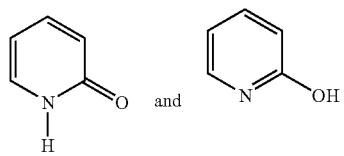

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the diseases or conditions noted below, and thus producing the desired therapeutic, ameliorative, inhibitory or preventative effect.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, ($C_1$-$C_4$)alkyl, or ($C_1$-$C_4$)alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a ($C_1$-$C_{20}$) alcohol or reactive derivative thereof, or by a 2,3-di-($C_6$-$C_{24}$)acyl glycerol.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Compounds of Formula I, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prod rug of enantiomers, stereoisomers, rotamers, tautomers, positional isomers, racemates or prodrugs of the inventive compounds.

Polymorphic forms of the compounds of Formula I, and of the salts, solvates, esters and prodrugs of the compounds of Formula I, are intended to be included in the present invention.

The compounds of Formula (I), or pharmaceutically acceptable salts, solvates, or esters thereof according to the invention have pharmacological properties; in particular, the compounds of Formula I can be kinase inhibitors, including but not limited to inhibitors of tyrosine protein kinases, inhibitors of serine/threonine protein kinases, and inhibitors of dual specific protein kinases.

The compounds of Formula (I) of the present invention, or pharmaceutically acceptable salts, solvates, or esters thereof are useful in treating diseases or conditions including immunodeficiencies, cancers, cardiovascular diseases and endocrine disorders, such as Parkinson's disease, metabolic diseases, tumorigenesis, Alzheimer's disease, heart disease, diabetes, neurodegeneration, proliferative disorders, inflammation, kidney disease, atherosclerosis and airway disease, particularly cancers and proliferative disorders.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The compounds of Formula (I), or pharmaceutically acceptable salts, solvates, or esters thereof, can be administered in any suitable form, e.g., alone, or in combination with a pharmaceutically acceptable carrier, excipient or diluent in a pharmaceutical composition, according to standard pharmaceutical practice. The compounds of Formula (I), or pharmaceutically acceptable salts, solvates, or esters thereof, can be administered orally or parenterally, including intravenous, intramuscular, interperitoneal, subcutaneous, rectal, or topical routes of administration.

Pharmaceutical compositions comprising at least one compound of Formula I, or a pharmaceutically acceptable salt, solvate, or ester thereof can be in a form suitable for oral administration, e.g., as tablets, troches, capsules, lozenges, aqueous or oily suspensions, dispersible powders or granules, emulsions, syrups, or elixirs. Oral compositions may be prepared by any conventional pharmaceutical method, and may also contain sweetening agents, flavoring agents, coloring agents, and preserving agents.

The amount of compound of Formula I, or a pharmaceutically acceptable salt, solvate, or ester thereof, administered to a patient can be determined by a physician based on the age, weight, and response of the patient, as well as by the severity of the condition treated. For example, the amount of compound of Formula I, or a pharmaceutically acceptable salt, solvate, or ester thereof, administered to the patient can range from about 0.1 mg/kg body weight per day to about 60 mg/kg/d, preferably about 0.5 mg/kg/d to about 40 mg/kg/d.

The compounds of Formula I, or pharmaceutically acceptable salts, solvates, or esters thereof, can also be administered in combination with other therapeutic agents. For example one or more compounds of Formula I, or pharmaceutically acceptable salts, solvates, or esters thereof, can be administered with one or more additional active ingredients selected from the group consisting of a second kinase inhibitor, an estrogen receptor modulator, an androgen receptor modulator, a retinoid receptor modulator, a cyclotoxic agent, a prenyl-protein transferase inhibitor, an HMG-CoA reductase inhibitor, an HIV protease inhibitor, a reverse transcriptase inhibitor, an angiogenesis inhibitor, an inhibitor of inherent multidrug resistance, an anti-emetic agent, an agent useful in the treatment of anemia, an agent useful in the treatment of neutropenia, and an immunologic-enhancing drug. Examples of such additional active ingredients may be found in *Cancer Princilles and Practice of Oncology*, V. T. Devita and S. Hellman (Eds.), 6$^{th}$ Ed. (Feb. 15, 2001), Lippincott Williams & Wilkins, Publ.

"Estrogen-receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include but are not limited to finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include but are not limited to bexarotene, tretinoin, 13-cis-retinoic acid, 9-cis-retinoic acid, α-difluoromethylornithine, ILX23-7553,trans-N-(4'-hydroxyphenyl) retinamide, and N-4-carboxyphenylretinarnide.

"Cytotoxic/cytostatic agents" refer to compounds which cause cell death or inhibit cell proliferation primarily by interfering directly with the cell's functioning or inhibit or interfere with cell myosis, including but not limited to alkylating agents, tumor necrosis factors, intercalators, hypoxia activatable compounds, microtubule inhibitors/microtubule-stabilizing agents, inhibitors of mitotic kinesins, anti-metabolites; biological response modifiers; hormonal/anti-hormonal therapeutic agents, haematopoietic growth factors, monoclonal antibody targeted therapeutic agents and topoisomerase inhibitors. Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro (2-methyl-pyridine) platinum, benzylguanine, glufosfamide, GPX100, (trans,trans,trans)-bis-mu-(hexane-1,6-diamine)-mu-[diamine-platinum(H)]bis[diamine(chloro) platinum(II)] tetrachloride, diarizidinylspermine, arsenic trioxide, 1(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

Antiproliferative agents" include but are not limited to antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl) urea, N6-[4-deoxy-4-[N2-[2(E),4(E)-tetradecadienoyl] glycylamino]-L-glycero-B-L-manno-heptopyranosyl] adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo (7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabinofuranosyl cytosine, 3-aminopyridine-2-carboxaldehydethiosemicarbazone and trastuzumab.

"Prenyl-protein transferase inhibitor" refers to a compound which inhibits any one or any combination of the prenyl-protein transferase enzymes, including but not limited to farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (+)-6-[amino(4-chlorophenyl)(1-methyl-1H-imidazol-5-yl)methyl]-4-(3-chlorophenyl)-1-methyl-2(1H)-quinolinone, (−)-6-[amino(4-chlorophenyl)(1-methyl-(1H)-imidazol-5-yl)methyl]-4-(3-chlorophenyl)-1-methyl-2(1H )-quinolinone, (+)-6-[amino(4-chlorophenyl)(1-methyl-1H-imidazol-5-yl)methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl]-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-15-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-oxo-2H-[1,2']bipyridin-6,10-metheno-22H-benzo[d]imidazo[4,3-k][1,6,9,12] oxatriaza-cyclooctadecine-9-carbonitrile, 19,20-dihydro-19-oxo-5H,17H-18,21-ethano-6,10:12,16-dimetheno-22H-imidazo[3,4-h][1,8,11,14]oxatriazacycloeicosine-9-carbonitrile, and ( )-19,20-dihydro-3-methyl-19-oxo-5H-18,21-ethano-12,14-etheno-6,10-metheno-22H-benzo[d] imidazo[4,3-k][1,6,9,12]oxa-triazacyclooctadecine-9-carbonitrile. Other examples of prenyl-protein transferase inhibitors can be found in the following publications and patents: WO 96/30343, WO 97/18813, WO 97/21701, WO 97/23478, WO97/38665, WO98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO95/25086, WO96/05529, WO 96/06138, WO 96/06193, WO 96/16443, WO96/21701, WO 96/21456, WO96/22278, WO 96/24611, WO 96/24612, WO 96/05168, WO 96/05169, WO 96/00736, U.S. Pat. No. 5,571,792, WO 96/17861, WO96/33159, WO96/34850, WO 96/34851, WO 96/30017, WO 96/30018, WO 96/30362, WO 96/30363, WO 96/31111, WO 96/31477, WO 96/31478, WO 96/31501, WO 97/00252, WO97/03047, WO97/03050, WO97/04785, WO97/02920, WO97/17070, WO97/23478, WO97/26246, WO97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein. Examples of HMG-CoA reductase inhibitors that may be used include but are not limited to lovastatin (MEVACOR®); see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of this invention. In HMG-CoA reductase inhibitors where an open-acid form can exist, salt and ester forms may preferably be formed from the open-acid and all such forms are included within the meaning of the term "HMG-CoA reductase inhibitor".

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-I/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105: 141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186). Other therapeutic agents that modulate or inhibit angiogenesis and may also be used in combination with the compounds of the instant invention include agents that modulate or inhibit the coagulation and fibrinolysis systems (see review in Clin. Chem. La. Med. 38: 679-692 (2000)). Examples of such agents that modulate or inhibit the coagulation and fibrinolysis pathways include, but are not limited to, heparin (see Thromb. Haemost. 80:10-23 (1998)), low molecular weight heparin and carboxypeptidase U inhibitors (also known as inhibitors of active thrombin activatable fibrinolysis inhibitor [TAFIa]) (see Thrombosis Res.

101: 329-354 (2001)). TAFIa inhibitors have been described in U.S. Ser. Nos. 60/310,927 (filed Aug. 8, 2001) and 60/349,925 (filed Jan. 18, 2002).

An "inhibitor of inherent multidrug resistance" (MDR), in particular MDR associated with high levels of expression of transporter proteins. Can include, for example, inhibitors of p-glycoprotein (P-gp), such as $LY_{335979}$, XR9576, OC144-093, R101922, VX853 and PSC833 (valspodar).

"Anti-emetic agents" may include, for example, neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an anti-dopaminergic, such as the phenothiazines (for example prochlorperazine, fluphenazine, thioridazine and mesoridazine), metoclopramide or dronabinol.

"Anemia treatment agents" include, for example, a continuous eythropoiesis receptor activator (such as epoetin alfa).

An "agent useful in the treatment of neutropenia" can include, for example, a hematopoietic growth factor which regulates the production and function of neutrophils such as a human granulocyte colony stimulating factor, (G-CSF). Examples of a G-CSF include filgrastim.

An "immunologic-enhancing drug" can include, for example, levamisole, isoprinosine and Zadaxin.

The compounds of this invention may also be useful in combination (administered together or sequentially) with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaeuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine.

EXAMPLES

Experimental

GENERAL SYNTHESIS OF [1,2,4]TRIAZINE COMPOUNDS

The compounds of Formula I can be prepared by the general method of Scheme 1, below, in which a carboximidic acid hydrazide 131 is treated with a ketoester (or thioketoester) 132 to provide a [1,2,4]triazin-5-one 133. The [1,2,4]triazin-5-one 133 can then be converted, e.g., by treatment with thionyl chloride, to a 5-chloro[1,2,4]triazine 134. The 5-chloro[1,2,4]triazine 134 can then be converted to other functionalized triazines, e.g., by treatment with an amine (primary, secondary or cyclic amine), to a [1,2,4]triazine 135. The group $R^b$ in Scheme 1 may also be further reacted or functionalized to provide a compound of Formula (I). For example, when $R^b$ is H, intermediate 133 may be di-chlorinated to provide intermediate 134 where $R^b$ is —Cl, which can then be further derivatized at the 6-position of the [1,2,4] triazine ring.

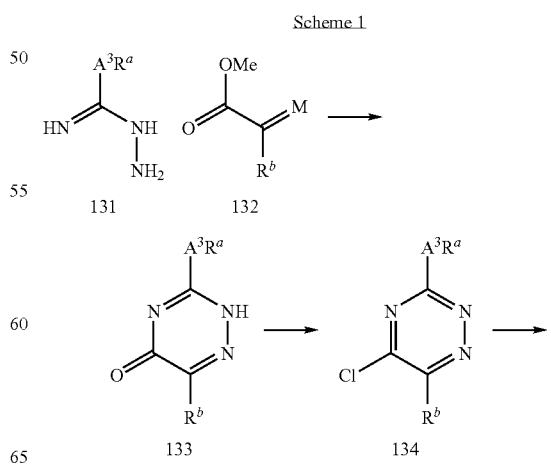

-continued

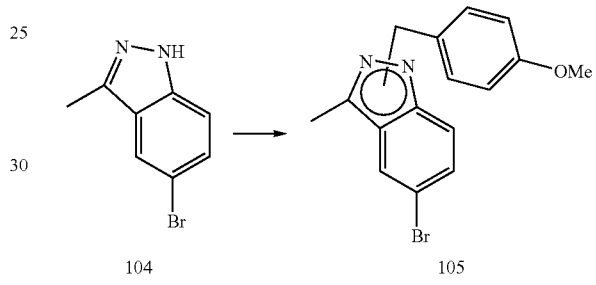

135

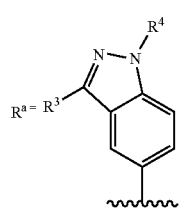

$R^b$ = H, -NH$_2$, alkyl, aryl, -C(O)-alkyl, -C(O)-aryl, etc.
M = O, S

The general procedure of Scheme 1 is further exemplified below.

Preparation of 5-bromo-3-methyl-1H-indazole 104

Scheme 2

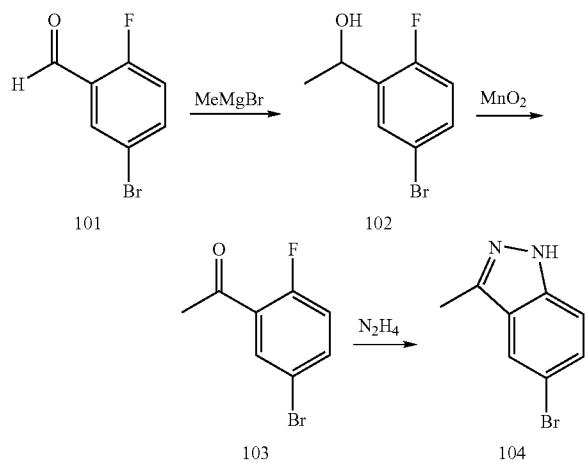

To a solution of 5-bromo-2-fluorobenzaldehyde 101 (100 g, 0.492 mol.) in ether (500 mL), cooled in an ice bath, was added a 3 M solution of methyl magnesium bromide in ether (i.e., diethyl ether) (173 mL, 0.516 mol.) in a dropwise manner. The reaction mixture was stirred for 30 minutes in the ice bath. The reaction mixture was allowed to warm to room temperature and was stirred for 15 minutes. The reaction mixture was cooled in an ice bath and the reaction was quenched by addition of water in a dropwise manner. The reaction mixture was acidified with dilute hydrochloric acid. The organic layer was separated. The aqueous layer was extracted with ether for two times. The combined organic layer was dried over magnesium sulfate and evaporated under reduced pressure to afford 1-(5-bromo-2-fluoro-phenyl)-ethanol 102 (106 g, 0.484 mol.) which was used in the next step without further purification.

To a solution of 1-(5-bromo-2-fluoro-phenyl)-ethanol 102 (105 g, 0.479 mol.) in dioxane (2 L) was added manganese dioxide (203 g, 2.35 mol.). The reaction mixture was heated under reflux for 5 hours. The reaction mixture was allowed to cool to room temperature. The reaction mixture was filtered through Celite (i.e., diatomaceous earth) and the solid was washed with ether (1 L). The combined filtrate was evaporated under reduced pressure to afford the 1-(5-bromo-2-fluoro-phenyl)-ethanone 103 (95.7 g, 0.441 mol.) which was used in the next step without further purification.

To 1-(5-bromo-2-fluoro-phenyl)-ethanone 103 (95.7 g, 0.441 mol.) was added anhydrous hydrazine (240 mL, 7.65 mol.). The reaction mixture was heated under reflux for 10 hours. The reaction mixture was allowed to cool to room temperature and was stirred for 16 hours. The reaction mixture was added to ice (1.4 L). The reaction mixture was stirred for 30 minutes. The reaction mixture was filtered and the white solid product was washed with water. The white solid was dried in a vacuum oven to afford the desired 5-bromo-3-methyl-1H-indazole 104 (86.1 g, 0.408 mol.) which was used without further purification.

Preparation of
5-bromo-N-(4-methoxybenzyl)-3-methylindazole
105

Scheme 3

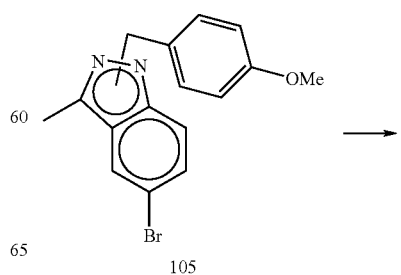

To a solution of 5-bromo-3-methylindazole 104 (0.2 g, 0.948 mmol) in anhydrous THF (3 mL), cooled in ice bath, was added potassium t-butoxide (0.127 g, 1.13 mmol) and 4-methoxybenzyl chloride (0.14 mL, 1.04 mmol). The reaction mixture was allowed to warmed to room temperature and was stirred for 16 hours. Ethyl acetate (100 mL) was added and the organic layer was washed with saturated ammonium chloride solution, water and brine. The organic layer was dried over sodium sulfate. The organic solvent was evaporated under reduced pressure. The crude product was purified by flash column chromatography to yield the desired 5-bromo-N-(4-methoxybenzyl)-3-methylindazole 105 (0.29 g, 0.932 mmol) as a mixture of the 1H- and 2H-indazole regioisomers.

Preparation of
5-cyano-N-(4-methoxybenzyl)-3-methylindazole 106

Scheme 4

-continued

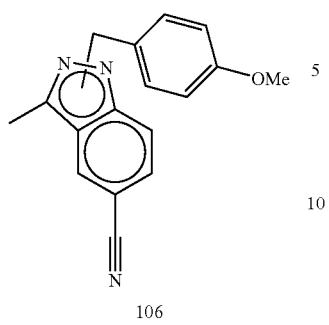

106

To a solution of 5-bromo-N-(4-methoxybenzyl)-3-methylindazole 105 (0.12 g, 0.363 mmol) in NMP (N-methylpyrrolidinone; 2 mL) was added sodium cyanide (0.035 g, 0.714 mmol) and nickel bromide (0.079 g, 0.362 mmol). The reaction mixture was heated in a microwave reactor at 180° C. for 20 minutes. Ethyl acetate (100 mL) was added and the organic layer was washer with water and brine. The organic layer was dried over sodium sulfate. The organic solvent was evaporated under reduced pressure. The crude product was purified by flash column chromatography to yield the desired 5-cyano-N-(4-methoxybenzyl)-3-methylindazole 106 (0.1 g, 0.361 mmol).

Preparation of 6-amino-3-[N-(4-methoxy-benzyl)-3-methylindazol-5-yl]-[1,2,4]triazin-5-one 109

Scheme 5

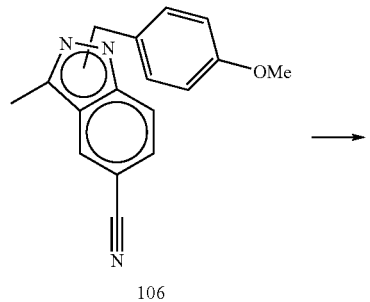

106

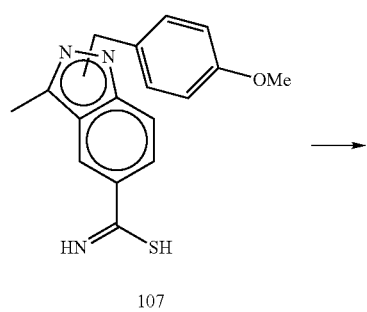

107

-continued

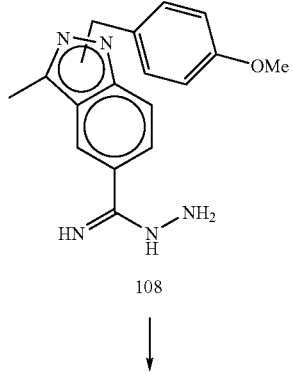

108

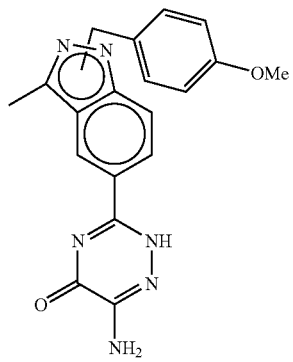

109

To a solution of 5-cyano-N-(4-methoxybenzyl)-3-methylindazole 106 (0.25 g, 0.903 mmol) in 10% v/v triethylamine-pyridine (10 mL) was bubbled hydrogen sulfide gas for 10 minutes. The reaction mixture was stirred at room temperature for 16 hours. Ethyl acetate (100 mL) was added and the organic layer was washed with water, 1% aqueous citric acid and brine. The organic layer was dried over sodium sulfate. The organic solvent was evaporated under reduced pressure to yield N-(4-methoxybenzyl)-3-methylindazole-5-carboximidothioic acid 107 which was used in the next step without further purification.

To a solution of 107 (~0.903 mmol) in ethanol (10 mL) was added hydrazine hydrate (1 mL). The organic solvent was evaporated under reduced pressure. The residue was dissolved in dichloromethane. The organic layer was washed with water and brine. The organic layer was dried over sodium sulfate. The organic solvent was evaporated under reduced pressure to yield N-(4-methoxybenzyl)-3-methylindazole-5-carboximidic acid hydrazide 108 (0.23 g, 0.744 mmol) which was used in the next step without further purification.

To a solution of 108 (0.23 g, 0.744 mmol) in ethanol (6 mL) was added ethyl thiooxamate (0.1 g, 0.84 mmol). The reaction mixture was heated at 77° C. for 5 hours. The reaction mixture was allowed to cool to room temperature and the solid product was filtered and washed with dichloromethane to yield the desired 6-amino-3-[N-(4-methoxy-benzyl)-3-methylindazol-5-yl]-[1,2,4]triazin-5-one 109 (0.126 g, 0.348 mmol) which was used in the next step without further purification.

GENERAL PROCEDURE FOR THE PREPARATION OF 5-SUBSTITUTED 6-AMINO-3-[N-(4-METHOXYBENZYL)-3-METHYLINDAZOL-5-YL]-[1,2,4]TRIAZINE

Preparation of 6-amino-3-[N-(4-methoxybenzyl)-3-methylindazol-5-yl]-5-(4-Boc-piperazin-1-yl)-[1,2,4]triazine 111

Scheme 6

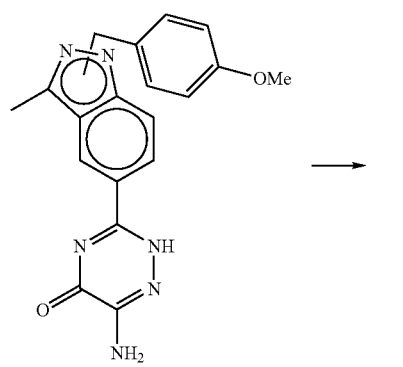
109

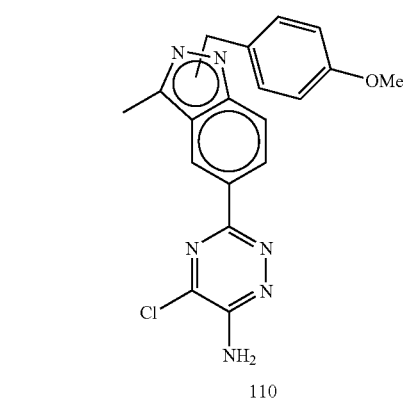
110

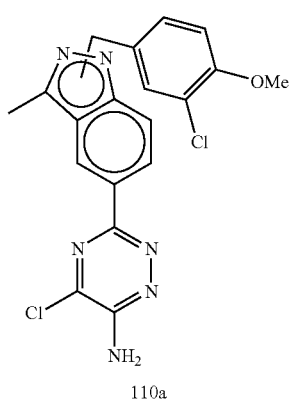
110a

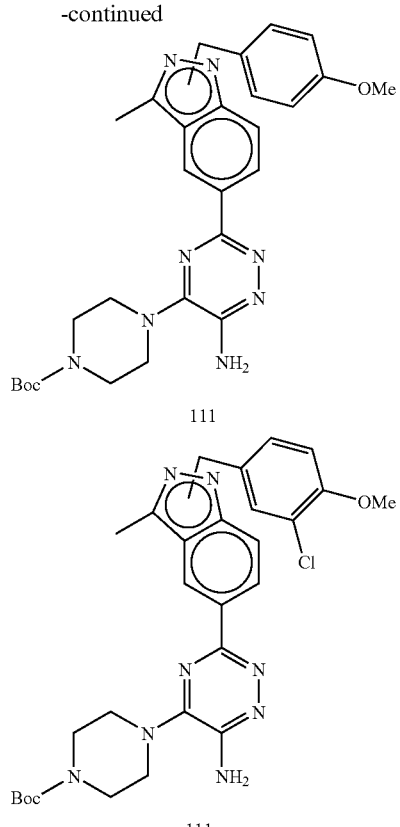
111

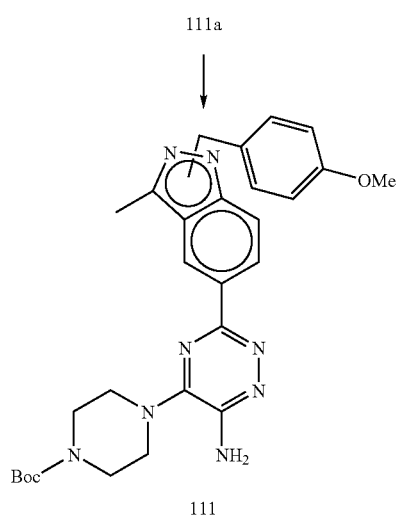
111a

↓

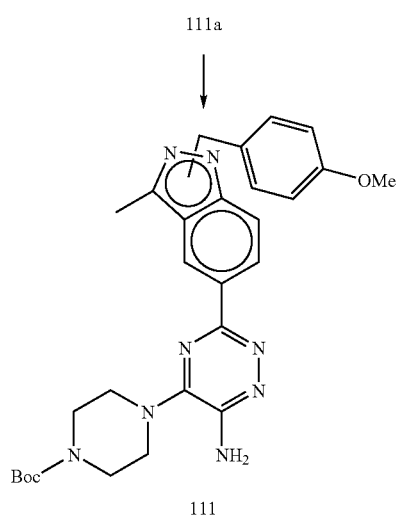
111

To thionyl chloride (12 mL), heated at 78° C., was added 6-amino-3-[N-(4-methoxy-benzyl)-3-methylindazol-5-yl]-[1,2,4]triazin-5-one 109 (0.08 g, 0.221 mmol) in small portions over 5 minutes. The reaction mixture was heated at 78° C. for 2 hours. The thionyl chloride was evaporated under reduced pressure. Anhydrous dichloromethane (20 mL) was added. The organic solvent was evaporated under reduced pressure to yield a mixture of the monochloride 110 and dichloride 110a which was used in the next step without further purification.

To a solution of 110 and 110a (~0.221 mmol) in dioxane (2 mL) and trifluoromethylbenzene (4 mL) was added N—Boc-piperazine (0.045 g, 0.242 mmol) and diisopropylethylamine (0.045 mL). The reaction mixture was heated in a microwave reactor at 140° C. for 40 minutes. The organic solvent was evaporated under reduced pressure. The crude product was purified by RP-HPLC to yield a mixture of 111 and 111a (0.05 g, ~0.09 mmol).

To a solution of 111 and 111a (0.04 g, ~0.073 mmol) in ethanol (5 mL) was added Pearlman's catalyst (palladium hydroxide, available from Aldrich) (0.03 g) and ammonium formate (0.017 g, 0.274 mmol). The reaction mixture was heated in a microwave reactor at 120° C. for 25 minutes. The reaction mixture was filtered through Celite. The filtrate was evaporated under reduced pressure to yield the desired 6-amino-3-[N-(4-methoxybenzyl)-3-methylindazol-5-yl]-5-(4-Boc-piperazin-1-yl)-[1,2,4]triazine 11 (0.03 g, 0.0566 mmol) which was used in the next step without further purification.

GENERAL PROCEDURE FOR THE DEPROTECTION OF N-(4-METHOXYBENZYL)INDAZOLES

Preparation of 6-amino-3-(3-methylindazol-5-yl)-5-(piperazin-1-yl)-[1,2,4]triazine 1

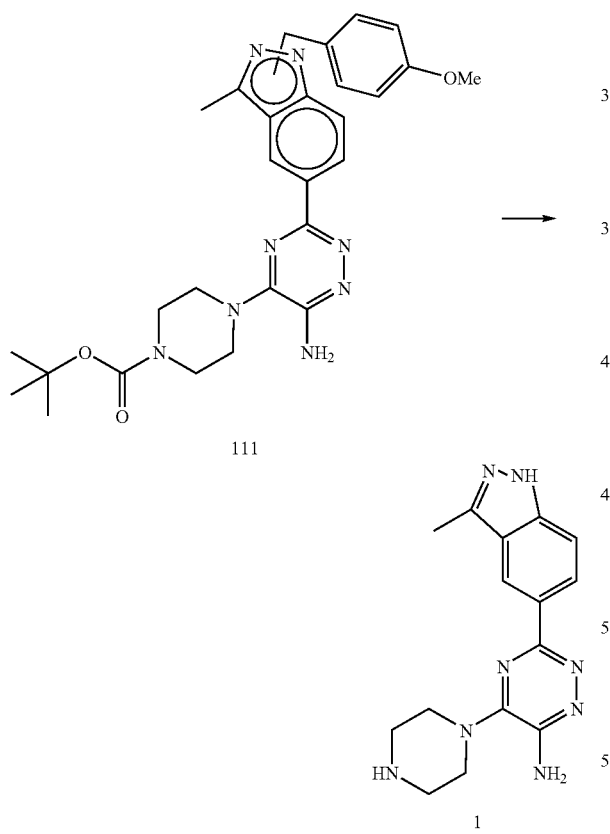

A solution of 6-amino-3-[N-(4-methoxybenzyl)-3-methylindazol-5-yl]-5-(4-Boc-piperazin-1-yl)-[1,2,4]triazine 111 (0.016 g, 0.0302 mmol) in trifluoroacetic acid (2.5 mL) was heated in a microwave reactor at 120° C. for 40 minutes. The organic solvent was evaporated under reduced pressure. Methanol (1 mL) and dichloromethane (9 mL) were added. The organic solvent was evaporated under reduced pressure. The crude product was purified by RP-HPLC to yield the desired 6-amino-3-(3-methylindazol-5-yl)-5-(piperazin-1-yl)-[1,2,4]triazine 1 (0.008 g, 0.0259 mmol).

GENERAL PROCEDURE FOR THE BENZYLATION OF 6-AMINO-3-[N-(4-METHOXYBENZYL)-3-METHYLINDAZOL-5-YL]-[1,2,4]TRIAZINE

Preparation of 6-benzylamino-3-[N-(4-methoxybenzyl)-3-methylindazol-5-yl]-5-(4-Boc-piperazin-1-yl)-[1,2,4]triazine 114

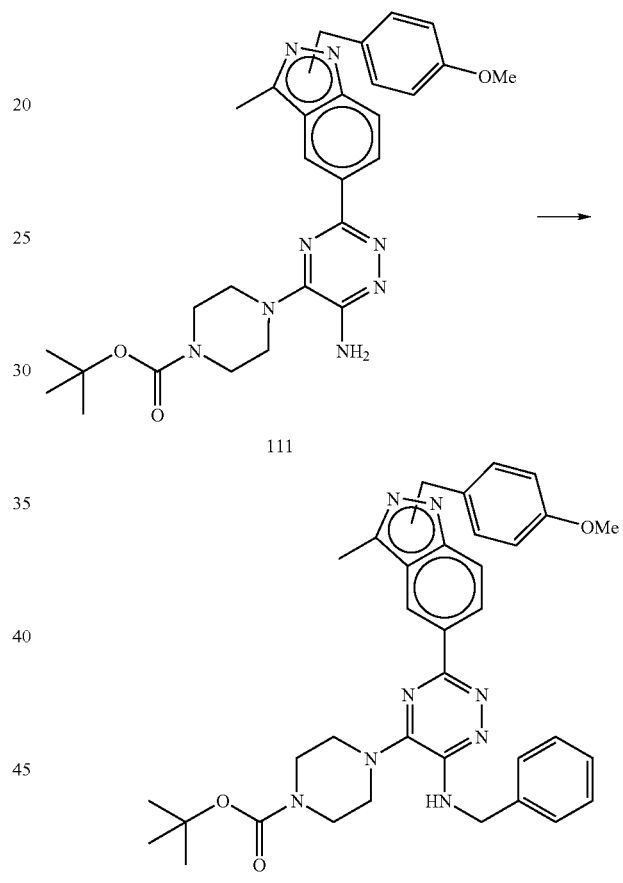

To a solution of 6-amino-3-[N-(4-methoxybenzyl)-3-methylindazol-5-yl]-5-(4-Boc-piperazin-1-yl)-[1,2,4]triazine 111 (0.04 g, 0.0755 mmol) in anhydrous THF (2 mL), cooled at −78° C., was added a 1.0 M solution of lithium bis(trimethylsilyl)amide (0.083 mL) and benzyl bromide (0.001 mL dissolved in 0.1 mL THF). The reaction mixture was allowed to warm to room temperature. The reaction mixture was heated at 70° C. for 3 hours. Dichloromethane (50 mL) was added. The organic layer was washed with 1% citric acid, water and brine. The organic layer was dried over sodium sulfate. The organic solvent was evaporated under reduced pressure. The crude product was purified by RP-HPLC to yield the desired 6-benzylamino-3-[N-(4-methoxybenzyl)-3-methylindazol-5-yl]-5-(4-Boc-piperazin-1-yl)-[1,2,4]triazine 114 (0.027 g, 0.0435 mmol).

Preparation of 5-bromo-3-methyl-N-(2-trimethylsilanylethoxymethyl)indazole 116

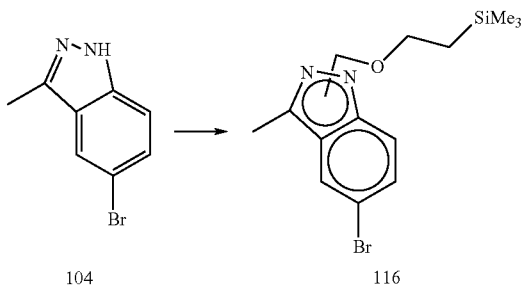

Scheme 9

To a solution of 5-bromo-3-methylindazole 104 (2 g, 9.48 mmol) in anhydrous DMF (20 mL), cooled in ice bath, was added sodium hydride (60% w/w, 0.57 g, 14.25 mmol) and (2-trimethylsilylethoxy)methyl chloride (2.5 mL, 14.16 mmol) in a dropwise manner. The reaction mixture was allowed to warm to room temperature and was stirred for 1 hour. Ethyl acetate (200 mL) was added. The organic layer was washed with saturated ammonium chloride solution, water and brine. The organic layer was dried over sodium sulfate. The organic solvent was evaporated under reduced pressure. The crude product was purified by flash column chromatography to yield the desired 5-bromo-3-methyl-N-(2-trimethylsilanylethoxymethyl)indazole 116 (2.95 g, 8.65 mmol) as a mixture of the 1H- and 2H-indazole regioisomers.

Preparation of 5-cyano-3-methyl-N-(2-trimethylsilanylethoxymethyl)indazole 117

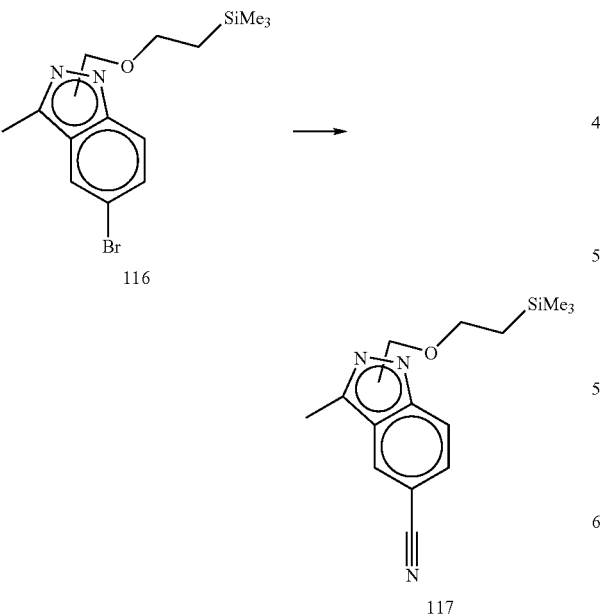

Scheme 10

To a solution of 5-bromo-3-methyl-N-(2-trimethylsilanylethoxymethyl)indazole 116 (0.5 g, 1.466 mmol) in NMP (10 mL) was added nickel bromide (0.321 g, 1.469 mmol) and sodium cyanide (0.144 g, 2.939 mmol). The reaction mixture was heated in a microwave reactor at 180° C. for 30 minutes. Ethyl acetate (100 mL) was added. The organic layer was washed with water and brine. The organic layer was dried over sodium sulfate. The organic solvent was evaporated under reduced pressure. The crude product was purified by flash column chromatography to yield the desired 5-cyano-3-methyl-N-(2-trimethylsilanylethoxymethyl)indazole 117. (0.36 g, 1.254 mmol).

Preparation of 3-[3-methyl-N-(2-trimethylsilanylethoxymethyl)indazol-5-yl]-[1,2,4]triazin-5-one 121

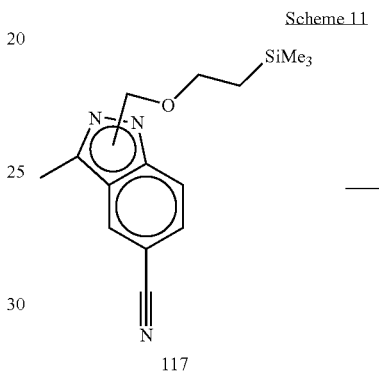

Scheme 11

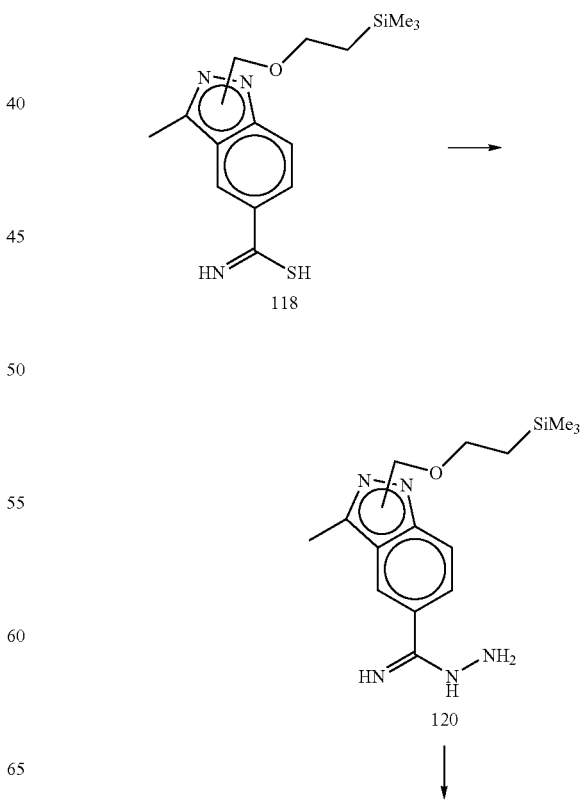

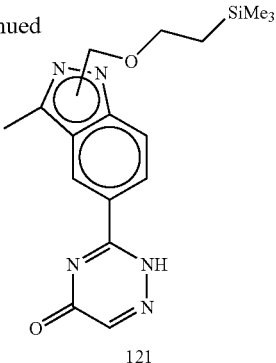

121

To a solution of 5-cyano-3-methyl-N-(2-trimethylsilanylethoxymethyl)indazole 117 (0.36 g, 1.254 mmol) in triethylamine (2 mL) and pyridine (18 mL) was bubbled hydrogen sulfide for 5 minutes. The reaction mixture was stirred at room temperature for 16 hours. Ethyl acetate (200 mL) was added. The organic layer was washed with water, 1% citric acid, water and brine. The organic layer was dried over sodium sulfate. The organic solvent was evaporated under reduced pressure to yield 3-methyl-N-(2-trimethylsilanylethoxymethyl)indazole-5-carboximidothioic acid 118 which was used in the next step without further purification.

To a solution of 118 (~1.25 mmol) in anhydrous ethanol (12 mL) was added hydrazine hydrate (1.3 mL). The reaction mixture was stirred at room temperature for 2 hours. The organic solvent was evaporated under reduced pressure. Dichloromethane (100 mL) was added. The organic layer was washed with water and brine. The organic layer was dried over sodium sulfate. The organic solvent was evaporated under reduced pressure to yield 3-methyl-N-(2-trimethylsilanylethoxymethyl)indazole-5-carboximidic acid hydrazide 120 (0.35 g, 1.097 mmol) which was used in the next step without further purification.

To a solution of 120 (0.1 g, 0.313 mmol) in ethanol (1.5 mL) was added a toluene solution of ethyl glyoxylate (50% w/w, 0.065 mL, 0.328 mmol). The reaction mixture was heated at 77° C. for 5 hours. The solid product was filtered and washed with ethanol. The crude product was purified by RP-HPLC to yield the desired 3-[3-methyl-N-(2-trimethylsilanylethoxymethyl)indazol-5-yl]-[1,2,4]triazin-5-one 121 (0.052 g, 0.146 mmol).

GENERAL PROCEDURE FOR THE PREPARATION OF 5-SUBSTITUTED 3-(3-METHYLINDAZOL-5-YL)-[1,2,4]TRIAZINE AND 5-SUBSTITUTED 6-CHLORO-3-(3-METHYLINDAZOL-5-YL)-[1,2,4]TRIAZINE

Preparation of 3-(3-methylindazol-5-yl)-5-[(S)-4-Boc-3-benzylpiperazin-1-yl]-[1,2,4]triazine 124 and 6-chloro-3-(3-methylindazol-5-yl)-5-[(S)-4-Boc-3-benzylpiperazin-1-yl]-[1,2,4]triazine 125

Scheme 12

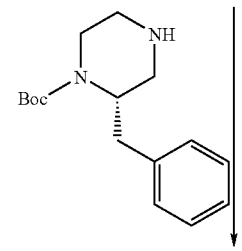

-continued

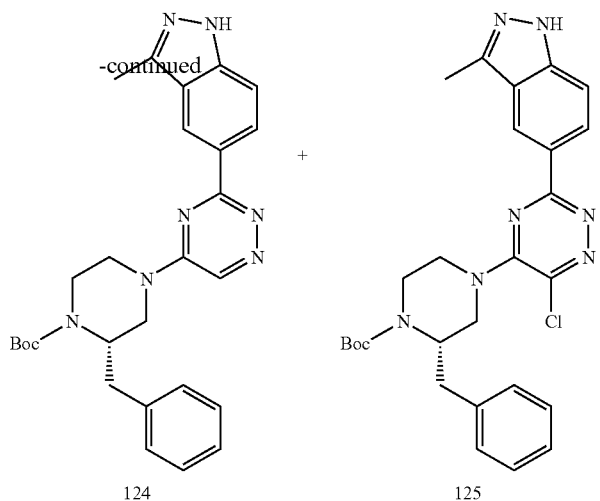

124       125

A solution of 3-[3-methyl-N-(2-trimethylsilanylethoxymethyl)indazol-5-yl]-[1,2,4]triazin-5-one 121 (0.077 mg, 0.216 mmol) in thionyl chloride (5 mL) was heated at 78° C. for 3 hours. The organic solvent was evaporated under reduced pressure. Dichloromethane (20 mL) was added. The organic solvent was evaporated under reduced pressure to yield a mixture of the monochloride 122 and dichloride 123 which was used in the next step without further purification.

To a solution of 122 and 123 (~0.216 mmol) in dioxane (3 mL) was added (S)—N-Boc-2-benzylpiperazine (0.07 g, 0.254 mmol) and diisopropylethylamine (0.077 mL, 0.443 mmol). The reaction mixture was heated at 60° C. for 1 hour. The organic solvent was evaporated under reduced pressure. The crude product mixture was purified by RP-HPLC to yield 3-(3-methylindazol-5-yl)-5-[(S)-4-Boc-3-benzyl piperazin-1-yl]-[1,2,4]triazine 124 (0.012 g, 0.025 mmol) and 6-chloro-3-(3-methylindazol-5-yl))-5-[(S)-4-Boc-3-benzylpiperazin-1-yl]-[1,2,4]triazine 125 (0.02 g, 0.038 mmol).

It is envisioned that intermediates of type 123 could provide additional compounds of formula (I) by sequential reaction with appropriate reagents such as nucleophiles.

GENERAL PROCEDURE FOR THE DEPROTECTION OF N—BOC-PIPERAZINES
Preparation of 3-(3-methylindazol-5-yl)-5-[(S)-3-benzylpiperazin-1-yl]-[1,2,4]triazine 12

Scheme 13

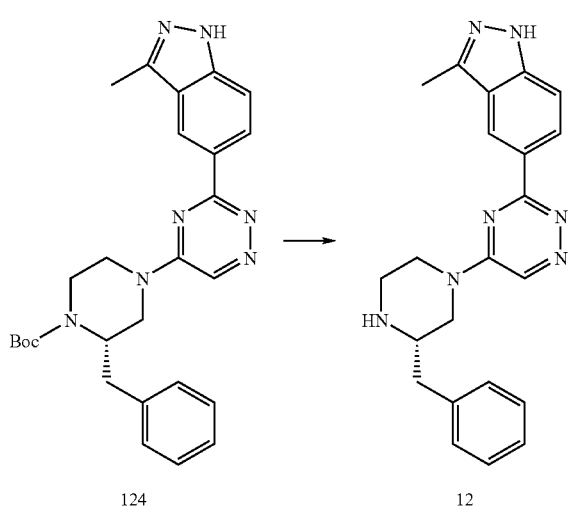

124       12

To a solution of 3-(3-methylindazol-5-yl)-5-[(S)-4-Boc-3-benzylpiperazin-1-yl]-[1,2,4]triazine 124 (0.012 g, 0.025 mmol) was added a solution of trifluoroacetic acid in dichloromethane (20% v/v, 2 mL). The reaction mixture was stirred at room temperature for 1 hour. The organic solvent was evaporated under reduced pressure. Methanol (1 mL) and dichloromethane (9 mL) were added. The organic solvent was evaporated under reduced pressure. The crude product was purified by RP-HPLC to yield the desired 3-(3-methylindazol-5-yl)-5-[(S)-3-benzylpiperazin-1-yl]-[1,2,4]triazine 12 (0.0041 g, 0.0106 mmol).

Those skilled in the art of organic synthesis will readily recognize that the compounds of Formula I, e.g., compounds 1-27 listed above, may be prepared by methods similar to those described above. For example, the 5-heterocycyl-6-amino-[1,2,4]triazines (e.g., examples 1, 3-12, and 14-18) may be prepared in a manner similar to that described in Scheme and 8, above, in which the appropriate 5-chloro-6-amino-[1,2,4]triazine intermediate (e.g., intermediate 134) is reacted at the 5-position with the appropriate heterocyclic amine (e.g., a substituted Boc-piperazine), then the 6-amino group is appropriately functionalized as in Scheme 8 (e.g., by benzylation).

5-hydroxy-[1,2,4]triazines (e.g., example 2) are tautomers of the corresponding 2H-[1,2,4]-triazine-5-one, prepared as shown in Scheme 1.

6-chloro- (e.g., examples 13, 20, 22, 24, and 25) and 6-H [1,2,4]triazines (e.g., examples 19, 21, 23, 26, and 27) may be prepared as shown in Scheme 12, by mono- or di-chlorination of the appropriate 2H-[1,2,4]-triazine-5-one.

In addition, compounds of Formula (I) where the $A^3$ group (as defined herein) is alkylene, —N($R^5$)—, —C(O)N($R^6$)—, or —N($R^6$)C(O)— may be prepared by selecting the appropriate carboximidic acid hydrazide (i.e., compound 131 of Scheme 1).

For example, compounds of Formula (I) where $A^3$ is alkylene may be prepared from indazolyl-alkylene-carboximidic acid hydrazides according to Scheme 1, above. Indazolyl-alkylene-carboximidic acid hydrazides could be prepared by the methods of Benson et al., *J. Org. Chem.*, (1992) 57, 5285-5287 and Li et al., *J. Org. Chem.* (1993), 58, 516-519, (both of which are herein incorporated by reference) except that the indolyl or pyrrolyl groups of Benson et al. and Li et al. could be replaced with indolyl. Alternatively, an indazolylmethylene-carboximidic acid hydrazide could be prepared from the corresponding cyanomethylindazole (the synthesis of the cyanomethylindazole has been described in U.S. published patent application No. 2004/127538, which is herein incorporated by reference). The resulting indazolyl-methylene-carboximidic acid hydrazide could then be reacted with the desired ketoester to provide a [1,2,4]triazin-5-one, which can in turn be converted to a functionalized 3-indazolylmethylene-[1,2,4]triazine as shown in Scheme 1.

Compounds of Formula (I) where $A^3$ is —C(O)N($R^6$)—, or —N($R^6$)C(O)-could be prepared, for example, by coupling a 5-aminoindazole (commercially available from Aldrich Chem. Co., Inc., and described in U.S. published patent application No. 2004/127538) with [1,2,4]triazine-3-carboxylic acids under standard amide bond formation conditions. [1,2,4]triazine-3-carboxylic acids could be prepared from the hydrolysis of the corresponding ester (e.g., using the method of Paulder et al., *J. Org. Chem.* (1966), 31, 1720-1722, herein incorporated by reference), and [1,2,4]triazine-3-carboxylic acid esters may be prepared from hydrazinoiminoacetic acid esters using the method of Stanforth et al., *Tet. Lett.* (2002), 43, 6015-6017 (herein incorporated by reference). Similarly, 3-amino-[1,2,4]triazines (e.g., prepared by the methods of Limanto et al., *Org. Lett.* (2003), 5, 2271-2274; herein incorporated by reference) could be coupled to an indazole-5-carboxylic acid (commercially available from Tyger Scientific Inc., and generally described in U.S. published patent application No. 2004/127538) under standard amide bond formation conditions.

Compounds of Formula (I) where $A^3$ is —N($R^5$)— could be prepared, for example, from the appropriate indazolyl-substituted aminoguanidines according to the method of Limanto et al. (above). The indazolyl-substituted aminoguanidines could be prepared from substituted S-methyl-isothiourea according to the method of Finnegan et al., *J. Org. Chem.* (1953), 18, 779-784 (herein incorporated by reference), which in turn could be prepared from aminoindazole using the method of Brands et al., *Bioorg. Med. Chem. Lett.* (2003), 13, 2641-2646.

Preparation of 3-[N-(4-methoxybenzyl)-3-methylindazol-5-yl]-6-phenethyl-[1,2,4]triazin-5-one 126

Scheme 14

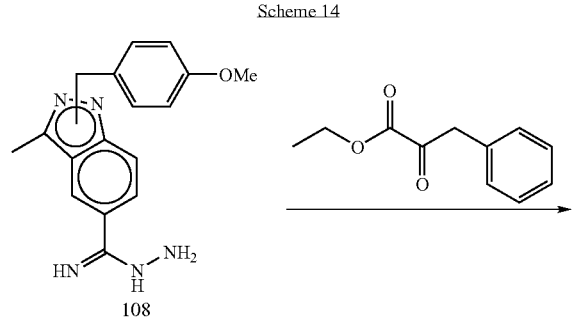

-continued

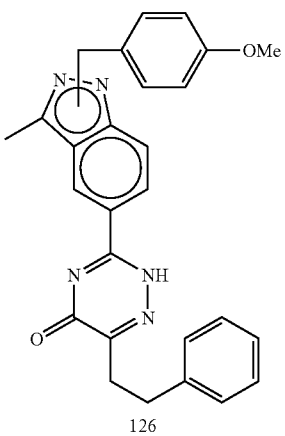

126

To a solution of N-(4-methoxybenzyl)-3-methylindazole-carboximidic acid hydrazide 108 (0.50 g, 1.62 mmol.) in anhydrous ethanol (5 mL) was added ethyl 2-oxo-4-phenyl-butyrate (0.325 g, 1.58 mmol.). The reaction mixture was heated in a microwave reactor at 150° C. for 45 minutes. The organic solvent was evaporated under reduced pressure. The solid product was crushed into fine powder and washed with trifluoromethylbenzene to afford 3-[N-(4-methoxybenzyl)-3-methylindazol-5-yl]-6-phenethyl-[1,2,4]triazin-5-one 126 (0.29 g, 0.64 mmol.) which was used in the next step without further purification.

Preparation of 5-(4-Boc-piperazin-1-yl)-3-[N-(4-methoxybenzyl)-3-methylindazol-5-yl]-6-phenethyl-[1,2,4]triazine 129

Scheme 15

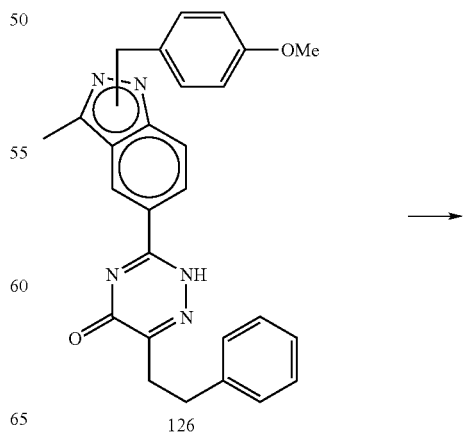

126

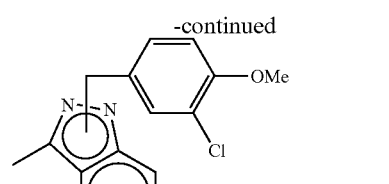

127

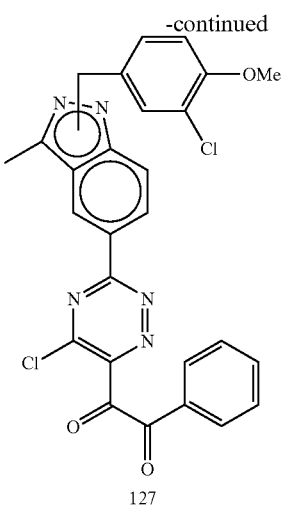

128

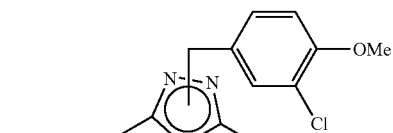

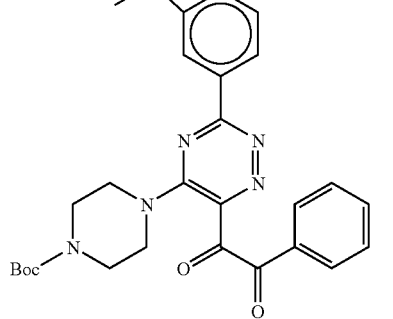

129

To 3-[N-(4-methoxybenzyl)-3-methylindazol-5-yl]-6-phenethyl-[1,2,4]triazin-5-one 126 (100 mg, 0.22 mmol.) was added thionyl chloride (20 mL). The reaction mixture was heated under gentle reflux for 1 hour. Excess thionyl chloride was evaporated under reduced pressure to afford the 3,6-disubstituted 5-chloro[1,2,4]triazine 127 which was used in the next step without further purification. To a solution of the 3,6-disubstituted 5-chloro[1,2,4]triazine 127 in anhydrous dioxane (3 mL) was added N-Boc-piperazine (49 mg, 0.26 mmol.) and diisopropylethylamine (57 mg, 0.44 mmol.). The reaction mixture was stirred at room temperature for 1 hour. Ethyl acetate (50 mL) was added. The organic layer was washed with saturated ammonium chloride solution. The organic layer was dried over sodium sulfate. The organic solvent was evaporated under reduced pressure. The crude product was purified by flash column chromatography to yield 3,6-disubstituted 5-(4-Boc-piperazin-1-yl)-[1,2,4]triazine 128 (80 mg, 0.12 mmol.). To a solution of the 3,6-disubstituted 5-(4-Boc-piperazin-1-yl)-[1,2,4]triazine 128 (80 mg, 0.12 mmol.) in ethanol (5 mL) was added Pearlman's catalyst (60 mg) and ammonium formate (30 mg, 0.48 mmol.). The reaction mixture was heated in a microwave reactor at 120° C. for 30 minutes. The reaction mixture was filtered through Celite and the filtrate was evaporated under reduced pressure. Ethyl acetate (100 mL) was added. The organic layer was washed with water and brine. The organic layer was dried over sodium sulfate. The organic solvent was evaporated under reduced pressure. The crude product was purified by flash column chromatography to yield the desired 5-(4-Boc-piperazin-1-yl)-3-[N-(4-methoxybenzyl)-3-methylindazol-5-yl]-6-phenethyl-[1,2,4]triazine 129 (18 mg, 0.029 mmol.).

Preparation of 3-(3-methylindazol-5-yl)-6-phenethyl-5-(piperazin-1-yl)-[1,2,4]triazine 92

Scheme 16

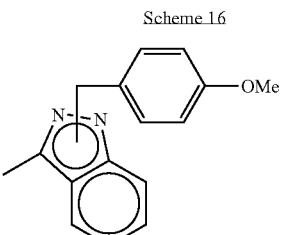

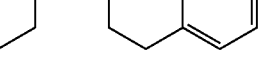

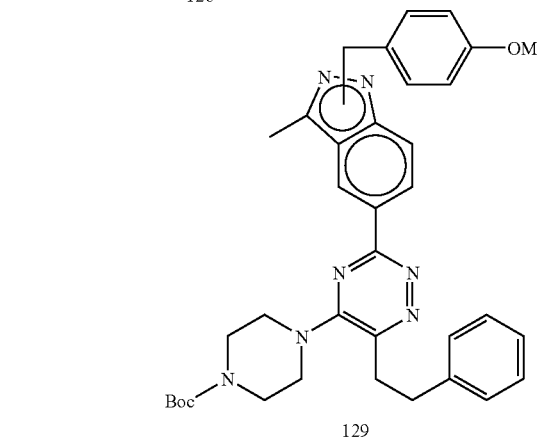

129

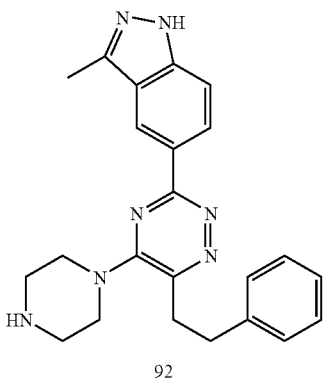

92

To 5-(4-Boc-piperazin-1-yl)-3-[N-(4-methoxybenzyl)-3-methylindazol-5-yl]-6-phenethyl-[1,2,4]triazine 129 (18 mg, 0.029 mmol.) was added trifluoroacetic acid (2.5 mL). The reaction mixture was heated in a microwave reactor at 120° C. for 40 minutes. Excess trifluoroacetic acid was evaporated under reduced pressure. The crude product was purified by RP-HPLC to yield the desired 3-(3-methylindazol-5-yl)-6-phenethyl-5-(piperazin-1-yl)-[1,2,4]triazine 92 (8.5 mg, 0.021 mmol.).

GENERAL SYNTHESIS OF 3,5-DISUBSTITUTED [1,2,4]TRIAZINE COMPOUNDS

The compounds of Formula I wherein $A^2$ is a covalent bond and $R^2$ is hydrogen can be prepared by the general method of Scheme 17, below, in which 6-azauracil 141 is treated with phosphorus oxychloride to provide 3,5-dichloro[1,2,4]triazine 142. The 3,5-dichloro[1,2,4]triazine 142 can then be converted to other functionalized [1,2,4]triazines, e.g., by treatment with an amine (primary, secondary or cyclic amine) to 3-chloro[1,2,4]triazine 143, followed by a metal catalyzed coupling reaction to provide 3,5-disubstituted[1,2,4]triazine 144.

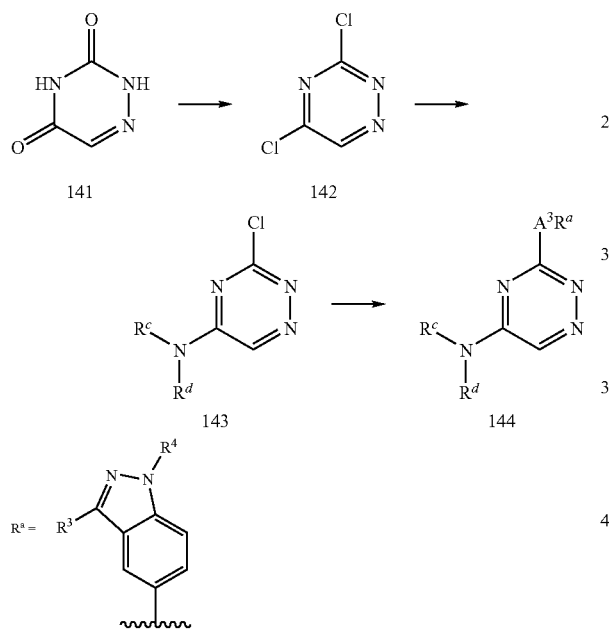

The general procedure of Scheme 17 is further exemplified below.

Preparation of 3,5-dichloro[1,2,4]triazine 142

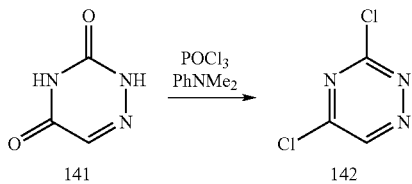

To 6-azauracil 141 (1.0 g, 8.85 mmol.) was added phosphorus oxychloride (10 mL, 108 mmol) and N,N-dimethylaniline (2 mL, 16 mmol). The reaction mixture was heated in a microwave reactor at 90° C. for 20 minutes. The reaction mixture was extracted with hexane (200 mL) twice. The combined hexane extract was filtered through Celite and sodium sulfate. The organic solvent was evaporated under reduced pressure to afford 3,5-dichloro[1,2,4]triazine 142 (0.53 g, 3.56 mmol.) which was used without further purification.

GENERAL PROCEDURE FOR THE PREPARATION OF 5-SUBSTITUTED 3-CHLORO[1,2,4]TRIAZINE

Preparation of 5-(4-Boc-piperazin-1-yl)-3-chloro[1,2,4]triazine 151

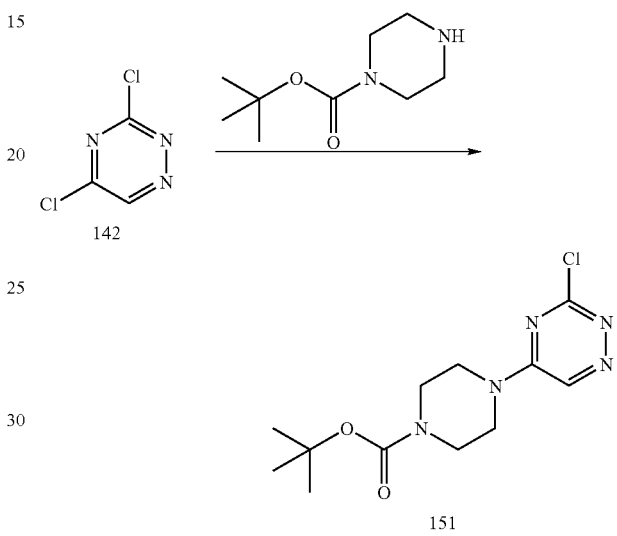

To a solution of 3,5-dichloro[1,2,4]triazine (0.34 g, 2.28 mmol.) in anhydrous dioxane (4 mL) was add diisopropylethylamine (0.44 g, 3.41 mmol.) and N—Boc-piperazine (0.424 g, 2.28 mmol.). The reaction mixture was stirred at room temperature for 40 minutes. Ethyl acetate (200 mL) was added. The organic solution was washed with saturated ammonium chloride solution, water and brine. The organic layer was dried over sodium sulfate. The organic solvent was evaporation under reduced pressure. The crude product was purified by RP-HPLC to yield the desired 5-(4-Boc-piperazin-1-yl)-3-chloro[1,2,4]triazine 151 (0.212 g, 0.71 mmol.).

Preparation of 3-methyl-5-trimethylstannanylindazole 152

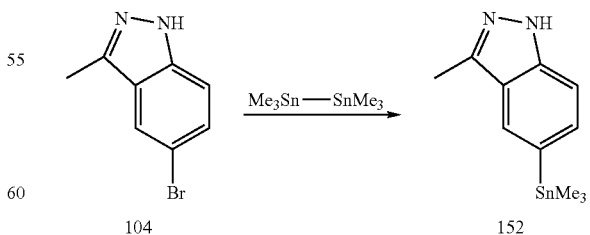

To a solution of 5-bromo-3-methylindazole 104 (2.0 g, 9.48 mmol.) in anhydrous toluene (20 mL) was added tetrakis (triphenylphosphine)palladium (1.1 g, 0.95 mmol.) and hexamethylditin (3.1 g, 9.46 mmol.). The reaction mixture was heated at 95° C. for 4 hours. Ethyl acetate (200 mL) was added. The organic layer was washed with water and brine. The organic layer was filtered through Celite and dried over sodium sulfate. The organic solvent was evaporated under reduced pressure. The crude product was purified by flash column chromatography to yield the desired 3-methyl-5-trimethylstannanylindazole 152 (1.85 g, 6.27 mmol.)

GENERAL PROCEDURE FOR THE PREPARATION OF 3,5-DISUBSTITUTED [1,2,4]TRIAZINE

Preparation of 3-(3-methylindazol-5-yl)-5-(4-Boc-piperazin-1-yl)-[1,2,4]triazine 153

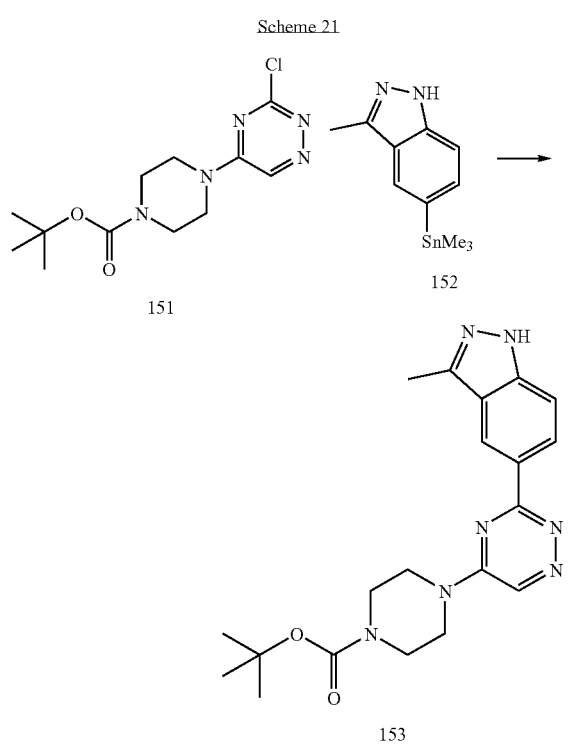

To a solution of 5-(4-Boc-piperazin-1-yl)-3-chloro[1,2,4]triazine 151 (50 mg, 0.167 mmol.) in anhydrous DMF (3 mL) was added 3-methyl-5-trimethylstannanylindazole 152 (49 mg, 0.166 mmol.), tris(dibenzylideneacetone)dipalladium (15 mg, 0.016 mmol.), tri-o-tolylphosphine (10 mg, 0.033 mmol.) and triethylamine (17 mg, 0.168 mmol.). The reaction mixture was heated in a microwave reactor at 180° C. for 20 minutes. Ethyl acetate (50 mL) was added. The organic layer was washed with water and brine. The organic layer was filtered through Celite and dried over sodium sulfate. The organic solvent was evaporated under reduced pressure. The crude product was purified by RP-HPLC to yield the desired 3-(3-methylindazol-5-yl)-5-(4-Boc-piperazin-1-yl)-[1,2,4]triazine 153 (5.1 mg, 0.013 mmol.).

Preparation of 3-(3-methylindazol-5-yl)-5-(piperazin-1-yl)-[1,2,4]triazine 46

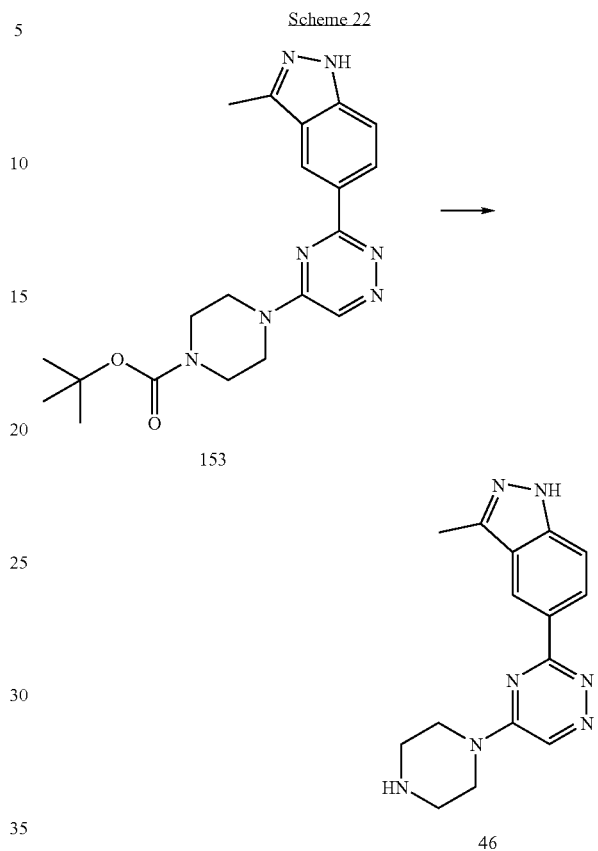

To 3-(3-methylindazol-5-yl)-5-(4-Boc-piperazin-1-yl)-[1,2,4]triazine 153 (5.1 mg, 0.013 mmol.) was added a 20% solution of trifluoroacetic acid in DCM. The reaction mixture was stirred at room temperature for 1 hour. The organic solvent was evaporated under reduced pressure. The crude product was purified by RP-HPLC to yield the desired 3-(3-methylindazol-5-yl)-5-(piperazin-1-yl)-[1,2,4]triazine 46 (2.6 mg, 0.0088 mmol.).

Preparation of 5-bromoindazole 162

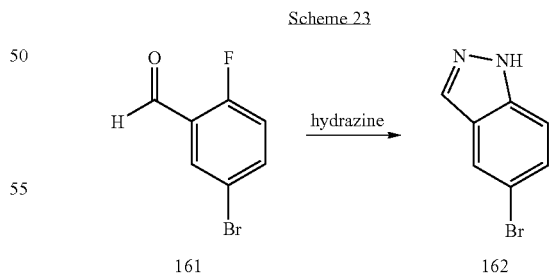

To 5-bromo-2-fluorobenzaldehyde 161 (2.0 g, 9.85 mmol.) was added hydrazine (10 mL). The reaction mixture was heated under gentle reflux for 4 hours. Excess hydrazine was evaporated under reduced pressure. Ethyl acetate (200 mL) was added. The organic layer was washed with water and brine. The organic layer was dried over sodium sulfate. The organic solvent was evaporated under reduced pressure. The crude product was purified by flash column chromatography to yield the desired 5-bromoindazole 162 (1.04 g, 5.28 mmol.).

Preparation of 5-bromo-3-chloroindazole 163

Scheme 24

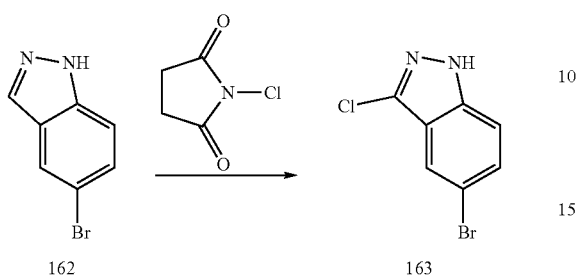

To a solution of 5-bromoindazole 162 (0.234 g, 1.19 mmol.) in anhydrous acetonitrile (8 mL) was added N-chlorosuccinamide (0.174 g, 1.31 mmol.). The reaction mixture was heated at 60° C. for 2 hours. The organic solvent was evaporated under reduced pressure. Ethyl acetate (100 mL) was added. The organic layer was washed was 1N sodium hydroxide solution, water and brine. The organic layer was dried over sodium sulfate. The organic solvent was evaporated under reduced pressure to yield 5-bromo-3-chloroindazole 163 (0.26 g, 1.13 mmol.). The crude product was used in the next step without further purification.

Preparation of 3-amino-5-bromoindazole 165

Scheme 25

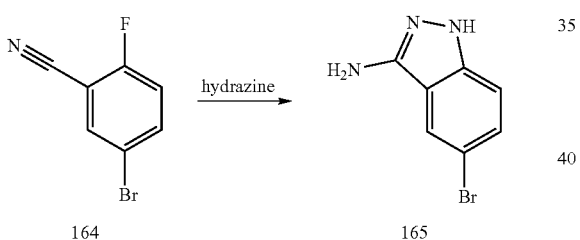

To a solution of 5-bromo-2-fluorobenzonitrile (0.40 g, 2.0 mmol.) in ethanol (3 mL) was added hydrazine (0.64 g, 20 mmol.). The reaction mixture was heated in a microwave reactor at 140° C. for 20 minutes. Ethyl acetate (100 mL) was added. The organic layer was washed with water and brine. The organic layer was dried over sodium sulfate. The organic solvent was evaporated under reduced pressure to yield 3-amino-5-bromoindazole 165 (0.41 g, 1.93 mmol.). The crude product was used in the next step without further purification.

Preparation of 5-bromo-3-ethylindazole 166

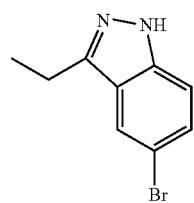

5-Bromo-3-ethylindazole 166 was prepared using methods shown in Scheme 2 wherein ethylmagnesium bromide was used in place of methylmagnesium bromide.

Preparation of 5-bromo-3-phenylindazole 167

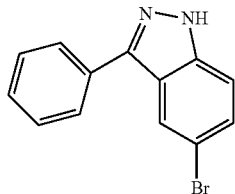

5-Bromo-3-phenylindazole 167 was prepared using methods shown in Scheme 2 wherein phenylmagnesium bromide was used in place of methylmagnesium bromide.

Preparation of 5-bromo-3-cyclopropylindazole 168

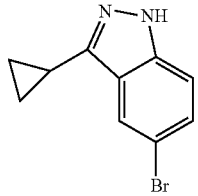

5-Bromo-3-cyclopropylindazole 168 was prepared using methods shown in Scheme 2 wherein cyclopropylmagesium bromide was used in place of methylmagnesium bromide.

Preparation of 5-bromo-2-fluoro-3-methylbenzaldehyde 170

Scheme 26

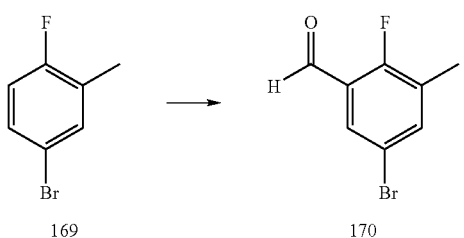

To a solution of 5-bromo-2-fluorotoluene 169 (1.0 g, 5.29 mmol.) in anhydrous THF (4 mL) cooled in dry ice/acetone bath was added a 2 M solution of lithium diisopropylamide (2.6 mL, 5.2 mmol.). The reaction mixture was stirred for 1 hour in the dry ice/acetone bath. Anhydrous dimethylformamide (0.46 g, 6.35 mmol.) was added in a dropwise manner. The reaction mixture was allowed to warm to room temperature in 3 hours. Ethyl acetate (100 mL) was added. The organic layer was washed with 1 N hydrochloric acid, water and brine. The organic layer was dried over sodium sulfate. The organic solvent was evaporated under reduced pressure to afford 5-bromo-2-fluoro-3-methylbenzaldehyde 170 (1.08 g, 4.98 mmol.). The crude product was used in the next step without further purification.

Preparation of 5-bromo-3,7-dimethylindazole 171

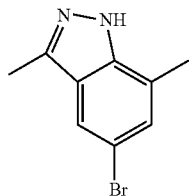

5-Bromo-3,7-dimethylindazole 171 was prepared using methods shown in Scheme 2 wherein 5-bromo-2-fluoro-3-methylbenzaldehyde 170 was used in place of 5-bromo-2-fluorobenzaldehyde 101.

Preparation of 5-trimethylstannanylindazole 172

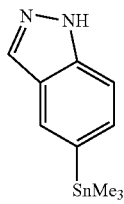

5-Trimethylstannanylindazole 172 was prepared using method shown in Scheme 20 wherein 5-bromoindazole 162 was used in place of 5-bromo-3-methylindazole 104.

Preparation of 3-chloro-5-trimethylstannanylindazole 173

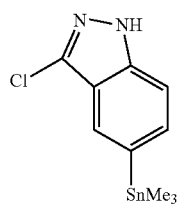

3-Chloro-5-trimethylstannanylindazole 173 was prepared using method shown in Scheme 20 wherein 5-bromo-3-chloroindazole 163 was used in place of 5-bromo-3-methylindazole 104.

Preparation of 3-amino-5-trimethylstannanylindazole 174

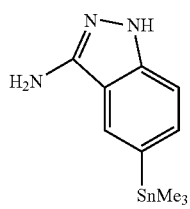

3-Amino-5-trimethylstannanylindazole 174 was prepared using method shown in Scheme 20 wherein 5-bromo-3-aminoindazole 165 was used in place of 5-bromo-3-methylindazole 104.

Preparation of 3-ethyl-5-trimethylstannanylindazole 175

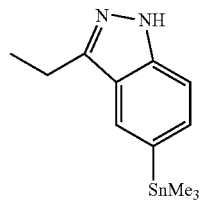

3-Ethyl-5-trimethylstannanylindazole 175 was prepared using method shown in Scheme 20 wherein 5-bromo-3-ethylindazole 166 was used in place of 5-bromo-3-methylindazole 104.

Preparation of 3-phenyl-5-trimethylstannanylindazole 176

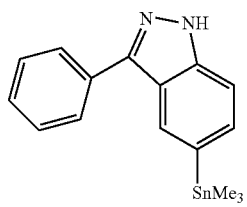

3-Phenyl-5-trimethylstannanylindazole 176 was prepared using method shown in Scheme 20 wherein 5-bromo-3-ethylindazole 167 was used in place of 5-bromo-3-methylindazole 104.

Preparation of 3-cyclopropyl-5-trimethylstannanylindazole 177

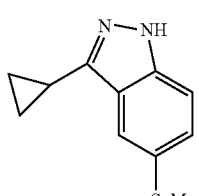

3-Cyclopropyl-5-trimethylstannanylindazole 177 was prepared using method shown in Scheme 20 wherein 5-bromo-3-cyclopropylindazole 168 was used in place of 5-bromo-3-methylindazole 104.

Preparation of 3,7-dimethyl-5-trimethylstannanylindazole 178

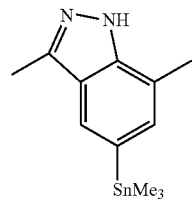

3,7-Dimethyl-5-trimethylstannanylindazole 178 was prepared using method shown in Scheme 20 wherein 5-bromo-3,7-dimethylindazole 171 was used in place of 5-bromo-3-methylindazole 104.

Preparation of 6-benzylamino-3-(3-methylindazol-5-yl)-5-(piperazin-1-yl)-[1,2,4]triazine 3

6-Benzylamino-3-(3-methylindazol-5-yl)-5-(piperazin-1-yl)-[1,2,4]triazine 3 was prepared using methods shown in Scheme 6, 8 and 7 wherein N-Boc-piperazine and benzyl bromide were used.

Preparation of 6-dibenzylamino-3-(3-methylindazol-5-yl)-5-(piperazin-1-yl)-[1,2,4]triazine 4

6-Dibenzylamino-3-(3-methylindazol-5-yl)-5-(piperazin-1-yl)-[1,2,4]triazine 4 was prepared using methods shown in Scheme 6, 8 and 7 wherein N—Boc-piperazine, excess base and excess benzyl bromide were used.

Preparation of 6-amino-5-[(S)-3-benzylpiperazin-1-yl]-3-(3-methylindazol-5-yl)-[1,2,4]triazine 5

6-Amino-5-[(S)-3-benzylpiperazin-1-yl]-3-(3-methylindazol-5-yl)-[1,2,4]triazine 5 was prepared using methods shown in Scheme 6 and 7 wherein (S)—N1-Boc-2-benzylpiperazine was used.

Preparation of 6-amino-3-(3-methylindazol-5-yl)-5-[(R)-3-phenylpiperazin-1-yl]-[1,2,4]triazine 6

6-Amino-3-(3-methylindazol-5-yl)-5-[(R)-3-phenylpiperazin-1-yl]-[1,2,4]triazine 6 was prepared using methods shown in Scheme 6 and 7 wherein (R)—N1-Boc-2-phenylpiperazine was used.

Preparation of 6-amino-5-[(S)-3-isopropylpiperazin-1-yl]-3-(3-methylindazol-5-yl)-[1,2,4]triazine 7

6-Amino-5-[(S)-3-isopropylpiperazin-1-yl]-3-(3-methylindazol-5-yl)-[1,2,4]triazine 7 was prepared using methods shown in Scheme 6 and 7 wherein (S)—N1-Boc-2-isopropylpiperazine was used.

Preparation of 6-amino-5-[(S)-3-isobutylpiperazin-1-yl]-3-(3-methylindazol-5-yl)-[1,2,4]triazine 8

6-Amino-5-[(S)-3-isobutylpiperazin-1-yl]-3-(3-methylindazol-5-yl)-[1,2,4]triazine 8 was prepared using methods shown in Scheme 6 and 7 wherein (S)—N1-Boc-2-isobutylpiperazine was used.

Preparation of 6-amino-3-(3-methylindazol-5-yl)-5-[(R)-3-methylpiperazin-1-yl]-[1,2,4]triazine 9

6-Amino-3-(3-methylindazol-5-yl)-5-[(R)-3-methylpiperazin-1-yl]-[1,2,4]triazine 9 was prepared using methods shown in Scheme 6 and 7 wherein (R)—N1-Boc-2-methylpiperazine was used.

Preparation of 6-amino-5-([1,4]diazepan-1-yl)-3-(3-methylindazol-5-yl)-[1,2,4]triazine 10

6-Amino-5-([1,4]diazepan-1-yl)-3-(3-methylindazol-5-yl)-[1,2,4]triazine 10 was prepared using methods shown in Scheme 6 and 7 wherein N-Boc-homopiperazine was used.

Preparation of 6-amino-5-(2,5-diazabicyclo[2.2.1]hept-2-yl)-3-(3-methylindazol-5-yl)-[1,2,4]triazine 11

6-Amino-5-(2,5-diazabicyclo[2.2.1]hept-2-yl)-3-(3-methylindazol-5-yl)-[1,2,4]triazine 11 was prepared using methods shown in Scheme 6 and 7 wherein N2-Boc-2,5-diazabicyclo[2.2.1]heptane was used.

Preparation of 5-[(S)-3-benzylpiperazin-1-yl]-6-chloro-3-(3-methylindazol-5-yl)-[1,2,4]triazine 13

5-[(S)-3-benzylpiperazin-1-yl]-6-chloro-3-(3-methylindazol-5-yl)-[1,2,4]triazine 13 was prepared using methods shown in Scheme 12 and 13 wherein (S)—N1-Boc-2-benzylpiperazine was used.

Preparation of 6-amino-3-(3-methylindazol-5-yl)-5-[(S)-3-methylpiperazin-1-yl]-[1,2,4]triazine 14

6-Amino-3-(3-methylindazol-5-yl)-5-[(S)-3-methylpiperazin-1-yl]-[1,2,4]triazine 14 was prepared using methods shown in Scheme 6 and 7 wherein (S)—N1-Boc-2-methylpiperazine was used.

Preparation of 6-benzylamino-3-(3-methylindazol-5-yl)-5-[(S)-3-methylpiperazin-1-yl]-[1,2,4]triazine 15

6-Benzylamino-3-(3-methylindazol-5-yl)-5-[(S)-3-methylpiperazin-1-yl]-[1,2,4]triazine 15 was prepared using methods shown in Scheme 6, 8 and 7 wherein (S)—N1-Boc-2-methylpiperazine and benzyl bromide were used.

Preparation of 6-benzylamino-5-[(S)-3-isopropylpiperazin-1-yl]-3-(3-methylindazol-5-yl)-[1,2,4]triazine 16

6-Benzylamino-5-[(S)-3-isopropylpiperazin-1-yl]-3-(3-methylindazol-5-yl)-[1,2,4]triazine 16 was prepared using methods shown in Scheme 6, 8 and 7 wherein (S)—N1-Boc-2-isopropylpiperazine and benzyl bromide were used.

Preparation of 6-benzylamino-5-[(S)-3-isobutylpiperazin-1-yl]-3-(3-methylindazol-5-yl)-[1,2,4]triazine 17

6-Benzylamino-5-[(S)-3-isobutylpiperazin-1-yl]-3-(3-methylindazol-5-yl)-[1,2,4]triazine 17 was prepared using methods shown in Scheme 6, 8 and 7 wherein (S)—N1-Boc-2-isobutylpiperazine and benzyl bromide were used.

Preparation of 6-benzylamino-5-[(S)-3-benzyl piperazin-1-yl]-3-(3-methylindazol-5-yl)-[1,2,4]triazine 18

6-Benzylamino-5-[(S)-3-benzylpiperazin-1-yl]-3-(3-methylindazol-5-yl)-[1,2,4]triazine 18 was prepared using methods shown in Scheme 6, 8 and 7 wherein (S)—N1-Boc-2-benzylpiperazine and benzyl bromide were used.

Preparation of 5-[(S)-3-isopropylpiperazin-1-yl]-3-(3-methylindazol-5-yl)-[1,2,4]triazine 19

5-[(S)-3-isopropylpiperazin-1-yl]-3-(3-methylindazol-5-yl)-[1,2,4]triazine 19 was prepared using methods shown in Scheme 12 and 13 wherein (S)—N1-Boc-2-isopropylpiperazine was used.

Preparation of 6-chloro-5-[(S)-3-isopropylpiperazin-1-yl]-3-(3-methylindazol-5-yl)-[1,2,4]triazine 20

6-Chloro-5-[(S)-3-isopropylpiperazin-1-yl]-3-(3-methylindazol-5-yl)-[1,2,4]triazine 20 was prepared using methods shown in Scheme 12 and 13 wherein (S)—N1-Boc-2-isopropylpiperazine was used.

Preparation of 5-[(S)-3-(3-indolylmethyl)piperazin-1-yl]-3-(3-methylindazol-5-yl)-[1,2,4]triazine 21

5-[(S)-3-(3-indolyl methyl)piperazin-1-yl]-3-(3-methylindazol-5-yl)-[1,2,4]triazine 21 was prepared using methods shown in Scheme 12 and 13 wherein (S)—N1-Boc-2-(3-indolylmethyl)piperazine was used.

Preparation of 6-chloro-5-[(S)-3-(3-indolylmethyl)piperazin-1-yl]-3-(3-methylindazol-5-yl)-[1,2,4]triazine 22

6-Chloro-5-[(S)-3-(3-indolylmethyl)piperazin-1-yl]-3-(3-methylindazol-5-yl)-[1,2,4]triazine 22 was prepared using methods shown in Scheme 12 and 13 wherein (S)—N1-Boc-2-(3-indolylmethyl)piperazine was used.

Preparation of 5-[(S)-3-isobutylpiperazin-1-yl]-3-(3-methylindazol-5-yl)-[1,2,4]triazine 23

5-[(S)-3-isobutylpiperazin-1-yl]-3-(3-methylindazol-5-yl)-[1,2,4]triazine 23 was prepared using methods shown in Scheme 12 and 13 wherein (S)—N1-Boc-2-isobutylpiperazine was used.

Preparation of 6-chloro-5-[(S)-3-isobutylpiperazin-1-yl]-3-(3-methylindazol-5-yl)-[1,2,4]triazine 24

6-Chloro-5-[(S)-3-isobutylpiperazin-1-yl]-3-(3-methylindazol-5-yl)-[1,2,4]triazine 24 was prepared using methods shown in Scheme 12 and 13 wherein (S)—N1-Boc-2-isobutylpiperazine was used.

Preparation of 5-[(R)-3-(benzyloxymethyl)piperazin-1-yl]-6-chloro-3-(3-methylindazol-5-yl)-[1,2,4]triazine 25

5-[(R)-3-(benzyloxymethyl)piperazin-1-yl]-6-chloro-3-(3-methylindazol-5-yl)-[1,2,4]triazine 25 was prepared using methods shown in Scheme 12 and 13 wherein (R)—N1-Boc-2-(benzyloxymethyl)piperazine was used.

Preparation of 5-[(R)-3-(benzyloxymethyl)piperazin-1-yl]-3-(3-methylindazol-5-yl)-[1,2,4]triazine 26

5-[(R)-3-(benzyloxymethyl)piperazin-1-yl]-3-(3-methylindazol-5-yl)-[1,2,4]triazine 26 was prepared using methods shown in Scheme 12 and 13 wherein (R)—N1-Boc-2-(benzyloxymethyl)piperazine was used.

Preparation of 5-[(S)-3-benzyl-4-methyl-piperazin-1-yl]-3-(3-methylindazol-5-yl)-[1,2,4]triazine 28

To a solution of 5-[(S)-3-benzylpiperazin-1-yl]-3-(3-methylindazol-5-yl)-[1,2,4]triazine 12 (14 mg, 0.036 mmol.) in 10% methanolic acetic acid was added 37% aqueous formaldehyde solution (0.06 mL, 0.74 mmol.) and cyanoborohydride resin (2.42 equiv./g, 44 mg, 0.11 mmol.). The reaction mixture was stirred at room temperature for 5 hours. The reaction mixture was filtered and the filtrate was evaporated under reduced pressure. The crude product was purified by RP-HPLC to yield the desired 5-[(S)-3-benzyl-4-methyl-piperazin-1-yl]-3-(3-methylindazol-5-yl)-[1,2,4]triazine 28 (7.1 mg, 0.018 mmol.).

Preparation of 5-(1,4-diazabicyclo[4.3.0]non-1-yl)-3-(3-methylindazol-5-yl)-[1,2,4]triazine 29

5-(1,4-Diazabicyclo[4.3.0]non-1-yl)-3-(3-methylindazol-5-yl)-[1,2,4]triazine 29 was prepared using methods shown in Scheme 12 and 13 wherein 1,4-diazabicyclo[4.3.0]nonane was used.

Preparation of 5-(1,4-diazabicyclo[4.4.0]dec-1-yl)-3-(3-methylindazol-5-yl)-[1,2,4]triazine 30

5-(1,4-Diazabicyclo[4.4.0]dec-1-yl)-3-(3-methylindazol-5-yl)-[1,2,4]triazine 30 was prepared using methods shown in Scheme 12 and 13 wherein 1,4-diazabicyclo[4.4.0]decane was used.

Preparation of 6-chloro-5-(1,4-diazabicyclo[4.3.0]non-1-yl)-3-(3-methylindazol-5-yl)-[1,2,4]triazine 31

6-Chloro-5-(1,4-diazabicyclo[4.3.0]non-1-yl)-3-(3-methylindazol-5-yl)-[1,2,4]triazine 31 was prepared using methods shown in Scheme 12 and 13 wherein 1,4-diazabicyclo[4.3.0]nonane was used.

Preparation of 6-chloro-5-(1,4-diazabicyclo[4.4.0]dec-1-yl)-3-(3-methylindazol-5-yl)-[1,2,4]triazine 32

6-Chloro-5-(1,4-diazabicyclo[4.4.0]dec-1-yl)-3-(3-methylindazol-5-yl)-[1,2,4]triazine 32 was prepared using methods shown in Scheme 12 and 13 wherein 1,4-diazabicyclo[4.4.0]decane was used.

Preparation of 5-(3-aminopiperidin-1-yl)-3-(3-methylindazol-5-yl)-[1,2,4]triazine 33

5-(3-Aminopiperidin-1-yl)-3-(3-methylindazol-5-yl)-[1,2,4]triazine 33 was prepared using methods shown in Scheme 12 and 13 wherein 3-(tert-butoxycarbonylamino)piperidine was used.

Preparation of 5-(3-aminopiperidin-1-yl)-6-chloro-3-(3-methylindazol-5-yl)-[1,2,4]triazine 34

5-(3-Aminopiperidin-1-yl)-6-chloro-3-(3-methylindazol-5-yl)-[1,2,4]triazine 34 was prepared using methods shown in Scheme 12 and 13 wherein 3-(tert-butoxycarbonylamino)piperidine was used.

Preparation of 5-(3-aminmethylopiperidin-1-yl)-3-(3-methylindazol-5-yl)-[1,2,4]triazine 35

5-(3-Aminopiperidin-1-yl)-3-(3-methylindazol-5-yl)-[1,2,4]triazine 35 was prepared using methods shown in Scheme 12 and 13 wherein 3-N—Boc-aminomethylpiperidine was used.

Preparation of 5-(3-aminmethyiopiperidin-1-yl)-6-chloro-3-(3-methylindazol-5-yl)-[1,2,4]triazine 36

5-(3-Aminopiperidin-1-yl)-6-chloro-3-(3-methylindazol-5-yl)-[1,2,4]triazine 36 was prepared using methods shown in Scheme 12 and 13 wherein 3-N—Boc-aminomethylpiperidine was used.

Preparation of 5-(3-aminopyrrolidin-1-yl)-3-(3-methylindazol-5-yl)-[1,2,4]triazine 37

5-(3-Aminopyrrolidin-1-yl)-3-(3-methylindazol-5-yl)-[1,2,4]triazine 37 was prepared using methods shown in Scheme 12 and 13 wherein 3-(tert-butoxycarbonylamino) pyrrolidine was used.

Preparation of 5-(3-aminopyrrolidin-1-yl)-6-chloro-3-(3-methylindazol-5-yl)-[1,2,4]triazine 38

5-(3-Aminopyrrolidin-1-yl)-6-chloro-3-(3-methylindazol-5-yl)-[1,2,4]triazine 34 was prepared using methods shown in Scheme 12 and 13 wherein 3-(tert-butoxycarbonylamino)pyrrolidine was used.

Preparation of 5-(3-methoxycarbonylpyrazin-1-yl)-3-(3-methylindazol-5-yl)-[1,2,4]triazine 39

5-(3-Methoxycarbonylpyrazin-1-yl)-3-(3-methylindazol-5-yl)-[1,2,4]triazine 39 was prepared using methods shown in Scheme 12 and 13 wherein N-1-Boc-2-piperazinecarboxylic acid methyl ester was used.

Preparation of 6-chloro-5-(3-methoxycarbonyl pyrazin-1-yl)-3-(3-methylindazol-5-yl)-[1,2,4]triazine 40

6-Chloro-5-(3-methoxycarbonylpyrazin-1-yl)-3-(3-methylindazol-5-yl)-[1,2,4]triazine 40 was prepared using methods shown in Scheme 12 and 13 wherein N-1-Boc-2-piperazinecarboxylic acid methyl ester was used.

Preparation of 5-(6,9-diaza-spiro[4.5]dec-9-yl)-3-(3-methylindazol-5-yl)-[1,2,4]triazine 41

5-(6,9-Diaza-spiro[4.5]dec-9-yl)-3-(3-methylindazol-5-yl)-[1,2,4]triazine 41 was prepared using methods shown in Scheme 12 and 13 wherein 6,9-diaza-spiro[4.5]decane was used.

Preparation of 3-(3-methylindazol-5-yl)-5-[(R)-3-phenylpiperazin-1-yl]-[1,2,4]triazine 42

3-(3-Methylindazol-5-yl)-5-[(R)-3-phenylpiperazin-1-yl]-[1,2,4]triazine 42 was prepared using methods shown in Scheme 12 and 13 wherein (R)—N1-Boc-2-phenylpiperazine was used.

Preparation of 6-chloro-3-(3-methylindazol-5-yl)-5-[(R)-3-phenylpiperazin-1-yl]-[1,2,4]triazine 43

6-Chloro-3-(3-methylindazol-5-yl)-5-[(R)-3-phenylpiperazin-1-yl]-[1,2,4]triazine 43 was prepared using methods shown in Scheme 12 and 13 wherein (R)—N1-Boc-2-phenylpiperazine was used.

Preparation of 5-(1,4-diaza-spiro[5.5]undec-4-yl)-3-(3-methylindazol-5-yl)-[1,2,4]triazine 44

5-(1,4-Diaza-spiro[5.5]undec-4-yl)-3-(3-methylindazol-5-yl)-[1,2,4]triazine 44 was prepared using methods shown in Scheme 12 and 13 wherein 1,4-diaza-spiro[5.5]undecane was used.

Preparation of 5-[3-(4-fluorobenzyl)piperazin-1-yl]-3-(3-methylindazol-5-yl)-[1,2,4]triazine 45

5-[3-(4-Fluorobenzyl)piperazin-1-yl]-3-(3-methylindazol-5-yl)-[1,2,4]triazine 45 was prepared using methods shown in Scheme 19, 21 and 22 wherein N1-Boc-2-(4-fluorobenzyl)piperazine was used.

Preparation of 5-[3-(3-fluorobenzyl)piperazin-1-yl]-3-(3-methylindazol-5-yl)-[1,2,4]triazine 47

5-[3-(3-Fluorobenzyl)piperazin-1-yl]-3-(3-methylindazol-5-yl)-[1,2,4]triazine 47 was prepared using methods shown in Scheme 19, 21 and 22 wherein N1-Boc-2-(3-fluorobenzyl)piperazine was used.

Preparation of 5-[3-(2-fluorobenzyl)piperazin-1-yl]-3-(3-methylindazol-5-yl)-[1,2,4]triazine 48

5-[3-(2-Fluorobenzyl)piperazin-1-yl]-3-(3-methylindazol-5-yl)-[1,2,4]triazine 48 was prepared using methods shown in Scheme 19, 21 and 22 wherein N1-Boc-2-(2-fluorobenzyl)piperazine was used.

Preparation of 3-(3-methylindazol-5-yl)-5-[3-(2-trifluoromethyl benzyl)piperazin-1-yl]-[1,2,4]triazine 49

3-(3-Methylindazol-5-yl)-5-[3-(2-trifluoromethylbenzyl)piperazin-1-yl]-[1,2,4]triazine 49 was prepared using methods shown in Scheme 19, 21 and 22 wherein N1-Boc-2-(2-trifluoromethylbenzyl)piperazine was used.

Preparation of 3-(3-methylindazol-5-yl)-5-[3-(2-trifluoromethoxybenzyl)piperazin-1-yl]-[1,2,4]triazine 50

3-(3-Methylindazol-5-yl)-5-[3-(2-trifluoromethoxybenzyl)piperazin-1-yl]-[1,2,4]triazine 50 was prepared using methods shown in Scheme 19, 21 and 22 wherein N1-Boc-2-(2-trifluoromethoxybenzyl)piperazine was used.

Preparation of 5-[3-(2-methoxybenzyl)piperazin-1-yl]-3-(3-methylindazol-5-yl)-1,2,4]triazine 51

5-[3-(2-Methoxybenzyl)piperazin-1-yl]-3-(3-methylindazol-5-yl)-[1,2,4]triazine 51 was prepared using methods shown in Scheme 19, 21 and 22 wherein N1-Boc-2-(2-methoxybenzyl)piperazine was used.

Preparation of 5-[3-(2-methylbenzyl)piperazin-1-yl]-3-(3-methylindazol-5-yl)-1,2,4]triazine 52

5-[3-(2-Methylbenzyl)piperazin-1-yl]-3-(3-methylindazol-5-yl)-[1,2,4]triazine 52 was prepared using methods shown in Scheme 19, 21 and 22 wherein N1-Boc-2-(2-methylbenzyl)piperazine was used.

Preparation of 6-benzylamino-3-(3-phenyl indazol-5-yl)-5-(piperazin-1-yl)-[1,2,4]triazine 53

6-Benzylamino-3-(3-phenylindazol-5-yl)-5-(piperazin-1-yl)-[1,2,4]triazine 53 was prepared using methods shown in Scheme 3, 4, 5, 6, 8 and 7 wherein 5-bromo-3-phenylindazole 167, N—Boc-piperazine and benzyl bromide were used.

Preparation of 5-(3,3-dibenzylpiperazin-1-yl)-3-(3-methylindazol-5-yl)-1,2,4]triazine 54

5-(3,3-dibenzyl piperazin-1-yl)-3-(3-methylindazol-5-yl)-[1,2,4]triazine 54 was prepared using methods shown in Scheme 19, 21 and 22 wherein N1-Boc-2,2-dibenzylpiperazine was used.

Preparation of 5-[(S)-3-benzylpiperazin-1-yl]-3-indazol-5-yl-[1,2,4]triazine 55

5-[(S)-3-Benzylpiperazin-1-yl]-3-indazol-5-yl-[1,2,4]triazine 55 was prepared using methods shown in Scheme 19, 21 and 22 wherein (S)—N1-Boc-2-benzylpiperazine and 5-trimethylstannanylindazole 172 were used.

Preparation of 5-[(S)-3-benzylpiperazin-1-yl]-3-(3-chloroindazol-5-yl)-[1,2,4]triazine 56

5-[(S)-3-Benzylpiperazin-1-yl]-3-(3-chloroindazol-5-yl)-[1,2,4]triazine 55 was prepared using methods shown in Scheme 19, 21 and 22 wherein (S)—N1-Boc-2-benzylpiperazine and 3-chloro-5-trimethylstannanylindazole 173 were used.

Preparation of 3-(3-methylindazol-5-yl)-5-[3-(Pyridin-3-ylmethyl)piperazin-1-yl]-[1,2,4]triazine 57

3-(3-Methylindazol-5-yl)-5-[3-(pyridin-3-ylmethyl)piperazin-1-yl]-[1,2,4]triazine 57 was prepared using methods shown in Scheme 19, 21 and 22 wherein N1-Boc-2-(pyridin-3-ylmethyl)piperazine was used.

Preparation of 3-(3-methylindazol-5-yl)-5-[3-(pyridin-2-ylmethyl)piperazin-1-yl]-[1,2,4]triazine 58

3-(3-Methylindazol-5-yl)-5-[3-(pyridin-2-ylmethyl)piperazin-1-yl]-[1,2,4]triazine 58 was prepared using methods shown in Scheme 19, 21 and 22 wherein N1-Boc-2-(pyridin-2-ylmethyl)piperazine was used.

Preparation of 5-(3-benzylpiperidin-1-yl)-3-(3-methylindazol-5-yl)-[1,2,4]triazine 59

5-(3-Benzylpiperidin-1-yl)-3-(3-methylindazol-5-yl)-[1,2,4]triazine 59 was prepared using methods shown in Scheme 19, 21 and 22 wherein 3-benzylpiperidine was used.

Preparation of 5-[(S)-3-benzyl-4-hydroxyethyl-piperazin-1-yl]-3-(3-methylindazol-5-yl)-[1,2,4]triazine 60

To a solution of 5-[(S)-3-benzylpiperazin-1-yl]-3-(3-methylindazol-5-yl)-[1,2,4]triazine 12 (28.5 mg, 0.074 mmol.) in acetonitrile (2 mL) was added sodium bicarbonate (6.2 mg, 0.074 mmol.) and 2-bromoethanol (9.2 mg, 0.11 mmol.). The reaction mixture was heated under gentle reflux overnight. Ethyl acetate (50 mL) was added. The organic layer was washed with water and brine. The organic layer was dried over sodium sulfate. The organic solvent was evaporated under reduced pressure. The crude product was purified by RP-HPLC to yield the desired 5-[(S)-3-benzyl-4-hydroxyethyl-piperazin-1-yl]-3-(3-methylindazol-5-yl)-[1,2,4]triazine 60 (2.3 mg, 0.0054 mmol.).

Preparation of 3-indazol-5-yl-5-[(S)-3-isobutylpiperazin-1-yl]-[1,2,4]triazine 61

3-Indazol-5-yl-5-[(S)-3-isobutylpiperazin-1-yl]-[1,2,4]triazine 61 was prepared using methods shown in Scheme 19, 21 and 22 wherein (S)—N1-Boc-2-isobutylpiperazine and 5-trimethylstannanylindazole 172 were used.

Preparation of 5-(3-benzyl-3-ethoxycarbonylpiperidin-1-yl)-3-(3-methylindazol-5-yl)-[1,2,4]triazine 62

5-(3-Benzyl-3-ethoxycarbonylpiperidin-1-yl)-3-(3-methylindazol-5-yl)-[1,2,4]triazine 62 was prepared using methods shown in Scheme 19, 21 and 22 wherein 3-benzylpiperidine-3-carboxylic acid ethyl ester was used.

Preparation of 3-(3-chloroindazol-5-yl)-5-[(S)-3-isobutyl piperazin-1-yl]-[1,2,4]triazine 64

3-(3-chloroindazol-5-yl)-5-[(S)-3-isobutylpiperazin-1-yl]-[1,2,4]triazine 64 was prepared using methods shown in Scheme 19, 21 and 22 wherein (S)—N1-Boc-2-isobutylpiperazine and 3-chloro-5-trimethylstannanylindazole 173 were used.

Preparation of 3-(3-aminoindazol-5-yl)-5-[(S)-3-benzylpiperazin-1-yl]-[1,2,4]triazine 67

3-(3-Aminoroindazol-5-yl)-5-[(S)-3-benzylpiperazin-1-yl]-[1,2,4]triazine 67 was prepared using methods shown in Scheme 19, 21 and 22 wherein (S)—N1-Boc-2-benzylpiperazine and 3-amino-5-trimethylstannanylindazole 174 were used.

Preparation of 3-(3-methylindazol-5-yl)-5-[3-(pyridin-4-ylmethyl)piperazin-1-yl]-[1,2,4]triazine 68

3-(3-Methylindazol-5-yl)-5-[3-(pyridin-4-ylmethyl)piperazin-1-yl]-[1,2,4]triazine 68 was prepared using methods shown in Scheme 19, 21 and 22 wherein N1-Boc-2-(pyridin-4-ylmethyl)piperazine was used.

Preparation of 3-(3-methylindazol-5-yl)-5-(3-benzylpyrrolidin-1-yl)-[1,2,4]triazine 69

3-(3-Methylindazol-5-yl)-5-(3-benzylpyrrolidin-1-yl)-[1,2,4]triazine 68 was prepared using methods shown in Scheme 19, 21 and 22 wherein 3-benzylpyrrolidine was used.

Preparation of 5-[(S)-3-benzylpiperazin-1-yl]-3-(3-phenylindazol-5-yl)-[1,2,4]triazine 70

5-[(S)-3-Benzylpiperazin-1-yl]-3-(3-phenylindazol-5-yl)-[1,2,4]triazine 70 was prepared using methods shown in Scheme 19, 21 and 22 wherein (S)—N1-Boc-2-benzylpiperazine and 3-phenyl-5-trimethylstannanylindazole 176 were used.

Preparation of 3-(3-phenylindazol-5-yl)-5-piperazin-1-yl-[1,2,4]triazine 71

3-(3-Phenylindazol-5-yl)-5-piperazin-1-yl-[1,2,4]triazine 71 was prepared using methods shown in Scheme 19, 21 and 22 wherein N—Boc-piperazine and 3-phenyl-5-trimethylstannanylindazole 176 were used.

Preparation of 5-[(S)-3-isobutylpiperazin-1-yl]-3-(3-phenylindazol-5-yl)-[1,2,4]triazine 72

5-[(S)-3-Isobutylpiperazin-1-yl]-3-(3-phenylindazol-5-yl)-[1,2,4]triazine 72 was prepared using methods shown in Scheme 19, 21 and 22 wherein (S)—N1-Boc-2-isobutylpiperazine and 3-phenyl-5-trimethylstannanylindazole 176 were used.

Preparation of 3-(3-methylindazol-5-yl)-5-[(S)-3-tert-butylpiperazin-1-yl]-[1,2,4]triazine 73

3-(3-Methylindazol-5-yl)-5-[(S)-3-tert-butylpiperazin-1-yl]-[1,2,4]triazine 73 was prepared using methods shown in Scheme 19, 21 and 22 wherein (S)—N1-Boc-2-tert-butylpiperazine was used.

Preparation of 3-indazol-5-yl-5-[3-(2-methylbenzyl)piperazin-1-yl]-[1,2,4]triazine 74

3-Indazol-5-yl-5-[3-(2-methyl benzyl)piperazin-1-yl]-[1,2,4]triazine 74 was prepared using methods shown in Scheme 19, 21 and 22 wherein N1-Boc-2-(2-methylbenzyl)piperazine and 5-trimethylstannanylindazole 172 were used.

Preparation of 3-(3-cyclopropylindazol-5-yl)-5-piperazin-1-yl-[1,2,4]triazine 75

3-(3-Cyclopropylindazol-5-yl)-5-piperazin-1-yl-[1,2,4]triazine 75 was prepared using methods shown in Scheme 19, 21 and 22 wherein N—Boc-piperazine and 3-cyclopropyl-5-trimethylstannanylindazole 177 were used.

Preparation of 3-(3-cyclopropylindazol-5-yl)-5-[(S)-3-isobutylpiperazin-1-yl]-[1,2,4]triazine 76

3-(3-Cyclopropylindazol-5-yl)-5-[(S)-3-isobutylpiperazin-1-yl]-[1,2,4]triazine 76 was prepared using methods shown in Scheme 19, 21 and 22 wherein (S)—N1-Boc-2-isobutylpiperazine and 3-cyclopropyl-5-trimethylstannanylindazole 177 were used.

Preparation of 5-[(S)-3-benzylpiperazin-1-yl]-3-(3-cyclopropylindazol-5-yl)-[1,2,4]triazine 77

5-[(S)-3-Benzylpiperazin-1-yl]-3-(3-cyclopropylindazol-5-yl)-[1,2,4]triazine 77 was prepared using methods shown in Scheme 19, 21 and 22 wherein (S)—N1-Boc-2-benzylpiperazine and 3-cyclopropyl-5-trimethylstannanylindazole 177 were used.

Preparation of 3-(3-ethylindazol-5-yl)-5-piperazin-1-yl-[1,2,4]triazine 78

3-(3-Ethylindazol-5-yl)-5-piperazin-1-yl-[1,2,4]triazine 78 was prepared using methods shown in Scheme 19, 21 and 22 wherein N—Boc-piperazine and 3-ethyl-5-trimethylstannanylindazole 175 were used.

Preparation of 3-(3-ethylindazol-5-yl)-5-[(S)-3-isobutylpiperazin-1-yl]-[1,2,4]triazine 79

3-(3-Ethylindazol-5-yl)-5-[(S)-3-isobutylpiperazin-1-yl]-[1,2,4]triazine 79 was prepared using methods shown in Scheme 19, 21 and 22 wherein (S)—N1-Boc-2-isobutylpiperazine and 3-ethyl-5-trimethylstannanylindazole 175 were used.

Preparation of 5-[(S)-3-benzylpiperazin-1-yl]-3-(3-ethylindazol-5-yl)-[1,2,4]triazine 80

5-[(S)-3-Benzyl piperazin-1-yl]-3-(3-ethyl indazol-5-yl)-[1,2,4]triazine 80 was prepared using methods shown in Scheme 19, 21 and 22 wherein (S)—N1-Boc-2-benzylpiperazine and 3-ethyl-5-trimethylstannanylindazole 175 were used.

Preparation of 6-amino-3-(3-methylindazol-5-yl)-5-[(S)-3-tert-butylpiperazin-1-yl]-[1,2,4]triazine 81

6-Amino-3-(3-methylindazol-5-yl)-5-[(S)-3-tert-butylpiperazin-1-yl]-[1,2,4]triazine 81 was prepared using methods shown in Scheme 6 and 7 wherein (S)—N1-Boc-2-tert-butylpiperazine was used.

Preparation of 6-amino-5-(1,4-diaza-spiro[5.5]undec-4-yl)-3-(3-methylindazol-5-yl)-[1,2,4]triazine 82

6-Amino-5-(1,4-diaza-spiro[5.5]undec-4-yl)-3-(3-methylindazol-5-yl)-[1,2,4]triazine 82 was prepared using methods shown in Scheme 6 and 7 wherein 1,4-diaza-spiro[5.5]undecane was used.

Preparation of 6-amino-5-(3-aminopyrrolidin-1-yl)-3-(3-methylindazol-5-yl)-[1,2,4]triazine 83

6-Amino-5-(3-aminopyrrolidin-1-yl)-3-(3-methylindazol-5-yl)-[1,2,4]triazine 83 was prepared using methods shown in Scheme 6 and 7 wherein 3-(tert-butoxycarbonylamino)pyrrolidine was used.

Preparation of 6-amino-5-(3-methylaminopyrrolidin-1-yl)-3-(3-methylindazol-5-yl)-[1,2,4]triazine 84

6-Amino-5-(3-methylaminopyrrolidin-1-yl)-3-(3-methylindazol-5-yl)-[1,2,4]triazine 84 was prepared using methods shown in Scheme 6 and 7 wherein 3-(N-tert-butoxycarbonyl-N-methylamino)pyrrolidine was used.

Preparation of 6-amino-5-(6,9-diaza-spiro[4.5]dec-9-yl)-3-(3-methylindazol-5-yl)-[1,2,4]triazine 85

6-Amino-5-(6,9-diaza-spiro[4.5]dec-9-yl)-3-(3-methylindazol-5-yl)-[1,2,4]triazine 85 was prepared using methods shown in Scheme 6 and 7 wherein 6,9-diaza-spiro[4.5]decane was used.

Preparation of 6-amino-5-(3-aminomethylpyrrolidin-1-yl)-3-(3-methylindazol-5-yl)-[1,2,4]triazine 86

6-Amino-5-(3-aminomethylpyrrolidin-1-yl)-3-(3-methylindazol-5-yl)-[1,2,4]triazine 86 was prepared using methods shown in Scheme 6 and 7 wherein 3-(tert-butoxycarbonylaminomethyl)pyrrolidine was used.

Preparation of 5-[(S)-3-benzylpiperazin-1-yl]-3-(3,7-dimethylindazol-5-yl)-[1,2,4]triazine 87

5-[(S)-3-Benzylpiperazin-1-yl]-3-(3,7-dimethylindazol-5-yl)-[1,2,4]triazine 87 was prepared using methods shown in Scheme 19, 21 and 22 wherein (S)—N1-Boc-2-benzylpiperazine and 3,7-dimethyl-5-trimethylstannanylindazole 178 were used.

Preparation of 6-amino-3-(3-methylindazol-5-yl)-5-[(R)-3-propylpiperazin-1-yl]-[1,2,4]triazine 88

6-Amino-3-(3-methylindazol-5-yl)-5-[(R)-3-propylpiperazin-1-yl]-[1,2,4]triazine 88 was prepared using methods shown in Scheme 6 and 7 wherein (R)—N1-Boc-2-propylpiperazine was used.

Preparation of 6-amino-3-(3-methylindazol-5-yl)-5-[(S)-3-propylpiperazin-1-yl]-[1,2,4]triazine 89

6-Amino-3-(3-methylindazol-5-yl)-5-[(S)-3-propylpiperazin-1-yl]-[1,2,4]triazine 89 was prepared using methods shown in Scheme 6 and 7 wherein (S)—N1-Boc-2-propylpiperazine was used.

Preparation of 6-amino-5-[(R)-3-isopropylpiperazin-1-yl]-3-(3-methylindazol-5-yl)-[1,2,4]triazine 90

6-Amino-5-[(S)-3-isopropylpiperazin-1-yl]-3-(3-methylindazol-5-yl)-[1,2,4]triazine 90 was prepared using methods shown in Scheme 6 and 7 wherein (R)—N1-Boc-2-isopropylpiperazine was used.

Preparation of 6-amino-5-[(R)-3-benzylpiperazin-1-yl]-3-(3-methylindazol-5-yl)-[1,2,4]triazine 91

6-Amino-5-[(R)-3-benzyl piperazin-1-yl]-3-(3-methylindazol-5-yl)-[1,2,4]triazine 91 was prepared using methods shown in Scheme 6 and 7 wherein (R)—N1-Boc-2-benzylpiperazine was used.

Preparation of 5-[(S)-3-isopropylpiperazin-1-yl]-3-(3-methylindazol-5-yl)-6-phenethyl-[1,2,4]triazine 93

5-[(S)-3-Isopropylpiperazin-1-yl]-3-(3-methylindazol-5-yl)-6-phenethyl-[1,2,4]triazine 93 was prepared using methods shown in Scheme 15 and 16 wherein (S)—N1-Boc-2-isopropylpiperazine was used.

Preparation of 3-(3-methylindazol-5-yl)-6-phenethyl-5-[(S)-3-propylpiperazin-1-yl]-[1,2,4]triazine 94

3-(3-Methylindazol-5-yl)-6-phenethyl-5-[(S)-3-propylpiperazin-1-yl]-[1,2,4]triazine-94 was prepared using methods shown in Scheme 15 and 16 wherein (S)—N1-Boc-2-proylpiperazine was used.

Preparation of 6-biphenyl-2-ylmethylamino-5-[(S)-3-isopropylpiperazin-1-yl]-3-(3-methylindazol-5-yl)-[1,2,4]triazine 95

6-Biphenyl-2-ylmethylamino-5-[(S)-3-isopropylpiperazin-1-yl]-3-(3-methylindazol-5-yl)-[1,2,4]triazine 95 was prepared using methods shown in Scheme 6, 8 and 7 wherein (S)—N1-Boc-2-isopropylpiperazine and 2-phenylbenzyl bromide were used.

Preparation of 6-biphenyl-3-ylmethylamino-5-[(S)-3-isopropylpiperazin-1-yl]-3-(3-methylindazol-5-yl)-[1,2,4]triazine 96

6-Biphenyl-3-ylmethylamino-5-[(S)-3-isopropyl piperazin-1-yl]-3-(3-methylindazol-5-yl)-[1,2,4]triazine 96 was prepared using methods shown in Scheme 6, 8 and 7 wherein (S)—N1-Boc-2-isopropylpiperazine and 3-phenylbenzyl bromide were used.

Preparation of 5-[(S)-3-isopropylpiperazin-1-yl]-3-(3-methylindazol-5-yl)-6-(1-phenylethylamino)-[1,2,4]triazine 97

5-[(S)-3-Isopropylpiperazin-1-yl]-3-(3-methylindazol-5-yl)-6-(1-phenylethylamino)-[1,2,4]triazine 97 was prepared using methods shown in Scheme 6, 8 and 7 wherein (S)—N1-Boc-2-isopropylpiperazine and (1-bromoethyl)benzene were used.

Preparation of 6-(2-chlorobenzylamino)-5-[(S)-3-isopropylpiperazin-1-yl]-3-(3-methylindazol-5-yl)-[1,2,4]triazine 98

6-(2-chlorobenzylamino)-5-[(S)-3-isopropylpiperazin-1-yl]-3-(3-methylindazol-5-yl)-[1,2,4]triazine 98 was prepared using methods shown in Scheme 6, 8 and 7 wherein (S)—N1-Boc-2-isopropylpiperazine and 2-chlorobenzyl bromide were used.

Preparation of 6-bis(biphenyl-2-ylmethyl)amino-5-[(S)-3-isopropylpiperazin-1-yl]-3-(3-methylindazol-5-yl)-[1,2,4]triazine 99

6-Bis(biphenyl-2-ylmethyl)amino-5-[(S)-3-isopropylpiperazin-1-yl]-3-(3-methylindazol-5-yl)-[1,2,4]triazine 99 was prepared using methods shown in Scheme 6, 8 and 7 wherein (S)—N1-Boc-2-isopropylpiperazine, excess base and excess 2-phenylbenzyl bromide were used.

Preparation of 6-bis(2-chlorobenzyl)amino-5-[(S)-3-isopropylpiperazin-1-yl]-3-(3-methylindazol-5-yl)-[1,2,4]triazine 100

6-bis(2-chlorobenzyl)amino-5-[(S)-3-isopropylpiperazin-1-yl]-3-(3-methylindazol-5-yl)-[1,2,4]triazine 100 was prepared using methods shown in Scheme 6, 8 and 7 wherein (S)—N1-Boc-2-isopropylpiperazine, excess base and excess 2-chlorobenzyl bromide were used.

Preparation of 6-(2-methoxybenzylamino)-5-[(S)-3-isopropylpiperazin-1-yl]-3-(3-methylindazol-5-yl)-[1,2,4]triazine 181

6-(2-methoxybenzylamino)-5-[(S)-3-isopropylpiperazin-1-yl]-3-(3-methylindazol-5-yl)-[1,2,4]triazine 181 as prepared using methods shown in Scheme 6, 8 and 7 wherein (S)—N1-Boc-2-isopropylpiperazine and 2-methoxybenzyl bromide were used.

Preparation of 6-(3-fluorobenzylamino)-5-[(S)-3-isopropylpiperazin-1-yl]-3-(3-methylindazol-5-yl)-[1,2,4]triazine 182

6-(3-fluorobenzylamino)-5-[(S)-3-isopropylpiperazin-1-yl]-3-(3-methylindazol-5-yl)-[1,2,4]triazine 182 was prepared using methods shown in Scheme 6, 8 and 7 wherein (S)—N1-Boc-2-isopropylpiperazine and 3-fluorobenzyl bromide were used.

Preparation of 6-bis(3-fluorobenzyl)amino-5-[(S)-3-isopropylpiperazin-1-yl]-3-(3-methylindazol-5-yl)-[1,2,4]triazine 183

6-Bis(3-fluorobenzyl)amino-5-[(S)-3-isopropylpiperazin-1-yl]-3-(3-methylindazol-5-yl)-[1,2,4]triazine 183 was prepared using methods shown in Scheme 6, 8 and 7 wherein (S)—N1-Boc-2-isopropylpiperazine, excess base and excess 3-fluorobenzyl bromide were used.

Preparation of 6-benzylamino-5-(3-methylaminopyrrolidin-1-yl)-3-(3-methylindazol-5-yl)-[1,2,4]triazine 184

6-Benzylamino-5-(3-methylaminopyrrolidin-1-yl)-3-(3-methylindazol-5-yl)-[1,2,4]triazine 184 was prepared using methods shown in Scheme 6, 8 and 7 wherein 3-(N-tert-butoxycarbonyl-N-methylamino)pyrrolidine and benzyl bromide were used.

Preparation of 6-(3-bromobenzylamino)-5-[(S)-3-isopropylpiperazin-1-yl]-3-(3-methylindazol-5-yl)-[1,2,4]triazine 185

6-(3-Bromobenzylamino)-5-[(S)-3-isopropylpiperazin-1-yl]-3-(3-methylindazol-5-yl)-[1,2,4]triazine 185 was prepared using methods shown in Scheme 6, 8 and 7 wherein (S)—N1-Boc-2-isopropylpiperazine and 3-bromobenzyl bromide were used.

Preparation of 6-bis(3-bromobenzyl)amino-5-[(S)-3-isopropylpiperazin-1-yl]-3-(3-methylindazol-5-yl)-[1,2,4]triazine 186

6-Bis(3-bromobenzyl)amino-5-[(S)-3-isopropylpiperazin-1-yl]-3-(3-methylindazol-5-yl)-[1,2,4]triazine 186 was prepared using methods shown in Scheme 6, 8 and 7 wherein (S)—N1-Boc-2-isopropylpiperazine, excess base and excess 3-bromobenzyl bromide were used.

Preparation of 6-(3-methoxybenzylamino)-5-[(S)-3-isopropylpiperazin-1-yl]-3-(3-methylindazol-5-yl)-[1,2,4]triazine 187

6-(3-Methoxybenzylamino)-5-[(S)-3-isopropylpiperazin-1-yl]-3-(3-methylindazol-5-yl)-[1,2,4]triazine 187 was prepared using methods shown in Scheme 6, 8 and 7 wherein (S)—N1-Boc-2-isopropylpiperazine and 3-methoxybenzyl bromide were used.

Preparation of 6-(3-nitrobenzylamino)-5-[(S)-3-isopropylpiperazin-1-yl]-3-(3-methylindazol-5-yl)-[1,2,4]triazine 188

6-(3-Nitrobenzylamino)-5-[(S)-3-isopropylpiperazin-1-yl]-3-(3-methylindazol-5-yl)-[1,2,4]triazine 188 was prepared using methods shown in Scheme 6, 8 and 7 wherein (S)—N1-Boc-2-isopropylpiperazine and 3-nitrobenzyl bromide were used.

Akt1 Kinase Assay

The assay described below measures the phosphorylation of a biotinylated peptide by active recombinant Akt1 and other kinase isoforms. The biotinylated peptide contains a consensus sequence derived from Akt substrate Gsk3 (Glycogen synthase kinase 3). The $^{33}$P-labeled peptide substrate was captured by streptavidin-coated Flash plates.

Enzyme and Substrate

Active recombinant Akt1 was expressed in Sf9 insect cells and purified as described by Kumar et al., *Biochim. Biophys. Acta*. Jun. 15, 2001, 1526(3), 257-268. Biotinylated peptide of the sequence Bio-ahx-RPRAASF was purchased from Syn Pep (Dublin, Calif., USA).

Cloning and Expression of Human Akt1 Sf9 Cells

Human Akt1 cDNA was amplified from a marathon-ready human lung cDNA library (Clonetech) using nested oligo primers as described below. The first round of amplification was carried out using the following primers; Akt1F1 (ATCAGAGGCTGTGGCCAGGCCAGCTGG) and Akt1R1 (TCCATC CCTCCAAGCGACGTGGCTATTG) and for the second round amplification, the primers of the following sequence were used; Akt1F2 (GGATCCTCGG GCACCATGAGCGACGTGGCTATTG) and AKT1R2 (GGTACCATCGTC CAGCCAGTCCACCGCCGCCTCA). The PCR product was subcloned into pCRScript plasmid as a BamHI/KpnI fragment and the sequence of the cDNA was confirmed by DNA sequencing. This plasmid was used as a template for reamplification of Akt1 using appropriate primers for subcloning into pBlueBaHis2B into BamH1/EcoRI sites to generate an in frame fusion to (His)$_6$ tag and an anti-Xpress antibody epitope tag at the N-terminus. This construct was sequenced to verify the junction sequences and used for generating a recombinant baculovirus. Growth of the recombinant virus, amplification and determination of viral titer were carried out according to the instructions from the manufacturer (InVitrogen, CA).

Purification of Akt1 from Sf9 Cells

Viral stocks were used to infect large scale Sf9 cells at a multiplicity of infection (MOI) of 2.5. Cells were maintained at 27° C. for 60 h and okadaic acid was added to the cultures to a concentration of 50 nM. Cells were harvested 4 h hours later by centrifugation at 1200 rpm for 30 min followed by freezing at −80° C. until further use. All purification steps were carried out at 4° C. Whole cell pellets were suspended in buffer A (20 mM sodium phosphate buffer pH 7.8, 500 mM NaCl, 1 mM sodium vanadate, 5 mM sodium fluoride, 40 mM β-glycerophosphate, 10 mM imidazole and protease inhibitor cocktail) and lysed using a microfluidizer. The cell extract was centrifuged at 16,000×g for 10 min to remove the debris and directly loaded onto Ni-NTA Superflow resin using a FPLC pump operated at 1 ml/min. The column was washed once with buffer A, once with wash buffer B (20 mM sodium phosphate pH 6.0, 1 mM sodium vanadate, 5 mM sodium fluoride and protease cocktail) and once with wash buffer B containing 0.05% Tween-20 followed by washing with buffer A until $OD_{260}$ returned to basal level. Proteins were eluted with buffer A containing 200 mM imidazole. Fractions were analyzed by electrophoresis on 10% denaturing polyacrylamide gels and fractions containing 85% pure protein band at 60 KDa were pooled and dialyzed against buffer C (20 mM Tris-HCl pH 7.5, 0.5 mM EDTA,-2 mM DTT, 145 mM NaCl, 0.1 mM sodium vanadate, 5 mM sodium fluoride, 10 mM, β-glycerophosphate and 20% glycerol). Purified protein was stored as aliquots at −80° C. Protein concentrations were determined using BCA protein assay reagent A (Catalog #23228). To examine the identity of the proteins, 2 μg of purified protein was electrophoresed on SDS-polyacrylamide gels and stained with coomassie blue dye or transferred to nitrocellulose membrane and probed with anti-Akt and anti-phospho-specific Akt antibodies using enhanced chemiluminescence (ECL) reagent according to the protocol described by the manufacturer (Amersham).

Kinase Assays

The kinase assay was performed in 96 well plates at room temperature. Assay solutions and plates were preincubated at room temperature for 5 min. To each well, we added 10 μL of peptide solution (5 μM) in kinase buffer (50 mM Tris-HCl pH 7.5, 10 mM $MgCl_2$, 1 mM Tris [2-Carboxyethyl] phosphine hydrochloride (TCEP) and 0.1 mM sodium ortho vanadate, 0.02% bovine serum albumin). The kinase buffer (10 μL) was dispensed to each well of a 96 well plate. Purified Akt1 was diluted to the proper concentration in kinase buffer and 10 μL of the diluted enzyme was dispensed to each well. Compounds diluted appropriately in reaction buffer containing 10% $Me_2SO$ were also dispensed in 10 μL aliquots. The reactions were started by adding 10 μL of ATP solution containing 5 μM ATP and 0.25 μCi of $[\gamma-^{33}P]$ATP in kinase buffer. The final concentrations of the components are, 1 μM biotinylated peptide, 200 ng of Akt1 enzyme, 0.25 μCi of $[\gamma-^{33}P]$-ATP, 2 μM cold ATP, 50 mM Tris-HCl pH 7.5, 10 mM $MgCl_2$, 1 mM TCEP, 0.02% bovine serum albumin, 2% $Me_2SO$ and 0.1 mM sodium vanadate. The plates were incubated at room temperature for 2 hr and at the end of the incubation, reactions were stopped by adding 200 μL of stop solution containing 1 mM ATP, 5 mM EDTA in phosphate buffered saline followed by transferring of 200 μL of the mixture to streptavidin-coated flash plates. Biotinylated peptides were allowed to bind to the flash plates for one hour at room temperature followed by two rinses with wash buffer. Plates were counted using a Top Count instrument.

CDK2 Assays

Baculovirus Constructions:

Cyclins A and E were cloned into pFASTBAC (Invitrogen) by PCR, with the addition of a GluTAG sequence (EYMPME) at the amino-terminal end to allow purification on anti-GluTAG affinity columns. The expressed proteins are approximately 46kDa (cyclin E) and 50kDa (cyclin A) in size. CDK2 was also cloned into pFASTBAC by PCR, with the addition of a haemaglutinin epitope tag at the carboxy-terminal end (YDVPDYAS). The expressed protein is approximately 34kDa in size.

Enzyme Production:

Recombinant baculoviruses expressing cyclins A, E and CDK2 were infected into Sf9 cells at a multiplicity of infection (MOI) of 5, for 48 hrs. Cells are harvested by centrifugation at 1000 RPM for 10 minutes. Cyclin-containing (E or A) pellets were combined with CDK2 containing cell pellets and lysed on ice for 30 minutes in five times the pellet volume of lysis buffer containing 50 mM Tris pH 8.0, 0.5% NP40, 1mM DTT and protease/phosphatase inhibitors (Roche Diagnostics GmbH, Mannheim, Germany). Mixtures were stirred for 30-60 minutes to promote cyclin-CDK2 complex formation. Mixed lysates were then spun down at 15000 RPM for 10 minutes and the supernatant retained. 5 mL of anti-GluTAG beads (for one liter of Sf9 cells) were then used to capture cyclin-CDK2 complexes. Bound beads were washed three times in lysis buffer. Proteins were competitively eluted with lysis buffer containing 100-200 μg/mL of the GluTAG peptide. Eluate was dialyzed overnight in 2 liters of kinase buffer containing 50 mM Tris pH 8.0, 1 mM DTT, 10 mM $MgCl_2$, 100 μM sodium orthovanadate and 20% glycerol. Enzyme was stored in aliquots at −70° C.

In Vitro Kinase Assay:

CDK2 kinase assays (either cyclin A or E-dependent) were performed in low protein binding 96-well plates (Corning Inc, Corning, N.Y.). Enzyme was diluted to a final concentration of 50 μg/mL in kinase buffer containing 50 mM Tris pH 8.0, 10 mM $MgCl_2$, 1 mM DTT, and 0.1 mM sodium orthovanadate. The substrate used in these reactions was a biotinylated peptide derived from Histone H1 (from Amersham, UK). The substrate was thawed on ice and diluted to 2 μM in kinase buffer. Compounds were diluted in 10% DMSO to desirable concentrations. For each kinase reaction, 20 μl of the 50 μg/mL enzyme solution (1 μg of enzyme) and 20 μL of the 1 μM substrate solution were mixed, then combined with 10 μL of diluted compound in each well for testing. The kinase reaction was started by addition of 50 μL of 4 μM ATP and 1 μCi of 33P-ATP (from Amersham, UK). The reaction was allowed to run for 1 hour at room temperature. The reaction was stopped by adding 200 μL of stop buffer containing 0.1% Triton X-100, 1 mM ATP, 5 mM EDTA, and 5 mg/mL streptavidine coated SPA beads (from Amersham, UK) for 15 minutes. The SPA beads were then captured onto a 96-well GF/B filter plate (Packard/Perkin Elmer Life Sciences) using a Filtermate universal harvester (Packard/Perkin Elmer Life Sciences.). Non-specific signals were eliminated by washing the beads twice with 2M NaCl then twice with 2 M NaCl with 1% phosphoric acid. The radioactive signal was then measured using a TopCount 96 well liquid scintillation counter (from Packard/Perkin Elmer Life Sciences).

$IC_{50}$ Determination

Dose-response curves were plotted from inhibition data generated each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values are derived by non-linear regression analysis.

Compounds 3, 5, 7, 8, 10, 12, 13, 16, 20, 23, and 24, described above, exhibited greater than 90% inhibition of Akt1 when assayed at a concentration of 1.1 mcg/mL.

$IC_{50}$ values of the compounds of Formula I of the present invention, are set forth in the Table below. The $IC_{50}$ values (AKT1 inhibition) are rated, "A" for $IC_{50}$ values less than about 100 nanomolar (nM) (<100 nM), "B" for $IC_{50}$ values in the range of from about 100 to about 1000 nM (100 nM-1000 nM), and "C" for $IC_{50}$ values greater than 1000 nM (>1000 nM).

| Compound Number | STRUCTURE | IC$_{50}$ rating |
|---|---|---|
| 1 | 3-(3-methyl-1H-indazol-5-yl)-5-(piperazin-1-yl)-1,2,4-triazin-6-amine | B |
| 2 | 6-amino-3-(3-methyl-1H-indazol-5-yl)-1,2,4-triazin-5-ol | C |
| 3 | 3-(3-methyl-1H-indazol-5-yl)-N-benzyl-6-(piperazin-1-yl)-1,2,4-triazin-5-amine | A |
| 4 | 3-(3-methyl-1H-indazol-5-yl)-N,N-dibenzyl-6-(piperazin-1-yl)-1,2,4-triazin-5-amine | C |
| 5 | 5-[(3S)-3-benzylpiperazin-1-yl]-3-(3-methyl-1H-indazol-5-yl)-1,2,4-triazin-6-amine | A |
| 6 | 3-(3-methyl-1H-indazol-5-yl)-5-[(3S)-3-phenylpiperazin-1-yl]-1,2,4-triazin-6-amine | B |
| 7 | 5-[(3S)-3-isopropylpiperazin-1-yl]-3-(3-methyl-1H-indazol-5-yl)-1,2,4-triazin-6-amine | A |

-continued
| Compound Number | STRUCTURE | IC$_{50}$ rating |
|---|---|---|
| 8 | 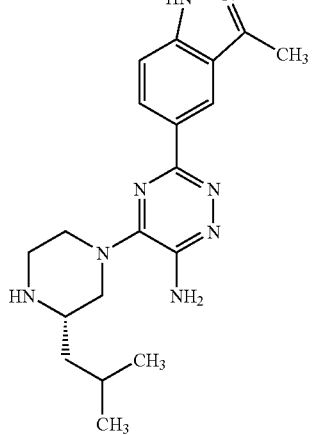 | A |
| 9 | 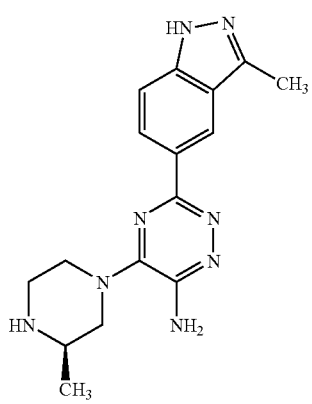 | C |
| 10 | 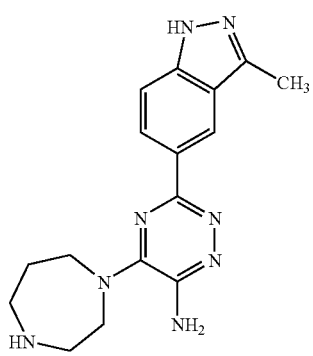 | B |
| 11 | 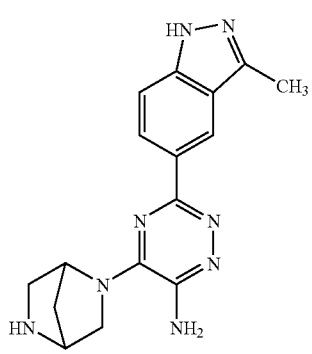 | C |
-continued
| Compound Number | STRUCTURE | IC$_{50}$ rating |
|---|---|---|
| 12 | 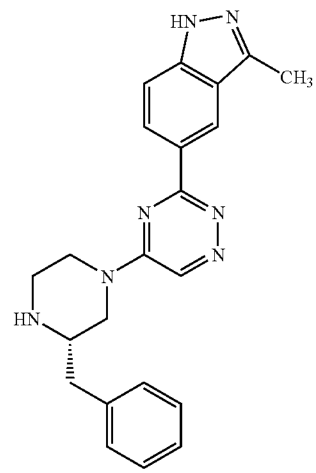 | A |
| 13 | 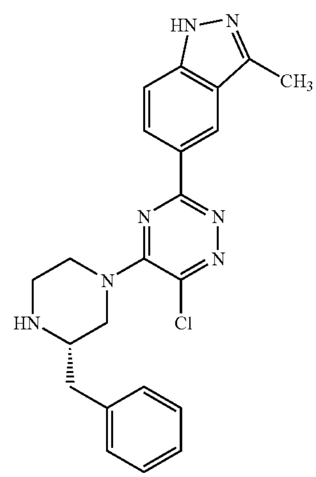 | A |
| 14 | 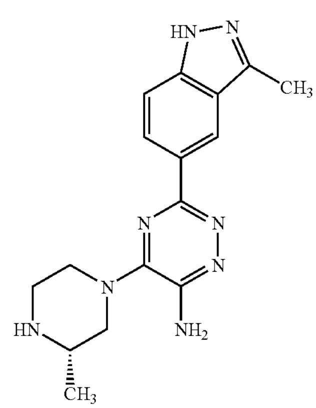 | B |

US 7,528,132 B2
139 140
-continued
| Compound Number | STRUCTURE | IC$_{50}$ rating |
|---|---|---|
| 15 | 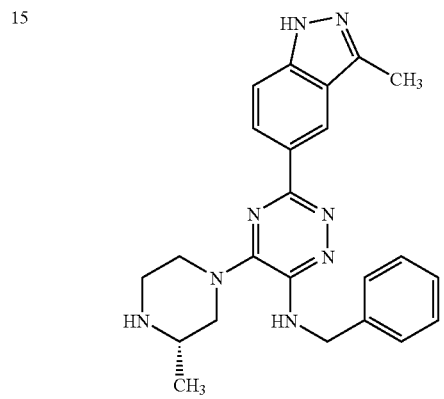 | B |
| 16 | 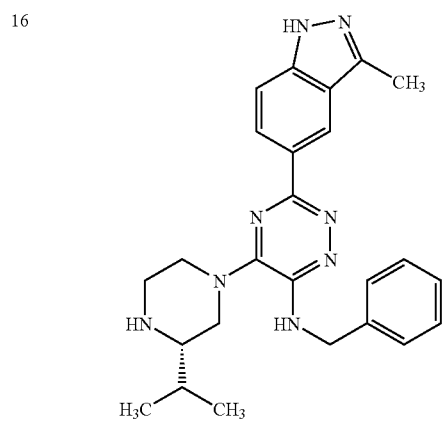 | A |
| 17 | 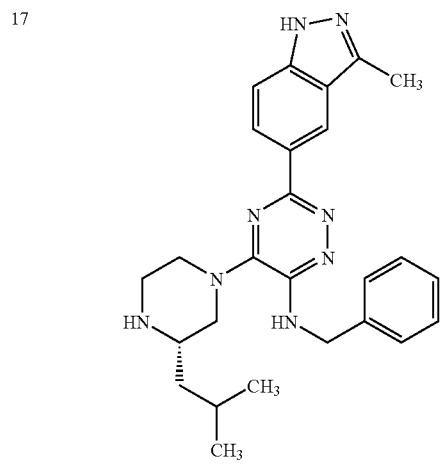 | C |
-continued
| Compound Number | STRUCTURE | IC$_{50}$ rating |
|---|---|---|
| 18 | 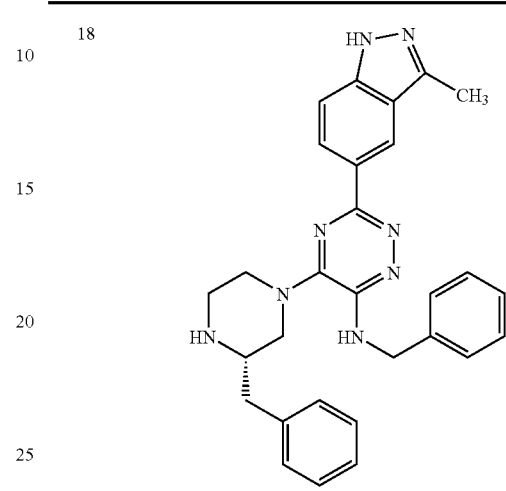 | C |
| 19 | 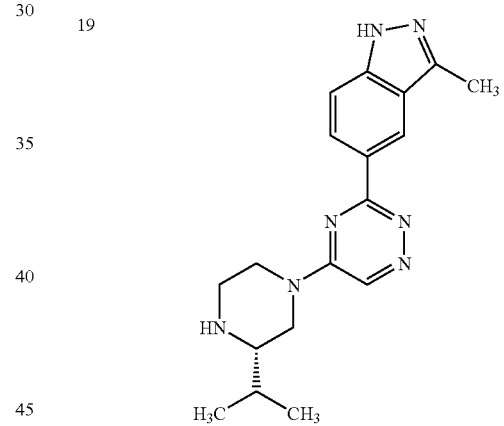 | A |
| 20 | 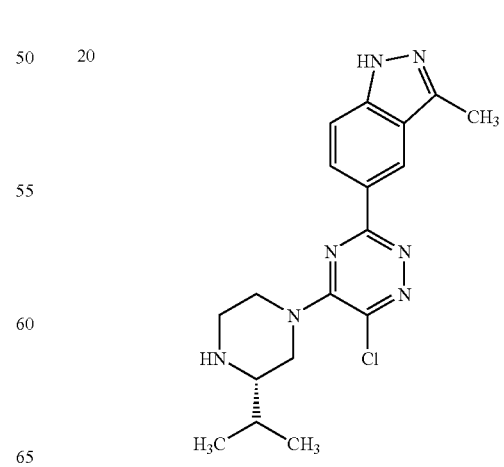 | A |

-continued
| Compound Number | STRUCTURE | IC$_{50}$ rating |
|---|---|---|
| 21 | 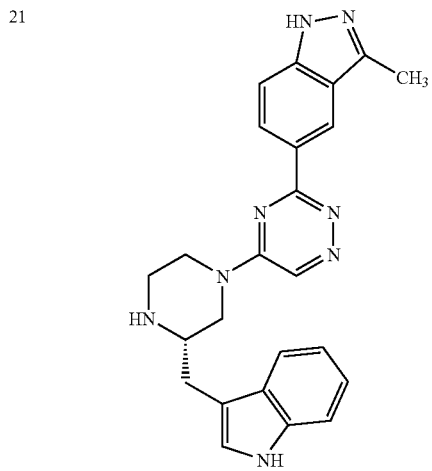 | B |
| 22 | 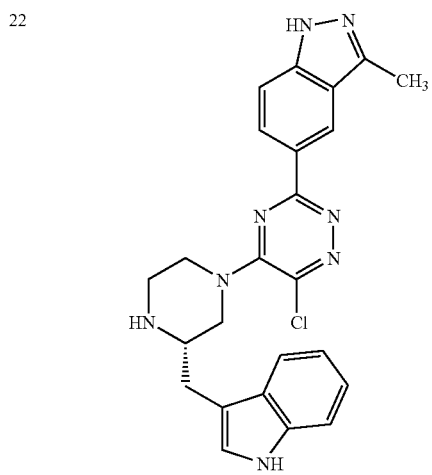 | C |
| 23 | 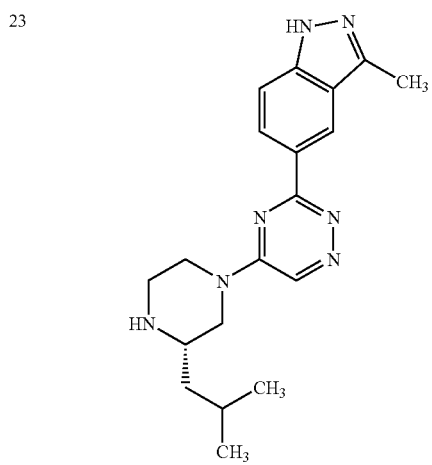 | A |
-continued
| Compound Number | STRUCTURE | IC$_{50}$ rating |
|---|---|---|
| 24 | 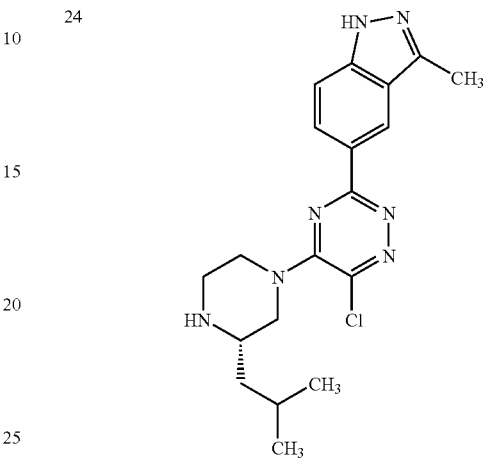 | A |
| 25 | 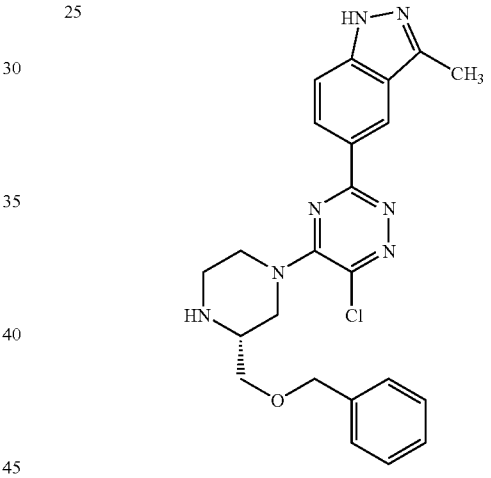 | C |
| 26 | 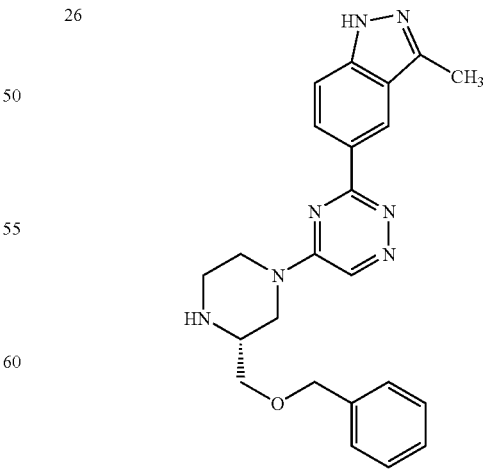 | C |

-continued
| Compound Number | STRUCTURE | IC$_{50}$ rating |
|---|---|---|
| 27 | 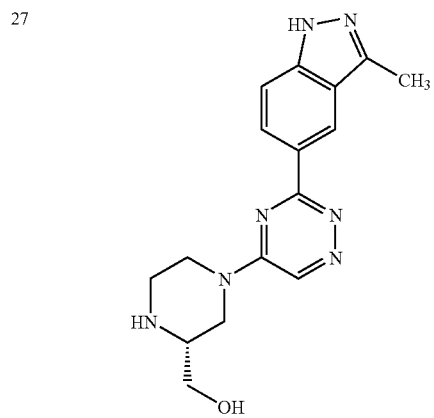 | C |
| 28 | 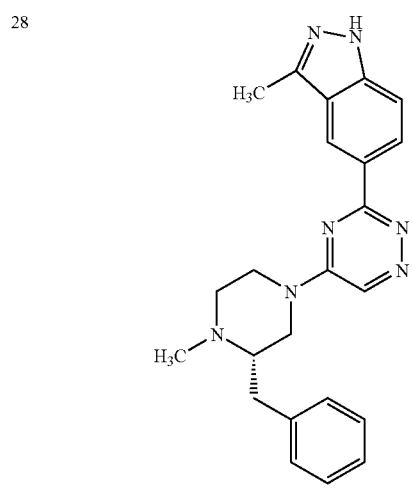 | A |
| 29 | 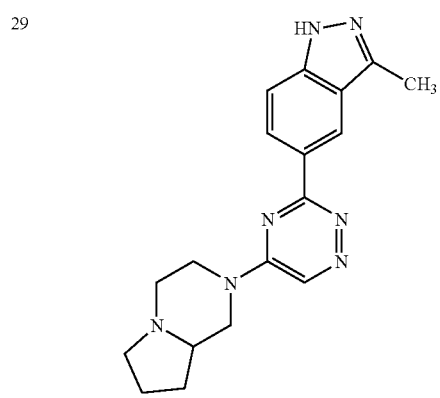 | C |
-continued
| Compound Number | STRUCTURE | IC$_{50}$ rating |
|---|---|---|
| 30 | 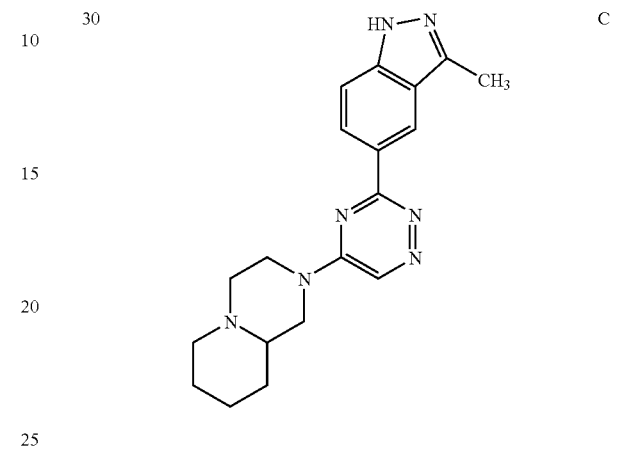 | C |
| 31 | 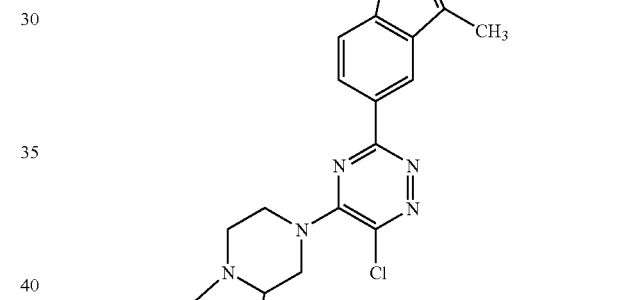 | C |
| 32 | 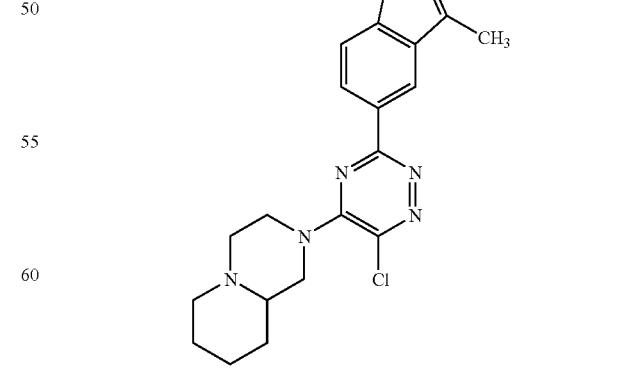 | C |

-continued
| Compound Number | STRUCTURE | IC$_{50}$ rating |
|---|---|---|
| 33 | 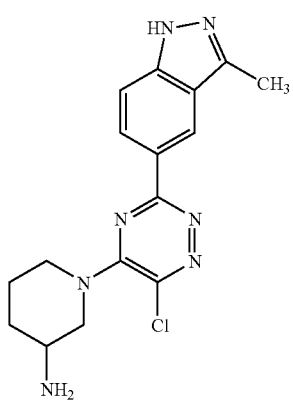 | B |
| 34 | 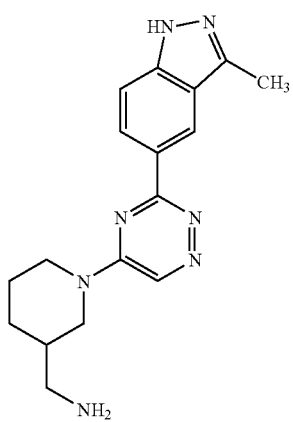 | B |
| 35 | 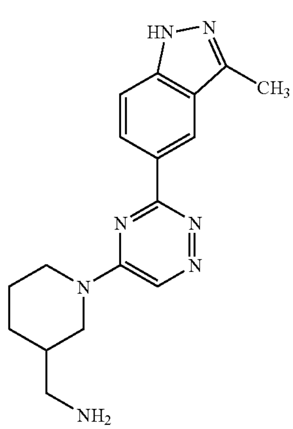 | C |
-continued
| Compound Number | STRUCTURE | IC$_{50}$ rating |
|---|---|---|
| 36 | 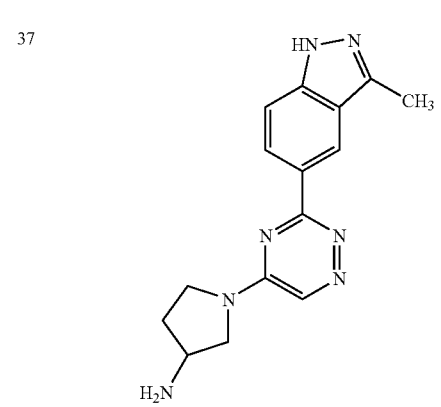 | B |
| 37 | 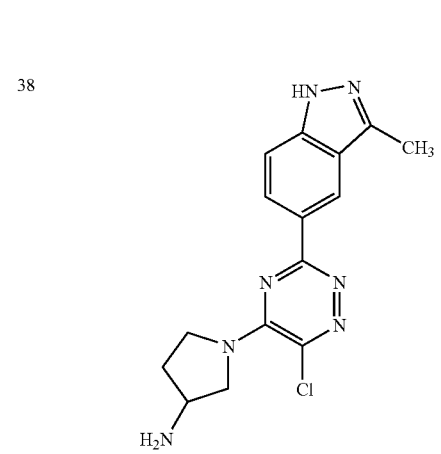 | B |
| 38 | 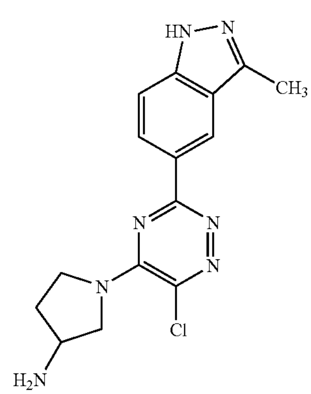 | A |

-continued
| Compound Number | STRUCTURE | IC$_{50}$ rating |
|---|---|---|
| 39 | 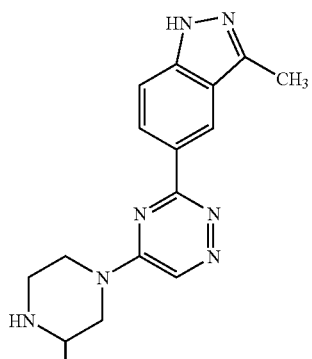 | C |
| 40 | 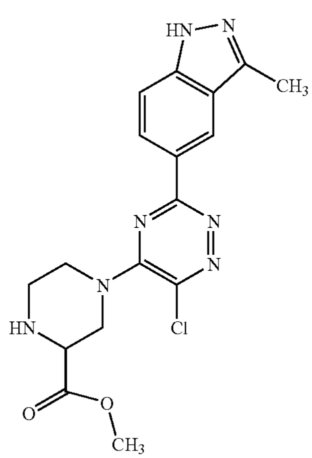 | C |
| 41 | 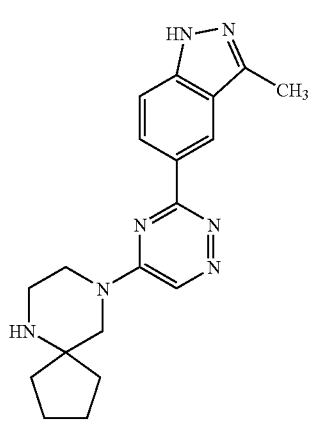 | B |
-continued
| Compound Number | STRUCTURE | IC$_{50}$ rating |
|---|---|---|
| 42 | 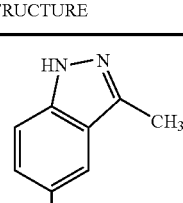 | B |
| 43 | 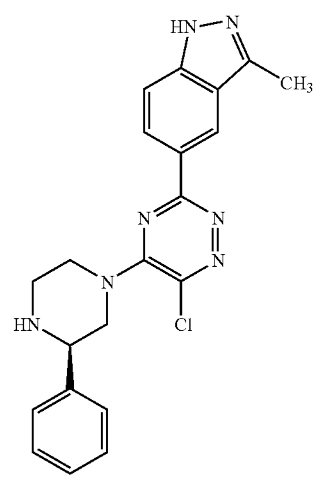 | B |
| 44 | 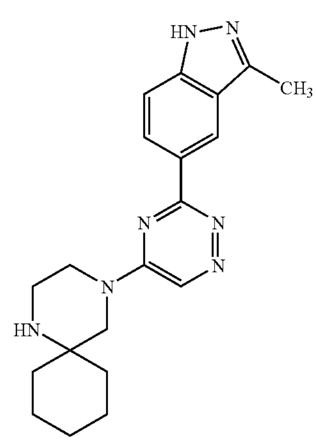 | A |

-continued
| Compound Number | STRUCTURE | IC$_{50}$ rating |
|---|---|---|
| 45 | 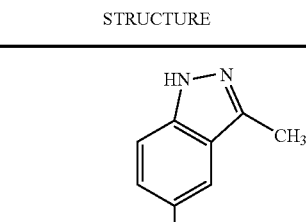 | A |
| 46 | 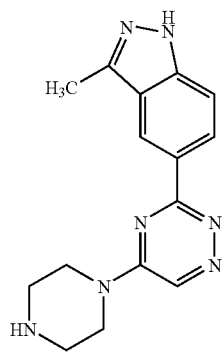 | B |
| 47 | 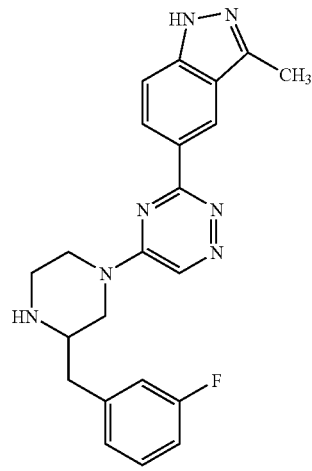 | A |
-continued
| Compound Number | STRUCTURE | IC$_{50}$ rating |
|---|---|---|
| 48 | 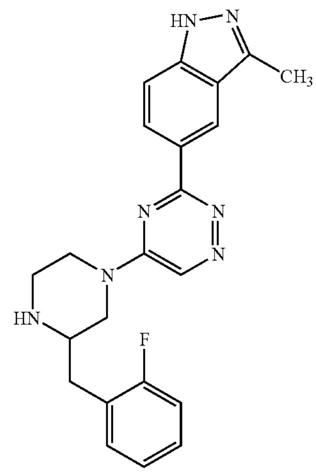 | A |
| 49 | 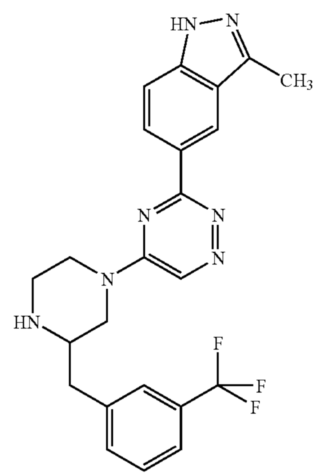 | C |
| 50 | 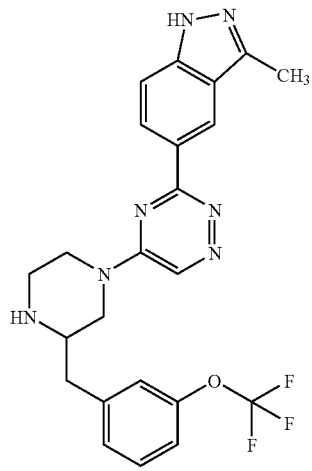 | C |

-continued
| Compound Number | STRUCTURE | IC$_{50}$ rating |
|---|---|---|
| 51 | 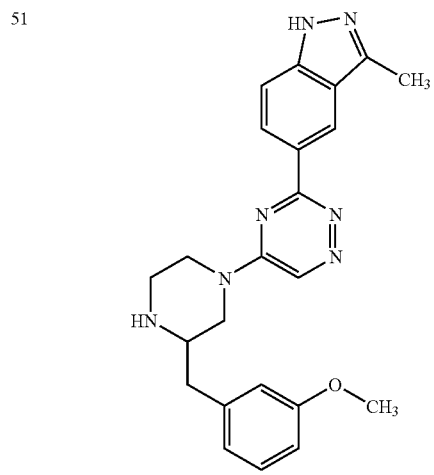 | B |
| 52 | 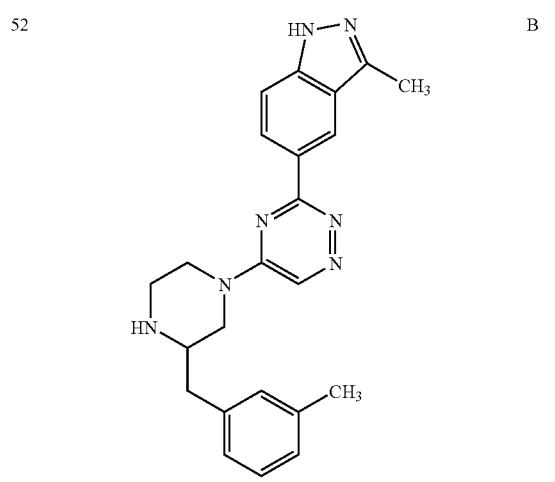 | B |
| 53 | 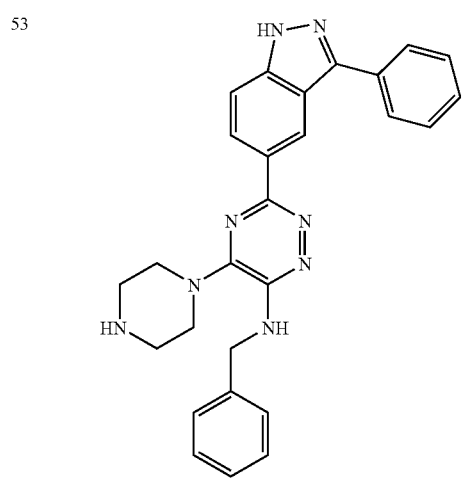 | C |
-continued
| Compound Number | STRUCTURE | IC$_{50}$ rating |
|---|---|---|
| 54 | 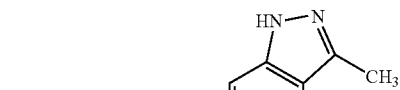 | B |
| 55 | 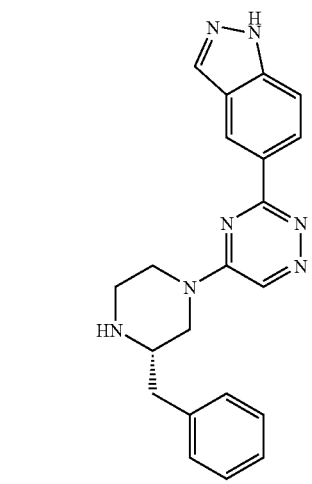 | A |
| 56 | 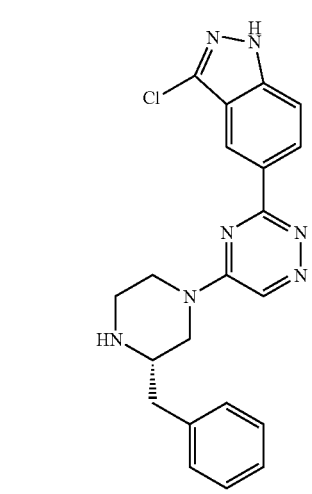 | A |

-continued

| Compound Number | STRUCTURE | IC$_{50}$ rating |
|---|---|---|
| 57 | 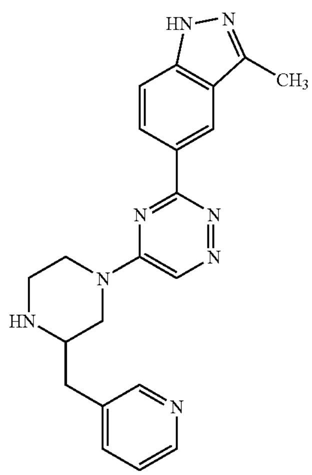 | B |
| 58 | 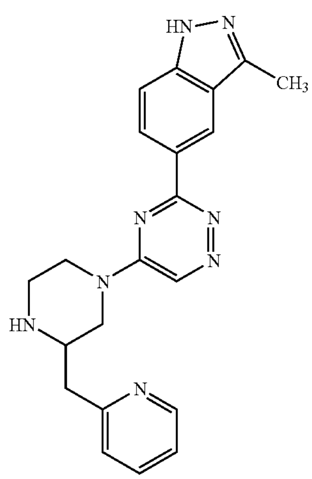 | C |
| 59 | 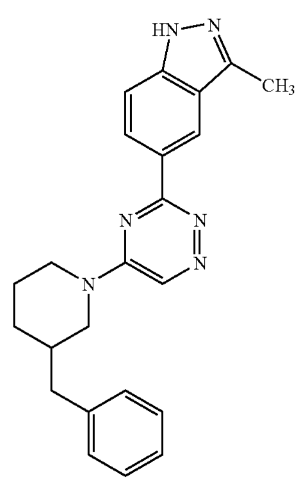 | B |
| 60 | | B |
| 61 | | A |
| 62 | | B |

-continued
| Compound Number | STRUCTURE | IC$_{50}$ rating |
|---|---|---|
| 63 | 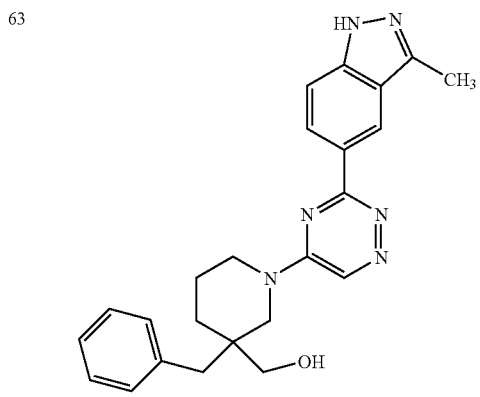 | B |
| 64 | 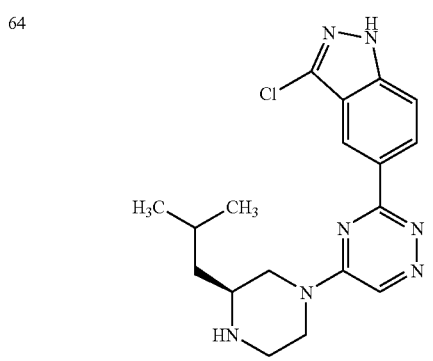 | A |
| 65 | 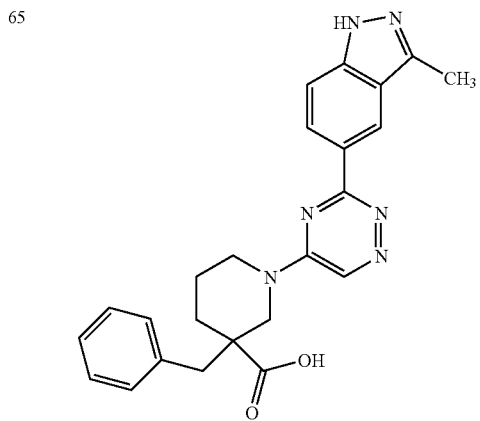 | C |
-continued
| Compound Number | STRUCTURE | IC$_{50}$ rating |
|---|---|---|
| 66 | 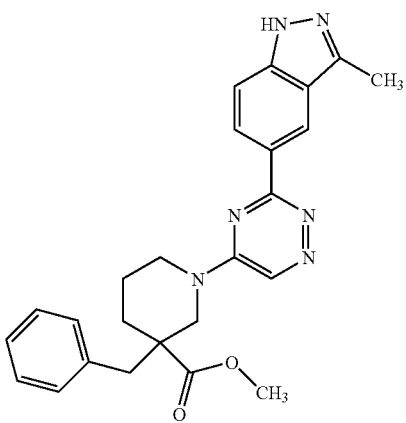 | C |
| 67 | 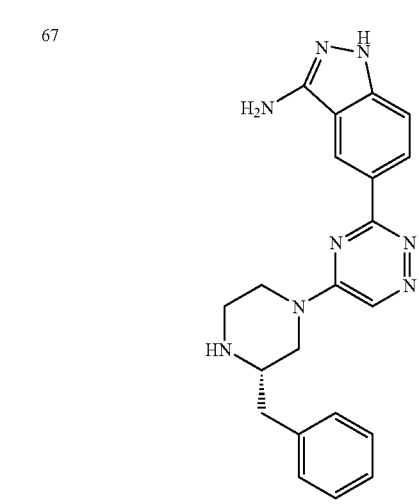 | C |
| 68 | 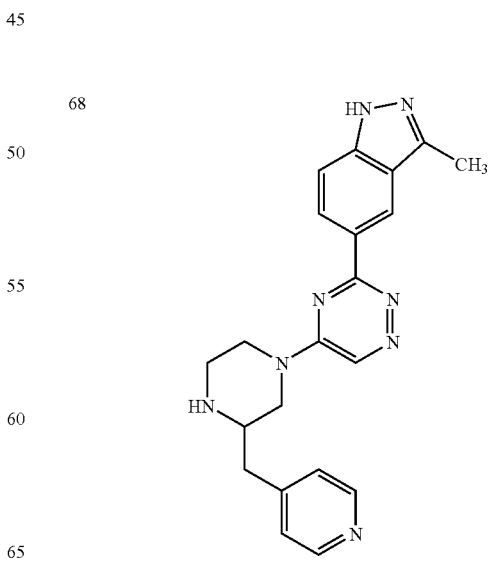 | B |

-continued
| Compound Number | STRUCTURE | IC$_{50}$ rating |
|---|---|---|
| 69 | 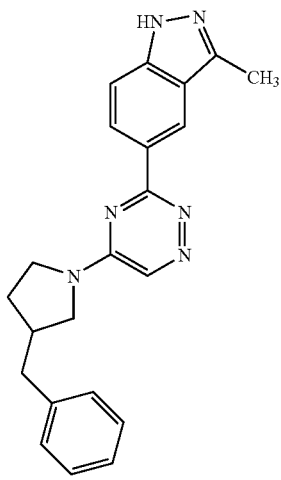 | B |
| 70 | 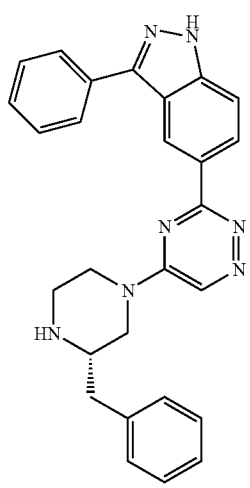 | C |
| 71 | 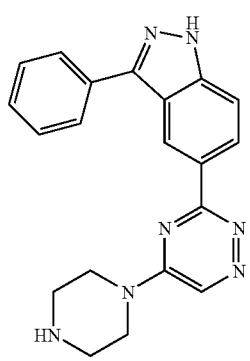 | B |
-continued
| Compound Number | STRUCTURE | IC$_{50}$ rating |
|---|---|---|
| 72 | 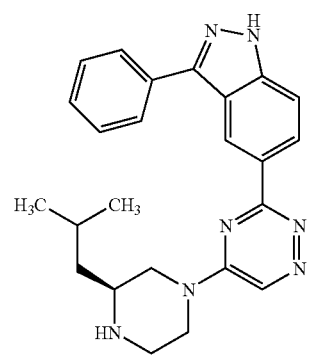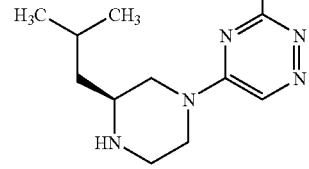 | C |
| 73 | 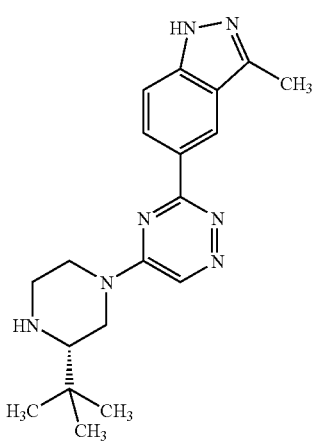 | B |
| 74 | 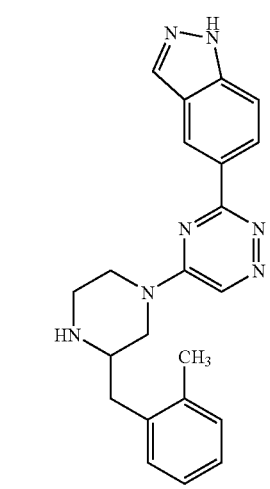 | B |

-continued

| Compound Number | STRUCTURE | IC$_{50}$ rating |
|---|---|---|
| 75 | 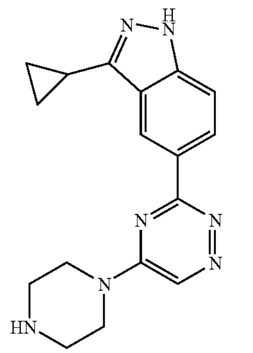 | C |
| 76 | 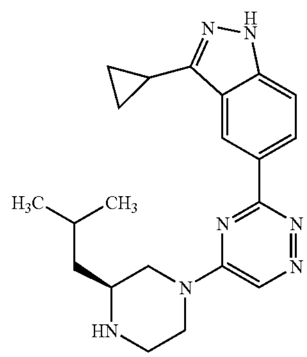 | B |
| 77 | 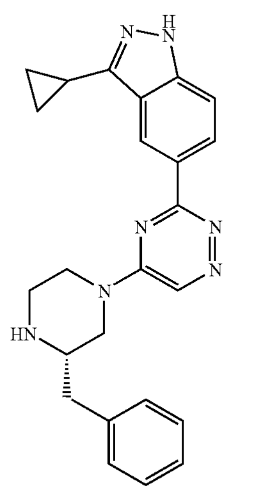 | B |
| 78 | 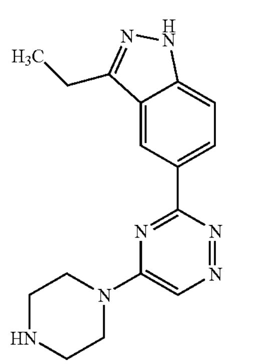 | C |
| 79 | 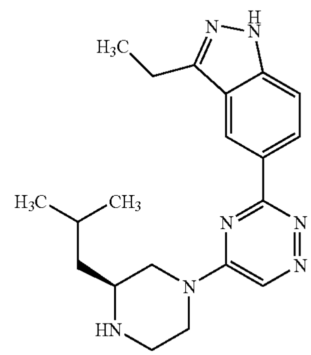 | B |
| 80 | 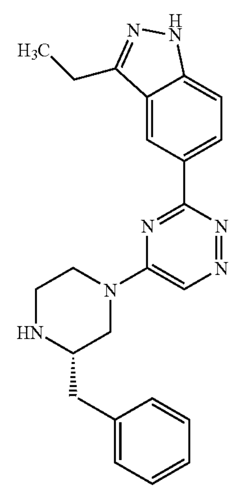 | A |
| 81 | 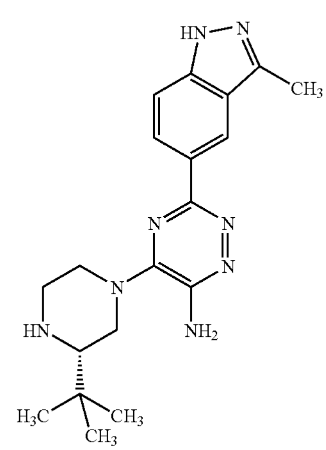 | A |

| Compound Number | STRUCTURE | IC$_{50}$ rating |
|---|---|---|
| 82 | 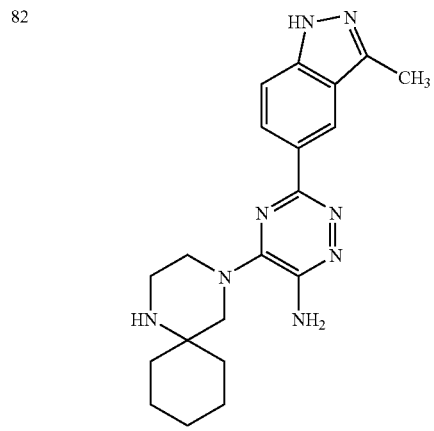 | B |
| 83 | 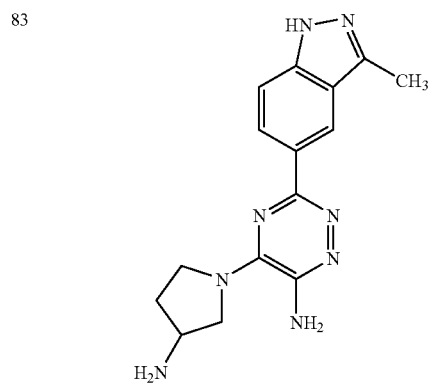 | B |
| 84 | 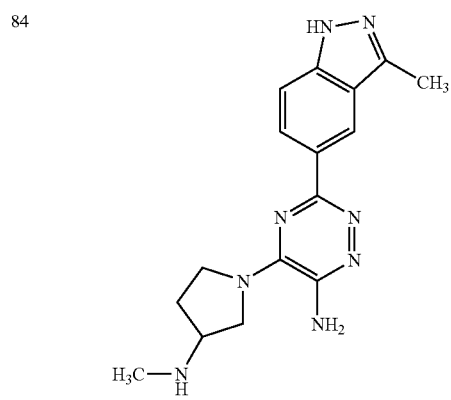 | B |
| Compound Number | STRUCTURE | IC$_{50}$ rating |
|---|---|---|
| 85 | 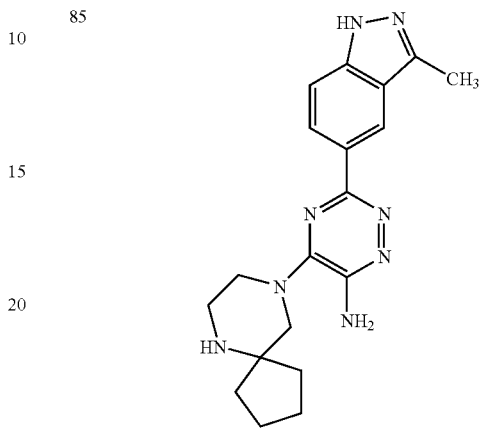 | B |
| 86 | 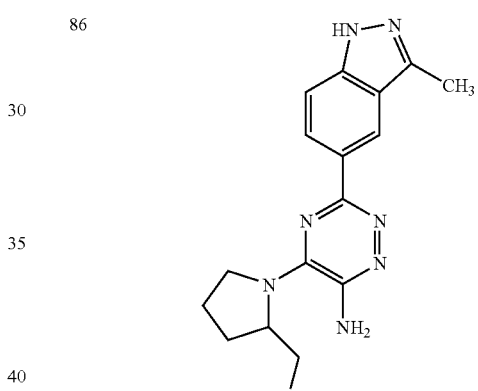 | C |
| 87 | 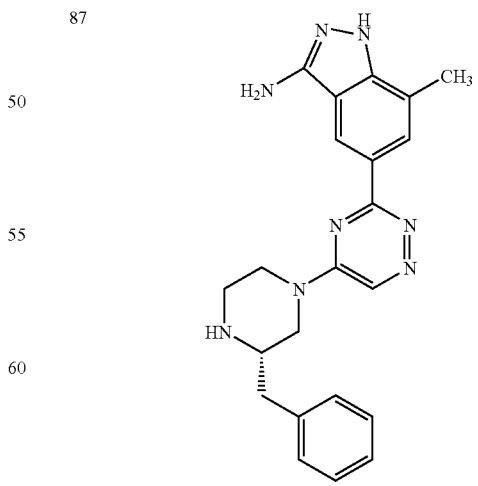 | C |

-continued
| Compound Number | STRUCTURE | IC$_{50}$ rating |
|---|---|---|
| 88 | 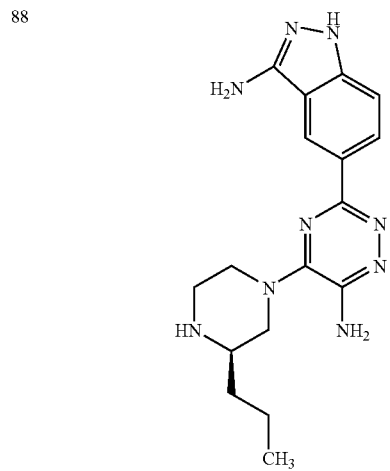 | B |
| 89 | 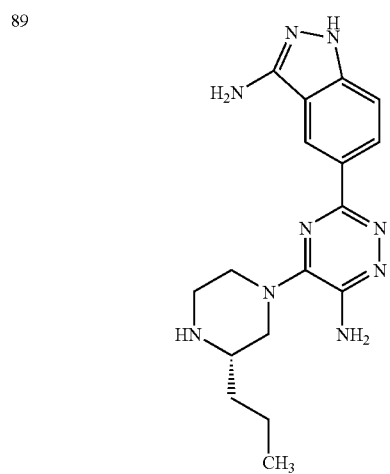 | A |
| 90 | 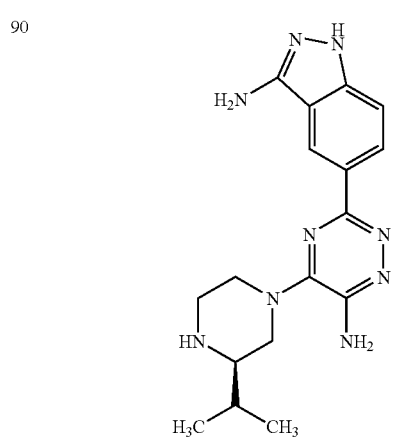 | B |
-continued
| Compound Number | STRUCTURE | IC$_{50}$ rating |
|---|---|---|
| 91 | 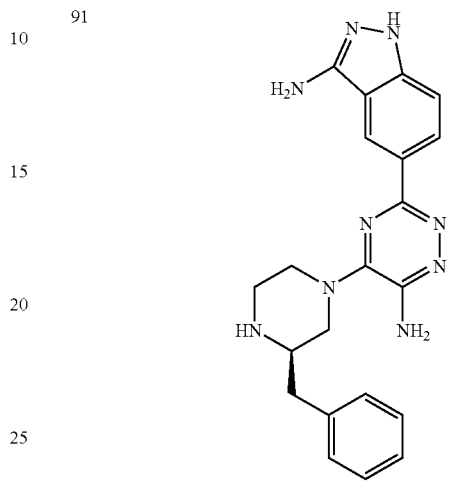 | B |
| 92 | 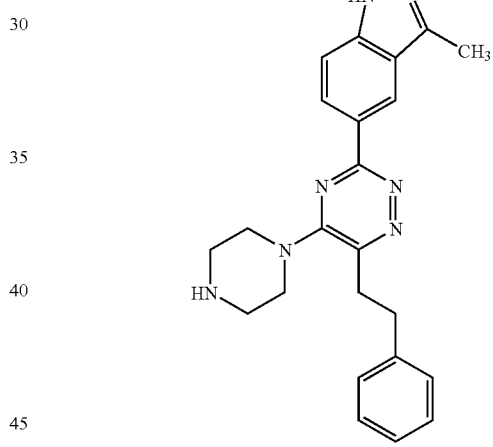 | A |
| 93 | 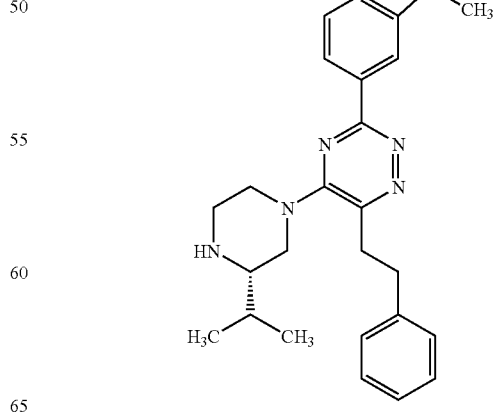 | A |

-continued
| Compound Number | STRUCTURE | IC$_{50}$ rating |
|---|---|---|
| 94 | 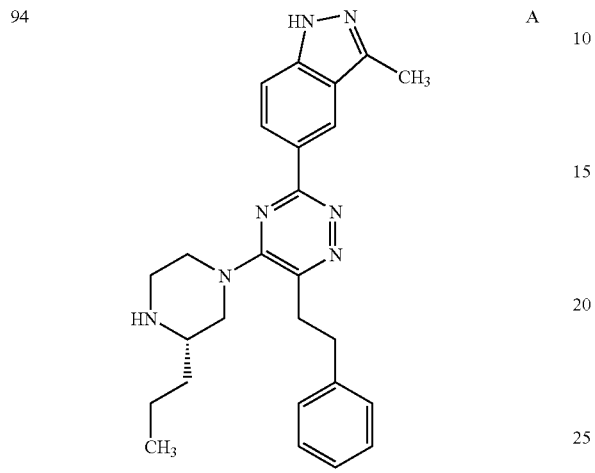 | A |
| 95 | 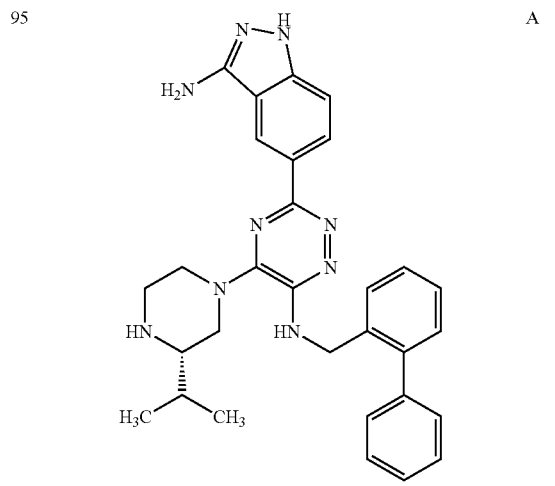 | A |
| 96 | 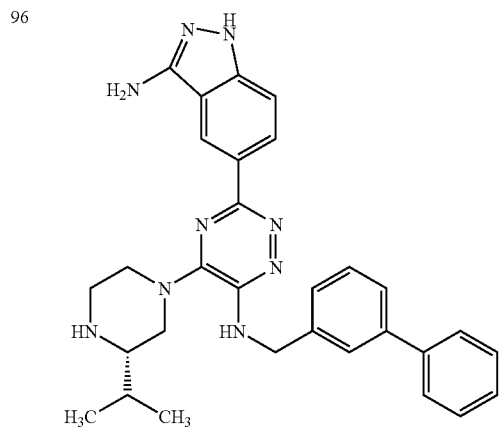 | B |
-continued
| Compound Number | STRUCTURE | IC$_{50}$ rating |
|---|---|---|
| 97 | 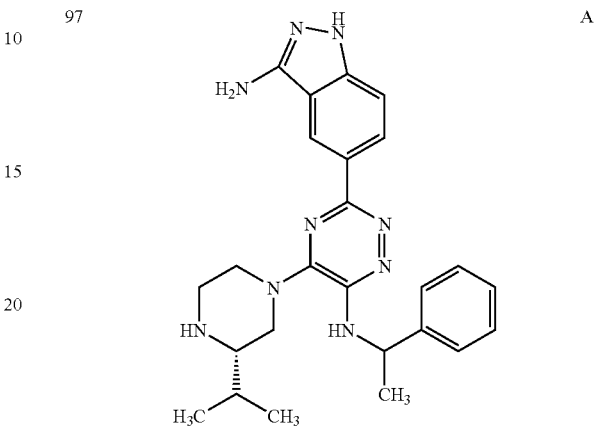 | A |
| 98 | 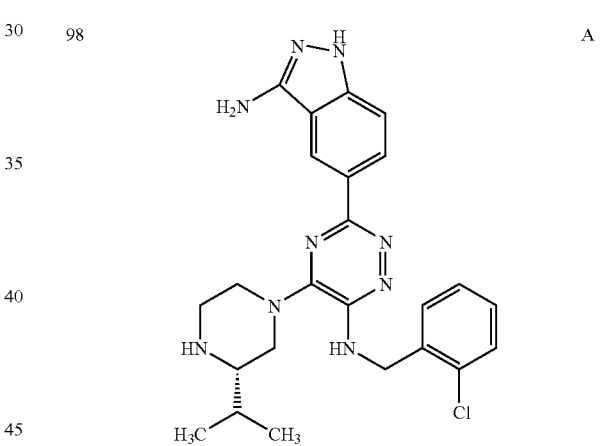 | A |
| 99 | 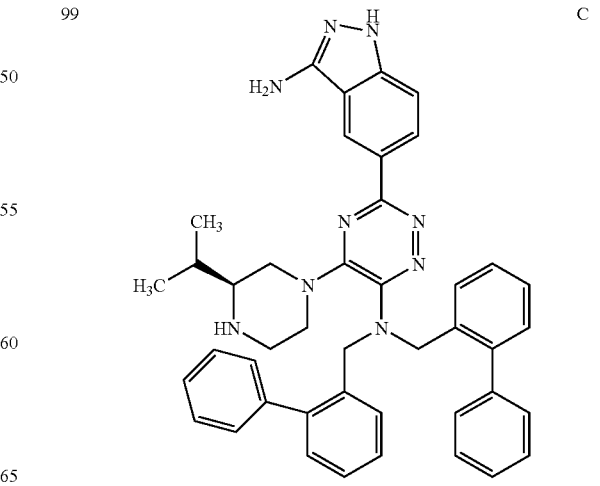 | C |

-continued
| Compound Number | STRUCTURE | IC$_{50}$ rating |
|---|---|---|
| 100 | 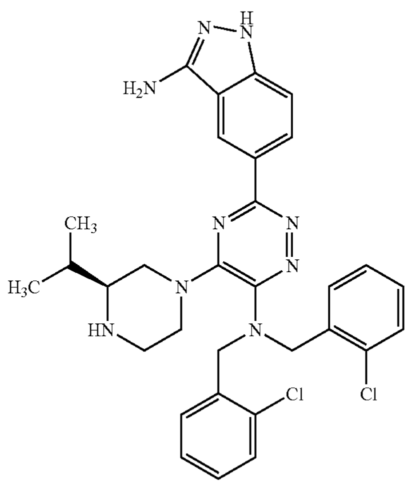 | B |
| 181 | 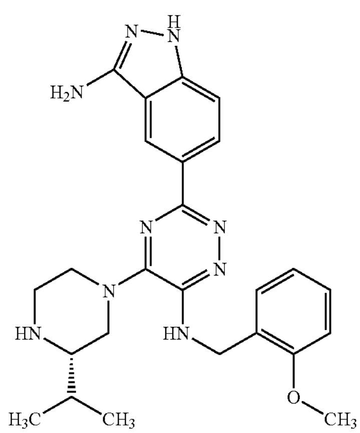 | A |
| 182 | 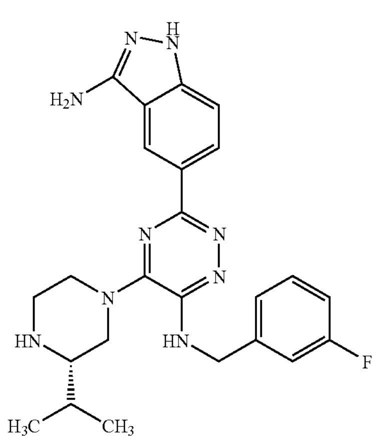 | A |
-continued
| Compound Number | STRUCTURE | IC$_{50}$ rating |
|---|---|---|
| 183 | 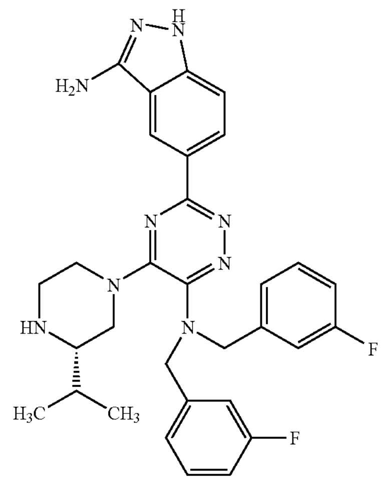 | C |
| 184 | 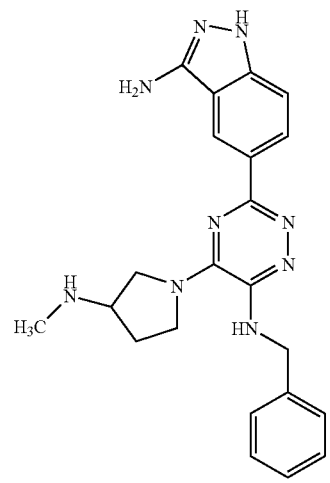 | B |
| 185 | 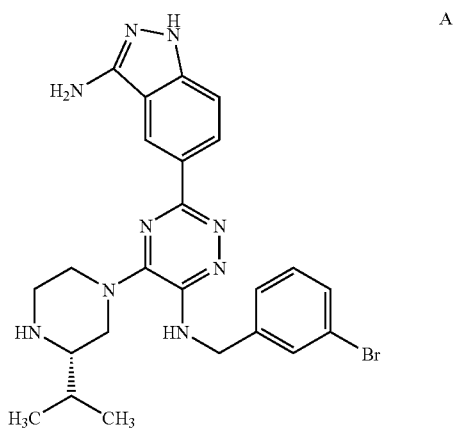 | A |

-continued
| Compound Number | STRUCTURE | IC$_{50}$ rating |
|---|---|---|
| 186 | 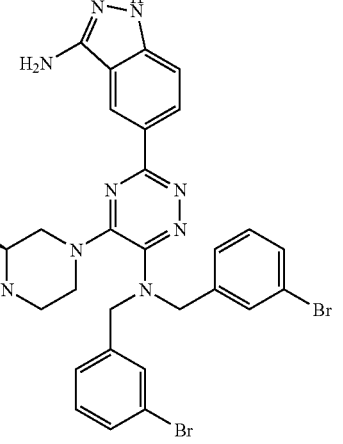 | C |
| 187 | 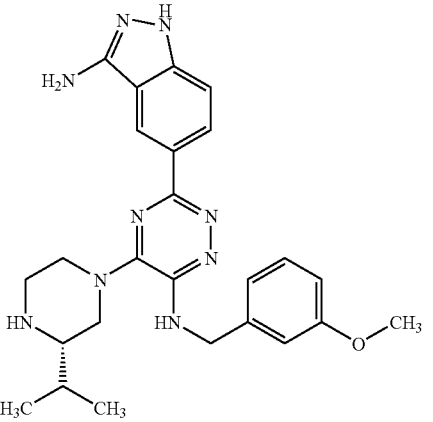 | A |
| 188 | 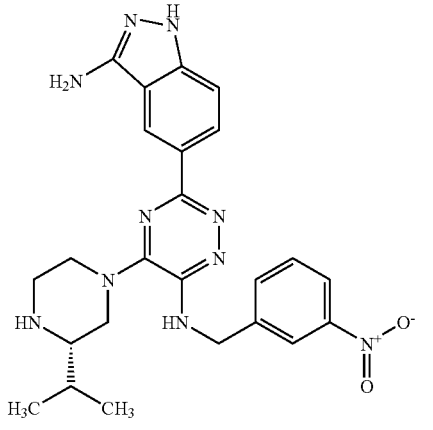 | B |
The Table below sets forth some representative compounds with their specific IC$_{50}$ (AKT1 inhibition) values:
| Compound Number | STRUCTURE | IC$_{50}$ (nM) |
|---|---|---|
| 12 | 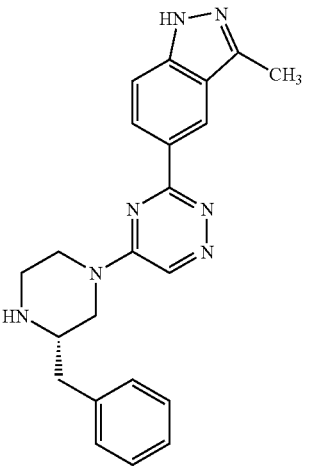 | 2.6 |
| 23 | 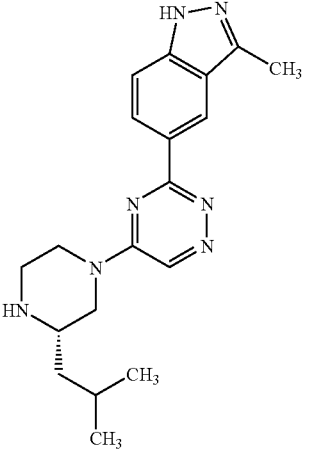 | 5.4 |
| 56 | 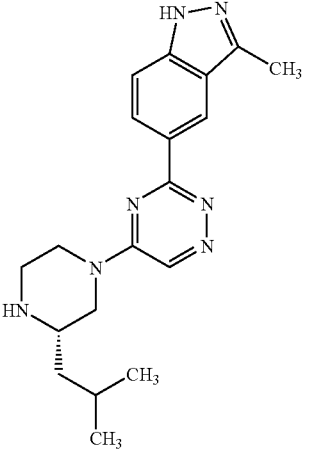 | 5.7 |

-continued

| Compound Number | STRUCTURE | IC$_{50}$ (nM) |
|---|---|---|
| 64 | 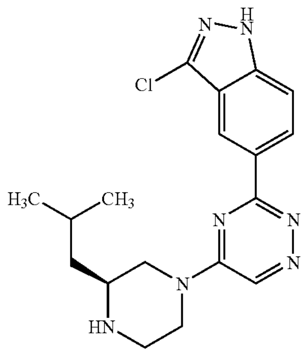 | 6.1 |
| 93 | 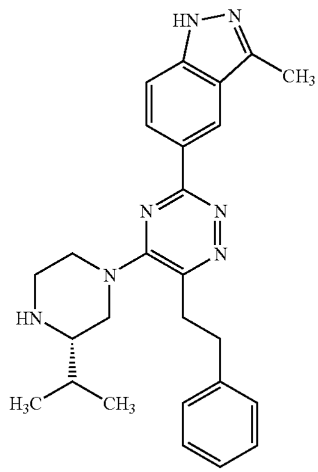 | 1.36 |

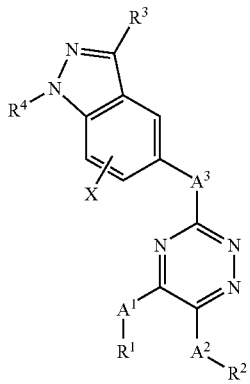

We claim:
1. A compound of Formula (I):

(I)

or a pharmaceutically acceptable salt thereof, wherein:
A$^1$ is selected from the group consisting of a covalent bond, and
A$^2$ is selected from the group consisting of a covalent bond, alkylene, alkenylene, alkynylene, cycloalkylene, —O—, —N(R$^5$)—, —C(O)—, —S—, —S(O)—, —S(O)$_2$—, —S(O)$_2$—N(R$^6$)—, —N(R$^6$)—S(O)$_2$—, —C(R$^7$)$_2$—N(R$^5$)—, —N(R$^5$)—C(R$^7$)$_2$—, —C(O)—N(R$^6$)—, —N(R$^6$)—C(O)—, —N(R$^6$)—C(O)—N(R$^6$)—, —C(R$^7$)$_2$—C═N—, and —N═C—C(R$^7$)$_2$—;

A$^3$ is selected from the group consisting of a covalent bond, cyclopropylene, alkenylene, alkynylene, —N(R$^5$)—, —O—, —S—, —S(O)$_2$—, —C(O)N(R$^6$)—, and —N(R$^6$)C(O)—;

R$^1$ and R$^2$ are each independently selected from the group consisting of H, alkyl, haloalkyl, one or more hydroxyl substituted alkyl, alkenyl, alkynyl, alkoxy, -alkylene-O-alkyl, aryl, -alkylene-aryl, —CN, halogen, heteroaryl, -alkylene-heteroaryl, cycloalkyl, heterocyclyl, and -alkylene-heterocyclyl,
wherein said aryl, heteroaryl, the aryl portion of said -alkylene-aryl, or the heteroaryl portion of said -alkylene-heteroaryl of R$^1$ or R$^2$ are unsubstituted or substituted with one or more groups Y which are independently selected; said heterocyclyl or the heterocyclyl portion of said -alkylene-heterocyclyl of R$^1$ or R$^2$ are unsubstituted or substituted with one or more groups Z which are independently selected; and with the proviso that:
1) if R$^1$ and/or R$^2$ are alkoxy, the oxygen atom of said alkoxy is not bonded to a S, N, or O atom of A$^1$ or A$^2$,
2) if R$^1$ and/or R$^2$ are —CN, said —CN is not bonded to a S, N, or O atom of A$^1$ or A$^2$,
3) if R$^1$ is halogen, A$^1$ is a covalent bond, and
4) if R$^2$ is halogen, A$^2$ is a covalent bond;

R$^3$ is selected from the group consisting of H, alkyl, haloalkyl, cycloalkyl, alkoxy, —N(R$^8$)$_2$, —N(R$^8$)—C(O)—R$^8$, —C(O)—N(R$^6$)$_2$, —N(R$^6$)—C(O)—N(R$^6$)$_2$, —N(R$^6$)—S(O)$_2$—R$^6$, —C(O)-alkyl, -alkylene-O-alkyl, —CN, halogen, aryl, heteroaryl, heterocyclyl, -alkylene-aryl, -alkylene-heteroaryl, alkylene-heterocyclyl, and alkynyl,
wherein said aryl, heteroaryl, the aryl portion of said -alkylene-aryl, or the heteroaryl portion of said -alkylene-heteroaryl of R$^3$ are unsubstituted or substituted with one or more groups Y which are independently selected; said heterocyclyl or the heterocyclyl portion of said alkylene-heterocyclyl of R$^3$ are unsubstituted or substituted with one or more groups Z which are independently selected;

R$^4$ is selected from the group consisting of H, alkyl, —C(O)-alkyl, —C(O)—O-alkyl, alkylene-O-alkyl, and -alkylene-O—C(O)-alkyl;

R$^5$ is selected from the group consisting of H, alkyl, cycloalkyl, haloalkyl, -alkylene-N(R$^8$)$_2$, alkoxy, aryl, heteroaryl, -alkylene-aryl, -alkylene-heteroaryl, —C(O)-alkyl, —S(O)$_2$-alkyl, —C(O)-aryl, —C(O)N(R$^9$)$_2$, —C(O)-aryl, —C(O)-alkylene-aryl, —C(O)-heteroaryl, C(O)-alkylene-heteroaryl, —S(O)$_2$-aryl, —S(O)$_2$-alkylene-aryl, —S(O)$_2$-heteroaryl, and —S(O)$_2$-alkylene-heteroaryl,
wherein said aryl, the aryl portion of —C(O)-aryl, the aryl portion of -alkylene-aryl, or the aryl portion of —S(O)$_2$-aryl of R$^5$ are unsubstituted or substituted with one or more groups Y which are independently selected;

each R$^6$ is independently selected from the group consisting of H, alkyl, cycloalkyl, haloalkyl, heterocyclyl, aryl, heteroaryl, -alkylene-heterocyclyl, -alkylene-aryl, and -alkylene-heteroaryl,
wherein said aryl or the aryl portion of alkylene-aryl of R$^6$ are unsubstituted or substituted with one or more groups Y which are independently selected;

each R$^7$ is independently selected from the group consisting of H, alkyl, cycloalkyl, haloalkyl, alkenyl, alkynyl, —N(R$^8$)$_2$, —CN, halo, aryl, heteroaryl, heterocyclyl, -alkylene-heterocyclyl, -alkylene-aryl, and -alkylene-heteroaryl, wherein said aryl, the aryl portion of said -alkylene-aryl, and said heteroaryl of R$^7$ are unsubstituted or substituted with one or more groups Y which are independently selected;

each R$^8$ is independently selected from the group consisting of H, alkyl, cycloalkyl, heterocyclyl, -alkylene-heterocyclyl, haloalkyl, -alkylene-aryl, aryl, heteroaryl, and -alkylene-heteroaryl, wherein said aryl of R$^8$ is unsubstituted or substituted with one or more groups Y which are independently selected;

X is one or more substituents independently selected from the group consisting of hydrogen, halogen, alkyl, alkoxy, haloalkyl, —OR$^9$, —N(R$^5$)$_2$, and —C(O)N(R$^6$)$_2$;

Y is one or more substituents independently selected from the group consisting of halogen, alkyl, haloalkyl, aryl, -alkylene-aryl, —OH, —OR$^9$, —CN, —NO$_2$, —N(R$^9$)$_2$, —N(R$^9$)—C(O)—R$^9$, —N(R$^9$)—C(O)—N(R$^9$)$_2$, —C(O)N(R$^9$)$_2$, —C(O)OH, —C(O)O-alkyl, —N(R$^9$)—S(O)$_2$—(R$^9$)$_2$ and —S(O)$_2$N(R$^9$)$_2$;

each R$^9$ is independently selected from the group consisting of H, alkyl, cycloalkyl, haloalkyl, heterocyclyl, -alkylene-heterocyclyl, aryl, -alkylene-aryl, heteroaryl, -alkylene-heteroaryl; and Z is one or more substituents independently selected from the group consisting of alkyl, one or more hydroxy substituted alkyl, aryl, -alkylene-aryl, -alkylene-O-alkyl, -alkylene-O-alkylene-aryl, -alkylene-O-aryl, —CN, haloalkyl, -alkylene-C(O)—N(R$^8$)$_2$, —C(O)—N(R$^8$)$_2$, —C(O)OH, —C(O)O-alkyl, —N(R$^8$)$_2$, and -alkylene-N(R$^8$)$_2$, —S(O)$_2$—N(R$^8$)$_2$, -alkylene-S(O)$_2$—N(R$^8$)$_2$, —N(R$^8$)—C(O)—R$^8$, —N(R$^8$)—C(O)—N(R$^8$)$_2$, -alkylene-N(R$^8$)—C(O)—N(R$^8$)$_2$, -alkylene-N(R$^8$)—C(O)—R$^8$, -alkylene-S(O)$_2$—R$^8$, —N(R$^8$)—S(O)$_2$—R$^8$, and -alkylene-N(R$^8$)—S(O)$_2$—R$^8$, cycloalkyl, heterocyclyl, -alkylene-heterocyclyl, heteroaryl, and -alkylene-heteroaryl, or wherein two Z substituents on adjacent carbon atoms, on a carbon atom and an adjacent heteroatom, or on a single carbon atom, together with the carbon atom(s) and/or the combination of the carbon atom and the adjacent heteroatom to which said Z substituents are attached form a four to seven-membered cycloalkyl, cycloalkenyl, heterocyclyl, aryl, or heteroaryl ring;

wherein said aryl, heteroaryl, the aryl portion of said -alkylene-aryl, -alkylene-O-alkylene-aryl, -alkylene-O-aryl, and the heteroaryl portion of said -alkylene-heteroaryl are unsubstituted or substituted with one or more R$^{10}$ substitutents which are independently selected; and R$^{10}$ is one or more substituents independently selected from the group consisting of halogen, cyano, alkyl, alkoxy, haloalkyl, haloalkoxy, nitro, —NH$_2$, —NH(alkyl), —N(alkyl)$_2$, hydroxyl, aryl, aryloxy, —O-alkylene-aryl, —NH(alkyl), —N(alkyl)$_2$, —NH(aryl), —N(aryl)$_2$, —NH-alkyene-aryl, —N(alkyl)-alkylene-aryl, -alkylene-aryl, —C(O)NH$_2$, —C(O)NH(alkyl), —C(O)N(alkyl)$_2$, —S(O)$_2$NH$_2$, —S(O)$_2$NH(alkyl), —S(O)$_2$N(alkyl)$_2$, —NHC(O)-alkyl, —N(alkyl)C(O)-alkyl, —NHC(O)-aryl, —N(alkyl)C(O)-aryl, —NH—S(O)$_2$-alkyl, —N(alkyl)-S(O)$_2$-alkyl, —NH—S(O)$_2$-aryl, and —N(alkyl)-S(O)$_2$-aryl.

2. The compound of claim 1, wherein A$^2$ is a covalent bond or —N(R$^5$).

3. The compound of claim 1, wherein A$^3$ is a covalent bond.

4. The compound of claim 1, wherein R$^1$ is H or (C$_2$-C$_6$)heterocyclyl.

5. The compound of claim 1, wherein R$^2$ is H, —(C$_1$-C$_4$)alkylene-(C$_6$-C$_{10}$)aryl, —(C$_1$-C$_4$)alkylene-(C$_2$-C$_{10}$)heteroaryl or halogen.

6. The compound of claim 1, wherein R$^3$ is H, (C$_1$-C$_6$)alkyl, (C$_3$-C$_6$)cycloalkyl, —(C$_6$-C$_{10}$)aryl, halogen, or —NH$_2$.

7. The compound of claim 1, wherein R$^4$ is H.

8. The compound of claim 1, wherein R$^5$ is H or —(C$_1$-C$_4$)alkylene-(C$_6$-C$_{10}$)aryl.

9. The compound of claim 1, wherein X is H or (C$_1$-C$_6$)alkyl.

10. The compound of claim 1, wherein Y is one or more substituents independently selected from the group consisting of halogen, alkyl, haloalkyl, aryl, —O-alkyl, —CN, and —NO$_2$.

11. The compound of claim 1, wherein Z is one or more substituents independently selected from the group consisting of (C$_1$-C$_6$)alkyl, (C$_6$-C$_{10}$)aryl, —(C$_1$-C$_4$)alkylene-(C$_6$-C$_{10}$)aryl, —(C$_1$-C$_4$)alkylene-(C$_2$-C$_{10}$)heteroaryl, —(C$_1$-C$_4$)alkylene-O—(C$_1$-C$_4$)alkylene-(C$_6$-C$_{10}$)aryl, —(C$_1$-C$_6$)alkylene-OH, —N(R$^8$)$_2$, —(C$_1$-C$_4$)alkylene-N(R$^8$)$_2$, —C(O)O—(C$_1$-C$_6$)alkyl, and —C(O)OH, or wherein two Z substitutents on adjacent carbon atoms, on a carbon atom and an adjacent heteroatom, or on a single carbon atom, together with the carbon atom(s) and/or the combination of the carbon atom and the adjacent heteroatom to which said Z substituents are attached together form a four to seven-membered cycloalkyl or heterocyclyl ring, wherein wherein said aryl, heteroaryl, the aryl portion of said -alkylene-aryl, -alkylene-O-alkylene-aryl, -alkylene-O-aryl, and the heteroaryl portion of said -alkylene-heteroaryl are unsubstituted or substituted with one or more R$^{10}$ substitutents which are independently selected; and R$^{10}$ is one or more substituents independently selected from the group consisting of halogen, alkyl, haloalkyl, alkoxy, haloalkoxy, and hydroxyalkyl.

12. The compound of claim 1, wherein:

A$^2$ is a covalent bond or —N(R$^5$)—;

A$^3$ is a covalent bond;

R$^1$ is H or (C$_2$-C$_6$)heterocyclyl; wherein said (C$_2$-C$_6$)heterocyclyl of R$^1$ is unsubstituted or substituted with one of more groups Z;

R$^2$ is H, —(C$_1$-C$_4$)alkylene-(C$_6$-C$_{10}$)aryl, —(C$_1$-C$_4$)alkylene-(C$_2$-C$_{10}$)heteroaryl or halogen; wherein said (C$_6$-C$_{10}$)aryl portion of —(C$_1$-C$_4$)alkylene-(C$_6$-C$_{10}$)aryl of R$^2$ and said (C$_2$-C$_{10}$)heteroaryl portion of —(C$_1$-C$_4$)alkylene-(C$_2$-C$_{10}$)heteroaryl of R$^2$ are independently unsubstituted or substituted with one or more groups Y;

R$^3$ is H, (C$_1$-C$_6$)alkyl, (C$_3$-C$_6$)cycloalkyl, —(C$_6$-C$_{10}$)aryl, halogen, or —NH$_2$;

R$^4$ is H;

R$^5$ is H or —(C$_1$-C$_4$)alkylene-(C$_6$-C$_{10}$)aryl;

X is H or (C$_1$-C$_6$)alkyl;

Y is one or more substituents independently selected from the group consisting of halogen, alkyl, haloalkyl, aryl, —O-alkyl, —CN, and —NO$_2$.

Z is one or more substituents independently selected from the group consisting of (C$_1$-C$_6$)alkyl, (C$_6$-C$_{10}$)aryl, —(C$_1$-C$_4$)alkylene-(C$_6$-C$_{10}$)aryl, —(C$_1$-C$_4$)alkylene-(C$_2$-C$_{10}$)heteroaryl, —(C$_1$-C$_4$)alkylene-O—(C$_1$-C$_4$)alkylene-(C$_6$-C$_{10}$)aryl, —(C$_1$-C$_6$)alkylene-OH, —N(R⁸)₂, —(C₁-C₄)alkylene-N(R⁸)₂, —C(O)O—(C₁-C₆)alkyl, and —C(O)OH, or wherein two Z substitutents on adjacent carbon atoms, on a carbon atom and an adjacent heteroatom, or on a single carbon atom, together with the carbon atom(s) and/or the combination of the carbon atom and the adjacent heteroatom to which said Z substituents are attached together form a four to seven-membered cycloalkyl or heterocyclyl ring.

13. The compound of claim 1, wherein:

A¹ is a covalent bond; and

R¹ is (C₂-C₆)heterocyclyl; wherein said (C₂-C₆)heterocyclyl of R¹ is unsubstituted or substituted with one of more groups Z.

14. The compound of claim 13, wherein:

R¹ is selected from the group consisting of unsubstituted piperazinyl, unsubstituted piperidinyl, unsubstituted pyrrolidinyl, and piperazinyl, piperidinyl and pyrrolidinyl each of which is substituted with one or more Z substituents which are independently selected, or wherein two Z substitutents on adjacent carbon atoms, on a carbon atom and an adjacent nitrogen atom, or on a single carbon atom, together with the carbon atom(s) and/or the combination of the carbon atom and the adjacent nitrogen atom to which said Z substituents are attached form a four to seven-membered cycloalkyl or heterocyclyl ring.

15. The compound of claim 1, wherein:

A is —N(R⁵)—;

R² is H or —(C₁-C₄)alkylene-(C₆-C₁₀)aryl; and

R⁵ is H or —(C₁-C₄)alkylene-(C₆-C₁₀)aryl.

16. The compound of claim 1, wherein:

A² is a covalent bond; and

R² is H or halogen.

17. The compound of claim 1, wherein:

A¹ is a covalent bond;

R¹ is selected from the group consisting of unsubstituted piperazinyl, unsubstituted piperidinyl, unsubstituted pyrrolidinyl, and piperazinyl, piperidinyl and pyrrolidinyl each of which is substituted with one or more Z substituents which are independently selected, or wherein two Z substitutents on adjacent carbon atoms, on a carbon atom and an adjacent nitrogen atom, or on a single carbon atom, together with the carbon atom(s) and/or the combination of the carbon atom and the adjacent nitrogen atom to which said Z substituents are attached form a four to seven-membered cycloalkyl or heterocyclyl ring;

A² is —N(R⁵)—;

R² is H or —(C₁-C₄)alkylene-(C₆-C₁₀)aryl; and

R⁵ is H or —(C₁-C₄)alkylene-(C₆-C₁₀)aryl.

18. The compound of claim 8, wherein:

R¹ is selected from the group consisting of

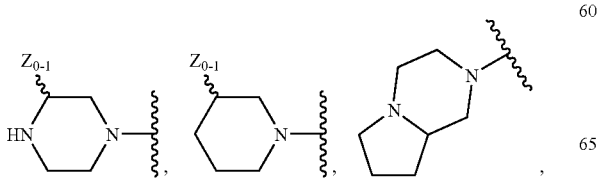

-continued

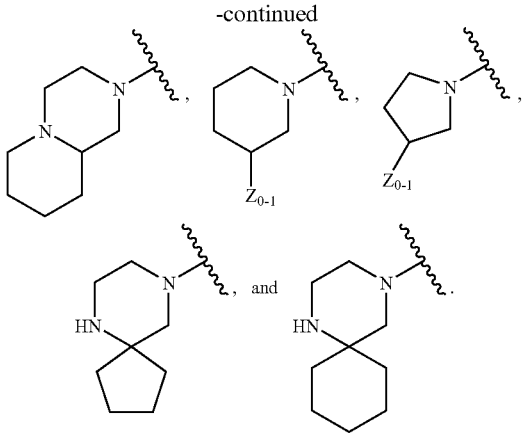

19. The compound of claim 1, wherein:

A¹ is a covalent bond;

R¹ is selected from the group consisting of unsubstituted piperazinyl, unsubstituted piperidinyl, unsubstituted pyrrolidinyl, and piperazinyl, puperidinyl and pyrrolidinyl each of which is substituted with one or more Z substitutents on adjacent carbon atoms, on a carbon atom and an adjacent nitrogen atom, or on a single carbon atom, together with the carbon atom(s) and/or the combination of the carbon atom and the adjacent nitrogen atom to which said Z substituents are attached form a four to seven-membered cycloalkyl or heterocyclyl ring;

A² is a covalent bond; and

R² is H or halogen. R² is H halogen.

20. The compound of claim 19, wherein:

Z is selected from the group consisting of (C₁-C₆)alkyl, (C₆-C₁₀)aryl, -(C₁-C₄)alkylene-(C₆-C₁₀)aryl, —(C₁-C₄)alkylene-O—(C₁-C₄)alkylene-(C₆-C₁₀)aryl, —N(R⁸)₂, —(C₁-C₄)alkylene-N(R⁸)₂, —C(O)OH, —C(O)O—(C₁-C₆)alkyl, and —(C₁-C₆)alkylene-OH, or wherein two Z substitutents on adjacent carbon atoms, on a carbon atom and an adjacent nitrogen atom, or on a single carbon atom, together with the carbon atom(s) and/or the combination of the carbon atom and the adjacent nitrogen atom to which said Z substituents are attached form a four to seven-membered cycloalkyl or heterocyclyl ring.

21. A purified compound of claim 1.

22. A compound having the structure of Formula (IA):

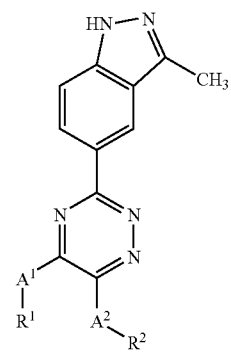

Formula (IA)

wherein A¹, A², R¹, R² are defined as shown in the Table below:

| Structure | A¹ | A² | R¹ | R² |
|---|---|---|---|---|
| A | covalent bond | —NH— | 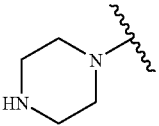 | H |
| B | —O— | —NH— | H | H |
| C | covalent bond | —NH— | 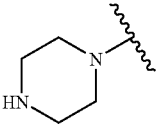 | 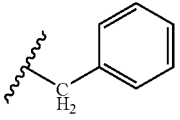 |
| D | covalent bond | 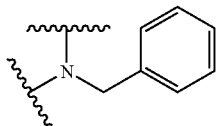 | 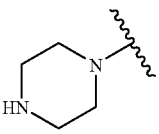 | 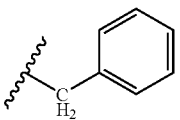 |
| E | covalent bond | —NH— | 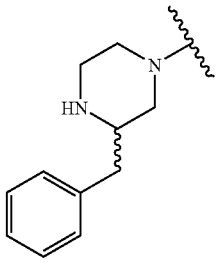 | H |
| F | covalent bond | —NH— | 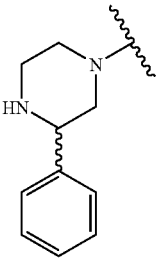 | H |
| G | covalent bond | —NH— | 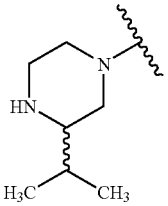 | H |
| H | covalent bond | —NH— | 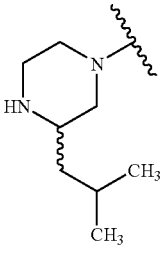 | H |

-continued
| Structure | A$^1$ | A$^2$ | R$^1$ | R$^2$ |
|---|---|---|---|---|
| I | covalent bond | —NH— | 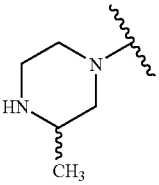 | H |
| J | covalent bond | —NH— | 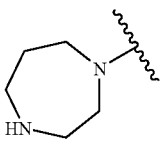 | H |
| K | covalent bond | —NH— | 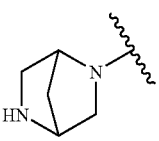 | H |
| L | covalent bond | covalent bond | 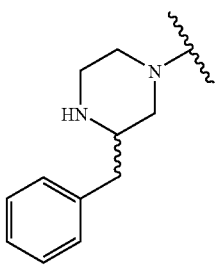 | H |
| M | covalent bond | covalent bond | 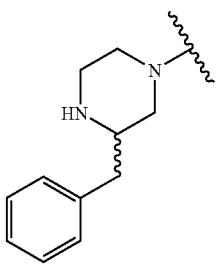 | Cl |
| N | covalent bond | —NH— | 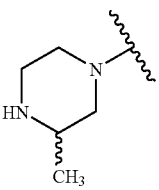 | 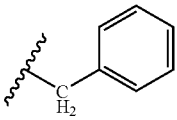 |
| O | covalent bond | —NH— | 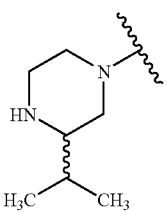 | 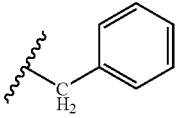 |

-continued
| Structure | A¹ | A² | R¹ | R² |
|---|---|---|---|---|
| P | covalent bond | —NH— | 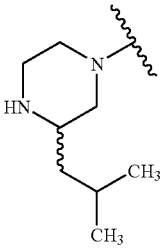 | 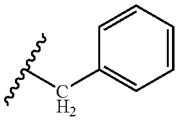 |
| Q | covalent bond | —NH— | 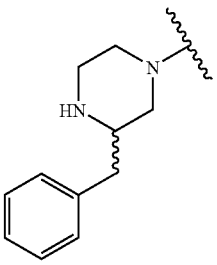 | 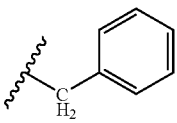 |
| R | covalent bond | covalent bond | 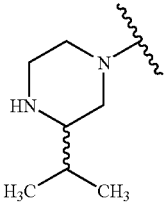 | H |
| S | covalent bond | covalent bond | 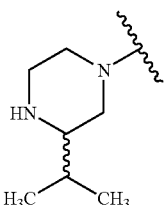 | Cl |
| T | covalent bond | covalent bond | 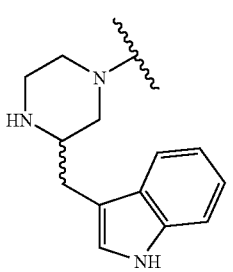 | H |
| U | covalent bond | covalent bond | 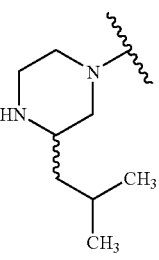 | Cl |

-continued
| Structure | A¹ | A² | R¹ | R² |
|---|---|---|---|---|
| V | covalent bond | covalent bond | 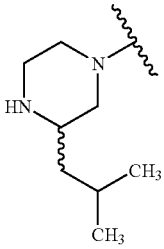 | H |
| W | covalent bond | covalent bond | 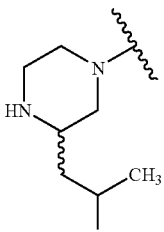 | Cl |
| X | covalent bond | covalent bond | 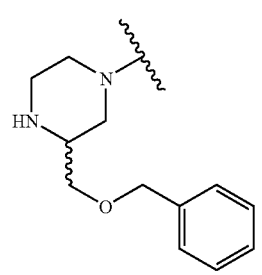 | Cl |
| Y | covalent bond | covalent bond | 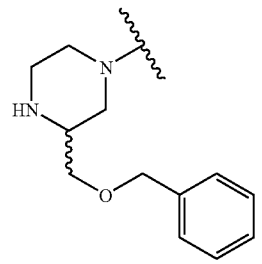 | H |
| Z | covalent bond | covalent bond | 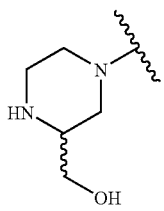 | H |
| AA | covalent bond | covalent bond | 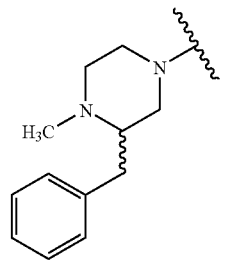 | H |

-continued
| Structure | A$^1$ | A$^2$ | R$^1$ | R$^2$ |
|---|---|---|---|---|
| AB | covalent bond | covalent bond | 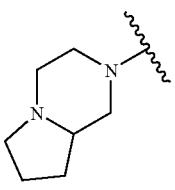 | H |
| AC | covalent bond | covalent bond | 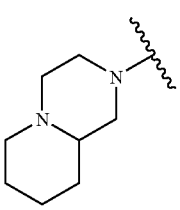 | H |
| AD | covalent bond | covalent bond | 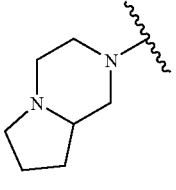 | Cl |
| AE | covalent bond | covalent bond | 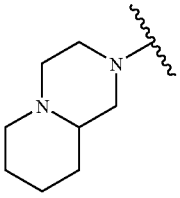 | Cl |
| AF | covalent bond | covalent bond | 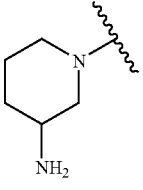 | H |
| AG | covalent bond | covalent bond | 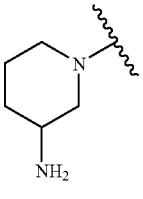 | Cl |
| AH | covalent bond | covalent bond | 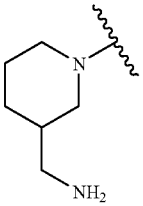 | H |

-continued

| Structure | A¹ | A² | R¹ | R² |
|---|---|---|---|---|
| AI | covalent bond | covalent bond | 3-(aminomethyl)piperidin-1-yl | Cl |
| AJ | covalent bond | covalent bond | 3-aminopyrrolidin-1-yl | H |
| AK | covalent bond | covalent bond | 3-aminopyrrolidin-1-yl | Cl |
| AL | covalent bond | covalent bond | 3-(methoxycarbonyl)piperazin-1-yl | H |
| AM | covalent bond | covalent bond | 3-(methoxycarbonyl)piperazin-1-yl | Cl |
| AN | covalent bond | covalent bond | 2,7-diazaspiro[4.5]decan-7-yl | H |
| AO | covalent bond | covalent bond | 3-phenylpiperazin-1-yl | H |

-continued
| Structure | A¹ | A² | R¹ | R² |
|---|---|---|---|---|
| AP | covalent bond | covalent bond | 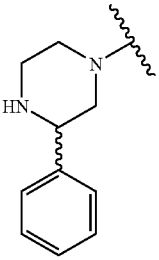 | Cl |
| AQ | covalent bond | covalent bond | 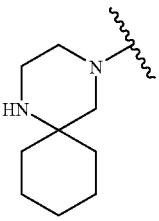 | H |
| AR | covalent bond | covalent bond | 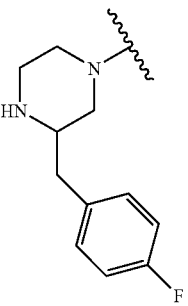 | H |
| AS | covalent bond | covalent bond | 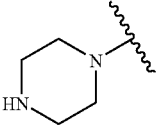 | H |
| AT | covalent bond | covalent bond | 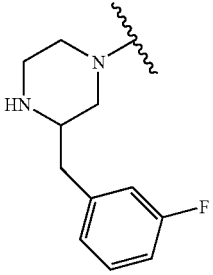 | H |
| AU | covalent bond | covalent bond | 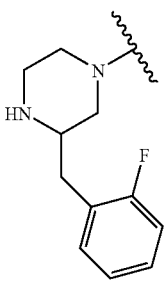 | H |

-continued
| Structure | A¹ | A² | R¹ | R² |
|---|---|---|---|---|
| AV | covalent bond | covalent bond | 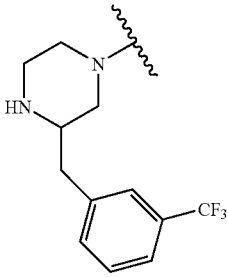 | H |
| AW | covalent bond | covalent bond | 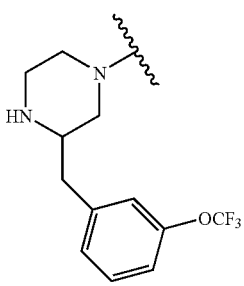 | H |
| AX | covalent bond | covalent bond | 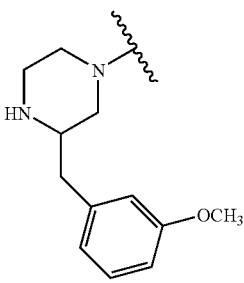 | H |
| AY | covalent bond | covalent bond | 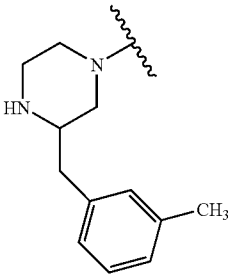 | H |
| AZ | covalent bond | covalent bond | 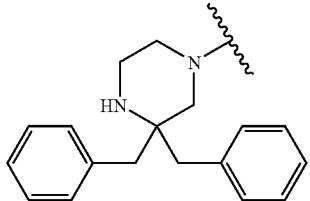 | H |

-continued
| Structure | A¹ | A² | R¹ | R² |
|---|---|---|---|---|
| AAA | covalent bond | covalent bond | 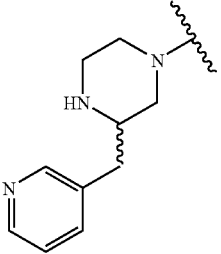 | H |
| AAB | covalent bond | covalent bond | 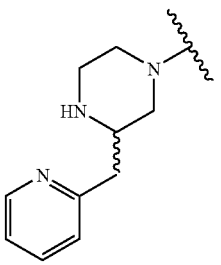 | H |
| AAC | covalent bond | covalent bond | 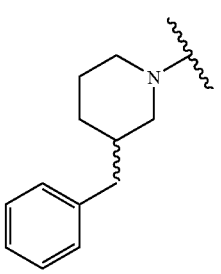 | H |
| AAD | covalent bond | covalent bond | 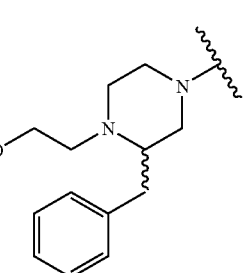 | H |
| AAE | covalent bond | covalent bond | 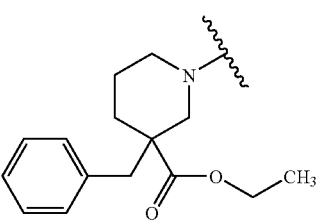 | H |
| AAF | covalent bond | covalent bond | 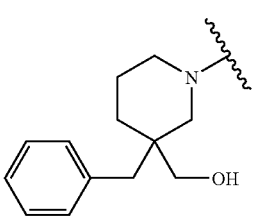 | H |

-continued
| Structure | A¹ | A² | R¹ | R² |
|---|---|---|---|---|
| AAG | covalent bond | covalent bond | 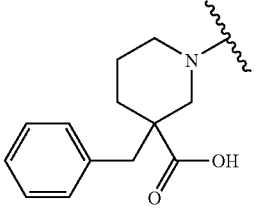 | H |
| AAH | covalent bond | covalent bond | 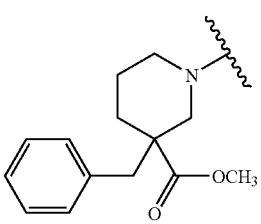 | H |
| AAI | covalent bond | covalent bond | 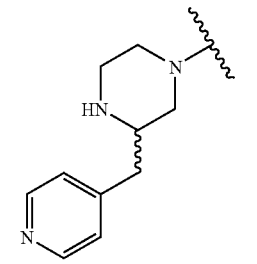 | H |
| AAJ | covalent bond | covalent bond | 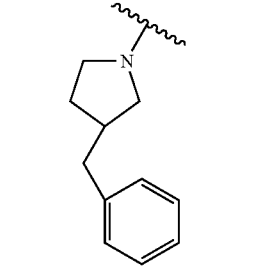 | H |
| AAK | covalent bond | covalent bond | 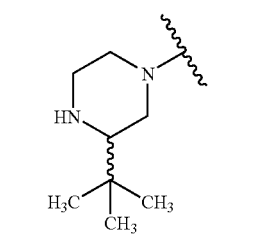 | H |
| AAL | covalent bond | —NH— | 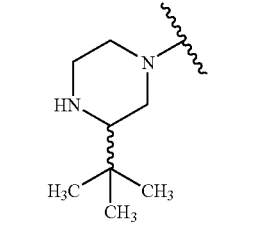 | H |

-continued
| Structure | A¹ | A² | R¹ | R² |
|---|---|---|---|---|
| AAM | covalent bond | —NH— | 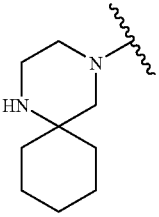 | H |
| AAN | covalent bond | —NH— | 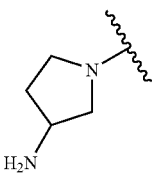 | H |
| AAO | covalent bond | —NH— | 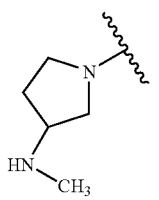 | H |
| AAP | covalent bond | —NH— | 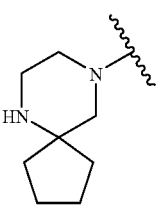 | H |
| AAQ | covalent bond | —NH— | 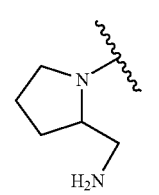 | H |
| AAR | covalent bond | —NH— | 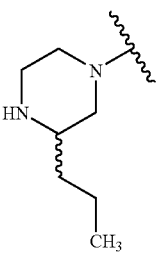 | H |
| AAT | covalent bond | —NH— | 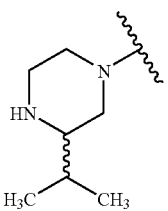 | H |

-continued
| Structure | $A^1$ | $A^2$ | $R^1$ | $R^2$ |
|---|---|---|---|---|
| AAU | covalent bond | —NH— | 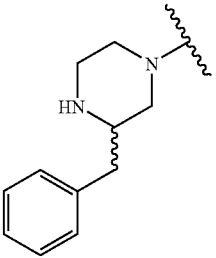 | H |
| AAV | covalent bond | covalent bond | 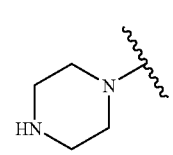 | —CH$_2$CH$_2$-phenyl |
| AAW | covalent bond | covalent bond | 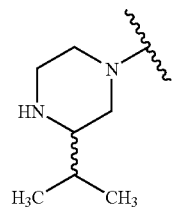 | —CH$_2$CH$_2$-phenyl |
| AAX | covalent bond | covalent bond | 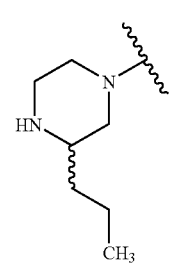 | —CH$_2$CH$_2$-phenyl |
| AAY | covalent bond | —NH— | 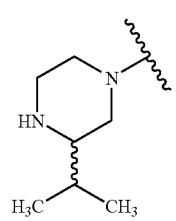 | 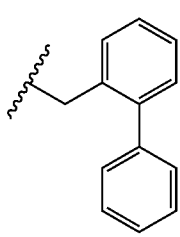 |
| AAZ | covalent bond | —NH— | 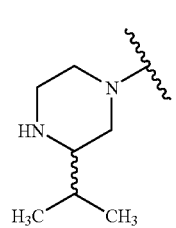 | 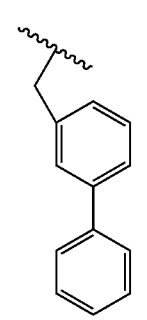 |

-continued
| Structure | A¹ | A² | R¹ | R² |
|---|---|---|---|---|
| AAAA | covalent bond | —NH— | 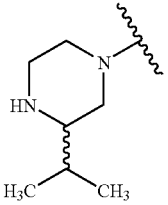 | 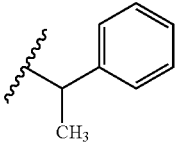 |
| AAAB | covalent bond | —NH— | 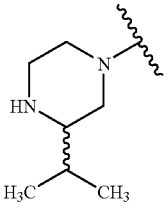 | 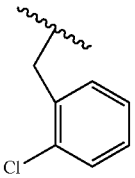 |
| AAAC | covalent bond | 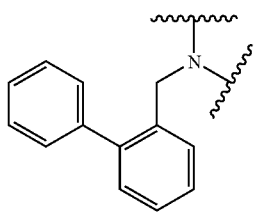 | 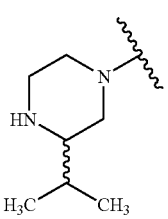 | 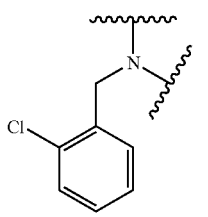 |
| AAAD | covalent bond | 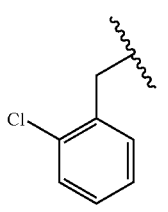 | 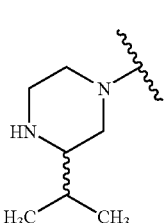 | 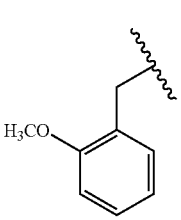 |
| AAAE | covalent bond | —NH— | 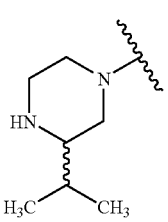 | 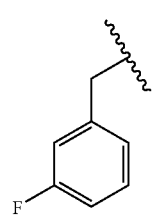 |
| AAAF | covalent bond | —NH— | | |

-continued

| Structure | A¹ | A² | R¹ | R² |
|---|---|---|---|---|
| AAAG | covalent bond | N-benzyl(3-fluorophenyl) | 3-isopropylpiperazin-1-yl | 3-fluorobenzyl |
| AAAH | covalent bond | —NH— | 3-(methylamino)pyrrolidin-1-yl | benzyl |
| AAAI | covalent bond | —NH— | 3-isopropylpiperazin-1-yl | 3-bromobenzyl |
| AAAJ | covalent bond | N-benzyl(3-bromophenyl) | 3-isopropylpiperazin-1-yl | 3-bromobenzyl |
| AAAK | covalent bond | —NH— | 3-isopropylpiperazin-1-yl | 3-methoxybenzyl |
| AAAL | covalent bond | —NH— | 3-isopropylpiperazin-1-yl | 3-nitrobenzyl | or a pharmaceutically acceptable salt thereof.

23. A compound selected from the group consisting of:
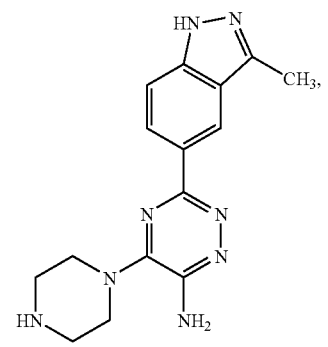
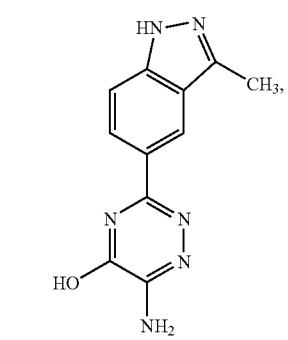
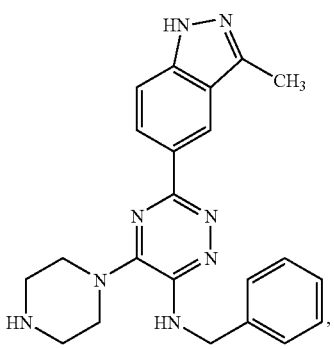
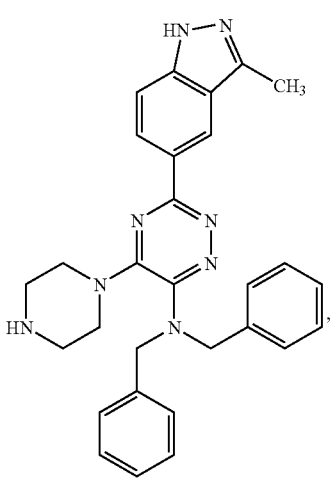
-continued
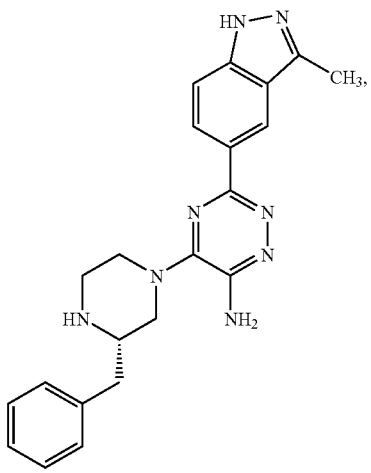
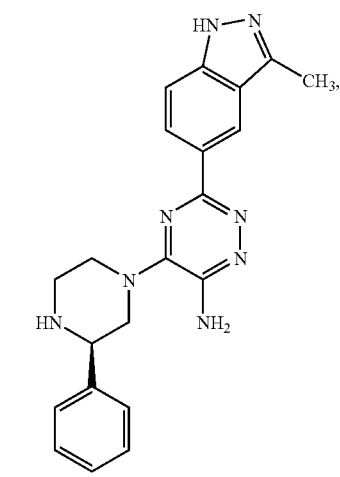
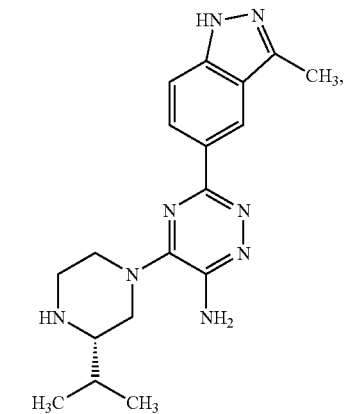

207
-continued
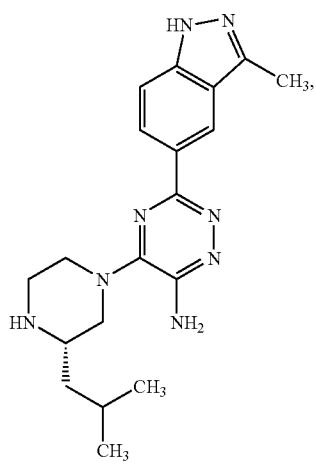
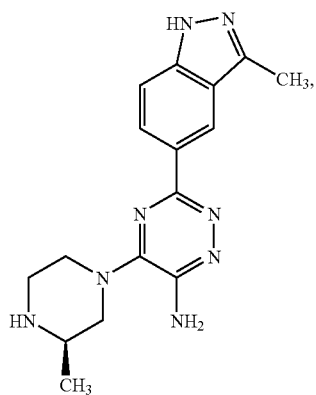
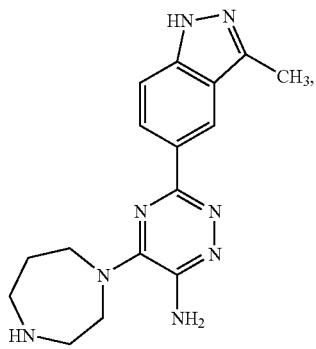
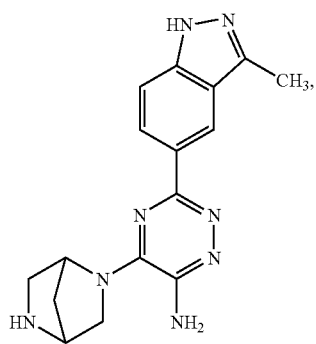
208
-continued
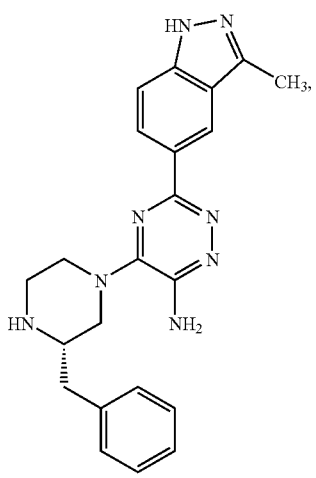
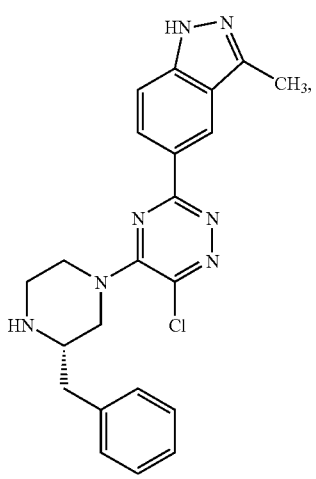
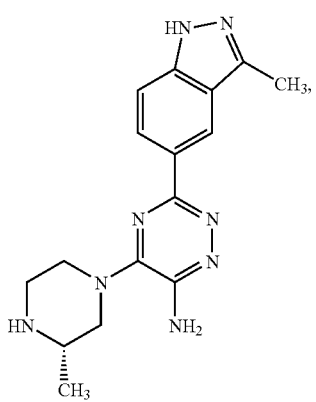

-continued
209
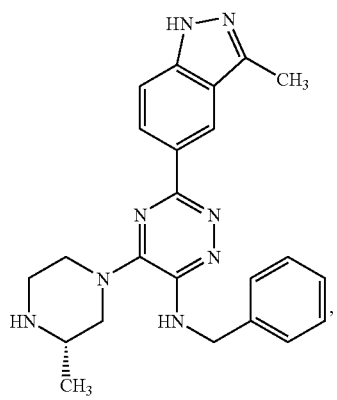
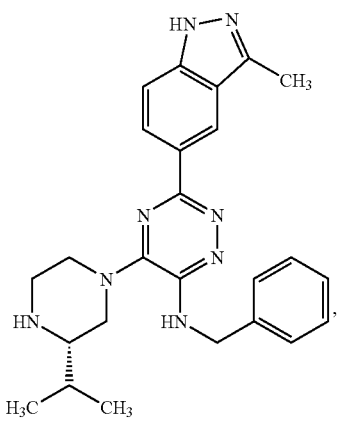
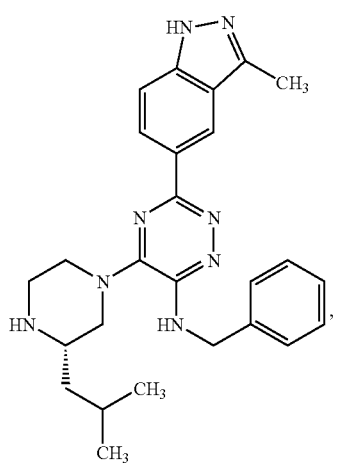
-continued
210
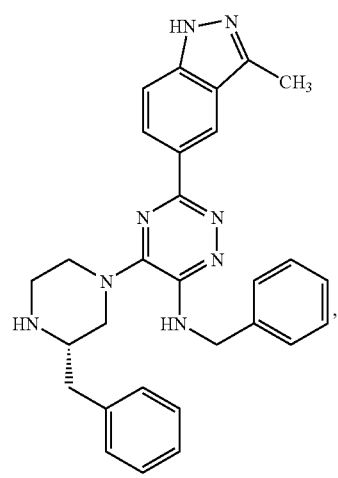
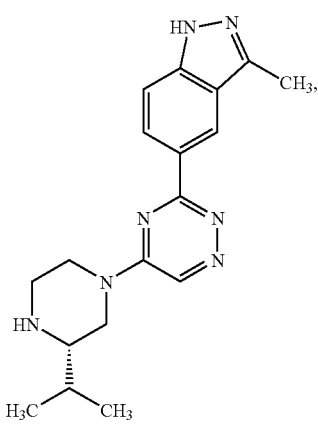
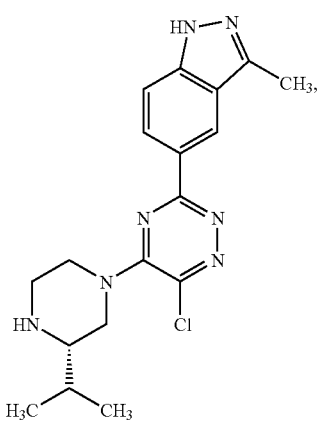

211
-continued
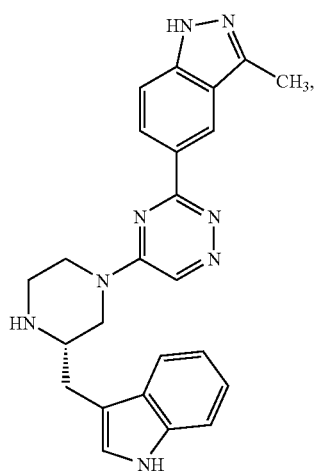
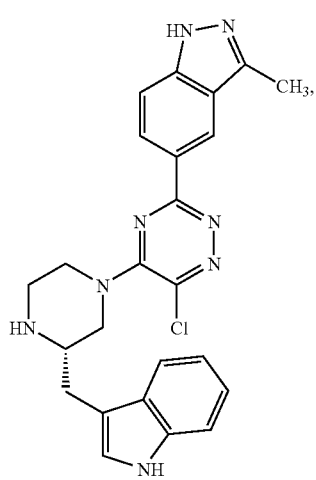
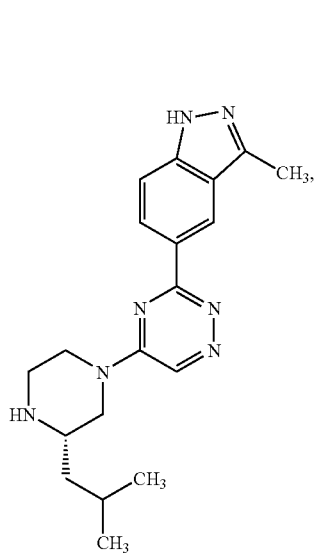
212
-continued
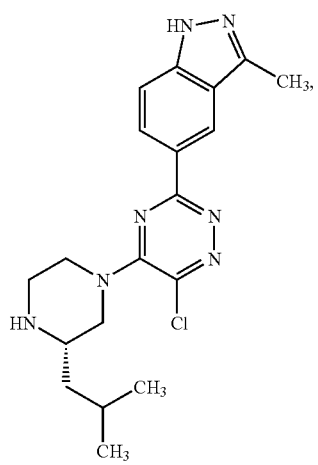
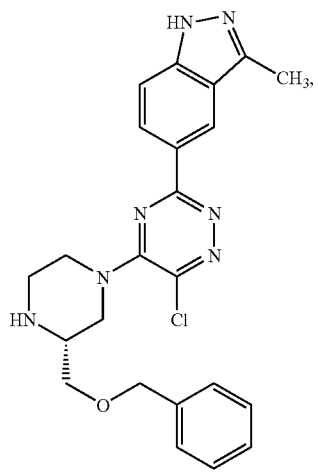
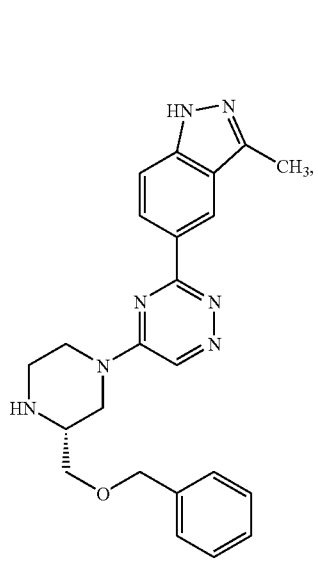

-continued
213
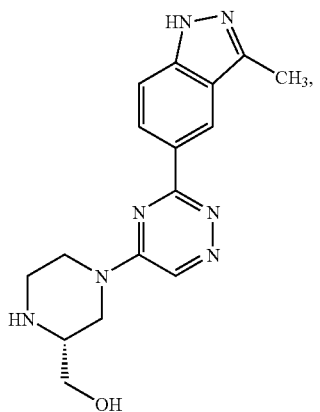
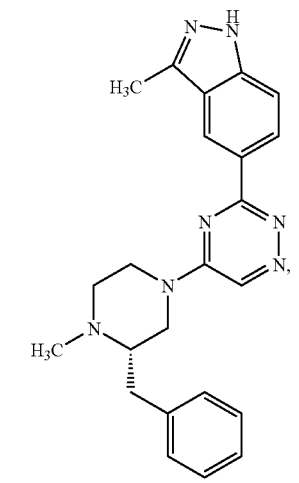
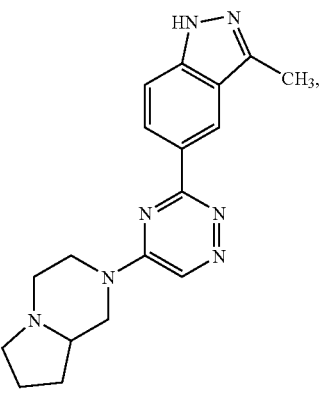
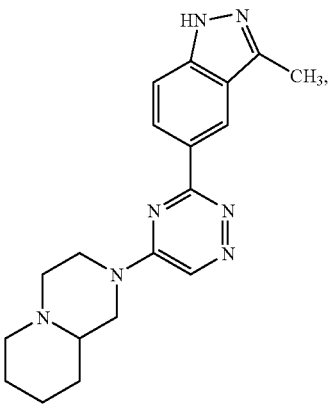
214
-continued
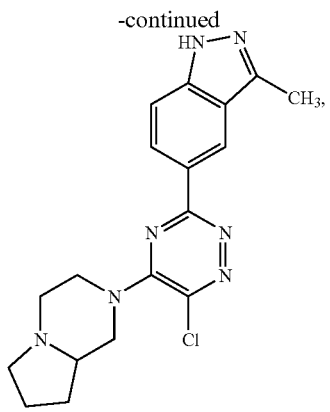
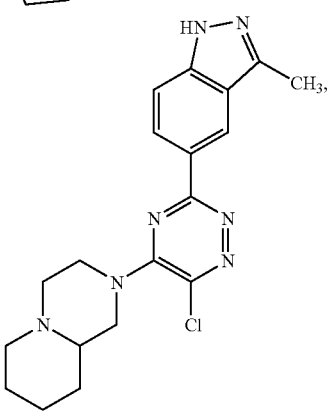
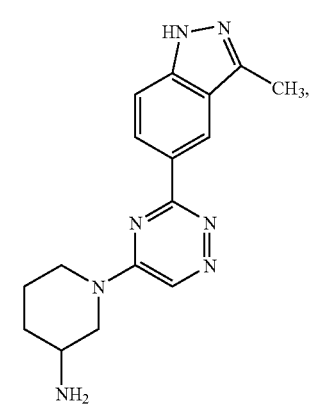
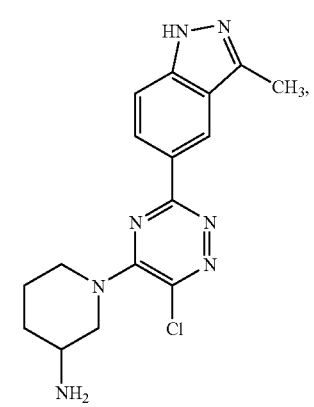

215
-continued
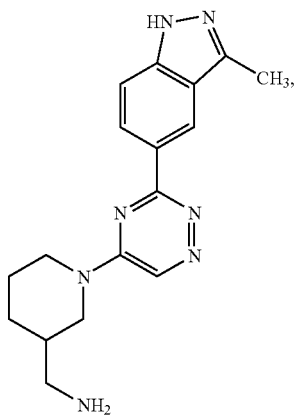
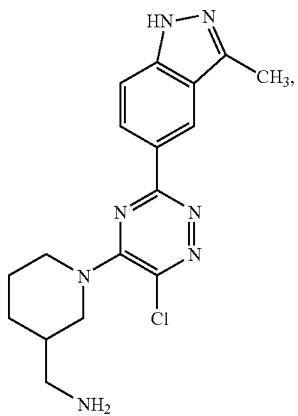
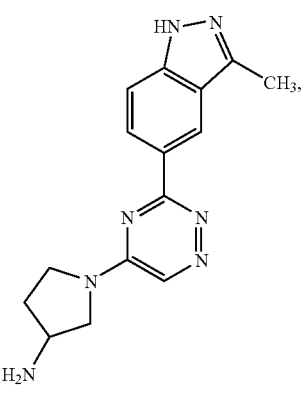
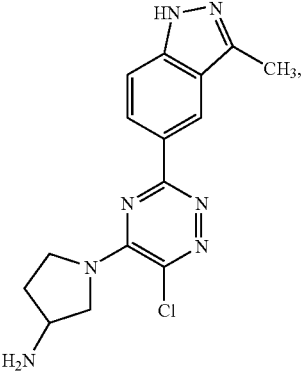
216
-continued
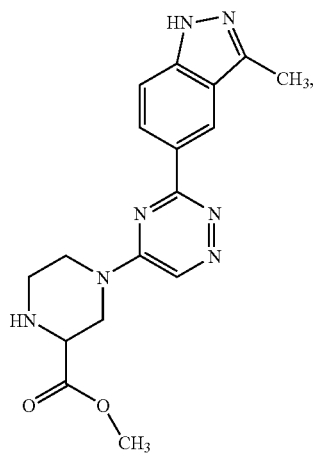
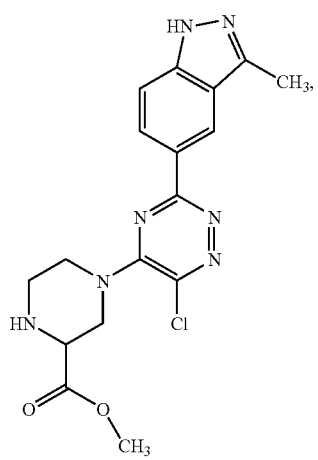
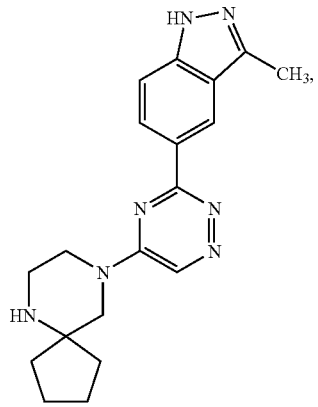

217
-continued
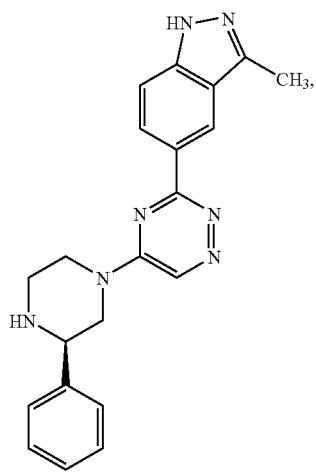
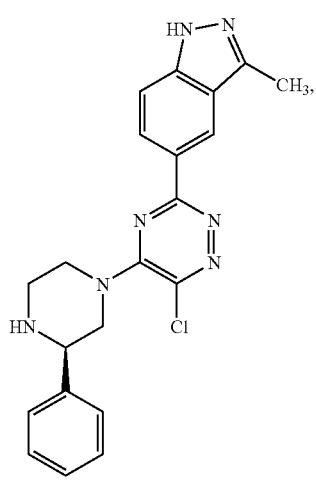
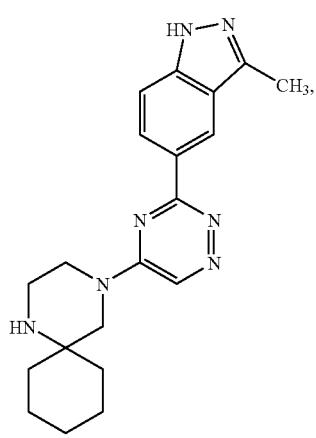
218
-continued
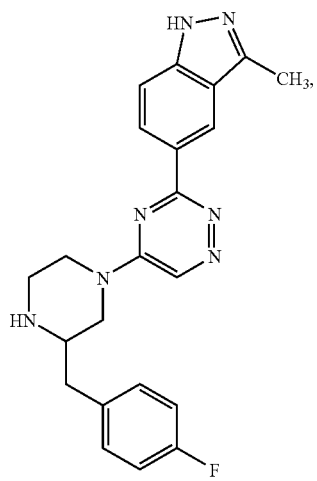
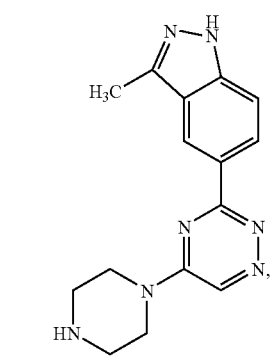
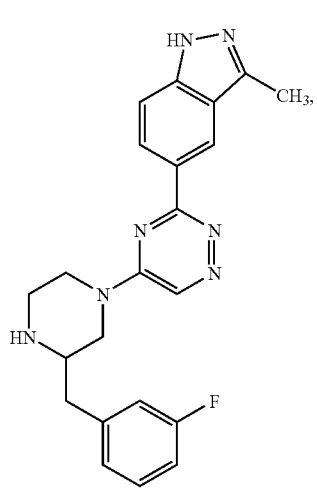

-continued
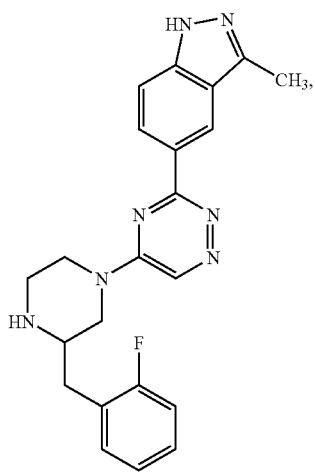
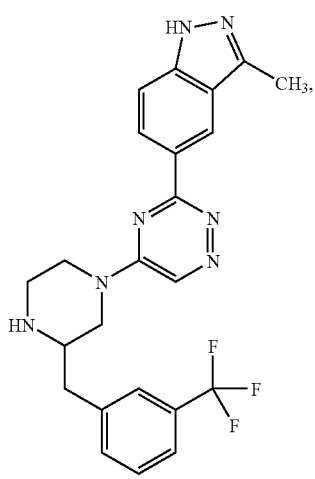
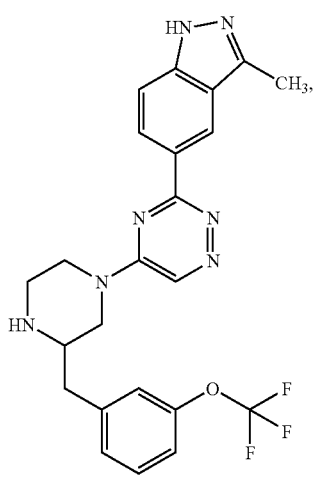
-continued
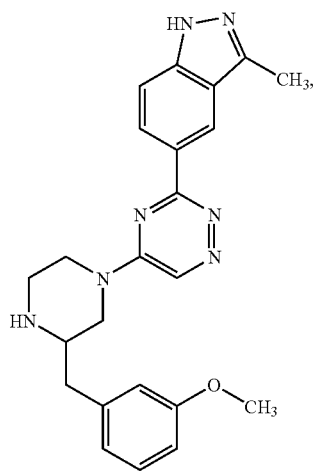
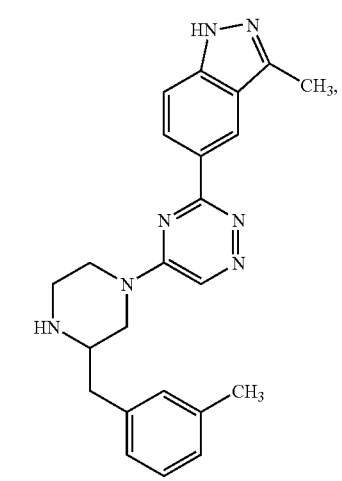
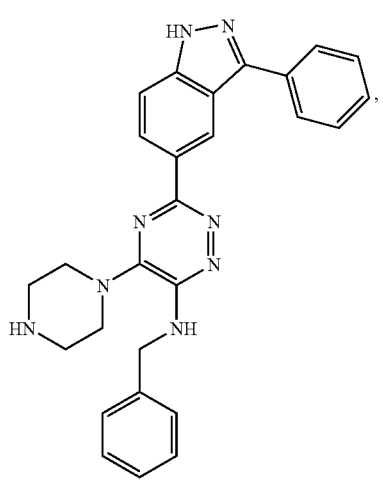

221
-continued
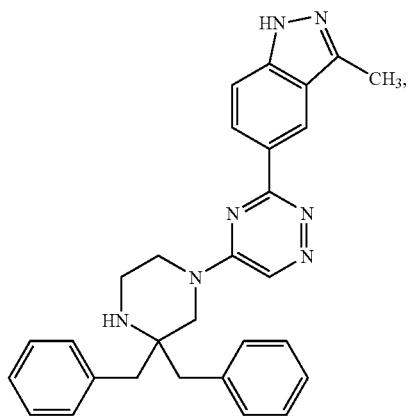
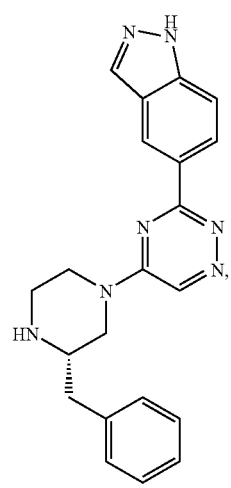
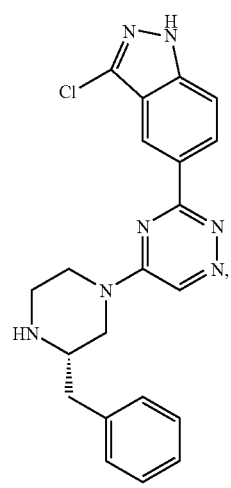
222
-continued
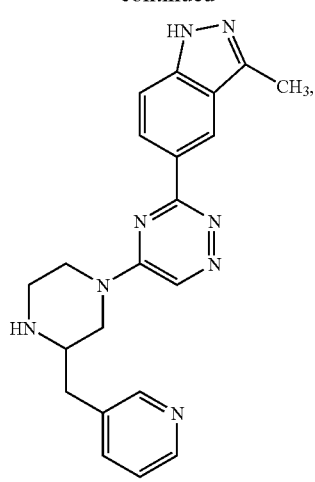
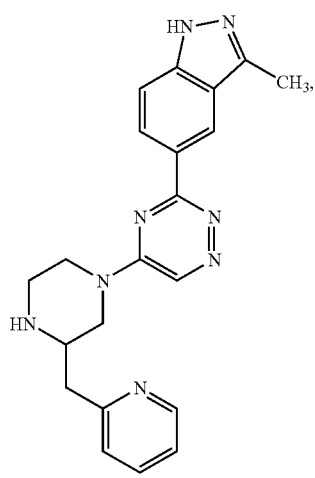
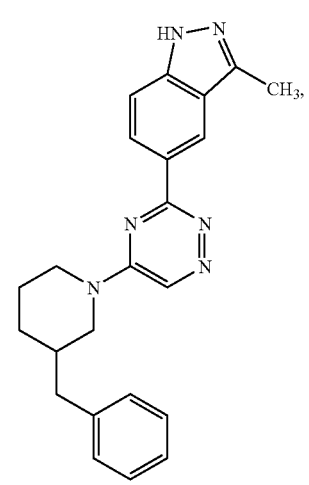

-continued
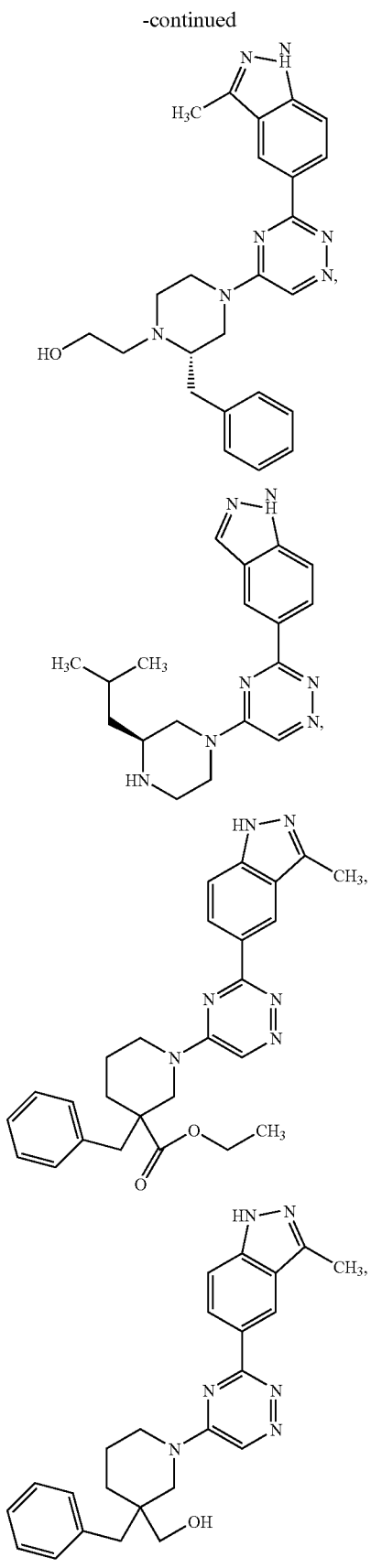
-continued
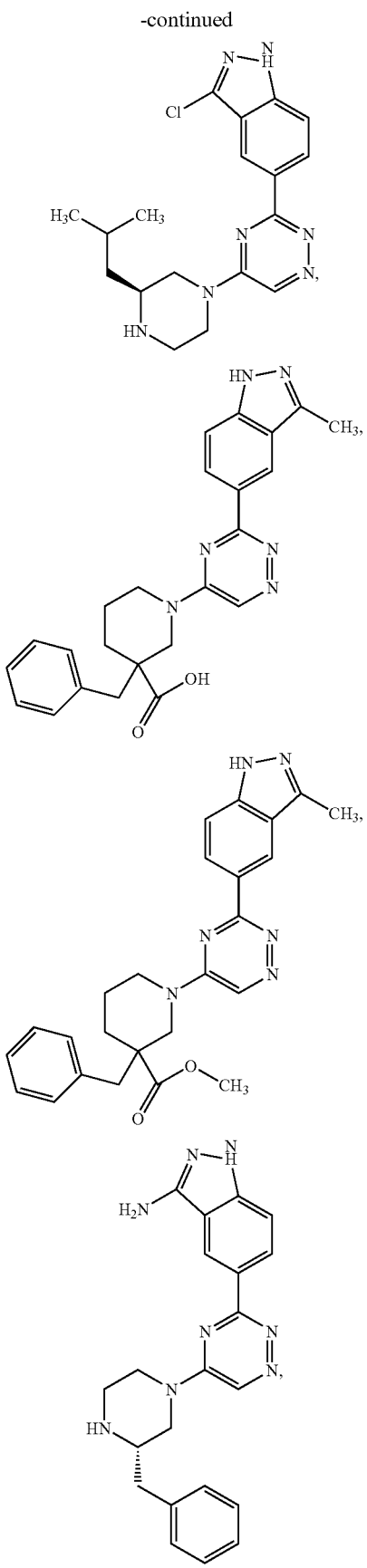

225
-continued
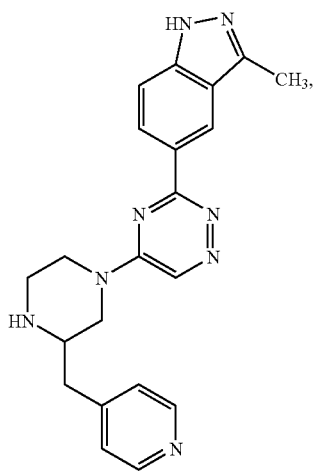
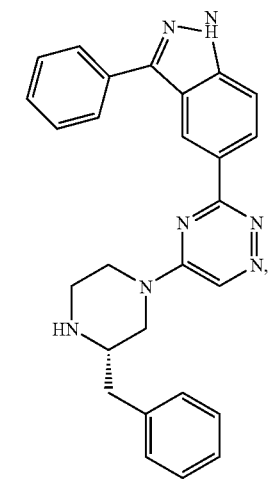
226
-continued
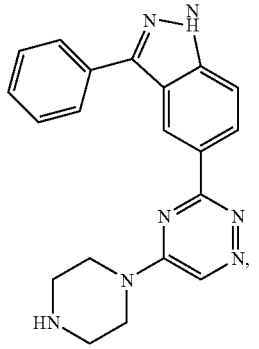
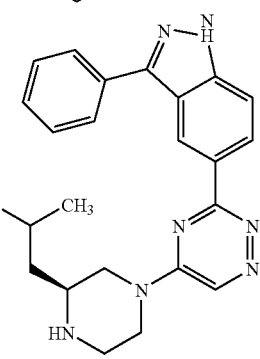
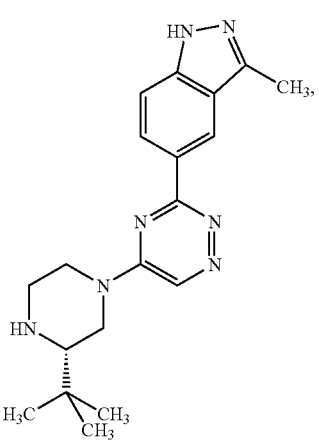
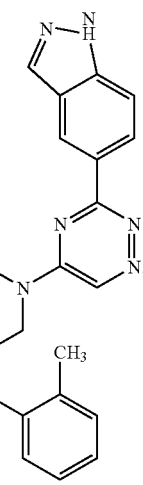

227
-continued
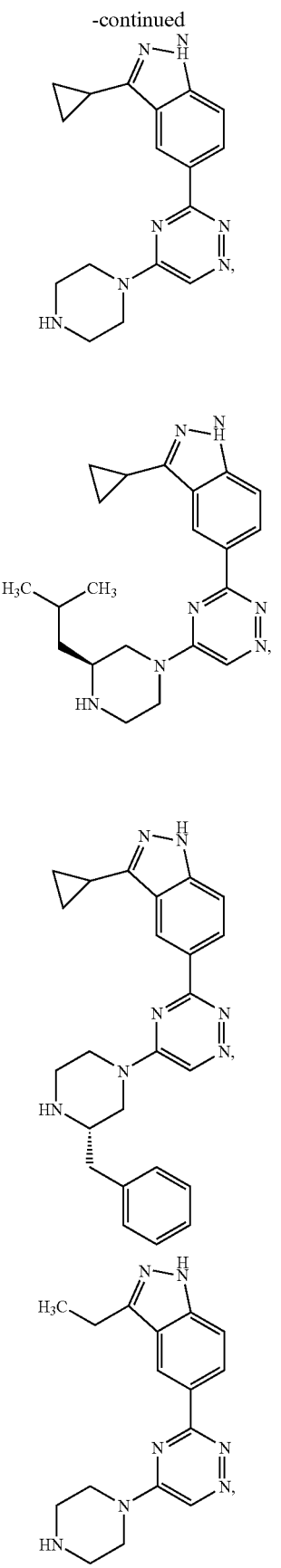
228
-continued
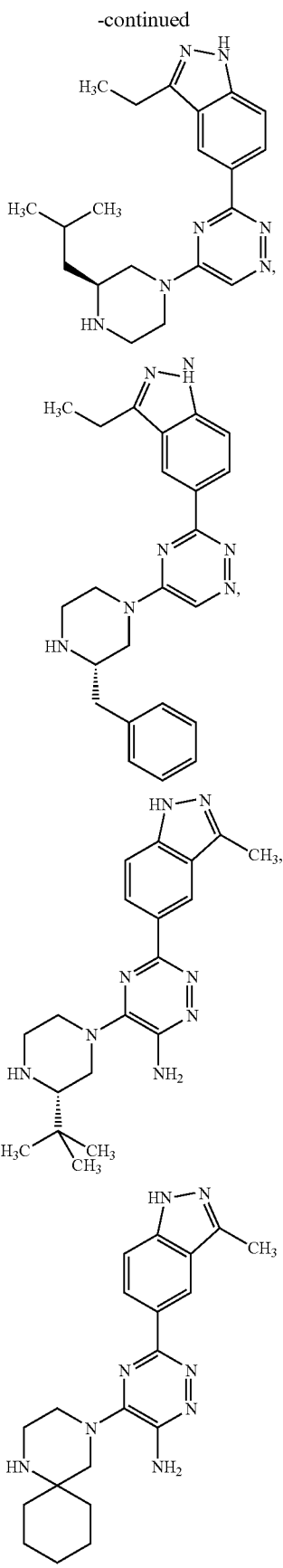

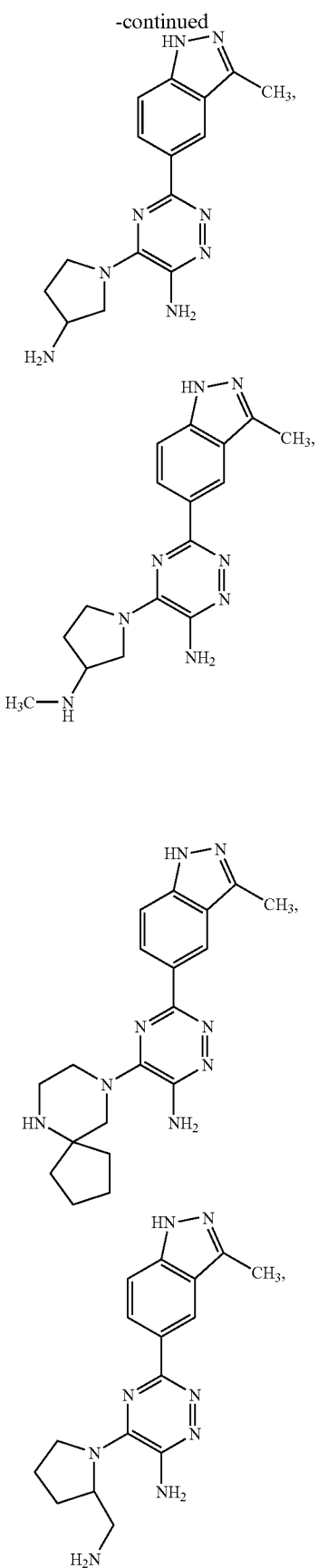
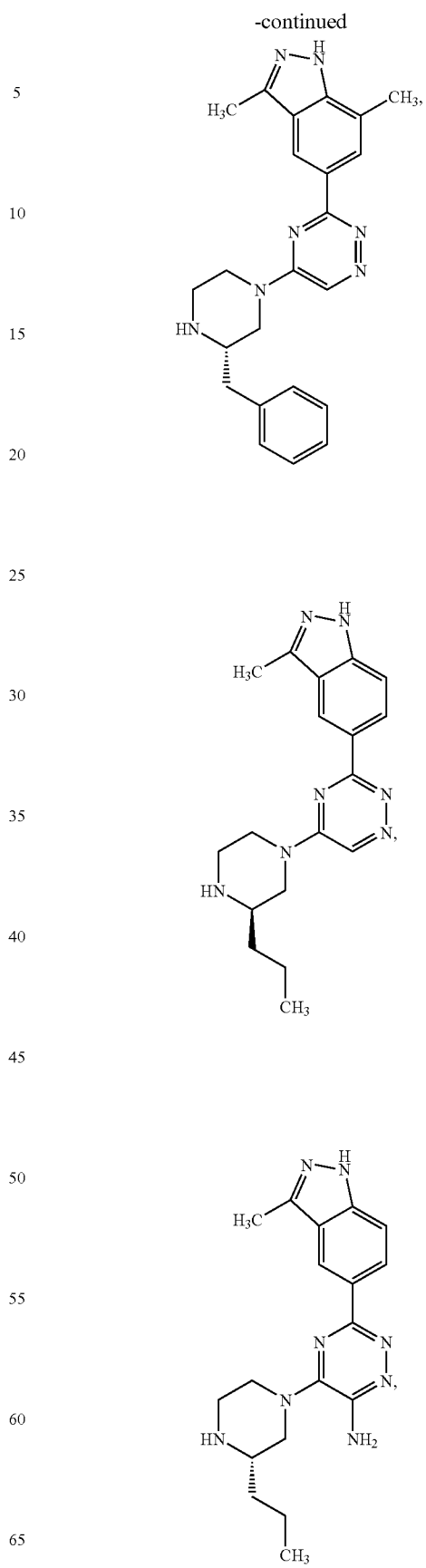

231
-continued
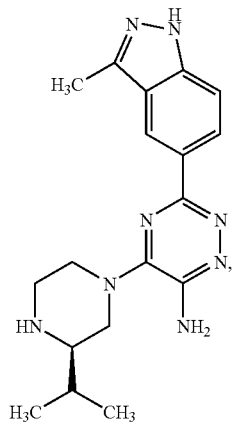
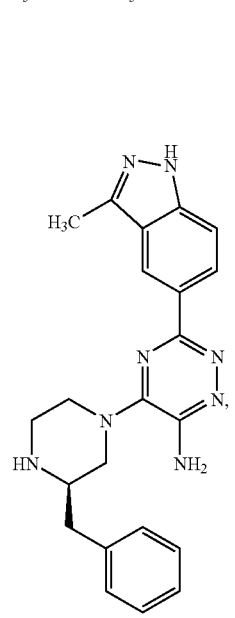
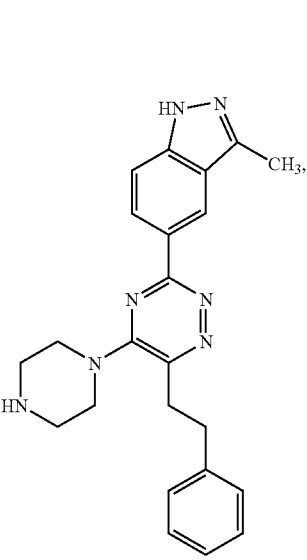
232
-continued
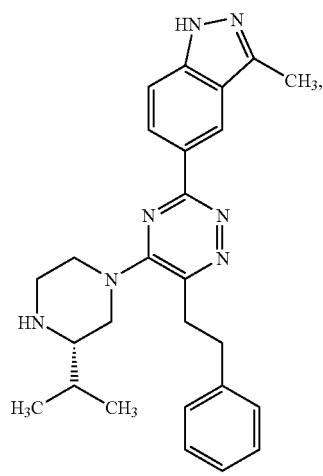
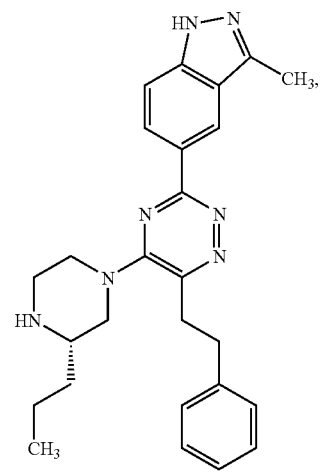
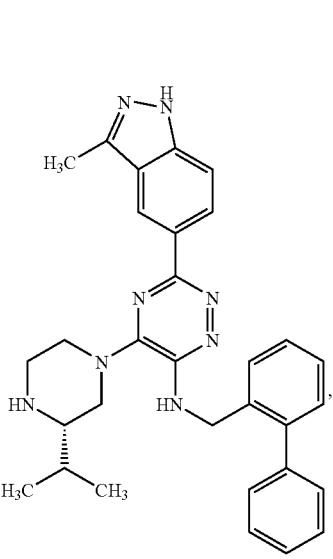

233
-continued
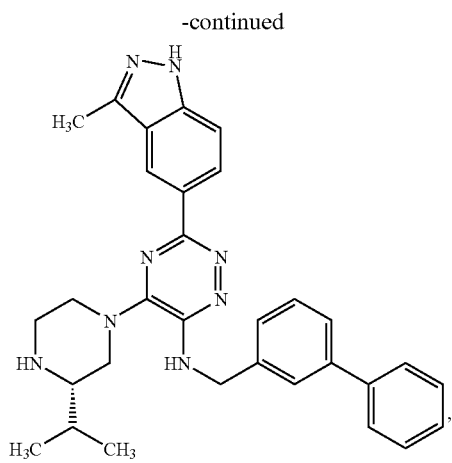
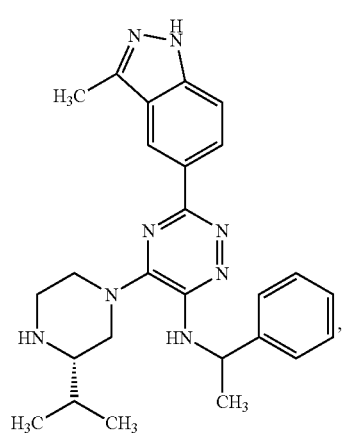
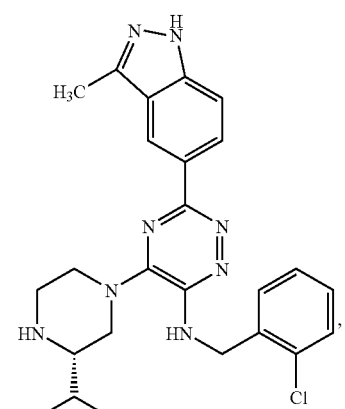
234
-continued
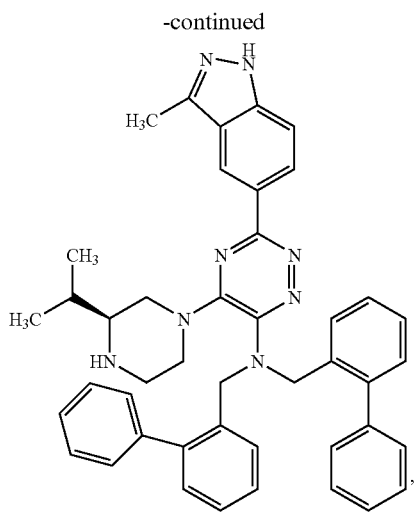
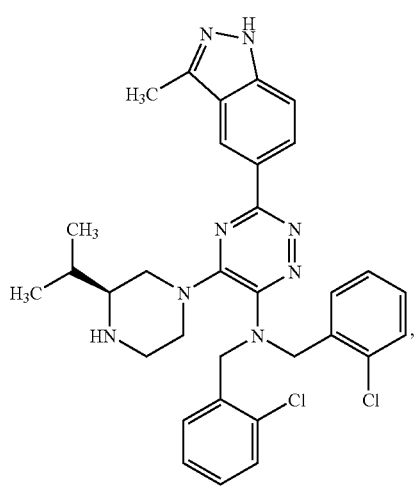
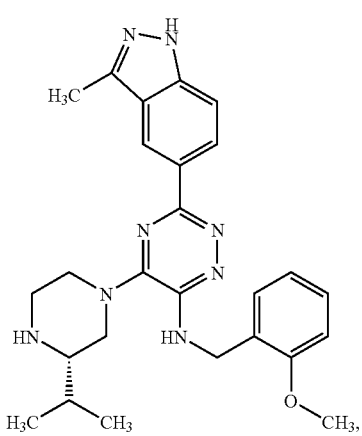

235
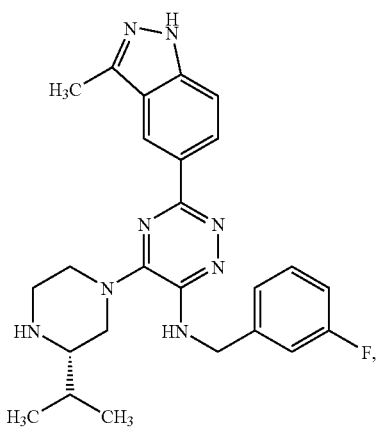
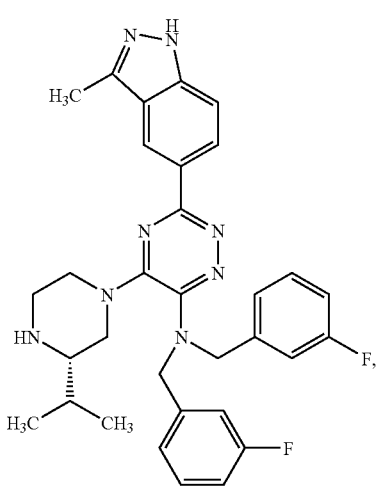
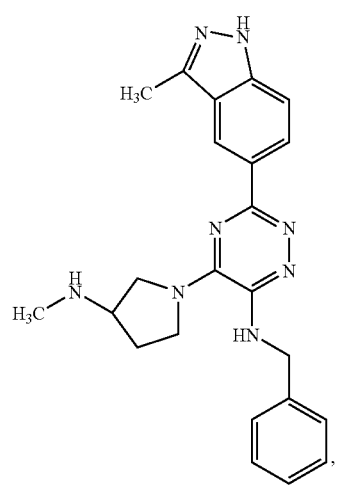
236
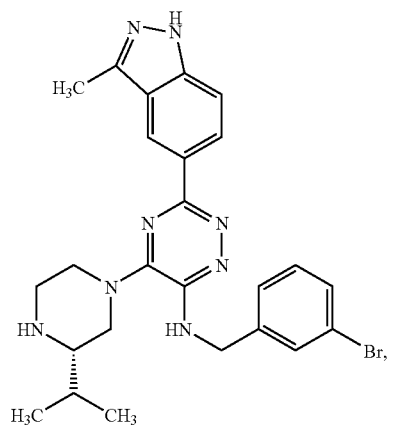
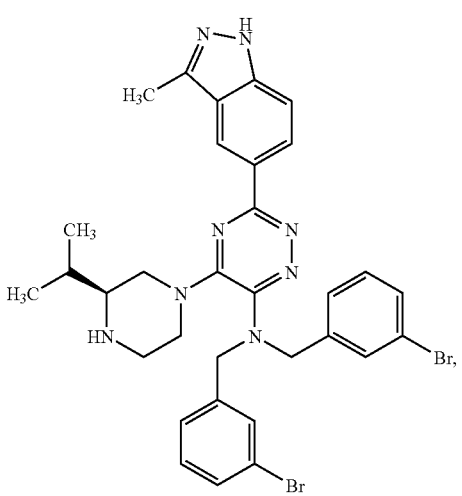
and

-continued
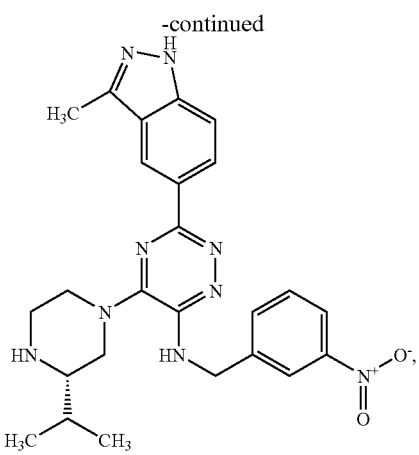
or a pharmaceutically acceptable salt thereof.
24. The compound of claim 23, selected from the group consisting of:
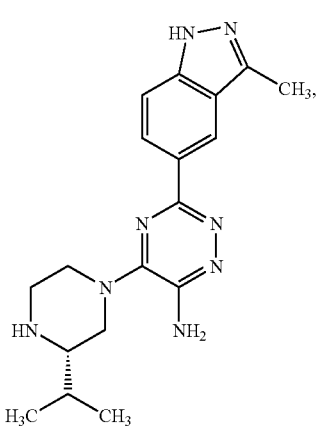
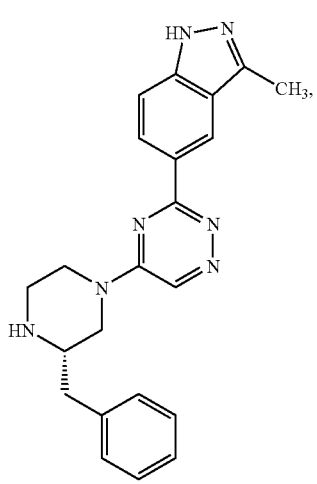
-continued
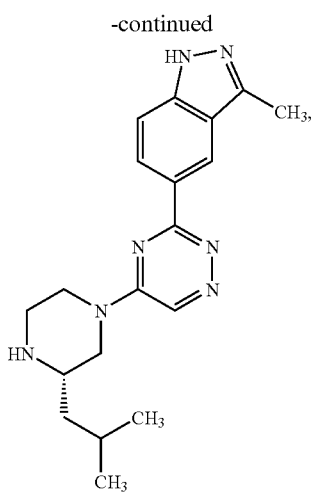
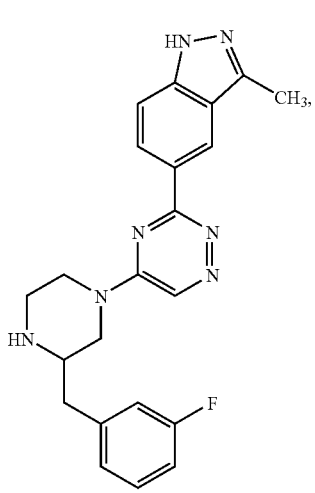

239
-continued
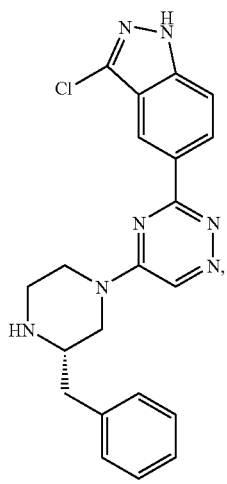
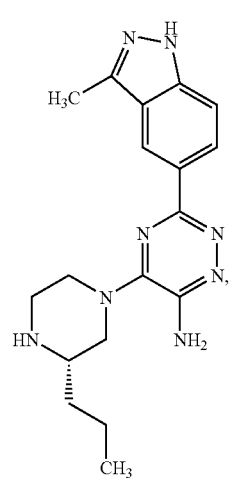
240
-continued
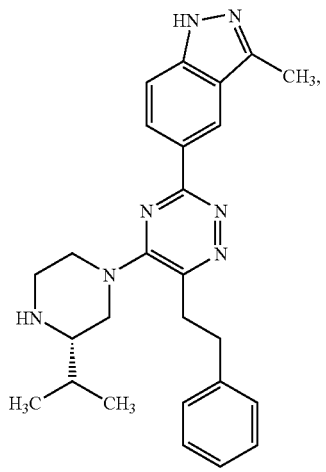
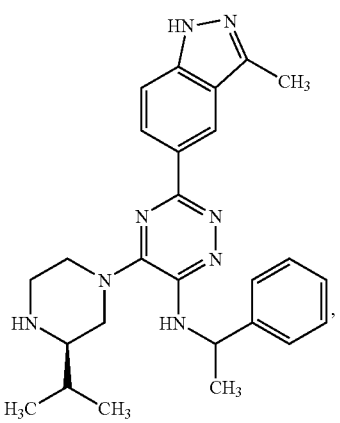
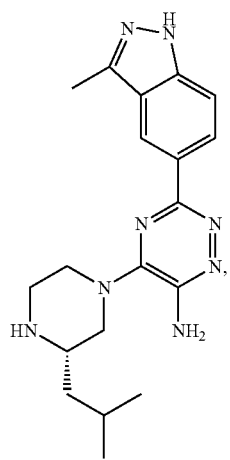

241
-continued
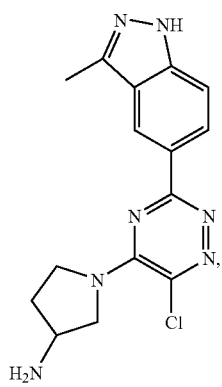
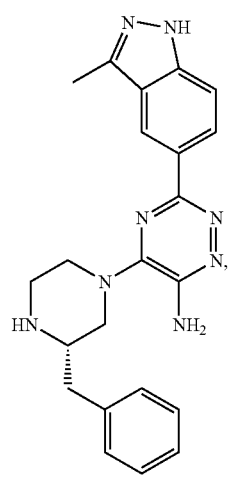
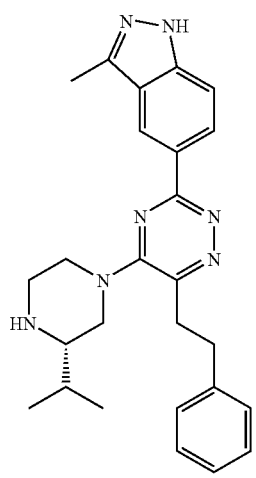
242
-continued
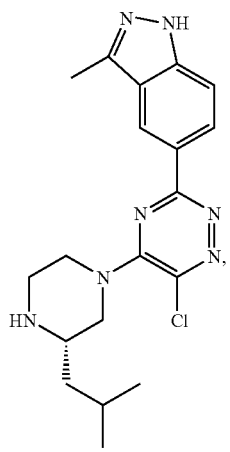
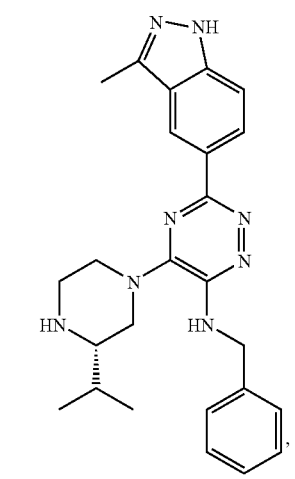
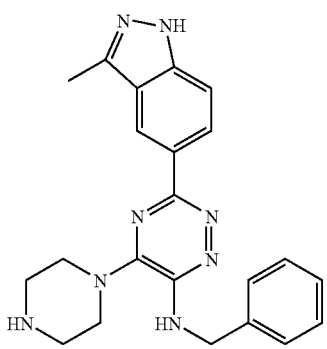

-continued
243
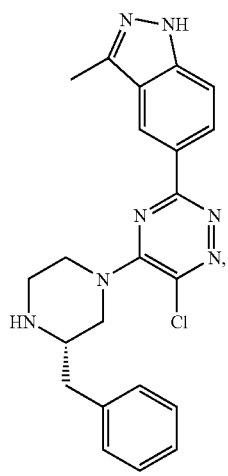
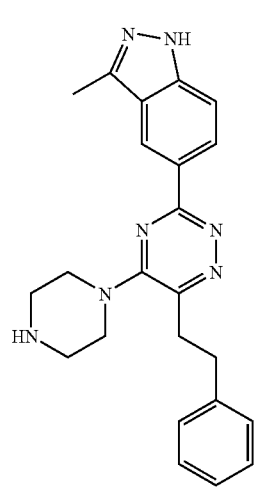
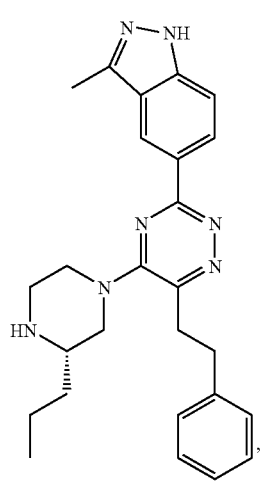
244
-continued
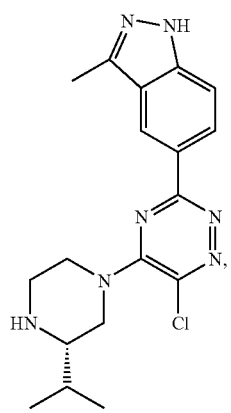
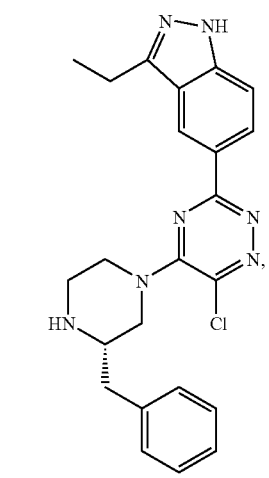
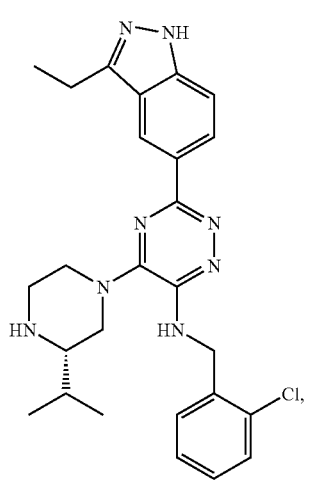

-continued

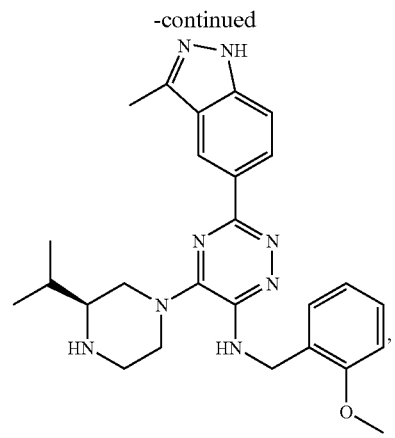

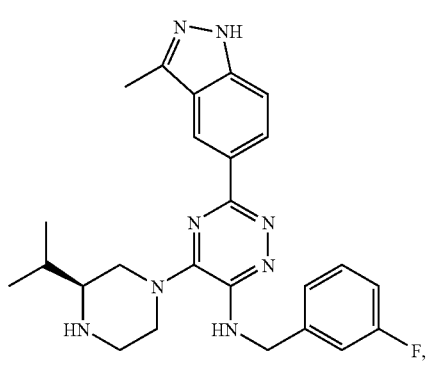

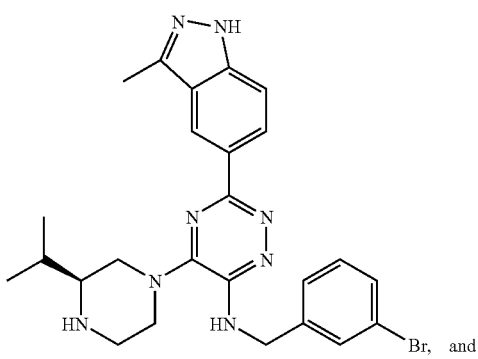

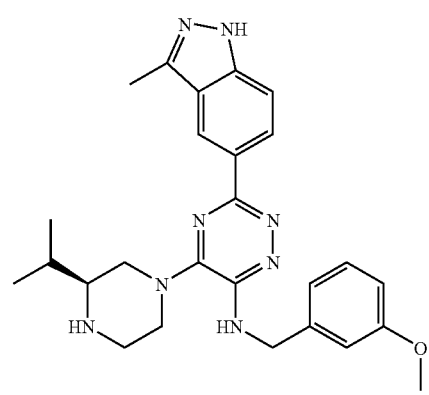

or a pharmaceutically acceptable thereof.

25. The compound of claim 24, wherein said compound is

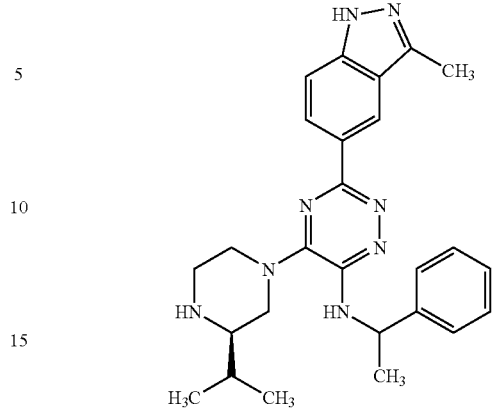

or a pharmaceutically acceptable salt thereof.

26. A pharmaceutical composition comprising:
  a compound of claim 1, or a pharmaceutically acceptable salt thereof; and
  at least one pharmaceutically acceptable carrier.

27. A pharmaceutical composition comprising:
  a compound of claim 12, or a pharmaceutically acceptable salt thereof; and
  at least one pharmaceutically acceptable carrier.

28. A method of treating a disease, disorder, or condition comprising:
  administering to a patient in need thereof a therapeutically effective amount of at least one compound of claim 1, or a pharmaceutically acceptable salt thereof;
  wherein said disease, disorder, or condition is breast cancer.

29. The method of claim 28, further comprising administering at least one additional active ingredient selected from the group consisting of a second kinase inhibitor, an estrogen receptor modulator, an androgen receptor modulator, a retinoid receptor modulator, a cyctotoxic agent, a prenyl-protein transferase inhibitor, an HMG-CoA reductase inhibitor, an HIV protease inhibitor, a reverse transcriptase inhibitor, an angiogenesis inhibitor, an inhibitor of inherent multidrug resistance, an anti-emetic agent, an agent useful in the treatment of anemia, an agent useful in the treatment of neutropenia, and an immunologic-enhancing agent.

30. A pharmaceutical composition comprising:
  a compound of claim 22, or a pharmaceutically acceptable salt thereof; and
  at least one pharmaceutically acceptable carrier.

31. A pharmaceutical composition comprising:
  a compound of claim 23, or a pharmaceutically acceptable salt thereof; and
  at least one pharmaceutically acceptable carrier.

32. A method of treating a disease, disorder, or condition comprising: administering to a patient in need thereof a therapeutically effective amount of at least one compound of claim 1, or a pharmaceutically acceptable salt thereof; wherein said disease, disorder or condition is selected from the group consisting of: ovarian tumor, pancreatic cancer, and prostrate cancer.

33. A method of treating a disease, disorder, or condition comprising: administering to a patient in need thereof a therapeutically effective amount of at least one compound of claim 22, or a pharmaceutically acceptable salt thereof; wherein said disease, disorder or condition is selected from the group consisting of: ovarian tumor, pancreatic cancer, and prostrate cancer.

34. A method of treating a disease, disorder, or condition comprising:
   administering to a patient in need thereof a therapeutically effective amount of at least one compound of claim 23, or a pharmaceutically acceptable salt thereof; wherein said disease, disorder or condition is selected from the group consisting of: ovarian tumor, pancreatic cancer, and prostrate cancer.

35. The method of claim 32, further comprising administering at least one additional active ingredient selected from the group consisting of a second kinase inhibitor, an estrogen receptor modulator, an androgen receptor modulator, a retinoid receptor modulator, a cyctotoxic agent, a prenyl-protein transferase inhibitor, an HMG-CoA reductase inhibitor, an HIV protease inhibitor, a reverse transcriptase inhibitor, an angiogenesis inhibitor, an inhibitor of inherent multidrug resistance, an anti-emetic agent, an agent useful in the treatment of anemia, an agent useful in the treatment of neutropenia, and an immunologic-enhancing agent.

* * * * *

UNITED STATES PATENT AND TRADEMARK OFFICE
CERTIFICATE OF CORRECTION

PATENT NO. : 7,528,132 B2  Page 1 of 1
APPLICATION NO. : 11/338501
DATED : May 5, 2009
INVENTOR(S) : Tin-Yau Chan et al.

It is certified that error appears in the above-identified patent and that said Letters Patent is hereby corrected as shown below:

In the Claims:

Claim 11, col. 174, line 34, please correct "wherein wherein" to:

-- wherein --

Claim 15, col. 175, line 31, please correct "A" to:

-- $A^2$ --

Claim 19, col. 176, line 24, please correct "puperidinyl" to:

-- piperidinyl --

Claim 19, col. 176, line 34, please correct "$R^2$ is H or halogen. $R^2$ is H halogen." to:

-- $R^2$ is H or halogen. --

Claim 24, col. 245, line 67, please correct "acceptable thereof." to:

-- acceptable salt thereof. --

Signed and Sealed this

Seventeenth Day of November, 2009

David J. Kappos
*Director of the United States Patent and Trademark Office*